United States Patent
Tafesse et al.

(10) Patent No.: US 9,975,854 B2
(45) Date of Patent: May 22, 2018

(54) BENZOMORPHAN ANALOGS AND USE THEREOF

(71) Applicant: Purdue Pharma L.P., Stamford, CT (US)

(72) Inventors: Laykea Tafesse, Robbinsville, NJ (US); Jiangchao Yao, Princeton, NJ (US); Jianming Yu, Plainsboro, NJ (US); R. Richard Goehring, Henderson, TX (US)

(73) Assignee: Purdue Pharma L.P., Stamford, CT (US)

( * ) Notice: Subject to any disclaimer, the term of this patent is extended or adjusted under 35 U.S.C. 154(b) by 0 days. days.

(21) Appl. No.: 15/308,987

(22) PCT Filed: May 5, 2015

(86) PCT No.: PCT/US2015/029161
§ 371 (c)(1),
(2) Date: Nov. 4, 2016

(87) PCT Pub. No.: WO2015/171553
PCT Pub. Date: Nov. 12, 2015

(65) Prior Publication Data
US 2017/0073313 A1    Mar. 16, 2017

Related U.S. Application Data

(60) Provisional application No. 61/989,129, filed on May 6, 2014.

(51) Int. Cl.
| C07D 221/06 | (2006.01) |
| C07D 221/26 | (2006.01) |
| C07D 403/12 | (2006.01) |
| C07D 401/12 | (2006.01) |
| C07D 405/12 | (2006.01) |
| C07D 409/12 | (2006.01) |

(Continued)

(52) U.S. Cl.
CPC ......... C07D 221/26 (2013.01); C07D 401/12 (2013.01); C07D 403/12 (2013.01); C07D 405/12 (2013.01); C07D 409/12 (2013.01); C07D 413/12 (2013.01); C07D 417/12 (2013.01)

(58) Field of Classification Search
CPC .................................................. C07D 221/26
See application file for complete search history.

(56) References Cited

U.S. PATENT DOCUMENTS 4,108,857 A * 8/1978 Albertson ............ C07D 221/26
546/97
4,150,032 A * 4/1979 Kavadias .............. C07C 49/755
546/97

(Continued)

FOREIGN PATENT DOCUMENTS

WO    WO-1998/054168    12/1998
WO    WO-1999/48492     9/1999

(Continued)

OTHER PUBLICATIONS

Jacobson, Journal of Medicinal Chemistry (1965), 8(5), 563-6.*
May, Journal of Organic Chemistry (1957), 22, 593-4.*
Iddon et al. Journal of the Chemical Society, Perkin Transactions 1: Organic and Bio-Organic Chemistry (1972-1999) (1990), (4), 1091-5.*
Wentland Bioorganic & Medicinal Chemistry Letters (2001), 11(5), 623-626.*
Wentland Bioorganic & Medicinal Chemistry Letters (2009), 19(1), 203-208.*
Altier, C. et al., "ORL-1 receptor-mediated internalization of N-type calcium channels." Nature Neuroscience, 2005, 9:31.

(Continued)

*Primary Examiner* — Nizal S Chandrakumar
(74) *Attorney, Agent, or Firm* — Purdue Pharma L.P.; Alan L. Koller; Weiying Yang

(57) ABSTRACT

The invention provides compounds as represented by Formula I or I' and pharmaceutically acceptable salts, solvates, and diastereomers thereof: Wherein $R^1$, $R^2$, $R^{2a}$, $R^3$, and $R^4$ are defined in the disclosure. The invention also provides compounds of Formulae II, III, and A-H, and pharmaceutically acceptable salts, solvates, and diastereomers thereof. In certain embodiments, Compounds of the Invention are useful for treating pain, constipation, and other conditions as delineated in the disclosure. Without wishing to be bound by any theory, it is believed that Compounds of the Invention are effective in treating conditions that are modulated by activity of opioid and/or ORL-1 receptors.

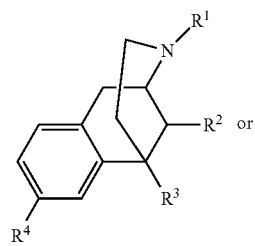

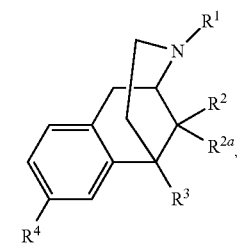

17 Claims, No Drawings

(51) Int. Cl.
*C07D 413/12* (2006.01)
*C07D 417/12* (2006.01)

(56) References Cited

U.S. PATENT DOCUMENTS

| | | | |
|---|---|---|---|
| 4,234,591 A * | 11/1980 | Akkerman | C07D 221/26 514/295 |
| 4,288,444 A * | 9/1981 | Akkerman | C07D 221/26 514/295 |
| 4,366,325 A | 12/1982 | Wedemeyer et al. | |
| 4,406,904 A | 9/1983 | Welle et al. | |
| 4,425,353 A | 1/1984 | Akkerman et al. | |
| 4,882,335 A * | 11/1989 | Sinclair | A61K 31/00 514/282 |
| 6,281,211 B1 | 8/2001 | Cai et al. | |
| 6,335,354 B2 | 1/2002 | Hogenkamp | |
| 6,414,011 B1 | 7/2002 | Hogenkamp et al. | |
| 6,479,484 B1 | 11/2002 | Lan et al. | |
| 6,500,825 B2 | 12/2002 | Lan et al. | |
| 6,613,803 B1 | 9/2003 | Wang et al. | |
| 6,638,947 B2 | 10/2003 | Wang et al. | |
| 6,696,442 B2 | 2/2004 | Wang et al. | |
| 6,737,418 B2 | 5/2004 | Hogenkamp et al. | |
| 6,770,661 B2 | 8/2004 | Shao et al. | |
| 6,867,210 B2 | 3/2005 | Hogenkamp et al. | |
| 6,919,363 B2 | 7/2005 | Hogenkamp et al. | |
| 7,022,714 B2 | 4/2006 | Sun et al. | |
| 7,078,426 B2 | 7/2006 | Hogenkamp et al. | |
| 7,091,210 B2 | 8/2006 | Lan et al. | |
| 7,105,549 B2 | 9/2006 | Shao et al. | |
| 7,169,782 B2 | 1/2007 | Sun et al. | |
| 7,229,993 B2 | 6/2007 | Goehring et al. | |
| 7,393,872 B2 | 7/2008 | Lan | |
| 7,541,465 B2 | 6/2009 | Lan et al. | |
| 7,579,367 B2 | 8/2009 | Shao et al. | |
| 7,872,127 B2 | 1/2011 | Lan et al. | |
| 7,943,643 B2 | 5/2011 | Shao et al. | |
| 8,426,431 B2 | 4/2013 | Lan et al. | |
| 8,771,643 B2 * | 7/2014 | Schachtel | A61K 31/167 424/9.2 |
| 9,045,435 B2 | 6/2015 | Goehring et al. | |
| 9,056,832 B2 | 6/2015 | Ni et al. | |
| 9,056,836 B2 * | 6/2015 | Lockman | C07D 221/26 |
| 9,120,752 B2 | 9/2015 | Kyle et al. | |
| 9,120,786 B2 | 9/2015 | Yu et al. | |
| 9,133,131 B2 | 9/2015 | Shao | |
| 9,163,008 B2 | 10/2015 | Ni et al. | |
| 9,168,255 B2 | 10/2015 | Goehring et al. | |
| 9,181,185 B2 | 11/2015 | Yao | |
| 9,206,127 B2 | 12/2015 | Tafesse et al. | |
| 9,212,139 B2 | 12/2015 | Kyle et al. | |
| 9,403,824 B2 | 8/2016 | Lockman | |
| 2002/0037926 A1 | 3/2002 | Lan | |
| 2003/0225080 A1 | 12/2003 | Wang et al. | |
| 2004/0097569 A1 | 5/2004 | Sun et al. | |
| 2004/0152696 A1 | 8/2004 | Sun et al. | |
| 2004/0176364 A1 | 9/2004 | Sun et al. | |
| 2004/0192691 A1 | 9/2004 | Hogenkamp et al. | |
| 2005/0043305 A1 | 2/2005 | Hogenkamp et al. | |
| 2005/0222027 A1 | 10/2005 | Chiang et al. | |
| 2008/0318932 A1 | 12/2008 | Lan | |
| 2010/0113436 A1 | 5/2010 | Amewu et al. | |
| 2012/0302591 A1 | 11/2012 | Wentland | |
| 2013/0303568 A1 | 11/2013 | Lan et al. | |
| 2014/0005212 A1 | 1/2014 | Ni et al. | |
| 2014/0187549 A1 | 7/2014 | Tafesse | |
| 2014/0309228 A1 | 10/2014 | Engel | |
| 2015/0057300 A1 | 2/2015 | Tafesse et al. | |
| 2015/0133500 A1 | 5/2015 | Tafesse et al. | |
| 2015/0141434 A1 | 5/2015 | Park et al. | |
| 2015/0175569 A1 | 6/2015 | Lynch et al. | |
| 2015/0203504 A1 | 7/2015 | Goehring | |
| 2015/0259293 A1 | 9/2015 | Ni et al. | |
| 2015/0284383 A1 | 10/2015 | Lynch et al. | |
| 2015/0335642 A1 | 11/2015 | Shao | |
| 2015/0336974 A1 | 11/2015 | Youngman | |
| 2015/0344465 A1 | 12/2015 | Kyle et al. | |
| 2015/0353512 A1 | 12/2015 | Tadesse et al. | |
| 2016/0009659 A1 | 1/2016 | Lockman et al. | |
| 2016/0031873 A1 | 2/2016 | Yao et al. | |
| 2016/0052911 A1 | 2/2016 | Yao | |
| 2016/0244459 A1 | 8/2016 | Kupper | |
| 2017/0037046 A1 | 2/2017 | Tafesse | |

FOREIGN PATENT DOCUMENTS

| | | | |
|---|---|---|---|
| WO | WO-2003/076414 | 9/2003 | |
| WO | WO-2011/158108 | 12/2011 | |
| WO | WO-2012/035421 | 3/2012 | |
| WO | WO 2013167963 | * 11/2013 | C07D 221/26 |
| WO | WO-2014/091298 | 6/2014 | |
| WO | WO-2015/102682 | 7/2015 | |
| WO | WO-2015/112801 | 7/2015 | |

OTHER PUBLICATIONS

Barlocco, D., et al., "The opioid-receptor-like 1 (ORL-1) as a potential target for new analgesics." Eur. J. Med.Chem., 2000, 35:275.

Foley, K. M. "Pain." Cecil Textbook of Medicine. Eds. J. C. Bennett and F. Plum. 20th ed. Philadelphia, P.A.: WB Saunders, 1996. 100-107.

Gutstein and Akil, "Opioid Analgesics." Brunton, LL, Lazo, JS, Parker, KI: Goodman & Gilman's The Pharmacological Basis of Therapeutics (547-590). Publisher City, State: McGraw Hill.

International Search Report from corresponding PCT Application No. PCT/US15/29161 dated Jul. 24, 2015 with Written Opinion.

Kawamoto et al., "Discovery of the first potent and selective small molecule opoid receptor-like )ORL-1) antagnoist: 1-[(3R,4R)-1-cyclooctylmethyl-3-hydroxymethyl-4-piperidy1]-3-ethyl-1,3-dihydro-2-h-benzimidazol-2-one (J-113397)" J. Med. Chem, 1999, 42:5061-6063.

Lufty, K. et al., "Buprenorphine-induced antinociception is mediated by μ-opioid receptors and compromised by concomitant activation of opioid receptor-like receptors." J. Neurosci., 2003, 23:10331-10337.

Mantovani, A. "Cancer: Inflammation by Remote Control." Nature 435.7043 (2005): 752-3.

Mogil, J.S. et al., "Orphanin FQ is a functional anti-opioid peptide." Neurosci., 1996, 75:333.

Morgan, M.M. et al., "Antinociception mediated by the periaqueductal gray is attenuated by orphanin FQ." NeuroReport, 1997, 8:3431.

Shinkai et al., "4-aminoquinolines: Novel nociceptin antagonists with analgesic activity", J. Med. Chem 2000, 43:4667-4677.

Tian J. et al., "Functional studies using antibodies against orphanin FQ/nociceptin." Peptides, 2000, 21:1047.

Tian, J. et al., "Involvement of endogenous Orphanin FQ in electroacupuncture-induced analgesia." NeuroReport,1997, 8:497.

Ueda, H. et al., "Enhanced Spinal Nociceptin Receptor Expression Develops Morphine Tolerance and Dependence."J. Neurosci., 2000, 20:7640.

Wood & Galligan, "Function of Opioids in the Enteric Nervous System." Neurogastroenterology & Motility 16 (Suppl.2): 17-28, 2004.

* cited by examiner

BENZOMORPHAN ANALOGS AND USE THEREOF

CROSS-REFERENCE TO RELATED APPLICATIONS

This application is the U.S. national phase, pursuant to 35 U.S.C. § 371, of PCT International Application Ser. No. PCT/US2015/029161, filed on May 5, 2015, designating the United States and published in English on Nov. 12, 2015 as publication WO 2015/171553 A1, which claims priority to U.S. Provisional Application Ser. No. 61/989,129, filed on May 6, 2014. The contents of the afore-mentioned patent applications are incorporated herein by their entirety.

BACKGROUND OF THE INVENTION

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone or oxymorphone).

Although the term "narcotic" is often used to refer to opioids, the term is not specifically applicable to opioids. The term "narcotic", derived from the Greek word for "stupor", originally referred to any drug that induced sleep, only later being associated with opioids (Gutstein, Howard B., Akil, Huda, "Chapter 21. Opioid Analgesics" (Chapter 21), Brunton, L L, Lazo, J S, Parker, K I: Goodman & Gilman's The Pharmacological Basis of Therapeutics, 11$^{th}$ Edition: http://www.accessmedicine.com/content.aspx?aID=940653). In the legal context, the term "narcotic" refers to a variety of mechanistically unrelated substances with abuse or addictive potential (Gutstein, Howard B., Akil, Huda, "Chapter 21. Opioid Analgesics" (Chapter 21), Brunton L L, Lazo J S, Parker K I: Goodman & Gilman's The Pharmacological Basis of Therapeutics, 11$^{th}$ Edition: http://www.accessmedicine.com/content.aspx?aID=940653). Thus, the term "narcotic" not only refers to opioids, but also refers to such drugs as cocaine, methamphetamine, ecstasy, etc., which exert their pharmacological effects via different receptors than opioids. Furthermore, because the term "narcotic" refers to such a wide variety of unrelated drugs, many of which do not possess analgesic properties, it cannot be assumed that a drug that has "narcotic" properties is necessarily analgesic. For example, drugs such as ecstasy and methamphetamine are not analgesic, and are not used to treat pain.

Until recently, there was evidence of three major classes of opioid receptors in the central nervous system (CNS), with each class having subtype receptors. These receptor classes are known as $\mu$, $\delta$ and $\kappa$. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This newly discovered receptor was classified as an opioid receptor based only on structural grounds, as the receptor did not exhibit pharmacological homology. It was initially demonstrated that non-selective ligands having a high affinity for $\mu$, $\delta$ and $\kappa$ receptors had low affinity for the ORL-1 receptor. This characteristic, along with the fact that an endogenous ligand had not yet been discovered, led to the ORL-1 receptor being designated as an "orphan receptor".

Subsequent research led to the isolation and structure of the endogenous ligand of the ORL-1 receptor. This ligand, nociceptin (also known as orphanin FQ (OFQ)), is a seventeen amino acid peptide structurally similar to members of the opioid peptide family. (C. Altier et al., "ORL-1 receptor-mediated internalization of N-type calcium channels." *Nature Neuroscience*, 2005, 9:31).

The discovery of the ORL-1 receptor and its endogenous ligand, presents an opportunity for the discovery of novel compounds that can be administered for pain management or other syndromes influenced by this receptor.

Many publications in the ORL-1/nociceptin field provide evidence that activation of ORL-1 receptors in the brain can inhibit opioid-mediated analgesia (e.g., D. Barlocco et al., "The opioid-receptor-like 1 (ORL-1) as a potential target for new analgesics." *Eur. J. Med. Chem.*, 2000, 35:275; J. S. Mogil et al., "Orphanin FQ is a functional anti-opioid peptide." *Neurosci.*, 1996, 75:333; K. Lutfy et al., "Tolerance develops to the inhibitory effect of orphanin FQ on morphine-induced antinociception in the rat." *NeuroReport*, 1999, 10:103; M. M. Morgan et al., "Antinociception mediated by the periaqueductal gray is attenuated by orphanin FQ." *NeuroReport*, 1997, 8:3431; and J. Tian et al., "Involvement of endogenous Orphanin FQ in electroacupuncture-induced analgesia." *NeuroReport*, 1997, 8:497).

A growing body of evidence supports a more generalized regulatory role for ORL-1 against the actions of the $\mu$ receptor, possibly contributing to the development of $\mu$-agonist tolerance in patients being treated with classical opiates (e.g., J. Tian et al., "Functional studies using antibodies against orphanin FQ/nociceptin." *Peptides*, 2000, 21:1047; and H. Ueda et al., "Enhanced Spinal Nociceptin Receptor Expression Develops Morphine Tolerance and Dependence." *J. Neurosci.*, 2000, 20:7640). Moreover, ORL-1 activation appears to have an inhibitory effect on the rewarding properties of several drugs of abuse, including $\mu$ agonists.

Use of opioid analgesics often leads to constipation as a side effect. Constipation associated with the use of opioid analgesics is presumed to occur primarily and mechanistically as a result of the action of mu opioid agonists directly upon mu opioid receptors located in the bowel (Wood & Galligan (2004), Function of opioids in the enteric nervous system. *Neurogastroenterology & Motility* 16(Suppl.2): 17-28.). Stimulation of the mu opioid receptors in the bowel causes inhibition of normal gastrointestinal (GI) motility, leading to constipation. The effect of $\mu$ opioid agonism on $\mu$ opioid receptors in the bowel can be observed via the action of loperamide (Imodium™) in treating diarrhea. Loperamide is a potent $\mu$ opioid agonist that is administered orally, but which has little to no absorption into the blood stream. As a result, loperamide exerts its action locally upon the $\mu$ opioid receptors in the bowel, and this results in inhibition of GI motility, which treats diarrhea.

There has been recent interest in developing combinations of $\mu$ receptor agonists and antagonists having defined biodistribution properties that might serve to limit opioid-induced constipation. For example, the co-administration of an orally bio-available μ opioid receptor agonist (such as morphine, codeine, oxycodone or hydormorphone) together with a potent μ opioid receptor antagonist (such as N-methylnaloxone or N-methylnaltrexone) that is not orally bio-available may serve to prevent or reduce the constipation otherwise associated with mu opioid receptor agonist therapy. The rationale is that the agonist component will be absorbed and distributed throughout the periphery and the central nervous system (CNS), resulting in the desired analgesia, while the antagonist component will remain in the bowel where it will prevent or reduce any agonist-induced constipation that might otherwise occur.

Benzomorphan analog compounds, such as 3,11,11-trimethyl-1,2,3,4,5,6-hexahydro-2,6-methanobenzo[d]azocine-6,8-diol and 8-methoxy-3,11,11-trimethyl-1,2,3,4,5,6-hexahydro-2,6-methanobenzo WI azocin-6-ol, having analgesic activity have been described (see, e.g. U.S. Pat. No. 4,425,353; U.S. Pat. No. 4,406,904; and U.S. Pat. No. 4,366,325).

In certain aspects, it is desirable to achieve benzomorphan analog compounds that have antagonist activity at the ORL-1 receptor which is greater than those currently-available compounds, e.g., JTC-801 (described in WO 99/48492; and Shinkai et al., "4-aminoquinolines: Novel nociceptin antagonists with analgesic activity", *J. Med. Chem.*, 2000, 43:4667-4677) and J-113397 (described in WO 98/54168; and Kawamoto et al., "Discovery of the first potent and selective small molecule opioid receptor-like (ORL-1) antagonist: 1-[(3R,4R)-1-cyclooctylmethyl-3-hydroxymethyl-4-piperidyl]-3-ethyl-1,3-dihydro-2H-benzimidazol-2-one (J-113397)", *J. Med. Chem.*, 1999, 42:5061-6063).

BRIEF SUMMARY OF THE INVENTION

The invention provides novel benzomorphan analogs that are useful for treating a variety of conditions, including pain, in particular chronic pain, and constipation. In one aspect, the invention provides compounds of Formulae I, I', II, III and A-H, and pharmaceutically acceptable salts, solvates, and diastereomers thereof (collectively, referred to hereinafter as "Compounds of the Invention") as novel compounds. In certain embodiments, Compounds of the Invention exhibit affinity for one or more of ORL-1, μ, δ, and κ opioid receptors.

Certain Compounds of the Invention have demonstrated agonist activity at the μ, δ and/or κ receptors greater than currently available compounds, e.g., morphine.

In certain embodiments, some Compounds of the Invention have both: (i) antagonist activity at the ORL-1 receptor; and (ii) agonist activity at one or more of the μ, δ and/or κ opioid receptors.

In a separate embodiment, certain Compounds of the Invention have both: (i) antagonist activity at the ORL-1 receptor; and (ii) agonist activity at the μ opioid receptor.

In another embodiment, certain compounds of the invention have both: (i) antagonist activity at the μ opioid receptor; and (ii) agonist activity at the κ opioid receptor.

Further, certain compounds of the invention have: (i) antagonist activity at the ORL-1 receptor; (ii) antagonist activity at the μ opioid receptor; and (iii) agonist activity at the κ opioid receptor.

Still further, certain compounds of the invention have: (i) antagonist activity at the μ opioid receptor; (ii) agonist activity at the κ opioid receptor; and (iii) antagonist activity at the δ opioid receptor.

In certain embodiments, compounds of the Invention are useful as analgesics; anti-inflammatories; diuretics; anesthetics; neuroprotective agents; anti-hypertensives; anxiolytics; agents for appetite control; hearing regulators; anti-tussives; anti-asthmatics; anti-epileptics; anti-convulsants; modulators of locomotor activity; modulators of learning and memory; regulators of neurotransmitter release; modulators of hormone release; kidney function modulators; anti-depressants; agents to treat memory loss due to Alzheimer's disease or other dementias; agents to treat withdrawal from alcohol and/or drugs of addiction; agents to control water balance or sodium excretion; agents to treat arterial blood pressure disorders, or any of the following: UI, ulcers, IBD, IBS, diarrhea, constipation, addictive disorders, Parkinson's disease, parkinsonism, anxiety, epilepsy, stroke, a seizure, pruritic conditions, psychosis, cognitive disorders, memory deficits, restricted brain function, Huntington's chorea, ALS, dementia, retinopathy, muscle spasms, migraines, vomiting, dyskinesia, and/or depression (each being a "Condition").

The invention further provides methods for treating a Condition, comprising administering to a subject in need thereof a therapeutically effective amount of a Compound of the Invention.

In certain embodiments, the Condition is pain (e.g., chronic or acute pain). In one embodiment, the Compounds of the Invention are particularly useful for treating chronic pain.

In certain embodiments, the Compound of the Invention is an ORL-1 receptor antagonist. In other embodiments, the Compound of the Invention is an agonist at one or more of μ, δ and/or κ opioid receptors.

In certain embodiments, the Compound of the Invention is both an ORL-1 receptor antagonist and an agonist at one or more of the μ, δ and/or κ opioid receptors. In other embodiments, the Compound of the Invention is both an ORL-1 receptor antagonist and an agonist at the μ opioid receptor.

In certain non-limiting embodiments, the Compound of the Invention produces fewer side effects and/or less severe side effects than currently available analgesic opioid compounds when administered at doses producing equivalent levels of analgesia and/or anti-hyperalgesia. In certain non-limiting embodiments, the Compound of the Invention exhibits a substantially linear dose response curve, such that the bell-shaped dose response curve observed for most opioid analgesics (i.e. low and high doses do not produce significant analgesia, whereas mid-range doses produce analgesia) is not observed for the Compound of the Invention.

In certain embodiments, it is expected, therefore, that it will be easier to titrate to an effective dose of a Compound of the Invention in a patient than it is for conventional opioid analgesics. It is further expected that, as one embodiment, a Compound of the Invention will produce effective analgesia and/or anti-hyperalgesia in a patient who has become tolerant to conventional opioids, and for whom a conventional opioid is no longer an effective treatment.

Also, in other embodiments, it is expected that a Compound of the Invention will produce effective analgesia and/or anti-hyperalgesia at doses that do not induce side effects, such as, respiratory depression in patients for whom a dose of a conventional opioid that is high enough to be an effective treatment also induces significant side effects such as respiratory depression.

The invention further provides methods for preventing a Condition, comprising administering to s a subject in need thereof a Condition-preventing effective amount of a Compound of the Invention.

In certain embodiments, the invention provides benzomorphan analog compounds that are useful for treating or preventing constipation, such as, μ opioid receptor-induced constipation. Thus, certain Compounds of the Invention act as μ opioid receptor antagonists.

In other embodiments, certain Compounds of the Invention demonstrate dual activity, that is, they act as both μ opioid receptor antagonists and κ opioid receptor agonists.

In further embodiments, certain Compounds of the Invention are expected to be μ opioid receptor antagonists, κ opioid receptor agonists, and δ opioid receptor antagonists, while being inactive at ORL-1 receptors.

In yet other embodiments, certain Compounds of the Invention are expected to be μ opioid receptor antagonists, κ opioid receptor agonists, δ opioid receptor antagonists, and ORL-1 receptor antagonists.

In other embodiments, certain Compounds of the Invention are expected to be μ opioid receptor antagonists, κ opioid receptor agonists, δ opioid receptor antagonists, and ORL-1 receptor partial agonists.

In separate embodiments, certain Compounds of the Invention are expected to be inactive at δ opioid receptors.

Further, certain Compounds of the Invention are expected to be substantially restricted to the GI tract. Compounds of the Invention that have μ opioid receptor antagonist activity and are substantially restricted to the GI tract will significantly reduce or prevent constipation that would otherwise occur in a patient as a result of treatment with a μ opioid receptor agonist. In one embodiment, the reduction or prevention of constipation is obtained without reducing the desired analgesic effect of the μ agonist. The Compounds of the Invention that also exhibit κ opioid receptor agonist activity should additionally stimulate GI motility via a non-μ receptor mediated mechanism.

In another aspect, the invention provides a method for treating or preventing a Condition in a subject. In certain embodiments, the Condition treated will be pain (e.g., acute or chronic pain).

The invention further provides a method for treating or preventing constipation (such as, constipation associated with μ-opioid agonist therapy) by administering an effective amount of a Compound of the Invention to a patient in need of such treatment or prevention. In one embodiment, the Compound of the Invention is a μ antagonist that is substantially restricted to the GI tract. In another embodiment, the Compound of the Invention is both a μ antagonist and a κ agonist, and is substantially restricted to the GI tract. In another embodiment, the method comprises co-administering to a patient both an effective amount of a Compound of the Invention that is a μ antagonist and is substantially restricted to the GI tract, and an analgesically effective amount of a μ agonist. In still another embodiment, the method comprises co-administration to a patient of both an effective amount of a Compound of the Invention, which is both a μ antagonist and a κ agonist, and which is substantially restricted to the GI tract, together with an analgesically effective amount of a μ agonist.

In still another aspect, the invention provides pharmaceutical compositions comprising a therapeutically effective amount of a Compound of the Invention admixed with a pharmaceutically acceptable carrier or excipient. Such compositions are useful for treating or preventing a Condition in a subject. The pharmaceutical compositions of the invention may be formulated as immediate release formulations, or as controlled or sustained release formulations.

Pharmaceutical compositions of the invention may be formulated for administration by any of a number of different routes known in the art, including but not limited to, oral, intradermal, intramuscular, intraperitoneal, parenteral, intravenous, subcutaneous, intranasal, epidural, sublingual, intracerebral, intravaginal, transdermal, transmucosal, rectal, by inhalation, or topical (particularly to the ears, nose, eyes, or skin).

Other apsects of the invention include methods for preparing a composition, comprising a step of admixing a Compound of the Invention and a pharmaceutically acceptable carrier or excipient to form a pharmaceutical composition. The invention also provides use of a Compound of the Invention in the manufacturing of a medicament useful to treat or prevent a Condition in a subject.

The invention further relates to a kit comprising a container (such as, sterile) containing an effective amount of a Compound of the Invention.

DETAILED DESCRIPTION OF THE INVENTION

In one aspect, the Invention provides novel benzomorphan analogs (also referred to as "Compounds of the Invention"). In certain embodiments, the benzomorphan analogs disclosed herein are useful for treating or preventing one or more Conditions, such as, pain and constipation. These benzomorphan analogs may provide a reduced liability for developing analgesic tolerance and physical dependence.

In certain embodiments, Compounds of the Invention are useful for modulating a pharmacodynamic response from ORL-1 receptors, either centrally or peripherally, or both. In other embodiments, Compounds of the Invention are useful for modulating a pharmacodynamic response from one or more opioid receptors (e.g., μ, δ, κ) either centrally or peripherally, or both. Without wishing to be bound by any theory, the pharmacodynamic response may be attributed to the compound stimulating (agonizing) or inhibiting (antagonizing) the one or more receptors.

In certain embodiments, Compounds of the Invention may inhibit (or antagonize) the ORL-1 receptor, while also stimulating (or agonizing) one or more other opioid receptors (e.g. as a μ, δ and/or κ agonist). Compounds of the Invention having agonist activity may be either full or partial agonists.

In certain embodiments, Compounds of the Invention can be used in combination with at least one other therapeutic agent. The other therapeutic agent can be, but is not limited to, a μ-opioid agonist, a non-opioid analgesic, a non-steroidal anti-inflammatory agent, a Cox-II inhibitor, an antiemetic, a β-adrenergic blocker, an anticonvulsant, an antidepressant, a $Ca^{2+}$-channel blocker, an anticancer agent, or a mixture thereof.

Various objects and advantages of the invention will become apparent from the following detailed description.

One aspect of the invention provides compounds of Formula I, and pharmaceutically acceptable salts, solvates, and diastereomers thereof:

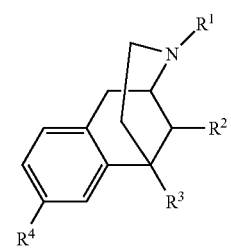

I wherein

R$^1$ is (C$_1$-C$_{10}$)alkyl, (C$_2$-C$_{10}$)alkenyl, or (C$_3$-C$_{12}$)cycloalkyl, wherein said (C$_2$-C$_{10}$)alkenyl is optionally substituted by one or two same or different (C$_1$-C$_6$)alkyl;

R$^2$ is (C$_1$-C$_{10}$)alkyl, —N(R$^5$)(R$^6$), or —C(=O)R$^7$;

R$^3$ is H or —(C$_1$-C$_6$)alkyl;

R$^4$ is selected from —H, —OH, —CN, —NR$^8$R$^9$, —(C$_1$-C$_5$)alkyl-NR$^8$R$^9$, —C(O)O(C$_1$-C$_5$)alkyl, —NHSO$_2$(C$_1$-C$_5$)alkyl, halo, —C(halo)$_3$, —CH(halo)$_2$, —CH$_2$(halo), —COOH, —CONH$_2$, —(C$_1$-C$_5$)alkyl, —(C$_2$-C$_5$)alkenyl, —(C$_2$-C$_5$)alkynyl, —(CH$_2$)$_n$—O—(CH$_2$)$_n$—CH$_3$, and —(C$_1$-C$_5$)alkoxy; each of which is optionally substituted with 1, 2, or 3 independently selected R$^a$ groups;

R$^5$ is selected from the group consisting of hydrogen, —(C$_1$-C$_{10}$)alkyl, —C(=O)—(C$_1$-C$_6$)alkyl-(6- to 14-membered)aryl, —C(=O)—(C$_1$-C$_6$)alkyl, —C(=O)—(C$_2$-C$_6$)alkenyl, —CONR$^8$R$^9$, —(C$_1$-C$_6$)alkyl-C(O)NR$^8$R$^9$, —CO—(CH$_2$)$_n$—C(O)NR$^8$R$^9$, ((6- to 14-membered)aryl)-(C$_1$-C$_6$)alkyl, ((3- to 12 membered)-heterocycle)-(C$_1$-C$_6$)alkyl-, —C(=O)—NH-((5- to 12-membered)heteroaryl), ((C$_3$-C$_{12}$)cycloalkyl)-(C$_1$-C$_6$)alkyl-, —SO$_2$—(C$_1$-C$_6$)alkyl, —SO$_2$—((6- to 14 membered)aryl), and ((5- to 12-membered)heteroaryl)-(C$_1$-C$_6$)alkyl-, each of which is optionally substituted with one, two, or three substituents independently selected from the group consisting of —OH, halo, —C(halo)$_3$, —CH(halo)$_2$, —CH$_2$(halo), —(C$_1$-C$_6$)alkyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, —NH$_2$, —NH(C$_1$-C$_6$)alkyl, —NH(C$_1$-C$_6$)alkyl-R$^{11}$, —CN, —SH, —OR$^{12}$, —NR$^8$R$^9$, —CONR$^8$R$^9$, —COOR$^{10}$, —(C$_1$-C$_6$)alkoxy-COOR$^{10}$, —(OCH$_2$CH$_2$)$_s$—O(C$_1$-C$_6$)alkyl, —SO$_2$—(C$_1$-C$_6$)alkyl, —SO$_2$—((C$_3$-C$_{12}$)cycloalkyl), —SO$_2$—(C$_1$-C$_6$)alkyl-(6- to 14 membered)aryl), —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)—(C$_1$-C$_6$)alkyl-(6- to 14-membered)aryl, —NH—(C$_1$-C$_6$)alkyl-CO—OR$^{10}$, —NH—C(=O)—(C$_1$-C$_6$)alkyl-CO—OR$^{10}$, —NH—C(=O)—CH(NH$_2$)—(C$_1$-C$_6$)alkyl-CO—OR$^{10}$, —(C$_3$-C$_{12}$)cycloalkyl, hydroxy(C$_3$-C$_{12}$)cycloalkyl-, -(6- to 14-membered)aryl, -(6- to 14-membered)aryloxy, —(C$_1$-C$_6$)alkoxy-C(O)NR$^8$R$^9$, —NH—(C$_1$-C$_6$)alkyl-C(O)NR$^8$R$^9$, —C(O)NH—(C$_1$-C$_6$)alkyl-COOR$^{10}$, —C(=O)—(C$_1$-C$_6$)alkyl, -(5- to 12-membered)heteroaryl, -(3- to 12-membered)heterocycle, and -(7- to 12-membered)-bicycloheterocycle;

R$^6$ is selected from the group consisting of H, —(C$_1$-C$_6$)alkyl, —(C$_1$-C$_6$)alkyl-CO—OR$^{10}$, —(C$_1$-C$_6$)alkyl-OR$^{10}$, —(C$_1$-C$_6$)alkyl-CONR$^8$R$^9$, —(C$_3$-C$_{12}$)cycloalkyl, ((C$_3$-C$_{12}$)cycloalkyl)-(C$_1$-C$_6$)alkyl-, —C(=O)(C$_1$-C$_6$)alkyl, and —SO$_2$(C$_1$-C$_6$)alkyl;

R$^7$ is selected from the group consisting of —(C$_1$-C$_{10}$)alkyl, —(C$_1$-C$_{10}$)alkoxy, —(OCH$_2$CH$_2$)$_s$—O(C$_1$-C$_6$)alkyl, —NH(C$_1$-C$_6$)alkyl, —NR$^c$R$^d$, —(C$_3$-C$_{12}$)cycloalkyl, ((C$_3$-C$_{12}$)cycloalkyl)-(C$_1$-C$_6$)alkyl-, and -(3- to 12-membered)heterocycle; each of which is optionally substituted with one, two, or three substituents independently selected from the group consisting of —OH, halo, —C(halo)$_3$, —CH(halo)$_2$, —CH$_2$(halo), —(C$_1$-C$_6$)alkyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, —NH$_2$, —NH(C$_1$-C$_6$)alkyl, —NH(C$_1$-C$_6$)alkyl-R$^{11}$, —CN, —SH, —OR$^{12}$, —NR$^8$R$^9$, —CONR$^8$R$^9$, —COOR$^{10}$, —(C$_1$-C$_6$)alkoxy-COOR$^{10}$, —(OCH$_2$CH$_2$)$_s$—O(C$_1$-C$_6$)alkyl, —SO$_2$—(C$_1$-C$_6$)alkyl, —SO$_2$—((C$_3$-C$_{12}$)cycloalkyl), —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)—(C$_1$-C$_6$)alkyl-(6- to 14-membered)aryl, —NH—(C$_1$-C$_6$)alkyl-CO—OR$^{10}$, —NH—C(=O)—(C$_1$-C$_6$)alkyl-CO—OR$^{10}$, —NH—C(=O)—CH(NH$_2$)—(C$_1$-C$_6$)alkyl-CO—OR$^{10}$, —(C$_3$-C$_{12}$)cycloalkyl, -(6- to 14-membered)aryl, -(6- to 14-membered)aryloxy, —(C$_1$-C$_6$)alkoxy-C(O)NR$^8$R$^9$, —NH—(C$_1$-C$_6$)alkyl-C(O)NR$^8$R$^9$, —C(O)NH—(C$_1$-C$_6$)alkyl-COOR$^{10}$, -(5- to 12-membered)heteroaryl, -(3- to 12-membered)heterocycle, and -(7- to 12-membered)bicycloheterocycle;

R$^8$ and R$^9$ are each independently selected from
a) hydrogen, —OH, halo, —C(halo)$_3$, —CH(halo)$_2$, —CH$_2$(halo);
b) —(C$_1$-C$_6$)alkyl, —(C$_2$-C$_5$)alkenyl, —(C$_2$-C$_5$)alkynyl, —(CH$_2$)$_n$—O—(CH$_2$)$_n$—CH$_3$, —(C$_1$-C$_6$)alkoxy, each of which is optionally substituted with 1, 2, or 3 substituents independently selected from —OH, halo, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_{12}$)cycloalkyl, —CHO, —C(O)OH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;
c) —(C$_3$-C$_8$)cycloalkyl, ((C$_3$-C$_8$)cycloalkyl)-(C$_1$-C$_6$)alkyl-, —COOR$^{10}$, —(C$_1$-C$_6$)alkyl-COOR$^{10}$, —CONH$_2$, and (C$_1$-C$_6$)alkyl-CONH—;
d) ((6- to 14-membered)aryl) optionally substituted with 1, 2, or 3 independently selected R$^b$ groups;
e) -((5- to 12-membered)heteroaryl) optionally substituted with 1, 2, or 3 independently selected R$^b$ groups; and
f) R$^8$ and R$^9$ together with the nitrogen atom to which they are attached form a (3- to 12-membered)heterocycle optionally substituted with 1, 2, or 3 independently selected R$^b$ groups;

each R$^{10}$ is independently selected from the group consisting of hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

each R$^{11}$ is independently selected from the group consisting of —COOR$^{10}$, —(C$_1$-C$_6$)alkyl-COOR$^{10}$, —C(=O)—(C$_1$-C$_6$)alkyl-COOR$^{10}$, —(C$_1$-C$_6$)alkyl-C(=O)—(C$_1$-C$_6$)alkyl-COOR$^{10}$, —CONH$_2$, and —(C$_1$-C$_6$)alkyl-CONH$_2$;

each R$^{12}$ is independently selected from the group consisting of —C(halo)$_3$, —CH(halo)$_2$, —CH$_2$(halo), —(C$_2$-C$_5$)alkenyl, —(C$_2$-C$_5$)alkynyl, —(CH$_2$)$_n$—O—(CH$_2$)$_n$—CH$_3$, (6- to 14-membered)aryl, ((6- to 14-membered)aryl)-(C$_1$-C$_6$)alkyl-, (5- to 12-membered)heteroaryl, and ((5- to 12-membered)heteroaryl)-(C$_1$-C$_6$)alkyl-, each of which is optionally substituted with 1, 2, or 3 independently selected R$^a$ groups;

each R$^a$ is independently selected from the group consisting of —OH, halo, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_2$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, and —CONR$^{5a}$R$^{6a}$;

each R$^b$ is independently selected from the group consisting of —C(halo)$_3$, —CH(halo)$_2$, —CH$_2$(halo), —COOR$^{10}$, —CONH$_2$, —CONH(C$_1$-C$_6$)alkyl, —CONH(C$_3$-C$_{12}$)cycloalkyl, —(C$_1$-C$_6$)alkyl, CN, -(3- to 12-membered)heteroaryl, ((3- to 12-membered)heteroaryl)-(C$_1$-C$_6$)alkyl-, —NH$_2$, halo, —SO$_2$—(C$_1$-C$_6$)alkyl, —SO$_2$—((C$_3$-C$_{12}$)cycloalkyl), and ((6- to 14-membered)aryl)-(C$_1$-C$_6$)alkoxy-;

n is an integer 0, 1, 2, 3, 4, 5, or 6;
s in an integer 1, 2, 3, 4, 5, or 6;
$R^{5a}$ and $R^{6a}$ are each independently selected from the group consisting of:
  a) hydrogen, —OH, halo, —C(halo)$_3$, —CH(halo)$_2$, and —CH$_2$(halo);
  b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 substituents independently selected from the group consisting of —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, and phenyl;
  c) —(C$_3$-C$_8$)cycloalkyl, ((C$_3$-C$_8$)cycloalkyl)-(C$_1$-C$_6$)alkyl-, —COOR$^{10}$, —(C$_1$-C$_6$)alkyl-COOR$^{10}$, —CONH$_2$, and (C$_1$-C$_6$)alkyl-CONH—;
  d) -(6- to 14-membered)aryl optionally substituted with 1, 2, or 3 independently selected R$^b$ groups;
  e) -((5- to 12-membered)heteroaryl) optionally substituted with 1, 2, or 3 independently selected R$^b$ groups; and
  f) $R^{5a}$ and $R^{6a}$ together with the nitrogen atom to which they are attached form a (3- to 12-membered)heterocycle optionally substituted with 1, 2, or 3 independently selected R$^b$ groups;

R$^c$ and R$^d$ together with the nitrogen atom to which they are attached form a (3- to 12-membered)heterocycle optionally substituted with 1, 2, or 3 independently selected R$^b$ groups;

Provided that
  i) when R$^4$ is hydrogen and when R$^1$ and R$^3$ are both methyl, then R$^2$ may not be NH$_2$ or NHC(O)CH$_3$;
  ii) when R$^1$ is methyl, R$^2$ is —N(R$^5$)(R$^6$), and R$^5$ is ((3- to 12 membered)-heterocycle)-(C$_1$-C$_6$)alkyl-, then the ((3- to 12 membered)heterocycle) moiety in said ((3- to 12 membered)heterocycle)-(C$_1$-C$_6$)alkyl- of R$^5$ is further substituted by a substituent selected from the group consisting of —SO$_2$—(C$_1$-C$_6$)alkyl, —CONR$^8$R$^9$, hydroxy(C$_1$-C$_6$)alkyl-, —C(=O)—(C$_1$-C$_6$)alkyl, and —SO$_2$—((C$_3$-C$_{12}$)cycloalkyl);
  iii) when both of R$^1$ and R$^3$ are methyl, R$^4$ is methoxy, and R$^2$ is —N(R$^5$)(R$^6$), then
    R$^6$ is —(C$_1$-C$_6$)alkyl, and R$^5$ is —C(=O)—(C$_1$-C$_6$) alkyl substituted by -(3- to 12-membered)heterocycle; and
  iv) when R$^1$ is methyl, R$^2$ is —N(R$^5$)(R$^6$), R$^6$ is H or —(C$_1$-C$_6$)alkyl, and R$^5$ is optionally-substituted —CONR$^8$R$^9$ or optionally-substituted —C(=O)—NH—((5- to 12-membered)heteroaryl), then
    R$^3$ is methyl, R$^4$ is —OH, and R$^5$ is selected from the group consisting of

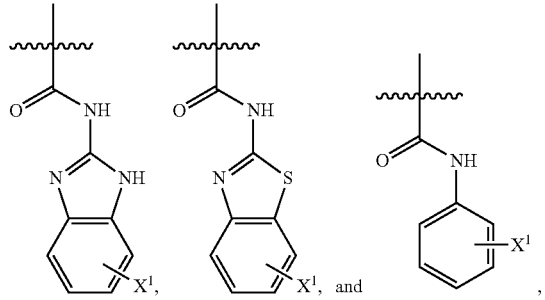

wherein X$^1$ is H, halo, CN, or —SO$_2$—(C$_1$-C$_6$)alkyl;
  v) when R$^1$ is methyl, R$^2$ is —N(R$^5$)(R$^6$), and R$^5$ is selected from the group consisting of a) —(C$_1$-C$_{10}$) alkyl substituted by -(6- to 14-membered)aryl or -(5- to 12-membered)heteroaryl; and b) ((6- to 14-membered) aryl)-(C$_1$-C$_6$)alkyl- optionally substituted by one or two substituents selected from the group of halo, —(C$_1$-C$_6$)alkyl, and —(C$_1$-C$_6$)alkoxy, then
    R$^6$ is a group other than H;
  vi) when each of R$^1$, R$^2$, and R$^3$, independently, is un-substituted —(C$_1$-C$_6$)alkyl, then R$^4$ is a group other than —OH; and
  vii) when R$^2$ is —N(R$^5$)(R$^6$), and R$^5$ is —SO$_2$—((6- to 14 membered)aryl), then said —SO$_2$—((6- to 14 membered)aryl) in R$^5$ is unsubstituted; and
  viii) when R$^2$ is —N(R$^5$)(R$^6$), and R$^5$ is —C(=O)—(C$_2$-C$_6$)alkenyl substituted by -(5- to 12-membered)heteroaryl, then
    R$^4$ is —OH; and R$^6$ is H;

and further provided that
  said compound of Formula I is NOT any compound selected from the group consisting of A1-A15 provided in TABLE 1 as follows:

TABLE 1

| Cpd # | Structure | Chemical name |
|---|---|---|
| A1 | 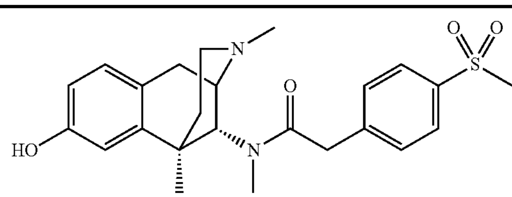 | N-((2R,6R,11S)-8-hydroxy-3,6-dimethyl-1,2,3,4,5,6-hexahydro-2,6-methano-benzo[d]azocin-11-yl)-N-methyl-2-(4-(methylsulfonyl)phenyl)acetamide |
| A2 | 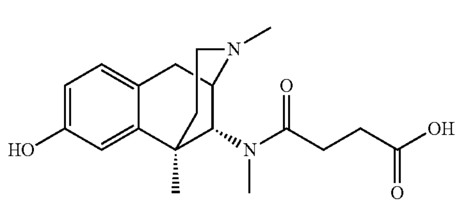 [SMILES: CN1CC[C@]2(C)c3cc(O)ccc3CC1[C@@H]2N(C)C(=O)CCC(=O)O] | 4-(((2R,6R,11S)-8-hydroxy-3,6-dimethyl-1,2,3,4,5,6-hexahydro-2,6-methano-benzo[d]azocin-11-yl)(methyl)amino)-4-oxobutanoic acid |

TABLE 1-continued

| Cpd # | Structure | Chemical name |
|---|---|---|
| A3 | 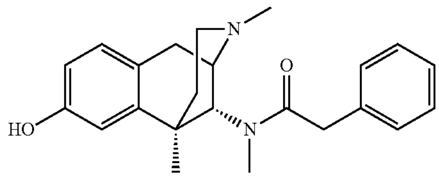 [SMILES: CN1CC[C@]2(C)c3cc(O)ccc3CC1[C@@H]2N(C)C(=O)Cc1ccccc1] | (2R,6R,11S)-3,6-dimethyl-11-(methyl(phenethyl)amino)-1,2,3,4,5,6-hexahydro-2,6-methanobenzo[d]azocin-8-ol |
| A4 | 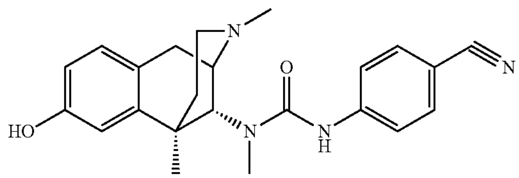 [SMILES: CN1CC[C@]2(C)c3cc(O)ccc3CC1[C@@H]2N(C)C(=O)Nc1ccc(C#N)cc1] | 3-(4-cyanophenyl)-1-((2R,6S,11R)-8-hydroxy-3,6-dimethyl-1,2,3,4,5,6-hexahydro-2,6-methano-benzo[d]azocin-11-yl)-1-methylurea |
| A5 | 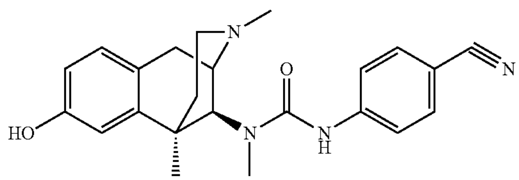 [SMILES: CN1CC[C@]2(C)c3cc(O)ccc3CC1[C@H]2N(C)C(=O)Nc1ccc(C#N)cc1] | 3-(4-cyanophenyl)-1-((2R,6S,11S)-8-hydroxy-3,6-dimethyl-1,2,3,4,5,6-hexahydro-2,6-methano-benzo[d]azocin-11-yl)-1-methylurea |
| A6 | 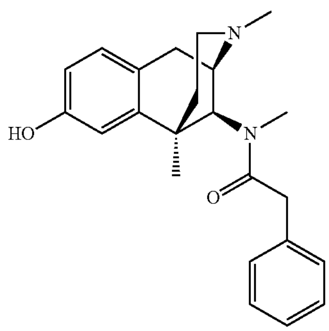 [SMILES: CN1CC[C@]2(C)c3cc(O)ccc3C[C@@H]1[C@H]2N(C)C(=O)Cc1ccccc1] | N-((2R,6S,11S)-8-hydroxy-3,6-dimethyl-1,2,3,4,5,6-hexahydro-2,6-methano-benzo[d]azocin-11-yl)-N-methyl-2-phenylacetamide |
| A7 | 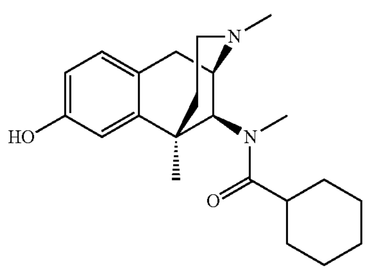 [SMILES: CN1CC[C@]2(C)c3cc(O)ccc3C[C@@H]1[C@H]2N(C)C(=O)C1CCCCC1] | N-((2R,6S,11S)-8-hydroxy-3,6-dimethyl-1,2,3,4,5,6-hexahydro-2,6-methano-benzo[d]azocin-11-yl)-N-methylcyclohexane-carboxamide |
| A8 | 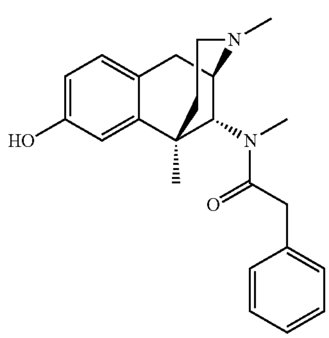 [SMILES: CN1CC[C@]2(C)c3cc(O)ccc3C[C@@H]1[C@@H]2N(C)C(=O)Cc1ccccc1] | N-((2R,6S,11R)-8-hydroxy-3,6-dimethyl-1,2,3,4,5,6-hexahydro-2,6-methanobenzo[d]azocin-11-yl)-N-methyl-2-phenylacetamide |

TABLE 1-continued

| Cpd # | Structure | Chemical name |
|---|---|---|
| A9 | 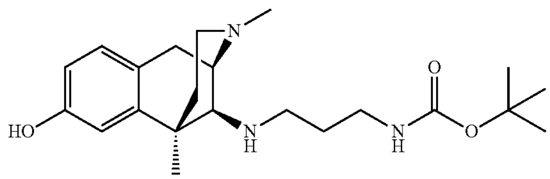 [SMILES: CN1CC[C@]2(C)c3cc(O)ccc3C[C@@H]1[C@H]2NCCCNC(=O)OC(C)(C)C] | tert-butyl (3-(((2R,6S,11S)-8-hydroxy-3,6-dimethyl-1,2,3,4,5,6-hexahydro-2,6-methanobenzo[d]azocin-11-yl)amino)propyl)carbamate |
| A10 | 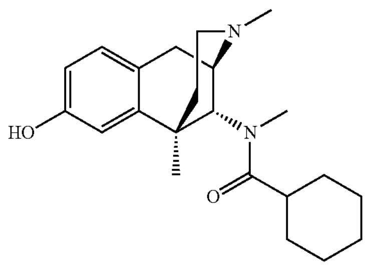 [SMILES: CN1CC[C@]2(C)c3cc(O)ccc3C[C@@H]1[C@@H]2N(C)C(=O)C1CCCCC1] | N-((2R,6S,11R)-8-hydroxy-3,6-dimethyl-1,2,3,4,5,6-hexahydro-2,6-methanobenzo[d]azocin-11-yl)-N-methylcyclohexane-carboxamide |
| A11 | 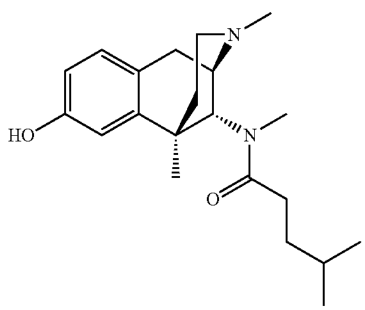 [SMILES: CC(C)CCC(=O)N(C)[C@H]1[C@H]2Cc3ccc(O)cc3[C@@]1(C)CCN2C] | N-((2R,6S,11R)-8-hydroxy-3,6-dimethyl-1,2,3,4,5,6-hexahydro-2,6-methanobenzo[d]azocin-11-yl)-N,4-dimethylpentanamide |
| A12 | 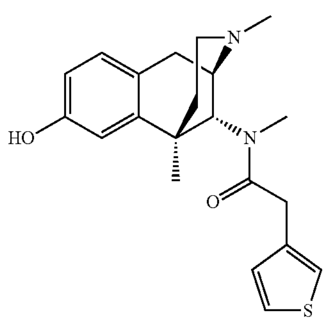 [SMILES: CN1CC[C@]2(C)c3cc(O)ccc3C[C@@H]1[C@@H]2N(C)C(=O)Cc1ccsc1] | N-((2R,6S,11R)-8-hydroxy-3,6-dimethyl-1,2,3,4,5,6-hexahydro-2,6-methanobenzo[d]azocin-11-yl)-N-methyl-2-(thiophen-2-yl)acetamide |
| A13 | 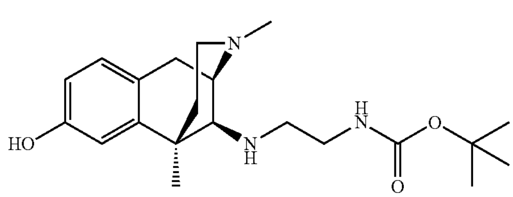 [SMILES: CN1CC[C@]2(C)c3cc(O)ccc3C[C@@H]1[C@H]2NCCNC(=O)OC(C)(C)C] | tert-butyl (2-(((2R,6S,11S)-8-hydroxy-3,6-dimethyl-1,2,3,4,5,6-hexahydro-2,6-methanobenzo[d]azocin-11-yl)amino)ethyl)carbamate |

TABLE 1-continued

| Cpd # | Structure | Chemical name |
|---|---|---|
| A14 | 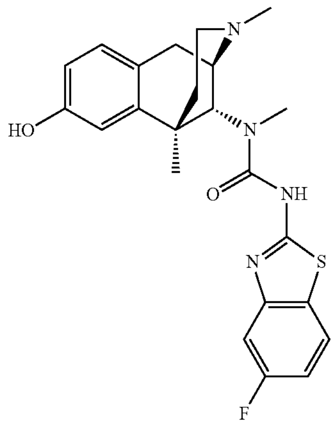 [SMILES: CN1CC[C@]2(C)c3cc(O)ccc3C[C@@H]1[C@@H]2N(C)C(=O)Nc1nc2cc(F)ccc2s1] | 3-(5-fluorobenzo[d]thiazol-2-yl)-1-((2R,6S,11R)-8-hydroxy-3,6-dimethyl-1,2,3,4,5,6-hexahydro-2,6-methanobenzo[d]azocin-11-yl)-1-methylurea |
| A15 | 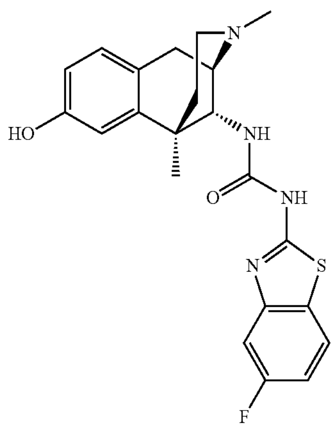 [SMILES: CN1CC[C@]2(C)c3cc(O)ccc3C[C@@H]1[C@@H]2NC(=O)Nc1nc2cc(F)ccc2s1] | 1-(5-fluorobenzo[d]thiazol-2-yl)-3-((2R,6S,11R)-8-hydroxy-3,6-dimethyl-1,2,3,4,5,6-hexahydro-2,6-methanobenzo[d]azocin-11-yl)urea |

In another aspect, the Invention provides compounds of Formula I', and pharmaceutically acceptable salts, solvates, and diastereomers thereof:

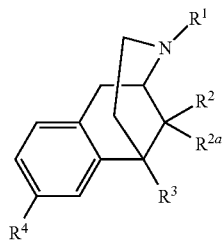

I' wherein $R^1$ is $(C_1-C_{10})$alkyl, $(C_2-C_{10})$alkenyl, or $(C_3-C_{12})$cycloalkyl, wherein said $(C_2-C_{10})$alkenyl is optionally substituted by one or two same or different $(C_1-C_6)$alkyl;

$R^2$ is —OH, $(C_1-C_6)$alkoxy, $(C_1-C_{10})$alkyl, —N($R^5$)($R^6$), or —C(=O)$R^7$;

$R^{2a}$ is H, —OH, or $(C_1-C_6)$alkoxy;

$R^3$ is H or —$(C_1-C_6)$alkyl;

$R^4$ is selected from —H, —OH, —CN, —$NR^8R^9$, —$(C_1-C_5)$alkyl-$NR^8R^9$, —C(O)O$(C_1-C_5)$alkyl, —NHSO$_2$$(C_1-C_5)$alkyl, halo, —C(halo)$_3$, —CH(halo)$_2$, —CH$_2$(halo), —COOH, —CONH$_2$, —$(C_1-C_5)$alkyl, —$(C_2-C_5)$alkenyl, —$(C_2-C_5)$alkynyl, —$(CH_2)_n$—O—$(CH_2)_n$—CH$_3$, and —$(C_1-C_5)$alkoxy; each of which is optionally substituted with 1, 2, or 3 independently selected $R^a$ groups;

$R^5$ is selected from the group consisting of hydrogen, —$(C_1-C_{10})$alkyl, —C(=O)—$(C_1-C_6)$alkyl-(6- to 14-membered)aryl, —C(=O)—$(C_1-C_6)$alkyl, —C(=O)—$(C_2-C_6)$alkenyl, —$CONR^8R^9$, —$(C_1-C_6)$alkyl-C(O)$NR^8R^9$, —CO—$(CH_2)_n$—C(O)$NR^8R^9$, ((6- to 14-membered)aryl)-$(C_1-C_6)$alkyl-, ((3- to 12 membered)-heterocycle)-$(C_1-C_6)$alkyl-, —C(=O)—NH—((5- to 12-membered)heteroaryl), (($C_3-C_{12}$)cycloalkyl)-$(C_1-C_6)$alkyl-, —SO$_2$—$(C_1-C_6)$alkyl, —SO$_2$—((6- to 14 membered)aryl), and ((5- to 12-membered)heteroaryl)-$(C_1-C_6)$alkyl-, each of which is optionally substituted with one, two, or three substituents independently selected from the group consisting of —OH, halo, —C(halo)$_3$, —CH(halo)$_2$, —CH$_2$(halo), —$(C_1-C_6)$alkyl, hydroxy($C_1-C_6$)alkyl-, dihydroxy($C_1-C_6$)alkyl-, —$(C_1-C_6)$alkoxy, (($C_1-C_6$)alkoxy)CO($C_1-C_6$)alkoxy-, —NH$_2$, —NH$(C_1-C_6)$alkyl, —NH$(C_1-C_6)$alkyl-$R^{11}$, —CN, —SH, —$OR^{12}$, —$NR^8R^9$, —$CONR^8R^9$, —$COOR^{10}$, —$(C_1-C_6)$alkoxy-$COOR^{10}$, —(OCH$_2$CH$_2$)$_s$—O$(C_1-C_6)$alkyl, —SO$_2$—$(C_1-C_6)$alkyl, —SO$_2$—(($C_3-C_{12}$)cycloalkyl), —SO$_2$—$(C_1-C_6)$alkyl-(6- to 14 membered)aryl), —NH—SO$_2(C_1-C_6)$alkyl, NH$_2$—SO$_2$$(C_1-C_6)$alkyl-, —N(SO$_2(C_1-C_6)$alkyl)$_2$, —C(=NH)NH$_2$, —NH—CO—$(C_1-C_6)$alkyl, —NH—CO—NH$_2$, —NH—C(=O)—NH—$(C_1-C_6)$alkyl, —NH—C(=O)-(6- to 14-membered)aryl, —NH—C(=O)—$(C_1-C_6)$alkyl-(6- to 14-membered)aryl, —NH—($C_1$-$C_6$)alkyl-CO—OR$^{10}$, —NH—C(=O)—($C_1$-$C_6$)alkyl-CO—OR$^{10}$, —NH—C(=O)—CH(NH$_2$)—($C_1$-$C_6$)alkyl-CO—OR$^{10}$, —($C_3$-$C_{12}$)cycloalkyl, hydroxy($C_3$-$C_{12}$)cycloalkyl-, -(6- to 14-membered)aryl, -(6- to 14-membered)aryloxy, —($C_1$-$C_6$)alkoxy-C(O)NR$^8$R$^9$, —NH—($C_1$-$C_6$)alkyl-C(O)NR$^8$R$^9$, —C(O)NH—($C_1$-$C_6$)alkyl-COOR$^{10}$, —C(=O)—($C_1$-$C_6$)alkyl, -(5- to 12-membered)heteroaryl, -(3- to 12-membered)heterocycle, and -(7- to 12-membered)-bicycloheterocycle;

R$^6$ is selected from the group consisting of H, —($C_1$-$C_6$)alkyl, —($C_1$-$C_6$)alkyl-CO—OR$^{10}$—, —($C_1$-$C_6$)alkyl-OR$^{10}$, —($C_1$-$C_6$)alkyl-CONR$^8$R$^9$, —($C_3$-$C_{12}$)cycloalkyl, (($C_3$-$C_{12}$)cycloalkyl)-($C_1$-$C_6$)alkyl-, —C(=O)($C_1$-$C_6$)alkyl-, and —SO$_2$($C_1$-$C_6$)alkyl;

R$^7$ is selected from the group consisting of —($C_1$-$C_{10}$)alkyl, —($C_1$-$C_{10}$)alkoxy, —(OCH$_2$CH$_2$)$_s$—O($C_1$-$C_6$)alkyl, —NH($C_1$-$C_6$)alkyl, —NR$^c$R$^d$, —($C_3$-$C_2$)cycloalkyl, (($C_3$-$C_{12}$)cycloalkyl)-($C_1$-$C_6$)alkyl-, and -(3- to 12-membered)heterocycle; each of which is optionally substituted with one, two, or three substituents independently selected from the group consisting of —OH, halo, —C(halo)$_3$, —CH(halo)$_2$, —CH$_2$(halo), —($C_1$-$C_6$)alkyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, —NH$_2$, —NH($C_1$-$C_6$)alkyl, —NH($C_1$-$C_6$)alkyl-R$^{11}$, —CN, —SH, —OR$^{12}$, —NR$^8$R$^9$, —CONR$^8$R$^9$, —COOR$^{10}$, —($C_1$-$C_6$)alkoxy-COOR$^{10}$, —(OCH$_2$CH$_2$)$_s$—O($C_1$-$C_6$)alkyl, —SO$_2$—($C_1$-$C_6$)alkyl, —SO$_2$—(($C_3$-$C_{12}$)cycloalkyl), —NH—SO$_2$($C_1$-$C_6$)alkyl, NH$_2$—SO$_2$($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—OR$^{10}$, —NH—C(=O)—($C_1$-$C_6$)alkyl-CO—OR$^{10}$, —NH—C(=O)—CH(NH$_2$)—($C_1$-$C_6$)alkyl-CO—OR$^{10}$, —($C_3$-$C_{12}$)cycloalkyl, -(6- to 14-membered)aryl, -(6- to 14-membered)aryloxy, —($C_1$-$C_6$)alkoxy-C(O)NR$^8$R$^9$, —NH—($C_1$-$C_6$)alkyl-C(O)NR$^8$R$^9$, —C(O)NH—($C_1$-$C_6$)alkyl-COOR$^{10}$, -(5- to 12-membered)heteroaryl, -(3- to 12-membered)heterocycle, and -(7- to 12-membered)bicycloheterocycle;

R$^8$ and R$^9$ are each independently selected from
a) hydrogen, —OH, halo, —C(halo)$_3$, —CH(halo)$_2$, —CH$_2$(halo);
b) —($C_1$-$C_6$)alkyl, —($C_2$-$C_5$)alkenyl, —($C_2$-$C_5$)alkynyl, —(CH$_2$)$_n$—O—(CH$_2$)$_n$—CH$_3$, —($C_1$-$C_6$)alkoxy, each of which is optionally substituted with 1, 2, or 3 substituents independently selected from —OH, halo, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, —CHO, —C(O)OH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;
c) —($C_3$-$C_8$)cycloalkyl, (($C_3$-$C_8$)cycloalkyl)-($C_1$-$C_6$)alkyl-, —COOR$^{10}$, —($C_1$-$C_6$)alkyl-COOR$^{10}$, —CONH$_2$, and —CON(H)($C_1$-$C_6$)alkyl;
d) ((6- to 14-membered)aryl) optionally substituted with 1, 2, or 3 independently selected R$^b$ groups;
e) -((5- to 12-membered)heteroaryl) optionally substituted with 1, 2, or 3 independently selected R$^b$ groups; and
f) R$^8$ and R$^9$ together with the nitrogen atom to which they are attached form a (3- to 12-membered)heterocycle optionally substituted with 1, 2, or 3 independently selected R$^b$ groups;

each R$^{10}$ is independently selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

each R$^{11}$ is independently selected from the group consisting of —COOR$^{10}$, —($C_1$-$C_6$)alkyl-COOR$^{10}$, —C(=O)—($C_1$-$C_6$)alkyl-COOR$^{10}$, —($C_1$-$C_6$)alkyl-C(=O)—($C_1$-$C_6$)alkyl-COOR$^{10}$, —CONH$_2$, and —($C_1$-$C_6$)alkyl-CONH$_2$;

each R$^{12}$ is independently selected from the group consisting of —C(halo)$_3$, —CH(halo)$_2$, —CH$_2$(halo), —($C_2$-$C_5$)alkenyl, —($C_2$-$C_5$)alkynyl, —(CH$_2$)$_n$—O—(CH$_2$)$_n$—CH$_3$, (6- to 14-membered)aryl, ((6- to 14-membered)aryl)-($C_1$-$C_6$)alkyl-, (5- to 12-membered)heteroaryl, and ((5- to 12-membered)heteroaryl)-($C_1$-$C_6$)alkyl-, each of which is optionally substituted with 1, 2, or 3 independently selected R$^a$ groups;

each R$^a$ is independently selected from the group consisting of —OH, halo, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, and —CONR$^{5a}$R$^{6a}$;

each R$^b$ is independently selected from the group consisting of —C(halo)$_3$, —CH(halo)$_2$, —CH$_2$(halo), —COOR$^{10}$, —CONH$_2$, —CONH($C_1$-$C_6$)alkyl, —CONH($C_3$-$C_{12}$)cycloalkyl, —($C_1$-$C_6$)alkyl, CN, -(3- to 12-membered)heteroaryl, ((3- to 12-membered)heteroaryl)-($C_1$-$C_6$)alkyl-, —NH$_2$, halo, —SO$_2$—($C_1$-$C_6$)alkyl, —SO$_2$—(($C_3$-$C_{12}$)cycloalkyl), and ((6- to 14-membered)aryl)-($C_1$-$C_6$)alkoxy-;

n is an integer 0, 1, 2, 3, 4, 5, or 6;
s in an integer 1, 2, 3, 4, 5, or 6;
R$^{5a}$ and R$^{6a}$ are each independently selected from the group consisting of:
a) hydrogen, —OH, halo, —C(halo)$_3$, —CH(halo)$_2$, and —CH$_2$(halo);
b) —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, and —($C_1$-$C_6$)alkoxy, each of which is optionally substituted with 1, 2, or 3 substituents independently selected from the group consisting of —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, and phenyl;
c) —($C_3$-$C_8$)cycloalkyl, (($C_3$-$C_8$)cycloalkyl)-($C_1$-$C_6$)alkyl-, —COOR$^{10}$, —($C_1$-$C_6$)alkyl-COOR$^{10}$, —CONH$_2$, and ($C_1$-$C_6$)alkyl-CONH—;
d) -(6- to 14-membered)aryl optionally substituted with 1, 2, or 3 independently selected R$^b$ groups;
e) -((5- to 12-membered)heteroaryl) optionally substituted with 1, 2, or 3 independently selected R$^b$ groups; and
f) R$^{5a}$ and R$^{6a}$ together with the nitrogen atom to which they are attached form a (3- to 12-membered)heterocycle optionally substituted with 1, 2, or 3 independently selected R$^b$ groups;

R$^c$ and R$^d$, each independently, are H or —($C_1$-$C_6$)alkyl;
or R$^c$ and R$^d$ together with the nitrogen atom to which they are attached form a (3- to 12-membered)heterocycle optionally substituted with 1, 2, or 3 independently selected R$^b$ groups;

Provided that
i) when R$^4$ is hydrogen and when R$^1$ and R$^3$ are both methyl, then R$^2$ may not be NH$_2$ or NHC(O)CH$_3$;
ii) when R$^1$ is methyl, R$^2$ is —N(R$^5$)(R$^6$), and R$^5$ is ((3- to 12 membered)-heterocycle)-($C_1$-$C_6$)alkyl-, then the ((3- to 12 membered)heterocycle) moiety in said ((3- to 12 membered)heterocycle)-(C$_1$-C$_6$)alkyl- of R$^5$ is further substituted by a substituent selected from the group consisting of —SO$_2$—(C$_1$-C$_6$)alkyl, —CONR$^8$R$^9$, hydroxy(C$_1$-C$_6$)alkyl-, —C(=O)—(C$_1$-C$_6$)alkyl, and —SO$_2$—((C$_3$-C$_{12}$)cycloalkyl);

iii) when both of R$^1$ and R$^3$ are methyl, R$^4$ is methoxy, and R$^2$ is —N(R$^5$)(R$^6$), then
R$^6$ is —(C$_1$-C$_6$)alkyl, and R$^5$ is —C(=O)—(C$_1$-C$_6$) alkyl substituted by -(3- to 12-membered)heterocycle; and iv) when R$^1$ is methyl, R$^2$ is —N(R$^5$)(R$^6$), R$^6$ is H or —(C$_1$-C$_6$)alkyl, and R$^5$ is optionally-substituted —CONR$^8$R$^9$ or optionally-substituted —C(=O)—NH—((5- to 12-membered)heteroaryl), then
R$^3$ is methyl, R$^4$ is —OH, and R$^5$ is selected from the group consisting of

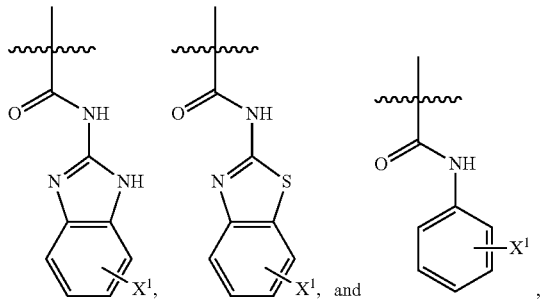

wherein X$^1$ is H, halo, CN, or —SO$_2$—(C$_1$-C$_6$)alkyl;

v) when R$^1$ is methyl, R$^2$ is —N(R$^5$)(R$^6$), and R$^5$ is selected from the group consisting of a) —(C$_1$-C$_{10}$) alkyl substituted by -(6- to 14-membered)aryl or -(5- to 12-membered)heteroaryl; and b) ((6- to 14-membered)aryl)-(C$_1$-C$_6$)alkyl- optionally substituted by one or two substituents selected from the group of halo, —(C$_1$-C$_6$)alkyl, and —(C$_1$-C$_6$)alkoxy, then
R$^6$ is a group other than H;

vi) when each of R$^1$, R$^2$, and R$^3$, independently, is un-substituted —(C$_1$-C$_6$)alkyl, then
R$^4$ is a group other than —OH; and vii) when R$^2$ is —N(R$^5$)(R$^6$), and R$^5$ is —SO$_2$—((6- to 14 membered)aryl), then
said —SO$_2$—((6- to 14 membered)aryl) in R$^5$ is unsubstituted; and viii) when R$^2$ is —N(R$^5$)(R$^6$), and R$^5$ is —C(=O)—(C$_2$-C$_6$)alkenyl substituted by -(5- to 12-membered)heteroaryl, then
R$^4$ is —OH; and R$^6$ is H;

and further provided that said compound is NOT selected from the group consisting of
1) N-((2R,6R,11S)-8-hydroxy-3,6-dimethyl-1,2,3,4,5,6-hexahydro-2,6-methanobenzo[d]azocin-11-yl)-N-methyl-2-(4-(methylsulfonyl)phenyl)acetamide;
2) 4-(((2R,6R,11S)-8-hydroxy-3,6-dimethyl-1,2,3,4,5,6-hexahydro-2,6-methanobenzo[d]azocin-11-yl)(methyl)amino)-4-oxobutanoic acid;
3) (2R,6R,11S)-3,6-dimethyl-11-(methyl(phenethyl)amino)-1,2,3,4,5,6-hexahydro-2,6-methanobenzo[d]azocin-8-ol;
4) 3-(4-cyanophenyl)-1-((2R,6S,11R)-8-hydroxy-3,6-dimethyl-1,2,3,4,5,6-hexahydro-2,6-methanobenzo[d]azocin-11-yl)-1-methylurea;
5) 3-(4-cyanophenyl)-1-((2R,6S,11S)-8-hydroxy-3,6-dimethyl-1,2,3,4,5,6-hexahydro-2,6-methanobenzo[d]azocin-11-yl)-1-methylurea;
6) N-((2R,6S,11S)-8-hydroxy-3,6-dimethyl-1,2,3,4,5,6-hexahydro-2,6-methanobenzo[d]azocin-11-yl)-N-methyl-2-phenylacetamide;
7) N-((2R,6S,11S)-8-hydroxy-3,6-dimethyl-1,2,3,4,5,6-hexahydro-2,6-methanobenzo[d]azocin-11-yl)-N-methylcyclohexanecarboxamide;
8) N-((2R,6S,11R)-8-hydroxy-3,6-dimethyl-1,2,3,4,5,6-hexahydro-2,6-methanobenzo[d]azocin-11-yl)-N-methyl-2-phenylacetamide;
9) tert-butyl (3-(((2R,6S,11S)-8-hydroxy-3,6-dimethyl-1,2,3,4,5,6-hexahydro-2,6-methanobenzo[d]azocin-11-yl)amino)propyl)carbamate;
10) N-((2R,6S,11R)-8-hydroxy-3,6-dimethyl-1,2,3,4,5,6-hexahydro-2,6-methanobenzo[d]azocin-11-yl)-N-methylcyclohexanecarboxamide;
11) N-((2R,6S,11R)-8-hydroxy-3,6-dimethyl-1,2,3,4,5,6-hexahydro-2,6-methanobenzo[d]azocin-11-yl)-N,4-dimethylpentanamide;
12) N-((2R,6S,11R)-8-hydroxy-3,6-dimethyl-1,2,3,4,5,6-hexahydro-2,6-methanobenzo[d]azocin-11-yl)-N-methyl-2-(thiophen-2-yl)acetamide;
13) tert-butyl (2-(((2R,6S,11S)-8-hydroxy-3,6-dimethyl-1,2,3,4,5,6-hexahydro-2,6-methanobenzo[d]azocin-11-yl)amino)ethyl)carbamate;
14) 3-(5-fluorobenzo[d]thiazol-2-yl)-1-((2R,6S,11R)-8-hydroxy-3,6-dimethyl-1,2,3,4,5,6-hexahydro-2,6-methanobenzo[d]azocin-11-yl)-1-methylurea; and
15) 1-(5-fluorobenzo[d]thiazol-2-yl)-3-((2R,6S,11R)-8-hydroxy-3,6-dimethyl-1,2,3,4,5,6-hexahydro-2, 6-methanobenzo[d]azocin-11-yl)urea.

In another aspect, the Invention provides compounds of Formula II, and pharmaceutically acceptable salts, solvates, and diastereomers thereof:

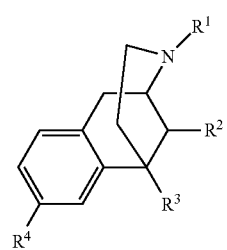

II wherein
R$^1$ is (C$_1$-C$_{10}$)alkyl, (C$_2$-C$_{10}$)alkenyl, or (C$_3$-C$_{12}$)cycloalkyl, wherein said (C$_2$-C$_{10}$)alkenyl is optionally substituted by one or two same or different (C$_1$-C$_6$)alkyl;
R$^2$ is (C$_1$-C$_{10}$)alkyl, —N(R$^5$)(R$^6$), or —C(=O)R$^7$;
R$^3$ is H or —(C$_1$-C$_6$)alkyl;
R$^4$ is selected from the group consisting of —CN, —NR$^8$R$^9$, —(C$_1$-C$_5$)alkyl-NR$^8$R$^9$, —C(O)O(C$_1$-C$_5$)alkyl, —NHSO$_2$(C$_1$-C$_5$)alkyl, halo, —C(halo)$_3$, —CH(halo)$_2$, —CH$_2$(halo), —COOH, —CONH$_2$, —(C$_5$-C$_5$)alkyl, —(C$_2$-C$_5$)alkenyl, and —(C$_2$-C$_5$)alkynyl; each of which is optionally substituted with 1, 2, or 3 independently selected R$^a$ groups;
R$^5$ is selected from the group consisting of hydrogen, —(C$_1$-C$_{10}$)alkyl, —C(=O)—(C$_1$-C$_6$)alkyl-(6- to 14-membered)aryl, —C(=O)—(C$_1$-C$_6$)alkyl, —C(=O)—(C$_2$-C$_6$) alkenyl, —CONR$^8$R$^9$, —(C$_1$-C$_6$)alkyl-C(O)NR$^8$R$^9$, —CO—(CH$_2$)$_n$—C(O)NR$^8$R$^9$, ((6- to 14-membered)aryl)-(C$_1$-C$_6$)alkyl-, ((3- to 12 membered)-heterocycle)-(C$_1$-C$_6$)alkyl-, —C(=O)—NH—((5- to 12-membered)heteroaryl), ((C$_3$-C$_{12}$)cycloalkyl)-(C$_1$-C$_6$)alkyl-, —SO$_2$—(C$_1$-C$_6$)alkyl, —SO$_2$—((6- to 14 membered)aryl), and ((5- to 12-membered)heteroaryl)-(C$_1$-C$_6$)alkyl-, each of which is optionally substituted with one, two, or three substituents independently selected from the group consisting of —OH, halo, —C(halo)$_3$, —CH(halo)$_2$, —CH$_2$(halo), —(C$_1$-C$_6$)alkyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, —NH$_2$, —NH(C$_1$-C$_6$)alkyl, —NH(C$_1$-C$_6$)alkyl-R$^{11}$, —CN, —SH, —OR$^{12}$, —NR$^8$R$^9$, —CONR$^8$R$^9$, —COOR$^{10}$, —(C$_1$-C$_6$)alkoxy-COOR$^{10}$, —(OCH$_2$CH$_2$)$_s$—O(C$_1$-C$_6$)alkyl, —SO$_2$—(C$_1$-C$_6$)alkyl, —SO$_2$—((C$_3$-C$_{12}$)cycloalkyl), —SO$_2$—(C$_1$-C$_6$)alkyl-(6- to 14 membered)aryl), —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)—(C$_1$-C$_6$)alkyl-(6- to 14-membered)aryl, —NH—(C$_1$-C$_6$)alkyl-CO—OR$^{10}$, —NH—C(=O)—(C$_1$-C$_6$)alkyl-CO—OR$^{10}$, —NH—C(=O)—CH(NH$_2$)—(C$_1$-C$_6$)alkyl-CO—OR$^{10}$, —(C$_3$-C$_{12}$)cycloalkyl, hydroxy(C$_3$-C$_{12}$)cycloalkyl-, -(6- to 14-membered)aryl, -(6- to 14-membered)aryloxy, —(C$_1$-C$_6$)alkoxy-C(O)NR$^8$R$^9$, —NH—(C$_1$-C$_6$)alkyl-C(O)NR$^8$R$^9$, —C(O)NH—(C$_1$-C$_6$)alkyl-COOR$^{10}$, —C(=O)—(C$_1$-C$_6$)alkyl, -(5- to 12-membered)heteroaryl, -(3- to 12-membered)heterocycle, and -(7- to 12-membered)-bicycloheterocycle;

R$^6$ is selected from the group consisting of H, —(C$_1$-C$_6$)alkyl, —(C$_1$-C$_6$)alkyl-CO—OR$^{10}$, —(C$_1$-C$_6$)alkyl-OR$^{10}$, —(C$_1$-C$_6$)alkyl-CONR$^8$R$^9$, —(C$_3$-C$_{12}$)cycloalkyl, ((C$_3$-C$_{12}$)cycloalkyl)-(C$_1$-C$_6$)alkyl-, —C(=O)(C$_1$-C$_6$)alkyl, and —SO$_2$(C$_1$-C$_6$)alkyl;

R$^7$ is selected from the group consisting of —(C$_1$-C$_{10}$)alkyl, —(C$_1$-C$_{10}$)alkoxy, —(OCH$_2$CH$_2$)$_s$—O(C$_1$-C$_6$)alkyl, —NH(C$_1$-C$_6$)alkyl, —NR$^c$R$^d$, —(C$_3$-C$_2$)cycloalkyl, ((C$_3$-C$_{12}$)cycloalkyl)-(C$_1$-C$_6$)alkyl-, and -(3- to 12-membered)heterocycle; each of which is optionally substituted with one, two, or three substituents independently selected from the group consisting of —OH, halo, —C(halo)$_3$, —CH(halo)$_2$, —CH$_2$(halo), —(C$_1$-C$_6$)alkyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, —NH$_2$, —NH(C$_1$-C$_6$)alkyl, —NH(C$_1$-C$_6$)alkyl-R$^{11}$, —CN, —SH, —OR$^{12}$, —NR$^8$R$^9$, —CONR$^8$R$^9$, —COOR$^{10}$, —(C$_1$-C$_6$)alkoxy-COOR$^{10}$, —(OCH$_2$CH$_2$)$_s$—O(C$_1$-C$_6$)alkyl, —SO$_2$—(C$_1$-C$_6$)alkyl, —SO$_2$—((C$_3$-C$_{12}$)cycloalkyl), —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)—(C$_1$-C$_6$)alkyl-(6- to 14-membered)aryl, —NH—(C$_1$-C$_6$)alkyl-CO—OR$^{10}$, —NH—C(=O)—(C$_1$-C$_6$)alkyl-CO—OR$^{10}$, —NH—C(=O)—CH(NH$_2$)—(C$_1$-C$_6$)alkyl-CO—OR$^{10}$, —(C$_3$-C$_{12}$)cycloalkyl, -(6- to 14-membered)aryl, -(6- to 14-membered)aryloxy, —(C$_1$-C$_6$)alkoxy-C(O)NR$^8$R$^9$, —NH—(C$_1$-C$_6$)alkyl-C(O)NR$^8$R$^9$, —C(O)NH—(C$_1$-C$_6$)alkyl-COOR$^{10}$, -(5- to 12-membered)heteroaryl, -(3- to 12-membered)heterocycle, and -(7- to 12-membered)bicycloheterocycle;

R$^8$ and R$^9$ are each independently selected from
a) hydrogen, —OH, halo, —C(halo)$_3$, —CH(halo)$_2$, —CH$_2$(halo);
b) —(C$_1$-C$_6$)alkyl, —(C$_2$-C$_5$)alkenyl, —(C$_2$-C$_5$)alkynyl, —(CH$_2$)$_n$—O—(CH$_2$)$_n$—CH$_3$, —(C$_1$-C$_6$)alkoxy, each of which is optionally substituted with 1, 2, or 3 substituents independently selected from —OH, halo, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_{12}$)cycloalkyl, —CHO, —C(O)OH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;
c) —(C$_3$-C$_8$)cycloalkyl, ((C$_3$-C$_8$)cycloalkyl)-(C$_1$-C$_6$)alkyl-, —COOR$^{10}$, —(C$_1$-C$_6$)alkyl-COOR$^{10}$, —CONH$_2$, and —CON(H)(C$_1$-C$_6$)alkyl;
d) ((6- to 14-membered)aryl) optionally substituted with 1, 2, or 3 independently selected R$^b$ groups; and
e) -((5- to 12-membered)heteroaryl) optionally substituted with 1, 2, or 3 independently selected R$^b$ groups;
or R$^8$ and R$^9$ together with the nitrogen atom to which they are attached form a (3- to 12-membered)heterocycle optionally substituted with 1, 2, or 3 independently selected R$^b$ groups;

each R$^{10}$ is independently selected from the group consisting of hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

each R$^{11}$ is independently selected from the group consisting of —COOR$^{10}$, —(C$_1$-C$_6$)alkyl-COOR$^{10}$, —C(=O)—(C$_1$-C$_6$)alkyl-COOR$^{10}$, —(C$_1$-C$_6$)alkyl-C(=O)—(C$_1$-C$_6$)alkyl-COOR$^{10}$, —CONH$_2$, and —(C$_1$-C$_6$)alkyl-CONH$_2$;

each R$^{12}$ is independently selected from the group consisting of —C(halo)$_3$, —CH(halo)$_2$, —CH$_2$(halo), —(C$_2$-C$_5$)alkenyl, —(C$_2$-C$_5$)alkynyl, —(CH$_2$)$_n$—O—(CH$_2$)$_n$—CH$_3$, (6- to 14-membered)aryl, ((6- to 14-membered)aryl)-(C$_1$-C$_6$)alkyl-, (5- to 12-membered)heteroaryl, and ((5- to 12-membered)heteroaryl)-(C$_1$-C$_6$)alkyl-, each of which is optionally substituted with 1, 2, or 3 independently selected R$^a$ groups;

each R$^a$ is independently selected from the group consisting of —OH, halo, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_{12}$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, and —CONR$^{5a}$R$^{6a}$;

each R$^b$ is independently selected from the group consisting of —C(halo)$_3$, —CH(halo)$_2$, —CH$_2$(halo), —COOR$^{10}$, —CONH$_2$, —CONH(C$_1$-C$_6$)alkyl, —CONH(C$_3$-C$_{12}$)cycloalkyl, —(C$_1$-C$_6$)alkyl, CN, -(3- to 12-membered)heteroaryl, ((3- to 12-membered)heteroaryl)-(C$_1$-C$_6$)alkyl-, —NH$_2$, halo, —SO$_2$—(C$_1$-C$_6$)alkyl, —SO$_2$—((C$_3$-C$_{12}$)cycloalkyl), and ((6- to 14-membered)aryl)-(C$_1$-C$_6$)alkoxy-;

n is an integer 0, 1, 2, 3, 4, 5, or 6;
s in an integer 1, 2, 3, 4, 5, or 6;
R$^{5a}$ and R$^{6a}$ are each independently selected from the group consisting of:
a) hydrogen, —OH, halo, —C(halo)$_3$, —CH(halo)$_2$, and —CH$_2$(halo);
b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 substituents independently selected from the group consisting of —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, and phenyl;
c) —(C$_3$-C$_8$)cycloalkyl, ((C$_3$-C$_8$)cycloalkyl)-(C$_1$-C$_6$)alkyl-, —COOR$^{10}$, —(C$_1$-C$_6$)alkyl-COOR$^{10}$, —CONH$_2$, and (C$_1$-C$_6$)alkyl-CONH—;

d) -(6- to 14-membered)aryl optionally substituted with 1, 2, or 3 independently selected $R^b$ groups;

e) -((5- to 12-membered)heteroaryl) optionally substituted with 1, 2, or 3 independently selected $R^b$ groups; and f) $R^{5a}$ and $R^{6a}$ together with the nitrogen atom to which they are attached form a (3- to 12-membered)heterocycle optionally substituted with 1, 2, or 3 independently selected $R^b$ groups;

$R^c$ and $R^d$, each independently, are H or —$(C_1\text{-}C_6)$alkyl; or $R^c$ and $R^d$ together with the nitrogen atom to which they are attached form a (3- to 12-membered)heterocycle optionally substituted with 1, 2, or 3 independently selected $R^b$ groups.

In one embodiment of Formula II, $R^4$ is selected from the group consisting of —CN, —COOH, and —CONH$_2$. In a separate embodiment of Formula II, $R^3$ is —$(C_1\text{-}C_6)$alkyl (e.g., methyl, ethyl, etc.). In another separate embodiment of Formula II, $R^1$ is —$(C_1\text{-}C_6)$alkyl (e.g., methyl, ethyl, etc.).

In another aspect, the Invention provides compounds of Formula III, and pharmaceutically acceptable salts, solvates, and diastereomers thereof:

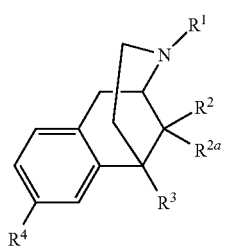

III wherein $R^1$ is $(C_1\text{-}C_{10})$alkyl, $(C_2\text{-}C_{10})$alkenyl, or $(C_3\text{-}C_{12})$cycloalkyl, wherein said $(C_2\text{-}C_{10})$alkenyl is optionally substituted by one or two same or different $(C_1\text{-}C_6)$alkyl;

$R^2$ is —OH, $(C_1\text{-}C_6)$alkoxy, $(C_1\text{-}C_{10})$alkyl, —N($R^5$)($R^6$), or —C(=O)$R^7$;

$R^{2a}$ is H, —OH, or $(C_1\text{-}C_6)$alkoxy;

$R^3$ is H or —$(C_1\text{-}C_6)$alkyl;

$R^4$ is selected from the group consisting of —CN, —NR$^8$R$^9$, —$(C_1\text{-}C_5)$alkyl-NR$^8$R$^9$, —C(O)O$(C_1\text{-}C_5)$alkyl, —NHSO$_2$$(C_1\text{-}C_5)$alkyl, halo, —C(halo)$_3$, —CH(halo)$_2$, —CH$_2$(halo), —COOH, —CONH$_2$, —$(C_1\text{-}C_5)$alkyl, —$(C_2\text{-}C_5)$alkenyl, and —$(C_2\text{-}C_5)$alkynyl; each of which is optionally substituted with 1, 2, or 3 independently selected $R^a$ groups;

$R^5$ is selected from the group consisting of hydrogen, —$(C_1\text{-}C_{10})$alkyl, —C(=O)—$(C_1\text{-}C_6)$alkyl-(6- to 14-membered)aryl, —C(=O)—$(C_1\text{-}C_6)$alkyl, —C(=O)—$(C_2\text{-}C_6)$alkenyl, —CONR$^8$R$^9$, —$(C_1\text{-}C_6)$alkyl-C(O)NR$^8$R$^9$, —CO—(CH$_2$)$_n$—C(O)NR$^8$R$^9$, ((6- to 14-membered)aryl)-$(C_1\text{-}C_6)$alkyl-, ((3- to 12 membered)-heterocycle)-$(C_1\text{-}C_6)$alkyl-, —C(=O)—NH—((5- to 12-membered)heteroaryl), (($C_3\text{-}C_{12}$)cycloalkyl)-$(C_1\text{-}C_6)$alkyl-, —SO$_2$—$(C_1\text{-}C_6)$alkyl, —SO$_2$—((6- to 14 membered)aryl), and ((5- to 12-membered)heteroaryl)-$(C_1\text{-}C_6)$alkyl-, each of which is optionally substituted with one, two, or three substituents independently selected from the group consisting of —OH, halo, —C(halo)$_3$, —CH(halo)$_2$, —CH$_2$(halo), —$(C_1\text{-}C_6)$alkyl, hydroxy$(C_1\text{-}C_6)$alkyl-, dihydroxy$(C_1\text{-}C_6)$alkyl-, —$(C_1\text{-}C_6)$alkoxy, (($C_1\text{-}C_6)$alkoxy)CO$(C_1\text{-}C_6)$alkoxy-, —NH$_2$, —NH$(C_1\text{-}C_6)$alkyl, —NH$(C_1\text{-}C_6)$alkyl-$R^{11}$, —CN, —SH, —OR$^{12}$, —NR$^8$R$^9$, —CONR$^8$R$^9$, —COOR$^{10}$, —$(C_1\text{-}C_6)$alkoxy-COOR$^{10}$, —(OCH$_2$CH$_2$)$_s$—O$(C_1\text{-}C_6)$alkyl, —SO$_2$—$(C_1\text{-}C_6)$alkyl, —SO$_2$—(($C_3\text{-}C_{12}$)cycloalkyl), —SO$_2$—$(C_1\text{-}C_6)$alkyl-(6- to 14 membered)aryl), —NH—SO$_2$$(C_1\text{-}C_6)$alkyl, NH$_2$—SO$_2$$(C_1\text{-}C_6)$alkyl-, —N(SO$_2$$(C_1\text{-}C_6)$alkyl)$_2$, —C(=NH)NH$_2$, —NH—CO—$(C_1\text{-}C_6)$alkyl, —NH—CO—NH$_2$, —NH—C(=O)—NH—$(C_1\text{-}C_6)$alkyl, —NH—C(=O)-(6- to 14-membered)aryl, —NH—C(=O)—$(C_1\text{-}C_6)$alkyl-(6- to 14-membered)aryl, —NH—$(C_1\text{-}C_6)$alkyl-CO—OR$^{10}$, —NH—C(=O)—$(C_1\text{-}C_6)$alkyl-CO—OR$^{10}$, —NH—C(=O)—CH(NH$_2$)—$(C_1\text{-}C_6)$alkyl-CO—OR$^{10}$, —$(C_3\text{-}C_{12})$cycloalkyl, hydroxy$(C_3\text{-}C_{12})$cycloalkyl-, -(6- to 14-membered)aryl, -(6- to 14-membered)aryloxy, —$(C_1\text{-}C_6)$alkoxy-C(O)NR$^8$R$^9$, —NH—$(C_1\text{-}C_6)$alkyl-C(O)NR$^8$R$^9$, —C(O)NH—$(C_1\text{-}C_6)$alkyl-COOR$^{10}$, —C(=O)—$(C_1\text{-}C_6)$alkyl, -(5- to 12-membered)heteroaryl, -(3- to 12-membered)heterocycle, and -(7- to 12-membered)-bicycloheterocycle;

$R^6$ is selected from the group consisting of H, —$(C_1\text{-}C_6)$alkyl, —$(C_1\text{-}C_6)$alkyl-CO—OR$^{10}$, —$(C_1\text{-}C_6)$alkyl-OR$^{10}$, —$(C_1\text{-}C_6)$alkyl-CONR$^8$R$^9$, —$(C_3\text{-}C_{12})$cycloalkyl, (($C_3\text{-}C_{12}$)cycloalkyl)-$(C_1\text{-}C_6)$alkyl-, —C(=O)$(C_1\text{-}C_6)$alkyl, and —SO$_2$$(C_1\text{-}C_6)$alkyl;

$R^7$ is selected from the group consisting of —$(C_1\text{-}C_{10})$alkyl, —$(C_1\text{-}C_{10})$alkoxy, —(OCH$_2$CH$_2$)$_s$—O$(C_1\text{-}C_6)$alkyl, —NH$(C_1\text{-}C_6)$alkyl, —NR$^c$R$^d$, —$(C_3\text{-}C_2)$cycloalkyl, (($C_3\text{-}C_{12}$)cycloalkyl)-$(C_1\text{-}C_6)$alkyl-, and -(3- to 12-membered)heterocycle; each of which is optionally substituted with one, two, or three substituents independently selected from the group consisting of —OH, halo, —C(halo)$_3$, —CH(halo)$_2$, —CH$_2$(halo), —$(C_1\text{-}C_6)$alkyl, hydroxy$(C_1\text{-}C_6)$alkyl-, dihydroxy$(C_1\text{-}C_6)$alkyl-, —$(C_1\text{-}C_6)$alkoxy, (($C_1\text{-}C_6)$alkoxy)CO$(C_1\text{-}C_6)$alkoxy-, —NH$_2$, —NH$(C_1\text{-}C_6)$alkyl, —NH$(C_1\text{-}C_6)$alkyl-$R^{11}$, —CN, —SH, —OR$^{12}$, —NR$^8$R$^9$, —CONR$^8$R$^9$, —COOR$^{10}$, —$(C_1\text{-}C_6)$alkoxy-COOR$^{10}$, —(OCH$_2$CH$_2$)$_s$—O$(C_1\text{-}C_6)$alkyl, —SO$_2$—$(C_1\text{-}C_6)$alkyl, —SO$_2$—(($C_3\text{-}C_{12}$)cycloalkyl), —NH—SO$_2$$(C_1\text{-}C_6)$alkyl, NH$_2$—SO$_2$$(C_1\text{-}C_6)$alkyl-, —N(SO$_2$$(C_1\text{-}C_6)$alkyl)$_2$, —C(=NH)NH$_2$, —NH—CO—$(C_1\text{-}C_6)$alkyl, —NH—CO—NH$_2$, —NH—C(=O)—NH—$(C_1\text{-}C_6)$alkyl, —NH—C(=O)-(6- to 14-membered)aryl, —NH—C(=O)—$(C_1\text{-}C_6)$alkyl-(6- to 14-membered)aryl, —NH—$(C_1\text{-}C_6)$alkyl-CO—OR$^{10}$, —NH—C(=O)—$(C_1\text{-}C_6)$alkyl-CO—OR$^{10}$, —NH—C(=O)—CH(NH$_2$)—$(C_1\text{-}C_6)$alkyl-CO—OR$^{10}$, —$(C_3\text{-}C_{12})$cycloalkyl, -(6- to 14-membered)aryl, -(6- to 14-membered)aryloxy, —$(C_1\text{-}C_6)$alkoxy-C(O)NR$^8$R$^9$, —NH—$(C_1\text{-}C_6)$alkyl-C(O)NR$^8$R$^9$, —C(O)NH—$(C_1\text{-}C_6)$alkyl-COOR$^{10}$, -(5- to 12-membered)heteroaryl, -(3- to 12-membered)heterocycle, and -(7- to 12-membered)bicycloheterocycle;

$R^8$ and $R^9$ are each independently selected from a) hydrogen, —OH, halo, —C(halo)$_3$, —CH(halo)$_2$, —CH$_2$(halo);

b) —$(C_1\text{-}C_6)$alkyl, —$(C_2\text{-}C_5)$alkenyl, —$(C_2\text{-}C_5)$alkynyl, —(CH$_2$)$_n$—O—(CH$_2$)$_n$—CH$_3$, —$(C_1\text{-}C_6)$alkoxy, each of which is optionally substituted with 1, 2, or 3 substituents independently selected from —OH, halo, —$(C_1\text{-}C_{10})$alkyl, —$(C_2\text{-}C_{10})$alkenyl, —$(C_2\text{-}C_{10})$alkynyl, —$(C_1\text{-}C_{10})$alkoxy, —$(C_3\text{-}C_{12})$cycloalkyl, —CHO, —C(O)OH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;

c) —$(C_3\text{-}C_8)$cycloalkyl, (($C_3\text{-}C_8$)cycloalkyl)-$(C_1\text{-}C_6)$alkyl-, —COOR$^{10}$, —$(C_1\text{-}C_6)$alkyl-COOR$^{10}$, —CONH$_2$, and —CON(H)$(C_1\text{-}C_6)$alkyl;

d) ((6- to 14-membered)aryl) optionally substituted with 1, 2, or 3 independently selected $R^b$ groups; and e) -((5- to 12-membered)heteroaryl) optionally substituted with 1, 2, or 3 independently selected $R^b$ groups;

or $R^8$ and $R^9$ together with the nitrogen atom to which they are attached form a (3- to 12-membered)heterocycle optionally substituted with 1, 2, or 3 independently selected $R^b$ groups;

each $R^{10}$ is independently selected from the group consisting of hydrogen, —$(C_1$-$C_6)$alkyl, —$(C_2$-$C_6)$alkenyl, —$(C_2$-$C_6)$alkynyl, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, and $((C_4$-$C_{12})$cycloalkenyl)-$(C_1$-$C_6)$alkyl-;

each $R^{11}$ is independently selected from the group consisting of —$COOR^{10}$, —$(C_1$-$C_6)$alkyl-$COOR^{10}$, —$C(=O)$—$(C_1$-$C_6)$alkyl-$COOR^{10}$, —$(C_1$-$C_6)$alkyl-$C(=O)$—$(C_1$-$C_6)$alkyl-$COOR^{10}$, —$CONH_2$, and —$(C_1$-$C_6)$alkyl-$CONH_2$;

each $R^{12}$ is independently selected from the group consisting of —$C(halo)_3$, —$CH(halo)_2$, —$CH_2(halo)$, —$(C_2$-$C_5)$alkenyl, —$(C_2$-$C_5)$alkynyl, —$(CH_2)_n$—O—$(CH_2)_n$—$CH_3$, (6- to 14-membered)aryl, ((6- to 14-membered)aryl)-$(C_1$-$C_6)$alkyl-, (5- to 12-membered)heteroaryl, and ((5- to 12-membered)heteroaryl)-$(C_1$-$C_6)$alkyl-, each of which is optionally substituted with 1, 2, or 3 independently selected $R^a$ groups;

each $R^a$ is independently selected from the group consisting of —OH, halo, —$(C_1$-$C_{10})$alkyl, —$(C_2$-$C_{10})$alkenyl, —$(C_2$-$C_{10})$alkynyl, —$(C_1$-$C_{10})$alkoxy, —$(C_3$-$C_2)$cycloalkyl, —CHO, —$C(O)OH$, —$C(halo)_3$, —$CH(halo)_2$, $CH_2(halo)$, —$(CH_2)_n$—O—$(CH_2)_n$—$CH_3$, phenyl, and —$CONR^{5a}R^{6a}$;

each $R^b$ is independently selected from the group consisting of —$C(halo)_3$, —$CH(halo)_2$, —$CH_2(halo)$, —$COOR^{10}$, —$CONH_2$, —$CONH(C_1$-$C_6)$alkyl, —$CONH(C_3$-$C_{12})$cycloalkyl, —$(C_1$-$C_6)$alkyl, CN, -(3- to 12-membered)heteroaryl, ((3- to 12-membered)heteroaryl)-$(C_1$-$C_6)$alkyl-, —$NH_2$, halo, —$SO_2$—$(C_1$-$C_6)$alkyl, —$SO_2$—$((C_3$-$C_{12})$cycloalkyl), and ((6- to 14-membered)aryl)-$(C_1$-$C_6)$alkoxy-;

n is an integer 0, 1, 2, 3, 4, 5, or 6;

s in an integer 1, 2, 3, 4, 5, or 6;

$R^{5a}$ and $R^{6a}$ are each independently selected from the group consisting of:

a) hydrogen, —OH, halo, —$C(halo)_3$, —$CH(halo)_2$, and —$CH_2(halo)$;

b) —$(C_1$-$C_6)$alkyl, —$(C_2$-$C_6)$alkenyl, —$(C_2$-$C_6)$alkynyl, —$(CH_2)_n$—O—$(CH_2)_n$—$CH_3$, and —$(C_1$-$C_6)$alkoxy, each of which is optionally substituted with 1, 2, or 3 substituents independently selected from the group consisting of —OH, halo, —$(C_1$-$C_{10})$alkyl, —$(C_2$-$C_{12})$alkenyl, —$(C_2$-$C_{12})$alkynyl, —$(C_1$-$C_{10})$alkoxy, —$(C_3$-$C_{12})$cycloalkyl, —CHO, —COOH, —$C(halo)_3$, —$CH(halo)_2$, —$CH_2(halo)$, —$(CH_2)_n$—O—$(CH_2)_n$—$CH_3$, and phenyl;

c) —$(C_3$-$C_8)$cycloalkyl, $((C_3$-$C_{58})$cycloalkyl)-$(C_1$-$C_6)$alkyl-, —$COOR^{10}$, —$(C_1$-$C_6)$alkyl-$COOR^{10}$, —$CONH_2$, and $(C_1$-$C_6)$alkyl-CONH—;

d) -(6- to 14-membered)aryl optionally substituted with 1, 2, or 3 independently selected $R^b$ groups;

e) -((5- to 12-membered)heteroaryl) optionally substituted with 1, 2, or 3 independently selected $R^b$ groups; and f) $R^{5a}$ and $R^{6a}$ together with the nitrogen atom to which they are attached form a (3- to 12-membered)heterocycle optionally substituted with 1, 2, or 3 independently selected $R^b$ groups;

$R^c$ and $R^d$, each independently, are H or —$(C_1$-$C_6)$alkyl; or $R^c$ and $R^d$ together with the nitrogen atom to which they are attached form a (3- to 12-membered)heterocycle optionally substituted with 1, 2, or 3 independently selected $R^b$ groups.

In one embodiment of Formula III, $R^4$ is selected from the group consisting of —CN, —COOH, and —$CONH_2$. In a separate embodiment of Formula III, $R^3$ is —$(C_1$-$C_6)$alkyl. In another separate embodiment of Formula III, $R^1$ is —$(C_1$-$C_6)$alkyl.

In certain embodiments, the invention provides compounds of Formula A, and pharmaceutically acceptable salts, solvates, and diastereomers thereof:

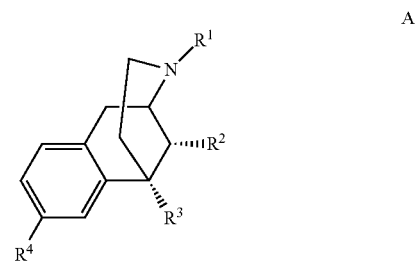

A wherein $R^1$, $R^2$, $R^3$, and $R^4$ are as above defined in connection with Formula I, I', II, or III.

In another embodiment, the invention provides compounds of Formula B, and pharmaceutically acceptable salts, solvates, and diastereomers thereof:

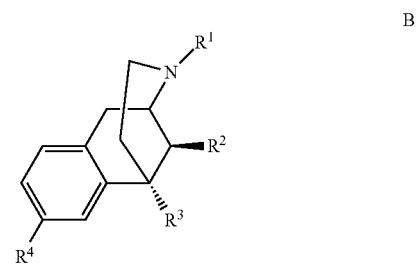

B wherein $R^1$, $R^2$, $R^3$, and $R^4$ are as above defined in connection with Formula I, I', II, or III.

Another embodiment of the invention provides compounds of Formula C, and pharmaceutically acceptable salts, solvates, and diastereomers thereof:

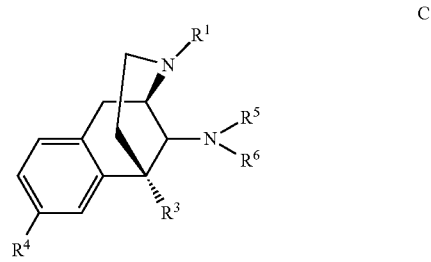

C wherein $R^1$, $R^3$, $R^4$, $R^5$, and $R^6$ are as above defined in connection with Formula I, I', II, or III.

Further, the invention provides compounds of Formula D, and pharmaceutically acceptable salts, solvates, and diastereomers thereof:

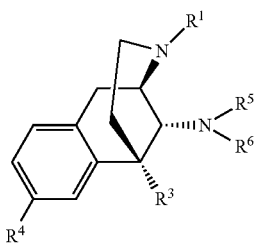

D wherein $R^1$, $R^3$, $R^4$, $R^5$, and $R^6$ are as above defined in connection with Formula I, I', II, or III.

In yet another embodiment, the invention provides compounds of Formula E, and pharmaceutically acceptable salts, solvates, and diastereomers thereof:

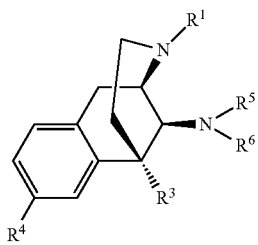

E wherein $R^1$, $R^3$, $R^4$, $R^5$, and $R^6$ are as above defined in connection with Formula I, I', II, or III.

In one embodiment, Compounds of the Invention are compounds represented by any one of Formulae I, I', II, III, and A-E, delineated supra., and the pharmaceutically acceptable salts, solvates, and diastereomers thereof, wherein $R^5$ is optionally-substituted —$(C_1$-$C_{10})$alkyl. For example, $R^5$ is optionally-substituted —$(C_1$-$C_6)$alkyl. In one embodiment, $R^5$ is —$(C_1$-$C_6)$alkyl optionally substituted by one, two, or three substituents independently selected from the group consisting of —OH, —CONR$^8$R$^9$, —NR$^8$R$^9$, —OR$^{12}$, —$(C_3$-$C_{12})$cycloalkyl, -(6- to 14-membered)aryl, and hydroxy($C_3$-$C_2$)cycloalkyl-.

For example, in accordance with any one of the above Formulae I, I', II, III, and A-E, $R^5$ is selected from the group consisting of methyl, ethyl, propyl, and butyl, each of which is further optionally substituted by one, two, or three substituents independently selected from the group of —OH, —OPh, cyclohexyl, (hydroxy)cyclohexyl-, phenyl, —NR$^8$R$^9$, and —CONR$^8$R$^9$. Certain instances provide that one of $R^8$ and $R^9$ is H, and the other is selected from the group consisting of —COOR$^{10}$; —CONH$_2$; —CON(H)($C_1$-$C_6$)alkyl; ((6- to 14-membered)aryl) that is optionally substituted with 1 or 2 independently selected $R^b$ groups; and -((5- to 12-membered)heteroaryl) that is optionally substituted with 1 or 2 independently selected $R^b$ groups. One embodiment provides that $R^b$ each independently is halo or —C(halo)$_3$.

In a separate embodiment, Compounds of the Invention are compounds represented by any one of Formulae I, I', II, III, and A-E, delineated supra., and the pharmaceutically acceptable salts, solvates, and diastereomers thereof, wherein $R^5$ is optionally-substituted —C(=O)—$(C_1$-$C_6)$alkyl. In one embodiment, $R^5$ is —C(=O)—$(C_1$-$C_6)$alkyl optionally substituted by -(3- to 12-membered)heterocycle or —CONR$^8$R$^9$. Non-limiting exemplary optionally-substituted -(3- to 12-membered)heterocycle groups include

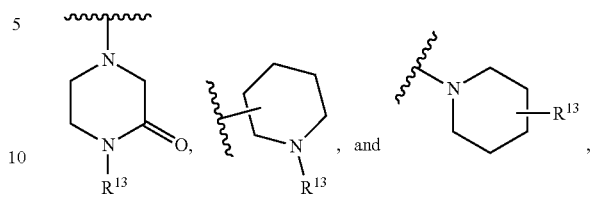

wherein $R^{13}$ is H, $(C_1$-$C_6)$alkyl, hydroxy$(C_1$-$C_6)$alkyl-, —SO$_2$—$(C_1$-$C_6)$alkyl, —SO$_2$—$((C_3$-$C_{12})$cycloalkyl), —SO$_2$—$(C_1$-$C_6)$alkyl-(6- to 14 membered)aryl), —C(O)($C_1$-$C_6)$alkyl, —C(O)—O($C_1$-$C_6)$alkyl, or —C(O)—NH($C_1$-$C_6)$alkyl. One example of the -(3- to 12-membered) heterocycle group is

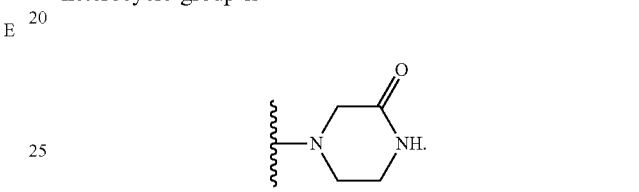

One embodiment of the invention provides that $R^5$ is —C(=O)—$(C_1$-$C_6)$alkyl optionally substituted by —CONR$^8$R$^9$, wherein one of $R^8$ and $R^9$ is H, and the other is ((6- to 14-membered)aryl) optionally substituted with 1 or 2 independently selected $R^b$ groups, or -((5- to 12-membered)heteroaryl) optionally substituted with 1 or 2 independently selected $R^b$ groups. In certain embodiments, $R^b$ each independently is halo or —C(halo)$_3$.

In another embodiment, Compounds of the Invention are compounds represented by any one of Formulae I, I', II, III, and A-E, delineated supra., and the pharmaceutically acceptable salts, solvates, and diastereomers thereof, wherein $R^5$ is optionally-substituted ((6- to 14-membered)aryl)-$(C_1$-$C_6)$ alkyl-. In one embodiment, $R^5$ is ((6- to 14-membered)aryl)-$(C_1$-$C_6)$alkyl- (e.g., —CH$_2$CH$_2$Ph) that is optionally substituted with 1 or 2 substituents independently selected from the group of halo, —C(halo)$_3$, CN, and —SO$_2$—$(C_1$-$C_6)$ alkyl.

In yet another embodiment in accordance with any one of Formulae I, I', II, III, and A-E, $R^5$ is ((3- to 12 membered)-heterocycle)-$(C_1$-$C_6)$alkyl- optionally substituted with 1 or 2 substituents independently selected from the group of —C(=O)—$(C_1$-$C_6)$alkyl, —SO$_2$—$(C_1$-$C_6)$alkyl (e.g., —SO$_2$CH$_3$, —SO$_2$CH$_2$CH$_3$, and —SO$_2$CH(CH$_3$)$_2$), —CONR$^8$R$^9$, hydroxy$(C_1$-$C_6)$alkyl-, —SO$_2$—$(C_1$-$C_6)$ alkyl-phenyl, and —SO$_2$—$((C_3$-$C_{12})$cycloalkyl).

One example provides that $R^5$ is ((3- to 12 membered)-heterocycle)-$(C_1$-$C_6)$alkyl-optionally substituted by —CONR$^8$R$^9$, wherein one of $R^8$ and $R^9$ is H, and the other is —$(C_1$-$C_6)$alkyl. Non-limiting exemplary optionally-substituted (3- to 12-membered)heterocycle groups, by itself or within another group, include

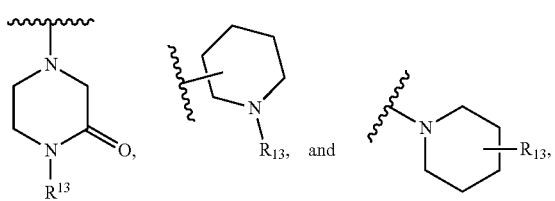

wherein R[13] is defined supra. Specific examples of the optionally-substituted ((3- to 12 membered)-heterocycle)-(C₁-C₆)alkyl- groups used as R⁵ include

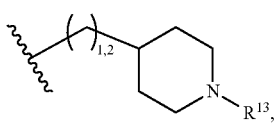

wherein R$^{13}$ is H, hydroxy(C$_1$-C$_6$)alkyl-, —SO$_2$—(C$_1$-C$_6$)alkyl, —SO$_2$—((C$_3$-C$_{12}$)cycloalkyl), —SO$_2$—(C$_1$-C$_6$)alkyl-phenyl, —C(O)(C$_1$-C$_6$)alkyl, —C(O)—O(C$_1$-C$_6$)alkyl, or —C(O)—NH(C$_1$-C$_6$)alkyl. In one embodiment, R$^5$ is ((3- to 12 membered)-heterocycle)-(C$_1$-C$_6$)alkyl- optionally substituted by —CONR$^8$R$^9$. As used herein, under certain instances, one of R$^8$ and R$^9$ is H, the other is (C$_1$-C$_6$)alkyl (e.g., tert-butyl). In a separate embodiment, R$^5$ is ((3- to 12 membered)-heterocycle)-(C$_1$-C$_6$)alkyl- optionally substituted by —SO$_2$—(C$_1$-C$_4$)alkyl or —SO$_2$—((C$_3$-C$_5$)cycloalkyl.

Another embodiment in accordance with Formulae I, I', II, III, and A-E provides that R$^5$ is —CONR$^8$R$^9$. In one embodiment, one of R$^8$ and R$^9$ is H, and the other is ((6- to 14-membered)aryl) optionally substituted with 1 or 2 independently selected R$^b$ groups, or -((5- to 12-membered)heteroaryl) optionally substituted with 1 or 2 independently selected R$^b$ groups. One embodiment of Formulae I, I', II, III, and A-E provides that R$^5$ is —CONR$^8$R$^9$, wherein one of said R and said R$^9$ is H, and the other is phenyl or benzoin[d]thiazolyl, and wherein each of said phenyl and said benzo[d]thiazolyl is optionally substituted with 1 or 2 R$^b$ groups independently selected from the group of CN, halo, and —C(halo)$_3$.

Further, the invention provides compounds represented by any one of Formulae I, I', II, III, and A-E, delineated supra., and the pharmaceutically acceptable salts, solvates, and diastereomers thereof, wherein R$^5$ is optionally-substituted —SO$_2$—(C$_1$-C$_6$)alkyl. In one embodiment, R$^5$ is —SO$_2$—(C$_1$-C$_6$)alkyl (such as, —SO$_2$CH$_3$) optionally substituted by -(6- to 14-membered)aryl (e.g., phenyl).

In yet another embodiment, the invention provides compounds of Formulae I, I', II, III, and A-E, delineated supra., and the pharmaceutically acceptable salts, solvates, and diastereomers thereof, wherein R$^5$ is optionally-substituted —C(=O)—(C$_2$-C$_6$)alkenyl. In one embodiment, R$^5$ is —C(=O)—(C$_2$-C$_6$)alkenyl substituted by -(5- to 12-membered)heteroaryl (e.g., furanyl).

In yet another embodiment, the invention provides compounds of Formulae I, I', II, III, and A-E, delineated supra., and the pharmaceutically acceptable salts, solvates, and diastereomers thereof, wherein R$^5$ is optionally-substituted —C(=O)—(C$_1$-C$_6$)alkyl-(6 to 14-membered)aryl. In one embodiment, R$^5$ is —C(=O)—(C$_1$-C$_6$)alkyl-Ph optionally substituted by —SO$_2$—(C$_1$-C$_6$)alkyl (such as, —SO$_2$CH$_3$) or halo (e.g., F).

In certain embodiments, the invention provides compounds of Formulae I, I', II, III, and A-E, delineated supra., and the pharmaceutically acceptable salts, solvates, and diastereomers thereof, wherein R$^6$ is H.

In another embodiment of the invention, R$^6$ is —(C$_1$-C$_6$)alkyl. Non-limiting exemplary (C$_1$-C$_6$)alkyl groups include methyl, ethyl, n-propyl, isopropyl, butyl, pentyl, and hexyl. In one embodiment, R$^6$ is selected from the group consisting of methyl, ethyl, and n-propyl.

In yet another embodiment, the invention provides compounds of Formulae I, I', II, III, and A-E, and the pharmaceutically acceptable salts, solvates, and diastereomers thereof, wherein R$^6$ is selected from the group consisting of —(C$_1$-C$_6$)alkyl-CO—OR$^{10}$, —(C$_1$-C$_6$)alkyl-OR$^{10}$, and —(C$_1$-C$_6$)alkyl-CONR$^8$R$^9$. In one embodiment, R$^{10}$ each independently is H or —(C$_1$-C$_6$)alkyl. In a separate embodiment, R$^8$ and R$^9$ each independently are H or —(C$_1$-C$_6$)alkyl. For example, R$^6$ is —CH$_2$—COOH, —CH$_2$CH$_2$OH, or —CH$_2$CONH$_2$.

Further, the invention provides compounds of Formula F, and pharmaceutically acceptable salts, solvates, and diastereomers thereof:

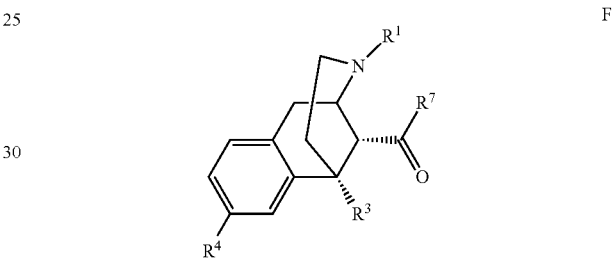

F wherein R$^1$, R$^3$, R$^4$, and R$^7$ are as above defined in connection with Formula I, I', II, or III.

In one embodiment in accordance with Formula I, I', II, III, or F, R$^7$ is optionally-substituted —NR$^c$R$^d$. In one embodiment, R$^c$ and R$^d$ together with the nitrogen atom to which they are attached form a (3- to 12-membered)heterocycle group (e.g., piperidinyl).

In another embodiment of Formula I, I', II, III, or F, R$^7$ is optionally-substituted -(3- to 12-membered)heterocycle (e.g., piperidyl).

In certain embodiments, Compounds of the Invention are compounds represented by any one of Formulae I, I', II, III, and A-F, and pharmaceutically acceptable salts, solvates, and diastereomers thereof, wherein R$^1$ is (C$_1$-C$_{10}$)alkyl. In one embodiment, R$^1$ is (C$_1$-C$_6$)alkyl. In another embodiment, R$^1$ is (C$_1$-C$_3$)alkyl. One example provides that R$^1$ is methyl.

Further, the invention provides compounds of Formulae I, I', II, III, and A-F, and pharmaceutically acceptable salts, solvates, and diastereomers thereof, wherein R$^1$ is optionally-substituted (C$_2$-C$_{10}$)alkenyl. One embodiment provides that R$^1$ is (C$_2$-C$_{10}$)alkenyl optionally substituted by one or two same or different (C$_1$-C$_3$)alkyl groups. One example provides that R$^1$ is 3-methylbut-2-en-1-yl (i.e.,

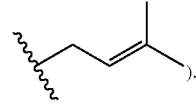 [SMILES: *CC=C(C)C]

).

In certain embodiments, Compounds of the Invention are compounds represented by any one of Formulae I, I', and A-F, and pharmaceutically acceptable salts, solvates, and diastereomers thereof, wherein $R^4$ is —OH.

In certain embodiments, Compounds of the Invention are compounds represented by any one of Formulae I, I', and A-F, and pharmaceutically acceptable salts, solvates, and diastereomers thereof, wherein $R^4$ is —($C_1$-$C_3$)alkoxy. In one embodiment, $R^4$ is —$OCH_3$.

In further embodiments, the invention provides compounds of Formula G, and pharmaceutically acceptable salts, solvates, and diastereomers thereof:

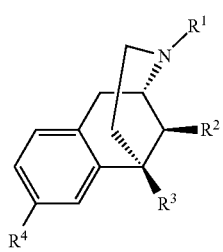

G wherein $R^1$, $R^2$, $R^3$, and $R^4$ are as above defined in connection with Formula I, I', II, or III.

In one embodiment, Compounds of the Invention are compounds represented by Formula I, I', or G, and pharmaceutically acceptable salts, solvates, and diastereomers thereof, wherein $R^4$ is —OH. In another embodiment, $R^4$ is —$OCH_3$.

In certain embodiments, Compounds of the Invention are compounds represented by Formula I, I', II, III, or G, and pharmaceutically acceptable salts, solvates, and diastereomers thereof, wherein $R^3$ is ($C_1$-$C_3$)alkyl (e.g., methyl).

In other embodiments, Compounds of the Invention are compounds represented by Formula I, I', II, III, or G, and pharmaceutically acceptable salts, solvates, and diastereomers thereof, wherein $R^2$ is ($C_1$-$C_6$)alkyl (e.g., methyl).

In yet another embodiment, Compounds of the Invention are compounds represented by Formula I, I', II, III, or G, and pharmaceutically acceptable salts, solvates, and diastereomers thereof, wherein $R^1$ is optionally-substituted ($C_2$-$C_{10}$) alkenyl. In one embodiment, $R^1$ is ($C_2$-$C_{10}$)alkenyl optionally substituted by one or two same or different ($C_1$-$C_3$) alkyl. One example provides that $R^1$ is 3-methylbut-2-en-1-yl (i.e.,

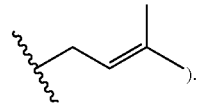 [SMILES: *CC=C(C)C]

).

In another embodiment, the Invention provides compounds of Formula H, and pharmaceutically acceptable salts, solvates, and diastereomers thereof:

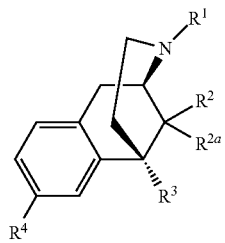

H wherein
$R^1$ is ($C_1$-$C_6$)alkyl;
$R^2$ is —OH or ($C_1$-$C_6$)alkoxy;
$R^{2a}$ is —OH or ($C_1$-$C_6$)alkoxy;
$R^3$ is —($C_1$-$C_6$)alkyl; and
$R^4$ is —OH, —($C_1$-$C_6$)alkoxy, —CN, —COOH, or —$CONH_2$.

In one embodiment of the compounds of Formula I', III, or H, and the pharmaceutically acceptable salts, solvates, and diastereomers thereof, $R^2$ and $R^{2a}$ are the same. For example, $R^2$ and $R^{2a}$ are both —OH. In another embodiment, $R^2$ and $R^{2a}$ are different. For example, $R^2$ and $R^{2a}$ are different alkoxy groups.

In another embodiment of the compounds of Formula I', III, or H, and the pharmaceutically acceptable salts, solvates, and diastereomers thereof, $R^4$ is —CN, —COOH, or —$CONH_2$.

Another embodiment provides compounds of Formula I', III, or H, and the pharmaceutically acceptable salts, solvates, and diastereomers thereof, wherein $R^1$ is ($C_1$-$C_3$)alkyl (e.g., methyl).

A separate embodiment provides compounds of Formula I', III, or H, and the pharmaceutically acceptable salts, solvates, and diastereomers thereof, wherein $R^3$ is ($C_1$-$C_3$) alkyl (e.g., methyl).

In certain embodiments, Compounds of the Invention include the compounds provided in TABLE 2 and the pharmaceutically acceptable salts, solvates, and diastereomers thereof.

TABLE 2

| Cpd # | Structure | Chemical name |
|---|---|---|
| 10 | 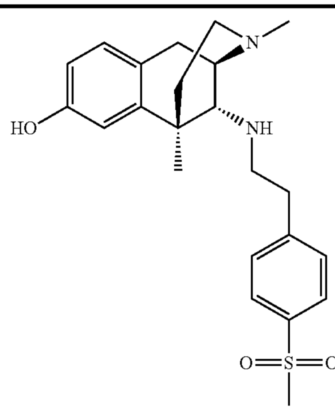 | (2R,6S,11R)-3,6-dimethyl-11-((4-(methylsulfonyl)-phenethyl)amino)-1,2,3,4,5,6-hexahydro-2,6-methano-benzo[d]azocin-8-ol |

TABLE 2-continued

| Cpd # | Structure | Chemical name |
|---|---|---|
| 11 | 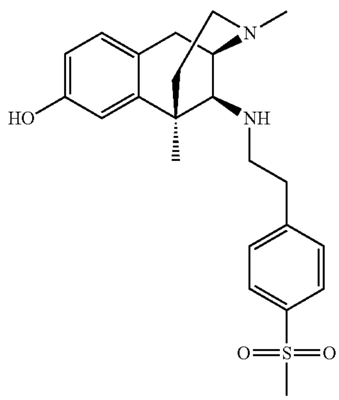 | (2R,6S,11S)-3,6-dimethyl-11-((4-(methylsulfonyl)phenethyl)-amino)-1,2,3,4,5,6-hexahydro-2,6-methanobenzo[d]azocin-8-ol |
| 12 | 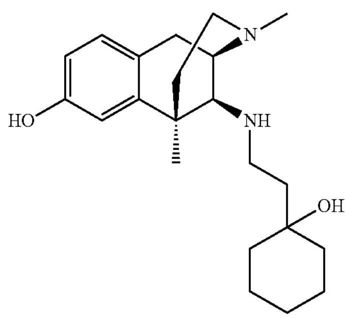 | (2R,6S,11S)-11-((2-(1-hydroxycyclohexyl)ethyl)amino)-3,6-dimethyl-1,2,3,4,5,6-hexahydro-2,6-methano-benzo[d]azocin-8-ol |
| 13 | 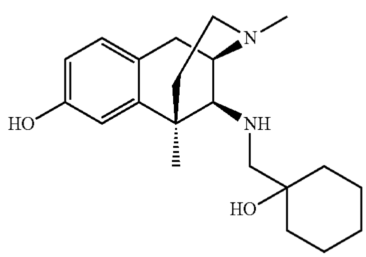 | (2R,6S,11S)-11-(((1-hydroxycyclohexyl)methyl)amino)-3,6-dimethyl-1,2,3,4,5,6-hexahydro-2,6-methano-benzo[d]azocin-8-ol |
| 14 | 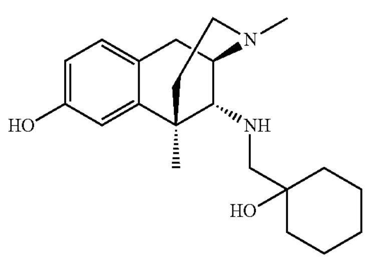 | (2R,6S,11R)-11-(((1-hydroxycyclohexyl)methyl)amino)-3,6-dimethyl-1,2,3,4,5,6-hexahydro-2,6-methano-benzo[d]azocin-8-ol |
| 15 | 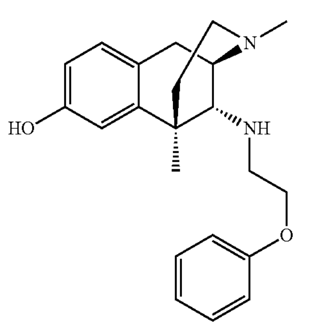 | (2R,6S,11R)-3,6-dimethyl-11-((2-phenoxyethyl)amino)-1,2,3,4,5,6-hexahydro-2,6-methanobenzo[d]azocin-8-ol |

TABLE 2-continued

| Cpd # | Structure | Chemical name |
|---|---|---|
| 16 | 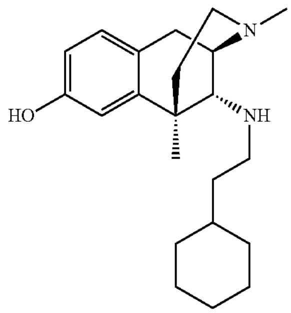 | (2R,6S,11R)-11-((2-cyclohexylethyl)amino)-3,6-dimethyl-1,2,3,4,5,6-hexahydro-2,6-methanobenzo[d]azocin-8-ol |
| 17 | 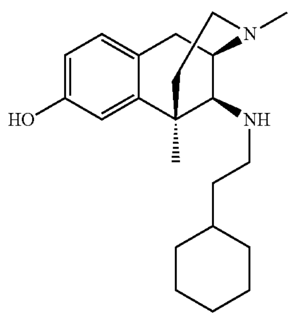 | (2R,6S,11S)-11-((2-cyclohexylethyl)amino)-3,6-dimethyl-1,2,3,4,5,6-hexahydro-2,6-methanobenzo[d]azocin-8-ol |
| 18 | 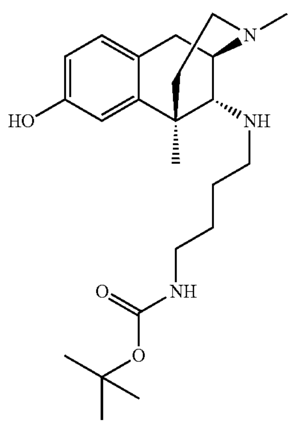 | tert-butyl (4-(((2R,6S,11R)-8-hydroxy-3,6-dimethyl-1,2,3,4,5,6-hexahydro-2,6-methanobenzo[d]azocin-11-yl)amino)butyl)carbamate |
| 19 | 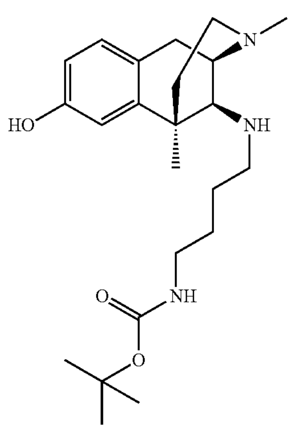 | tert-butyl (4-(((2R,6S,11S)-8-hydroxy-3,6-dimethyl-1,2,3,4,5,6-hexahydro-2,6-methanobenzo[d]azocin-11-yl)amino)butyl)carbamate |

TABLE 2-continued

| Cpd # | Structure | Chemical name |
|---|---|---|
| 26 | 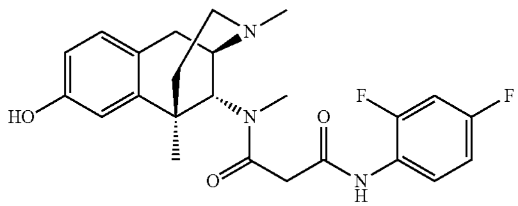 | $N^1$-(2,4-difluorophenyl)-$N^3$-((2R,6S,11R)-8-hydroxy-3,6-dimethyl-1,2,3,4,5,6-hexahydro-2,6-methanobenzo[d]azocin-11-yl)-$N^3$-methylmalonamide |
| 27 | 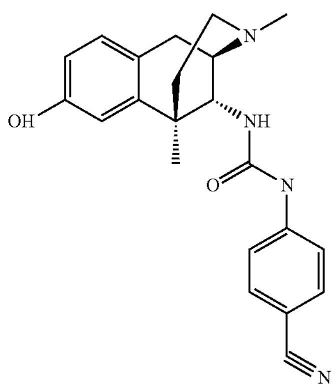 | 1-(4-cyanophenyl)-3-((2R,6S,11R)-8-hydroxy-3,6-dimethyl-1,2,3,4,5,6-hexahydro-2,6-methanobenzo[d]azocin-11-yl)urea |
| 28 | 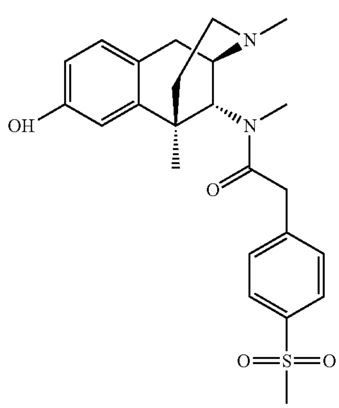 | N-((2R,6S,11R)-8-hydroxy-3,6-dimethyl-1,2,3,4,5,6-hexahydro-2,6-methanobenzo[d]azocin-11-yl)-N-methyl-2-(4-(methylsulfonyl)phenyl)acetamide |
| 29 | 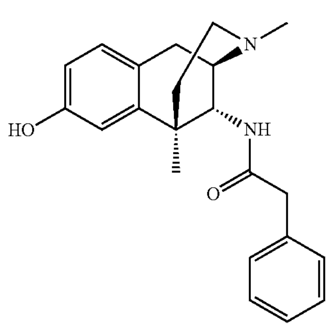 | N-((2R,6S,11S)-8-hydroxy-3,6-dimethyl-1,2,3,4,5,6-hexahydro-2,6-methanobenzo[d]azocin-11-yl)-2-phenylacetamide |

TABLE 2-continued

| Cpd # | Structure | Chemical name |
|---|---|---|
| 30 | 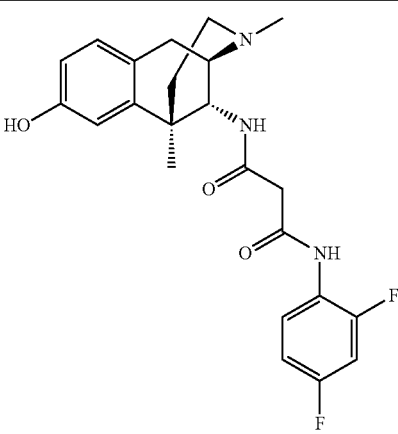 | N[1]-(2,4-difluorophenyl)-N[3]-((2R,6S,11R)-8-hydroxy-3,6-dimethyl-1,2,3,4,5,6-hexahydro-2,6-methanobenzo[d]azocin-11-yl)malonamide |
| 31 | 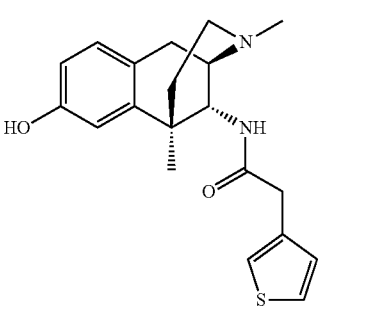 | N-((2R,6S,11S)-8-hydroxy-3,6-dimethyl-1,2,3,4,5,6-hexahydro-2,6-methanobenzo[d]azocin-11-yl)-2-(thiophen-3-yl)acetamide |
| 32 | 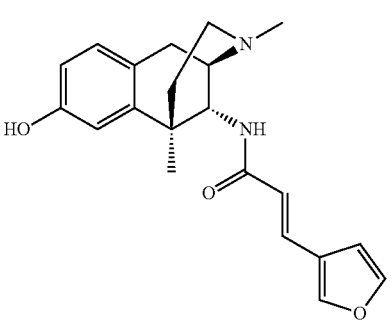 | (E)-3-(furan-3-yl)-N-((2R,6S,11S)-8-hydroxy-3,6-dimethyl-1,2,3,4,5,6-hexahydro-2,6-methanobenzo[d]azocin-11-yl)acrylamide |
| 33 | 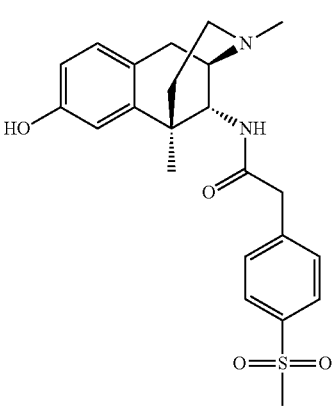 | N-((2R,6S,11R)-8-hydroxy-3,6-dimethyl-1,2,3,4,5,6-hexahydro-2,6-methanobenzo[d]azocin-11-yl)-2-(4-(methylsulfonyl)phenyl)acetamide |

TABLE 2-continued

| Cpd # | Structure | Chemical name |
| --- | --- | --- |
| 34 | 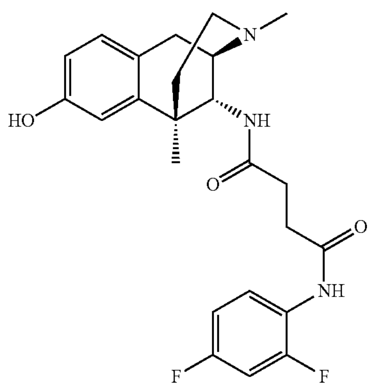 | N¹-(2,4-difluorophenyl)-N⁴-(((2R,6S,11S)-8-hydroxy-3,6-dimethyl-1,2,3,4,5,6-hexahydro-2,6-methanobenzo[d]azocin-11-yl)succinamide |
| 35 | 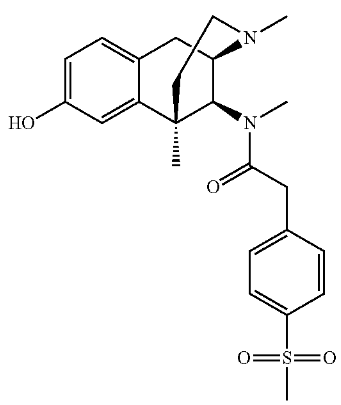 | N-((2R,6S,11S)-8-hydroxy-3,6-dimethyl-1,2,3,4,5,6-hexahydro-2,6-methanobenzo[d]azocin-11-yl)-N-methyl-2-(4-(methyl-sulfonyl)-phenyl)acetamide |
| 40 | 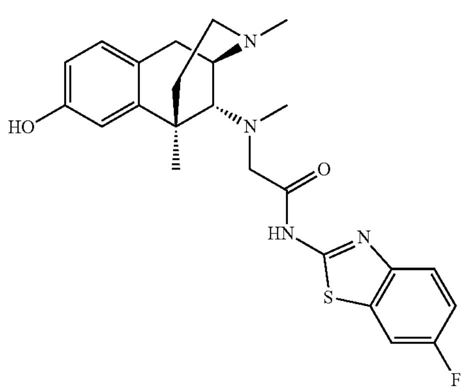 | N-(6-fluorobenzo[d]thiazol-2-yl)-2-(((2R,6S,11R)-8-hydroxy-3,6-dimethyl-1,2,3,4,5,6-hexahydro-2,6-methano-benzo[d]azocin-11-yl)-(methyl)amino)acetamide |
| 41 | 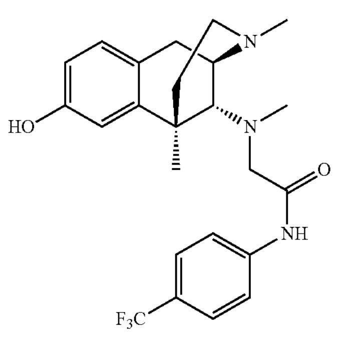 | 2-(((2R,6S,11R)-8-hydroxy-3,6-dimethyl-1,2,3,4,5,6-hexahydro-2,6-methanobenzo[d]azocin-11-yl)(methyl)amino)-N-(4-(tri-fluoromethyl)phenyl)acetamide |

TABLE 2-continued

| Cpd # | Structure | Chemical name |
|---|---|---|
| 44 | 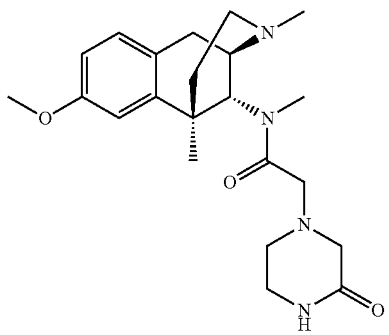 | N-((2R,6S,11R)-8-methoxy-3,6-dimethyl-1,2,3,4,5,6-hexahydro-2,6-methanobenzo[d]azocin-11-yl)-N-methyl-2-(3-oxopiperazin-1-yl)acetamide |
| 49 | 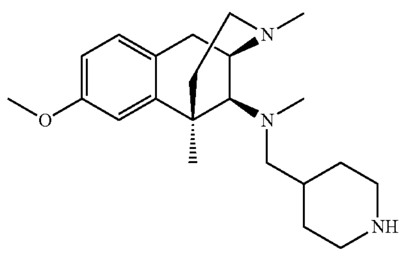 | (2R,6S,11S)-8-methoxy-N,3,6-trimethyl-N-(piperidin-4-ylmethyl)-1,2,3,4,5,6-hexahydro-2,6-methanobenzo[d]azocin-11-amine |
| 52 | 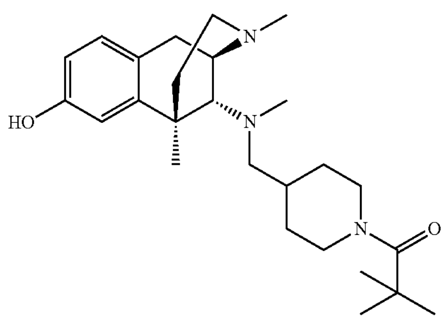 | 1-(4-((((2R,6S,11R)-8-hydroxy-3,6-dimethyl-1,2,3,4,5,6-hexahydro-2,6-methano-benzo[d]azocin-11-yl)-(methyl)amino)methyl)piperidin-1-yl)-2,2-dimethylpropan-1-one |
| 54 | 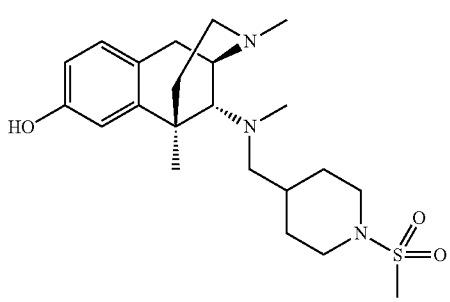 | (2R,6S,11R)-3,6-dimethyl-11-(methyl((1-(methylsulfonyl)-piperidin-4-yl)methyl)amino)-1,2,3,4,5,6-hexahydro-2,6-methanobenzo[d]azocin-8-ol |
| 55 | 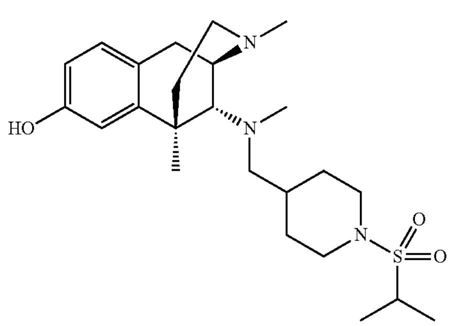 | (2R,6S,11R)-11-(((1-(isopropylsulfonyl)piperidin-4-yl)methyl)(methyl)amino)-3,6-dimethyl-1,2,3,4,5,6-hexahydro-2,6-methanobenzo[d]azocin-8-ol |

TABLE 2-continued

| Cpd # | Structure | Chemical name |
|---|---|---|
| 56 | 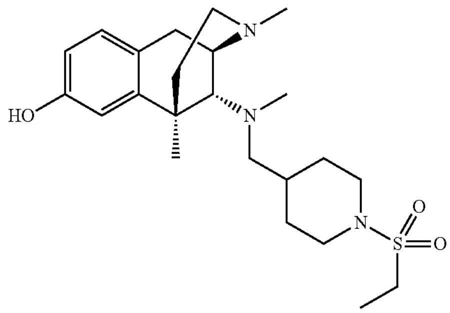 | (2R,6S,11R)-11-(((1-(ethylsulfonyl)piperidin-4-yl)methyl)(methyl)amino)-3,6-dimethyl-1,2,3,4,5,6-hexahydro-2,6-methanobenzo[d]azocin-8-ol |
| 57 | 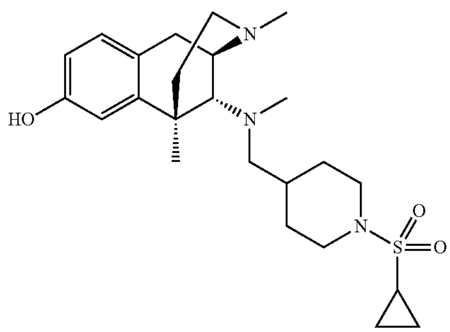 | (2R,6S,11R)-11-(((1-(cyclopropylsulfonyl)piperidin-4-yl)methyl)(methyl)amino)-3,6-dimethyl-1,2,3,4,5,6-hexahydro-2,6-methanobenzo[d]azocin-8-ol |
| 58 | 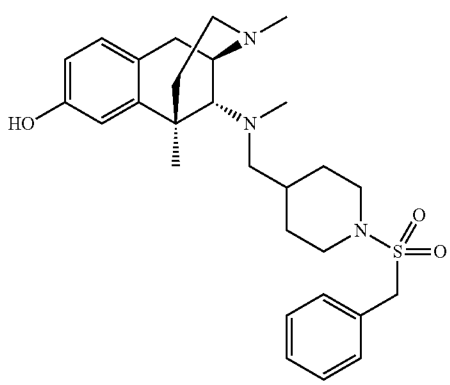 | (2R,6S,11S)-11-(((1-(benzylsulfonyl)piperidin-4-yl)methyl)(methyl)amino)-3,6-dimethyl-1,2,3,4,5,6-hexahydro-2,6-methanobenzo[d]azocin-8-ol |
| 59 | 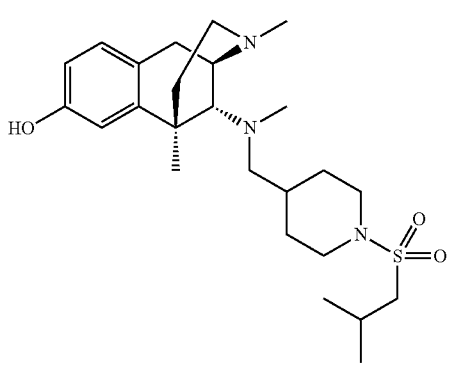 | (2R,6S,11S)-11-(((1-(isobutylsulfonyl)piperidin-4-yl)methyl)(methyl)amino)-3,6-dimethyl-1,2,3,4,5,6-hexahydro-2,6-methanobenzo[d]azocin-8-ol |

TABLE 2-continued

| Cpd # | Structure | Chemical name |
|---|---|---|
| 60 | 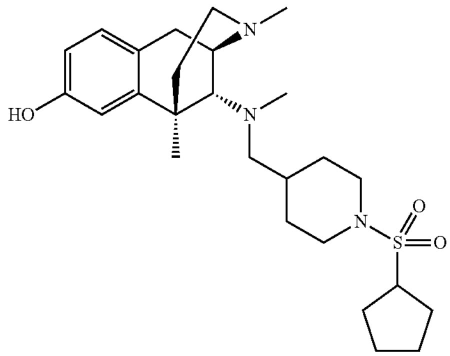 | (2R,6S,11S)-11-(((1-(cyclopentylsulfonyl)piperidin-4-yl)methyl)(methyl)amino)-3,6-dimethyl-1,2,3,4,5,6-hexahydro-2,6-methanobenzo[d]azocin-8-ol |
| 65 | 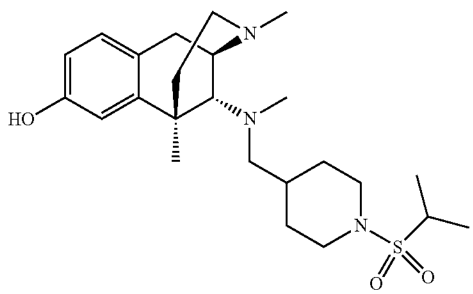 | (2R,6S,11S)-11-(((1-(isopropylsulfonyl)piperidin-4-yl)methyl)amino)-3,6-dimethyl-1,2,3,4,5,6-hexahydro-2,6-methanobenzo[d]azocin-8-ol |
| 72 | 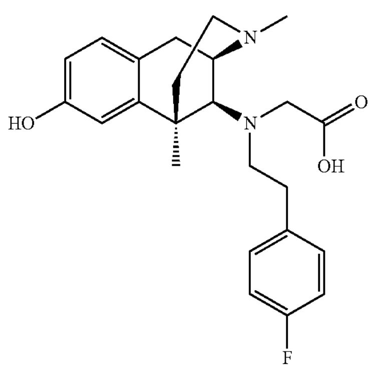 | N-(4-fluorophenethyl)-N-((2R,6S,11S)-8-hydroxy-3,6-dimethyl-1,2,3,4,5,6-hexahydro-2,6-methanobenzo[d]azocin-11-yl)glycine |
| 73 | 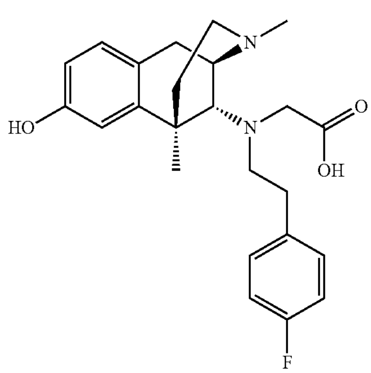 | N-(4-fluorophenethyl)-N-((2R,6S,11R)-8-hydroxy-3,6-dimethyl-1,2,3,4,5,6-hexahydro-2,6-methanobenzo[d]azocin-11-yl)glycine |

TABLE 2-continued

| Cpd # | Structure | Chemical name |
|---|---|---|
| 74 | 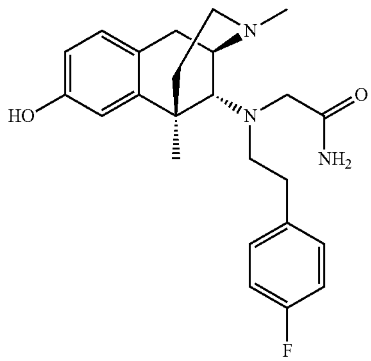 | 2-((4-fluorophenethyl)-((2R,6S,11R)-8-hydroxy-3,6-dimethyl-1,2,3,4,5,6-hexahydro-2,6-methanobenzo[d]azocin-11-yl)amino)acetamide |
| 77 | 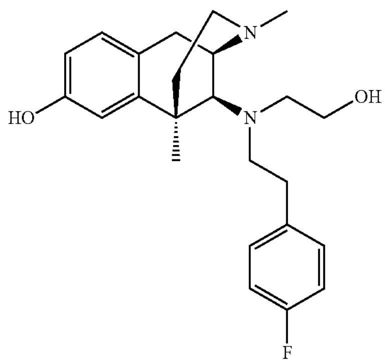 | (2R,6S,11S)-11-((4-fluoro-phenethyl)(2-hydroxyethyl)-amino)-3,6-dimethyl-1,2,3,4,5,6-hexahydro-2,6-methanobenzo-[d]azocin-8-ol |
| 81 | 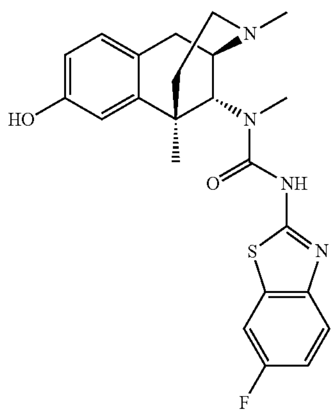 | 3-(6-fluorobenzo[d]thiazol-2-yl)-1-((2R,6S,11R)-8-hydroxy-3,6-dimethyl-1,2,3,4,5,6-hexahydro-2,6-methanobenzo[d]azocin-11-yl)-1-methylurea |
| 82 | 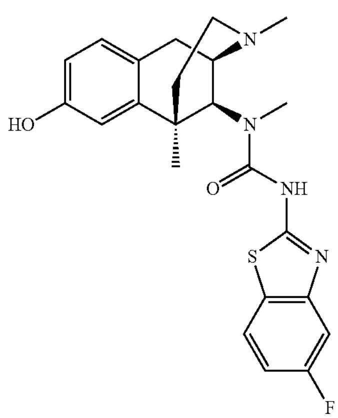 | 3-(5-fluorobenzo[d]thiazol-2-yl)-1-((2R,6S,11S)-8-hydroxy-3,6-dimethyl-1,2,3,4,5,6-hexahydro-2,6-methanobenzo[d]azocin-11-yl)-1-methylurea |

TABLE 2-continued

| Cpd # | Structure | Chemical name |
|---|---|---|
| 91 | 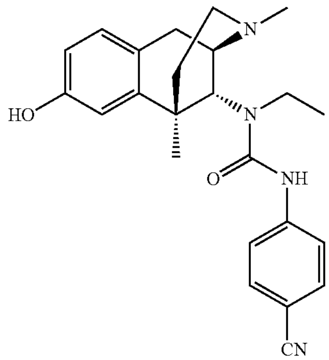 | 3-(4-cyanophenyl)-1-ethyl-1-(((2R,6S,11R)-8-hydroxy-3,6-dimethyl-1,2,3,4,5,6-hexahydro-2,6-methanobenzo[d]azocin-11-yl)urea |
| 92 | 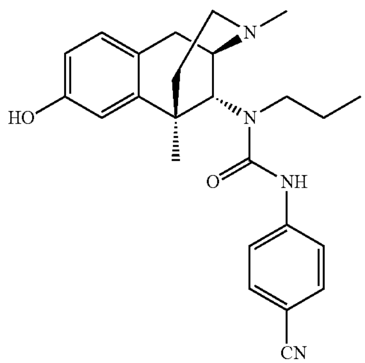 | 3-(4-cyanophenyl)-1-(((2R,6S,11R)-8-hydroxy-3,6-dimethyl-1,2,3,4,5,6-hexahydro-2,6-methanobenzo[d]azocin-11-yl)-1-propylurea |
| 93 | 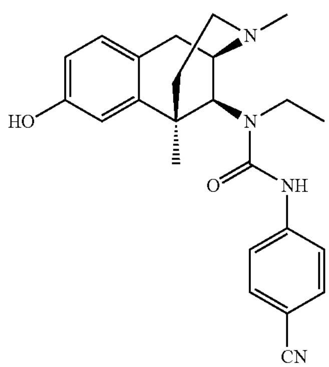 | 3-(4-cyanophenyl)-1-ethyl-1-(((2R,6S,11S)-8-hydroxy-3,6-dimethyl-1,2,3,4,5,6-hexahydro-2,6-methanobenzo[d]azocin-11-yl)urea |
| 95 | 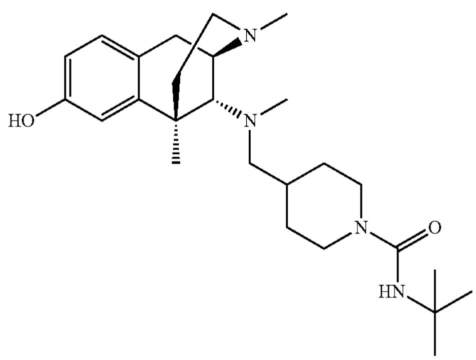 | N-(tert-butyl)-4-(((((2R,6S,11R)-8-hydroxy-3,6-dimethyl-1,2,3,4,5,6-hexahydro-2,6-methanobenzo[d]azocin-11-yl)(methyl)amino)methyl)piperidine-1-carboxamide |

TABLE 2-continued

| Cpd # | Structure | Chemical name |
|---|---|---|
| 97 | 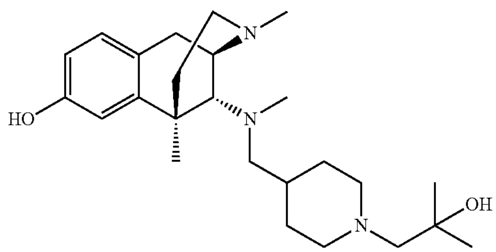 | (2R,6S,11R)-11-(((1-(2-hydroxy-2-methylpropyl)piperidin-4-yl)methyl)(methyl)amino)-3,6-dimethyl-1,2,3,4,5,6-hexahydro-2,6-methanobenzo[d]azocin-8-ol |
| 98 | 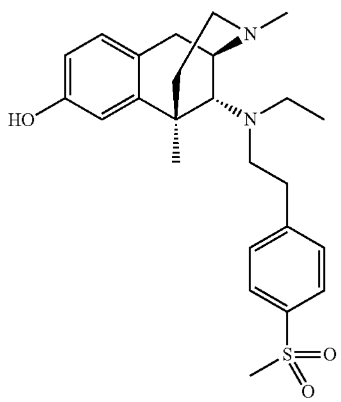 | (2R,6S,11R)-11-(ethyl(4-(methylsulfonyl)phenethyl)amino)-3,6-dimethyl-1,2,3,4,5,6-hexahydro-2,6-methano-benzo[d]azocin-8-ol |
| 100 | 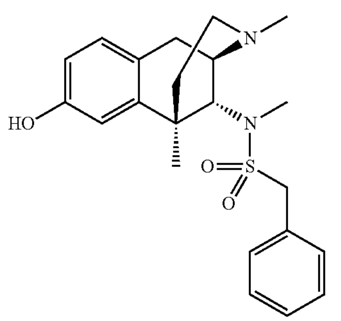 | N-((2R,6S,11R)-8-hydroxy-3,6-dimethyl-1,2,3,4,5,6-hexahydro-2,6-methanobenzo[d]azocin-11-yl)-N-methyl-1-phenylmethane-sulfonamide |
| 101 | 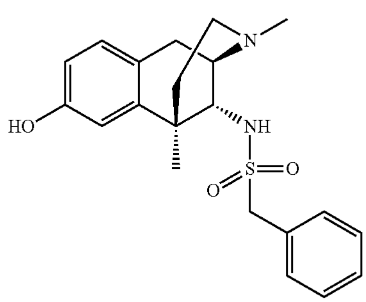 | N-((2R,6S,11S)-8-hydroxy-3,6-dimethyl-1,2,3,4,5,6-hexahydro-2,6-methanobenzo[d]azocin-11-yl)-1-phenylmethanesulfonamide |
| 102 | 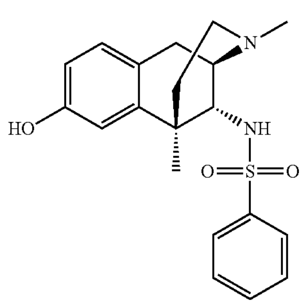 | N-((2R,6S,11S)-8-hydroxy-3,6-dimethyl-1,2,3,4,5,6-hexahydro-2,6-methanobenzo[d]azocin-11-yl)benzenesulfonamide |

TABLE 2-continued

| Cpd # | Structure | Chemical name |
|---|---|---|
| 106 | 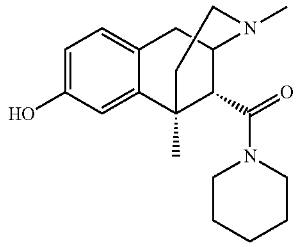 [SMILES: CN1CC[C@]2(C)c3cc(O)ccc3CC1[C@@H]2C(=O)N1CCCCC1] | ((6S,11R)-8-hydroxy-3,6-dimethyl-1,2,3,4,5,6-hexahydro-2,6-methanobenzo[d]azocin-11-yl)(piperidin-1-yl)methanone |
| 107 | 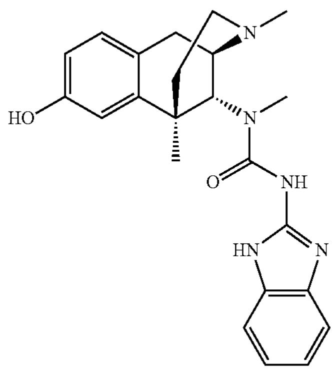 | 3-(1H-benzo[d]imidazol-2-yl)-1-((2R,6S,11R)-8-hydroxy-3,6-dimethyl-1,2,3,4,5,6-hexahydro-2,6-methanobenzo[d]azocin-11-yl)-1-methylurea |

In another embodiment, Compounds of the Invention also include the compounds of TABLE 2A and the pharmaceutically acceptable salts, solvates, and diastereomers thereof.

TABLE 2A

| Cpd# | Structure | Chemical name |
|---|---|---|
| 108 | 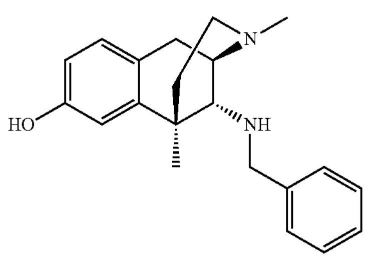 | (2R,6S,11R)-11-(benzylamino)-3,6-dimethyl-1,2,3,4,5,6-hexahydro-2,6-methanobenzo[d]azocin-8-ol |
| 109 | 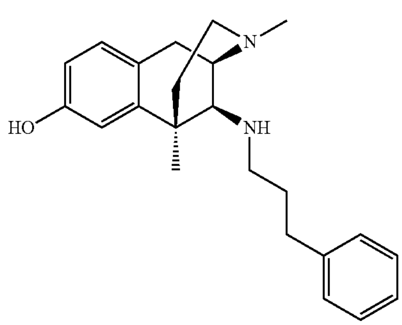 | (2R,6S,11S)-3,6-dimethyl-11-((3-phenylpropyl)amino)-1,2,3,4,5,6-hexahydro-2,6-methanobenzo[d]azocin-8-ol |

TABLE 2A-continued

| Cpd# | Structure | Chemical name |
|---|---|---|
| 110 | 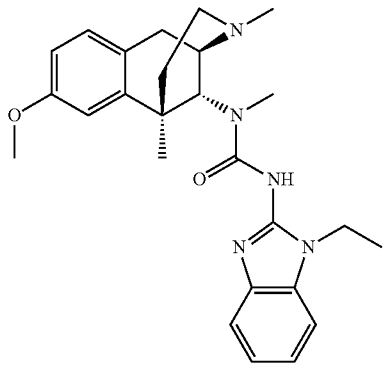 | 3-(1-ethyl-1H-benzo[d]imidazol-2-yl)-1-((2R,6S,11R)-8-methoxy-3,6-dimethyl-1,2,3,4,5,6-hexahydro-2,6-methanobenzo[d]azocin-11-yl)-1-methylurea |
| 111 | 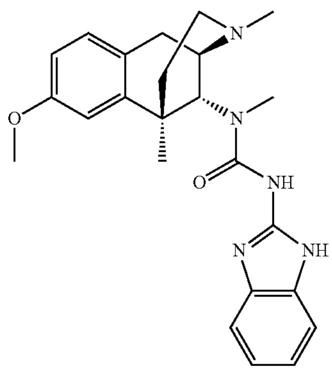 | 3-(1H-benzo[d]imidazol-2-yl)-1-((2R,6S,11R)-8-methoxy-3,6-dimethyl-1,2,3,4,5,6-hexahydro-2,6-methanobenzo[d]azocin-11-yl)-1-methylurea |
| 112 | 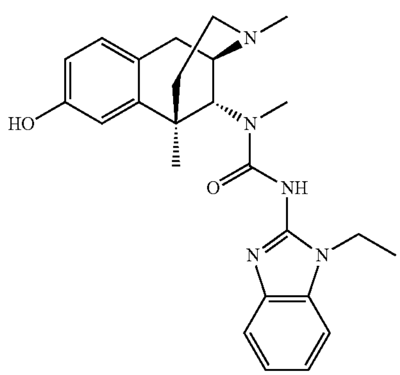 | 3-(1-ethyl-1H-benzo[d]imidazol-2-yl)-1-((2R,6S,11R)-8-hydroxy-3,6-dimethyl-1,2,3,4,5,6-hexahydro-2,6-methanobenzo[d]azocin-11-yl)-1-methylurea |
| 113 | 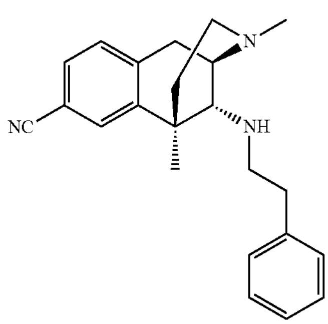 | (2R,6S,11R)-3,6-dimethyl-11-(phenethylamino)-1,2,3,4,5,6-hexahydro-2,6-methanobenzo[d]azocine-8-carbonitrile |

TABLE 2A-continued

| Cpd# | Structure | Chemical name |
|---|---|---|
| 114 | 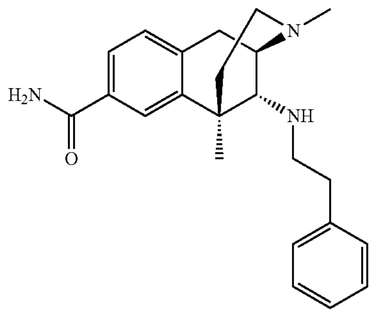 | (2R,6S,11R)-3,6-dimethyl-11-(phenethylamino)-1,2,3,4,5,6-hexahydro-2,6-methanobenzo[d]azocine-8-carboxamide |
| 115 | 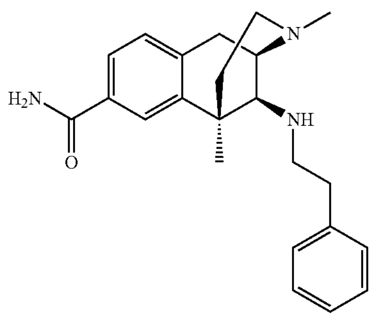 | (2R,6S,11S)-3,6-dimethyl-11-(phenethylamino)-1,2,3,4,5,6-hexahydro-2,6-methanobenzo[d]azocine-8-carboxamide |
| 116 | 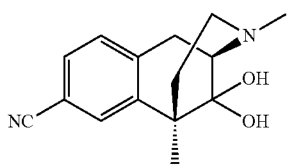 | (2R,6S)-11,11-dihydroxy-3,6-dimethyl-1,2,3,4,5,6-hexahydro-2,6-methanobenzo[d]azocine-8-carbonitrile |
| 117 | 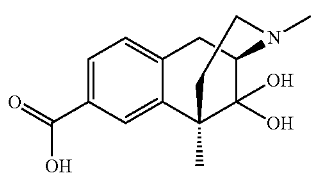 | (2R,6S)-11,11-dihydroxy-3,6-dimethyl-1,2,3,4,5,6-hexahydro-2,6-methanobenzo[d]azocine-8-carboxylic acid |
| 118 | 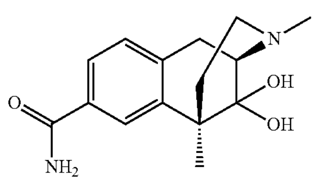 | (2R,6S)-11,11-dihydroxy-3,6-dimethyl-1,2,3,4,5,6-hexahydro-2,6-methanobenzo[d]azocine-8-carboxamide |
| 119 | 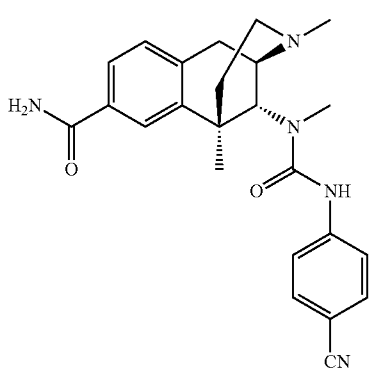 | (2R,6S,11R)-11-(3-(4-cyanophenyl)-1-methylureido)-3,6-dimethyl-1,2,3,4,5,6-hexahydro-2,6-methanobenzo[d]azocine-8-carboxamide |

TABLE 2A-continued

| Cpd# | Structure | Chemical name |
| --- | --- | --- |
| 120 | 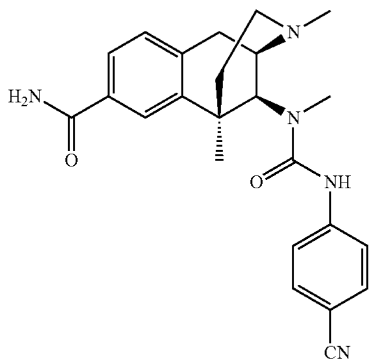 | (2R,6S,11S)-11-(3-(4-cyanophenyl)-1-methylureido)-3,6-dimethyl-1,2,3,4,5,6-hexahydro-2,6-methanobenzo[d]azocine-8-carboxamide |
| 121 | 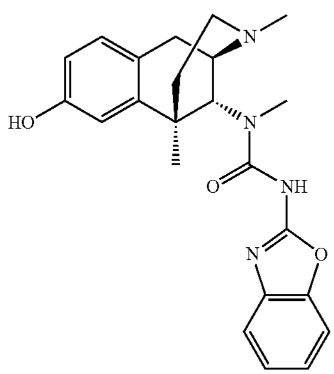 | 3-(benzo[d]oxazol-2-yl)-1-((2R,6S,11R)-8-hydroxy-3,6-dimethyl-1,2,3,4,5,6-hexahydro-2,6-methanobenzo[d]azocin-11-yl)-1-methylurea |
| 122 | 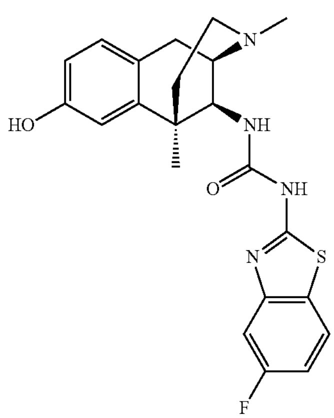 | 1-(5-fluorobenzo[d]thiazol-2-yl)-3-((2R,6S,11S)-8-hydroxy-3,6-dimethyl-1,2,3,4,5,6-hexahydro-2,6-methanobenzo[d]azocin-11-yl)urea |
| 123 | 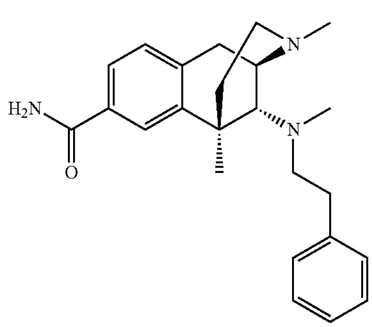 | (2R,6S,11R)-3,6-dimethyl-11-(methyl(phenethyl)amino)-1,2,3,4,5,6-hexahydro-2,6-methanobenzo[d]azocine-8-carboxamide |

TABLE 2A-continued

| Cpd# | Structure | Chemical name |
| --- | --- | --- |
| 124 | 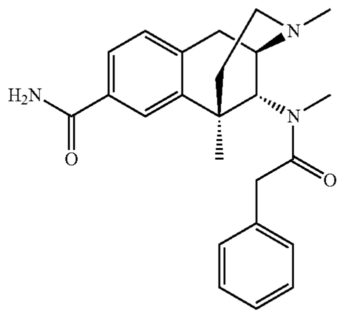 | (2R,6S,11R)-3,6-dimethyl-11-(N-methyl-2-phenylacetamido)-1,2,3,4,5,6-hexahydro-2,6-methanobenzo[d]azocine-8-carboxamide |
| 125 | 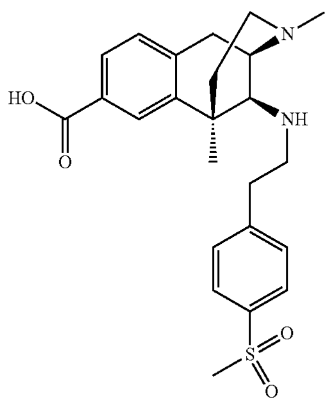 | (2R,6S,11S)-3,6-dimethyl-11-((4-(methylsulfonyl)phenethyl)amino)-1,2,3,4,5,6-hexahydro-2,6-methanobenzo[d]azocine-8-carboxylic acid |
| 126 | 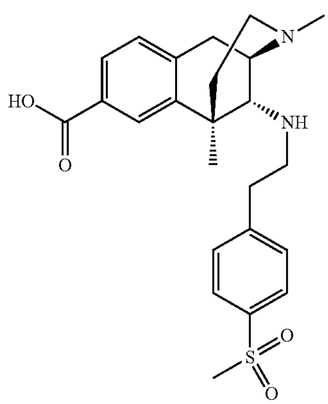 | (2R,6S,11R)-3,6-dimethyl-11-((4-(methylsulfonyl)phenethyl)amino)-1,2,3,4,5,6-hexahydro-2,6-methanobenzo[d]azocine-8-carboxylic acid |

In certain embodiments, Compounds of the Invention do not include any one of the compounds disclosed in WO 2014/072809 (International Patent Application No. PCT/IB2013/002511). Specifically, Compounds of the Invention do not include any compound selected from the group consisting of Compound Nos. 1-140 provided in TABLE 3 of WO 2014/072809 (Application No. PCT/IB2013/002511).

As used herein, the term "—($C_1$-$C_{10}$)alkyl" refers to straight-chain and branched non-cyclic saturated hydrocarbons having from 1 to 10 carbon atoms. Representative straight chain —($C_1$-$C_{10}$) alkyl groups include methyl, -ethyl, -n-propyl, -n-butyl, -n-pentyl, -n-hexyl, n-heptyl, n-octyl, n-nonyl and n-decyl. Representative branched —($C_1$-$C_{10}$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 5-methylhexyl, 6-methylheptyl, and the like.

As used herein, the term "—($C_1$-$C_6$)alkyl" refers to straight-chain and branched non-cyclic saturated hydrocarbons having from 1 to 6 carbon atoms. Representative straight chain —($C_1$-$C_6$)alkyl groups include methyl, -ethyl, -n-propyl, -n-butyl, -n-pentyl, and -n-hexyl. Representative branched-chain —($C_1$-$C_6$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-mehtylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like.

As used herein, the term "—($C_2$-$C_{10}$)alkenyl" refers to straight chain and branched non-cyclic hydrocarbons having from 2 to 10 carbon atoms and including at least one carbon-carbon double bond. Representative straight chain and branched —($C_2$-$C_{10}$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, 3-hexenyl, and the like.

As used herein, the term "—($C_2$-$C_6$)alkenyl" refers to straight chain and branched non-cyclic hydrocarbons having from 2 to 6 carbon atoms and including at least one carbon-carbon double bond. Representative straight chain and branched —($C_2$-$C_6$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, and the like.

As used herein, the term "—($C_2$-$C_{10}$)alkynyl" refers to straight chain and branched non-cyclic hydrocarbons having from 2 to 10 carbon atoms and including at least one carbon-carbon triple bond. Representative straight chain and branched —($C_2$-$C_{10}$)alkynyl groups include -acetylenyl, -propynyl, -1 butynyl, -2-butynyl, -1-pentynyl, -2-pentynyl, -3-methyl-1-butynyl, -4-pentynyl, -1-hexynyl, -2-hexynyl, -5-hexynyl, and the like.

As used herein, the term "—($C_2$-$C_6$)alkynyl" refers to straight chain and branched non-cyclic hydrocarbons having from 2 to 6 carbon atoms and including at least one carbon-carbon triple bond. Representative straight chain and branched —($C_2$-$C_6$)alkynyl groups include -acetylenyl, -propynyl, -1 butynyl, -2-butynyl, -1-pentynyl, -2-pentynyl, -3-methyl-1-butynyl, -4-pentynyl, and the like.

As used herein, "—($C_1$-$C_{10}$)alkoxy" means a straight chain or branched non-cyclic hydrocarbon having one or more ether groups and from 1 to 10 carbon atoms. Representative straight chain and branched ($C_1$-$C_{10}$)alkoxys include -methoxy, -ethoxy, -propoxy, -butyloxy, -pentyloxy, -hexyloxy, -heptyloxy, -methoxymethyl, -2-methoxyethyl, -5-methoxypentyl, -3-ethoxybutyl and the like.

As used herein, "—($C_1$-$C_6$)alkoxy" means a straight chain or branched non-cyclic hydrocarbon having one or more ether groups and from 1 to 6 carbon atoms. Representative straight chain and branched ($C_1$-$C_5$)alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

As used herein, "—($C_1$-$C_5$)alkoxy" means a straight chain or branched non-cyclic hydrocarbon having one or more ether groups and from 1 to 5 carbon atoms. Representative straight chain and branched ($C_1$-$C_5$)alkoxys include -methoxy, -ethoxy, -propoxy, -butyloxy, -pentyloxy, -methoxymethyl, -2-methoxyethyl, -5-methoxypentyl, -3-ethoxybutyl and the like.

As used herein, the term "—($C_3$-$C_{12}$)cycloalkyl" refers to a cyclic saturated hydrocarbon having from 3 to 12 carbon atoms. Representative ($C_3$-$C_{12}$)cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As used herein, "—($C_6$-$C_{14}$)bicycloalkyl" means a bicyclic hydrocarbon ring system having from 6 to 14 carbon atoms and at least one saturated cyclic alkyl ring. Representative —($C_6$-$C_{14}$)bicycloalkyls include -indanyl, -norbornyl, -1,2,3,4-tetrahydronaphthalenyl, -5,6,7,8-tetrahydronaphthalenyl, -perhydronaphthalenyl, and the like.

As used herein, "—($C_8$-$C_{20}$)tricycloalkyl" means a tricyclic hydrocarbon ring system having from 8 to 20 carbon atoms and at least one saturated cyclic alkyl ring. Representative —($C_8$-$C_{20}$)tricycloalkyls include -pyrenyl, -adamantyl, -1,2,3,4-tetrahydro-anthracenyl, -perhydroanthracenyl -aceanthrenyl, -1,2,3,4-tetrahydro-penanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydro-cyclohepta[a]heptalenyl, tricyclo-pentadecanyl, tricyclo-octadecanyl, tricyclo-nonadecanyl, tricyclo-icosanyl, and the like.

As used herein, the term "—($C_4$-$C_{12}$)cycloalkenyl" refers to a cyclic hydrocarbon having from 4 to 12 carbon atoms, and including at least one carbon-carbon double bond. Representative —($C_4$-$C_{12}$)cycloalkenyls include -cyclobutenyl, -cyclopentenyl, cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, and the like.

As used herein, "—($C_7$-$C_{14}$)bicycloalkenyl" means a bicyclic hydrocarbon ring system having at least one carbon-carbon double bond in at least one of the rings and from 7 to 14 carbon atoms. Representative —($C_7$-$C_{14}$)bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, and the like.

As used herein, "—($C_8$-$C_{20}$)tricycloalkenyl" means a tri-cyclic hydrocarbon ring system having at least one carbon-carbon double bond in one of the rings and from 8 to 20 carbon atoms. Representative —($C_8$-$C_{20}$)tricycloalkenyls include -anthracenyl, phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a,c]cyclooctenyl, 2,3,4,5,6,7,8,9,10,11,12,13-dodecahydro-1H-dibenzo[a,d]cyclononenyl, and the like.

As used herein, "-(3- to 12-membered)heterocycle" or "-(3- to 12-membered)heterocyclo" means a 3- to 12-membered monocyclic heterocyclic ring which is either saturated, or partially saturated, or non-aromatic. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(3- to 12-membered)heterocycle can be attached via a nitrogen or carbon atom. Representative -(3- to 12-membered)heterocycles include aziridinyl, thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, oxepanyl, thiepinyl, 3,4,5,6-tetrahydro-2H-azepinyl, 1,4-thiazepinyl, azocinyl, thiocanyl, and the like.

As used herein, "-(5- to 12-membered)heterocycle" or "-(5- to 12-membered)heterocyclo" means a 5- to 12-membered monocyclic heterocyclic ring which is either saturated, or unsaturated, or non-aromatic. A 5-membered heterocycle can contain up to 4 heteroatoms; a 6-membered heterocycle can contain up to 4 heteroatoms; and a 7-membered heterocycle can contain up to 5 heteroatoms. Representative (5- to 12-membered)heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, oxepanyl, thiepinyl, 3,4,5,6-tetrahydro-2H-azepinyl, 1,4-thiazepinyl, azocinyl, thiocanyl, and the like.

As used herein, "-(4- to 8-membered)heterocycle" or "-(4- to 8-membered)heterocyclo" means a 4- to 8-membered monocyclic heterocyclic ring which is either saturated or unsaturated, or non-aromatic. A 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to heteroatoms. Each heteroatom is independently selected from nitrogen (which can be quaternized), oxygen, and sulfur (including sulfoxide and sulfone). The -(4- to 8-membered)heterocycle can be attached via a nitrogen or carbon atom. Representative -(4- to 8-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(7- to 12-membered)bicycloheterocycle" or "-(7- to 12-membered)bicycloheterocyclo" means a 7- to 12-membered bicyclic, heterocyclic ring which is either saturated, unsaturated, or non-aromatic. At least one ring of the bicycloheterocycle contains at least one heteroatom. A -(7- to 12-membered)bicycloheterocycle contains from 1 to 4 heteroatoms independently selected from nitrogen (which can be quaternized), oxygen, and sulfur (including sulfoxide and sulfone). The -(7- to 12-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -benzo[d][1,3]dioxolyl, -indazolyl, -purinyl, -4H-quinolizinyl, -isoquinolyl, -quinolyl, -phthalazinyl, naphthyridinyl, -carbazolyl, -β-carbolinyl, -indolinyl, isoindolinyl, -1,2,3,4-tetrahydroquinolinyl, -1,2,3,4-tetrahydroisoquinolinyl, pyrrolopyrrolyl and the like.

As used herein a "-(6- to 14-membered)aryl" means an aromatic carbocyclic ring containing 6 to 14 carbon atoms, including both mono- and bicyclic ring systems. Representative -(5- to 14-membered)aryl groups include -indenyl, -phenyl, -naphthyl, and the like.

As used herein a "-(7- to 12-membered)bicyclic aryl" means an bicyclic aromatic carbocyclic ring containing 7 to 12 carbon atoms. Representative -(7- to 12-membered) bicyclic aryl groups include -indenyl, -naphthyl, and the like.

As used herein a "-(6- to 14-membered)aryloxy" means an oxygen substituted by an aromatic carbocyclic ring containing 6 to 14 carbon atoms, including both mono- and bicyclic ring systems. Representative -(6- to 14-membered) aryloxy groups include phenoxy and 4-fluorophenoxy, and the like.

As used herein a "hydroxy($C_1$-$C_6$)alkyl" means any of the above-mentioned $C_{1-6}$ alkyl groups substituted by one or more hydroxy groups. Representative hydroxy($C_1$-$C_6$)alkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein a "dihydroxy($C_1$-$C_6$)alkyl" means any of the above-mentioned $C_{1-6}$ alkyl groups substituted by two hydroxy groups. Representative dihydroxy($C_1$-$C_6$)alkyl groups include dihydroxyethyl, dihydroxypropyl and dihydroxybutyl groups, and especially 1,2-dihydroxyethyl, 1,3-dihydroxypropyl, 2,3-dihydroxypropyl, 1,3-dihydroxybutyl, 1,4-dihydroxybutyl, and 1,3-dihydroxyprop-2-yl.

As used herein a "-(5- to 12-membered)carbocyclic ring" means a mono- or bicyclic hydrocarbon ring system having from 5 to 12 carbon atoms, which is either saturated, unsaturated, non-aromatic or aromatic. Representative -(5- to 12-membered)carbocyclic rings include cyclopentyl, cyclohexyl, cycloheptyl, cyclooctyl, cyclononyl, cyclodecyl, cycloundecyl, cyclododecyl, -indanyl, -norbornyl, -1,2,3,4-tetrahydronaphthalenyl, -5,6,7,8-tetrahydronaphthalenyl, -perhydronaphthalenyl, adamantyl, cyclopentenyl, cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, heptalenyl, and the like.

As used herein, a "-(7- to 12-membered)bicyclic ring system" means a 7- to 12-membered carbocyclic or heterocyclic ring, which may be either unsaturated, saturated, non-aromatic or aromatic. Representative -(7- to 12-membered)bicyclic ring systems include azulenyl, -norbornyl, -1,2,3,4-tetrahydronaphthalenyl, -5,6,7,8-tetrahydronaphthalenyl, -perhydronaphthalenyl, bicyclo[3.2.0]hept-2-enyl, -indenyl, naphthyl, -pentalenyl, -naphthalenyl, -azulenyl, -heptalenyl, -1,2,7,8-tetrahydronaphthalenyl, -quinolinyl, -isoquinolinyl, -chromonyl, -coumarinyl, -indolyl, -indolizinyl, -benzo[b]furanyl, -benzo[b]thiophenyl, -benzo[d][1,3]dioxolyl, -indazolyl, -purinyl, -4H-quinolizinyl, -isoquinolyl, -quinolyl, -phthalazinyl, -naphthyridinyl, -carbazolyl, -β-carbolinyl, -indolinyl, isoindolinyl, -1,2,3,4-tetrahydroquinolinyl, -1,2,3,4-tetrahydroisoquinolinyl, pyrrolopyrrolyl, and the like.

As used herein, "-(5- to 12-membered)heteroaryl" means an aromatic heterocycle ring of 5 to 12 members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the bicyclic -(5- to 12-membered)heteroaryl rings contains at least one carbon atom. In another embodiment, both of the bicyclic -(5- to 12-membered)heteroaryl rings contain at least one carbon atom. Representative -(5- to 12-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, the terms "halo" and "halogen" refer to fluoro, chloro, bromo or iodo.

As used herein, "—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

As used herein, "—CH(halo)$_2$" means a methyl group where two of the hydrogens of the methyl group have been replaced with a halogen. Representative —CH(halo)$_2$ groups include —CHF$_2$, —CHCl$_2$, —CHBr$_2$, —CHBrCl, —CHClI, and —CHI$_2$.

As used herein, "—C(halo)$_3$" means a methyl group where each of the hydrogens of the methyl group has been replaced with a halogen. Representative —C(halo)$_3$ groups include —CF$_3$, —CCl$_3$, —CBr$_3$, and —CI$_3$.

As used herein, the term "optionally substituted" refers to a group that is either unsubstituted or substituted.

Optional substituents on optionally substituted groups, when not otherwise indicated, include 1, 2, or 3 groups each independently selected from the group consisting of —(C$_1$-C$_6$)alkyl, OH, halo, —C(halo)$_3$, —CH(halo)$_2$, —CH$_2$(halo), NH$_2$, —NH(C$_1$-C$_6$)alkyl, CN, SH, -(5- to 12-membered)carbocyclic ring, -(5- to 12-membered)heterocycle, phenyl, benzyl, (=O), halo(C$_1$-C$_6$)alkyl-, —(C$_2$-C$_6$)alkenyl, —(C$_2$-C$_6$)alkynyl, hydroxy(C$_1$-C$_6$)alkyl-, OR$^{4a}$ (such as —OC(halo)$_3$ and —O(C$_1$-C$_6$)alkyl), —CONR$^{5b}$R$^{6B}$, and —COOR$^{7a}$; where R$^{4a}$ is selected from the group consisting of —(C$_1$-C$_6$)alkyl, —(C$_2$-C$_6$)alkenyl, —(C$_2$-C$_6$)alkynyl, —C(halo)$_3$, hydroxy(C$_1$-C$_6$)alkyl-, —(C$_3$-C$_{12}$)cycloalkyl, —(C$_6$-C$_4$)bicycloalkyl, —(C$_8$-C$_{20}$)tricycloalkyl, —(C$_4$-C$_{12}$)cycloalkenyl, —(C$_7$-C$_{14}$)bicycloalkenyl, —(C$_8$-C$_{20}$)tricycloalkenyl, -(5- to 12-membered)aryl, -(5- to 12-membered)heteroaryl, -(3- to 12-membered)heterocycle, and -(7- to 12-membered)bicycloheterocycle; R$^{5b}$ and R$^{6b}$ are each independently selected from the group consisting of —(C$_1$-C$_6$)alkyl, —(C$_3$-C$_8$)cycloalkyl, ((C$_3$-C$_8$)cycloalkyl)-(C$_1$-C$_6$)alkyl-, or together with the nitrogen atom to which they may both be attached form a (4- to 8-membered)heterocycle; and R$^{7a}$ is selected from the group consisting of hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, —(C$_1$-C$_6$)alkoxy-COOR$^7$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-COOR$^7$, —NH—C(=O)—(C$_1$-C$_6$)alkyl-COOR$^7$, —NH—C(=O)—CH(NH$_2$)—(C$_1$-C$_6$)alkyl-COOR$^7$, —(C$_3$-C$_{12}$)cycloalkyl, -(5- to 12-membered)aryl, -(5- to 12-membered)aryloxy, —(C$_1$-C$_6$)alkoxy-CONR$^5$R$^6$, —NH—(C$_1$-C$_6$)alkyl-CONR$^5$R$^6$, —C(O)NH—(C$_1$-C$_6$)alkyl-COOR$^7$, —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, and ((3- to 12 membered)heterocycle)-(C$_1$-C$_6$)alkoxy-(C$_1$-C$_6$)alkyl-; wherein R$^5$, R$^6$, and R$^7$ are as defined above for Formula I.

As used herein, the term "Z is unsubstituted" means that Z is "—(CH$_2$)$_m$—" and m is selected from 1, 2, 3, 4, 5, or 6.

As used herein, the term "Z is substituted" means that Z is "—(CH$_2$)$_m$—" and m is selected from 1, 2, 3, 4, 5, or 6 and one or two of the hydrogen atoms has been independently replaced by a —(C$_1$-C$_6$)alkyl group.

As used herein, compounds that bind to receptors and mimic the regulatory effects of endogenous ligands are defined as "agonists". Compounds that bind to receptors and are only partly effective as agonists are defined as "partial agonists". Compounds that bind to receptors but produce no regulatory effect, but rather block the binding of ligands to the receptors are defined as "antagonists". (Ross and Kenakin, "Ch. 2: Pharmacodynamics: Mechanisms of Drug Action and the Relationship Between Drug Concentration and Effect", pp. 31-32, in Goodman & Gilman's the Pharmacological Basis of Therapeutics, 10$^{th}$ Ed. (J. G. Hardman, L. E. Limbird and A. Goodman-Gilman eds., 2001).

Compounds of the Invention can be in the form of prodrugs of the compounds of Formula I, Formula I', Formula II, Formula III, Formula A, Formula B, Formula C, Formula D, Formula E, Formula F, Formula G, or Formula H. Prodrugs are covalently bonded carrier molecules that release an active compound of Formula I, Formula I', Formula II, Formula III, Formula A, Formula B, Formula C, Formula D, Formula E, Formula F, Formula G, or Formula H in vivo. Non-limiting examples of prodrugs will typically include esters of the Compounds of the Invention that can be metabolized to the active compound by the action of enzymes in the body. Such prodrugs may be prepared by reacting a compound of Formula I, Formula I', Formula II, Formula III, Formula A, Formula B, Formula C, Formula D, Formula E, Formula F, Formula G, or Formula H, with an anhydride such as succinic anhydride.

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C $^{15}$N, $^{18}$O, $^{17}$O, $^{31}$P, $^{32}$P, $^{35}$S, $^{18}$F and $^{36}$Cl, respectively, and preferably $^3$H, $^{11}$C, and $^{14}$C. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds are generally described in Filer, Isotopes in the Physical and Biomedical Sciences, Vol. 1, Labeled Compounds (Part A), Chapter 6 (1987). $^{14}$C-labeled compounds can be prepared by employing starting materials having a $^{14}$C carbon.

Isotopically labeled Compounds of the Invention, as well as the pharmaceutically acceptable salts, prodrugs and solvates thereof, can be used as radioligands to test for the binding of compounds to an opioid or ORL-1 receptor. For example, a radio-labeled Compound of the Invention can be used to characterize specific binding of a test or candidate compound to the receptor. Binding assays utilizing such radio-labeled compounds can provide an alternative to animal testing for the evaluation of chemical structure-activity relationships. In a non-limiting embodiment, the present invention provides a method for screening a candidate compound for the ability to bind to an opioid or ORL-1 receptor, comprising the steps of: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Compounds of the Invention disclosed herein may contain one or more asymmetric centers, thus giving rise to diastereomers, enantiomers, and other stereoisomeric forms. The present invention encompasses all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, they include both E and Z geometric isomers. All tautomers are intended to be encompassed by the present invention as well.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active such that the enantiomer rotates the plane of polarized light in one direction and its mirror image compound rotates the plane of polarized light in the opposite direction.

The term "racemic" refers to a mixture of equal parts of enantiomers and which mixture is optically inactive. Racemic compounds can be separated into their enantiomers by chiral chromatography.

The term "resolution" refers to the separation or concentration or depletion of one of the two enantiomeric forms of a molecule.

The terms "a" and "an" refer to one or more.

Compounds of the Invention encompass all salts of the disclosed compounds of any one of Formulae I, I', II, III, A, B, C, D, E, F, G, and H. The present invention preferably includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicylohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

Compounds of the Invention also encompass solvates of the disclosed compounds of any one of Formulae I, I', II, III, A, B, C, D, E, F, G, and H. The term "solvate" as used herein is a combination, physical association and/or solvation of a compound of any one of Formulae I, I', II, III, A, B, C, D, E, F, G, and H with a solvent molecule such as, e.g. a disolvate, monosolvate or hemisolvate, where the ratio of solvent molecule to compound of any one of Formulae I, I', II, III, A, B, C, D, E, F, G, and H is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A compound of any one of Formulae I, I', II, III, A, B, C, D, E, F, G, and H may be present as a solvated form with a pharmaceutically acceptable solvent, such as water, methanol, ethanol, and the like, and it is intended that the invention include both solvated and unsolvated forms of compounds of any one of Formulae I, I', II, III, A, B, C, D, E, F, G, and H.

One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.*, 603-604 (2001). A typical, non-limiting, process of preparing a solvate would involve dissolving a compound of any one of Formulae I, I', II, III, A, B, C, D, E, F, G, and H in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides the use of a Compound of the Invention in the manufacture of a medicament for treating or preventing a Condition. In one embodiment, the Condition is pain, such as acute or chronic pain. In one embodiment, a Compound of the Invention has agonist activity at the μ, δ and/or κ receptors. In another embodiment a Compound of the Invention has agonist activity at the t receptor. In another embodiment, a Compound of the Invention has antagonist activity at the ORL-1 receptor. In another embodiment, certain Compounds of the invention can stimulate one receptor (e.g., a μ, δ and/or κ agonist) and inhibit a different receptor (e.g., an ORL-1 antagonist). In another embodiment, the Compound of the Invention is an agonist at the μ receptor, and an antagonist at the ORL-1 receptor. In another embodiment, the Compound of the Invention is an antagonist at the μ receptor, and an agonist at the κ receptor.

List of Abbreviations

ACN acetonitrile
AcOH acetic acid

AIBN 2,2-azobisisobutyronitrile
Alloc allyloxycarbonyl
aq. aqueous
atm atmosphere(s)
Bn benzyl
Boc tert-butoxycarbonyl
Boc$_2$O di-tert-butyl dicarbonate
Bz benzoyl
° C. degrees Celcius
CAN ceric ammonium nitrate
Cbz benzyloxycarbonyl
CSA 10-camphorsulfonic acid
d day(s)
DABCO 1,4-diazabicyclo[2.2.2]octane
DBU 1,8-diazabicyclo[5.4.0]undec-7-ene
DCM dichloromethane
DDQ 2,3-dichloro-5,6-dicyano-1,4-benzoquinone
DEAD diethyl azodicarboxylate
DIAD diisopropyl azodicarboxylate
DIBAL diisobutylaluminum hydride
DIPEA diisopropylethylamine
DMAC dimethylacetamide
DMAP 4-dimethylaminopyridine
DME 1,2-dimethoxyethane
DMF dimethylformamide
DMPU N,N-dimethylpropyleneurea
DMSO dimethylsulfoxide
EDCI 1-ethyl-3-(3-dimethylaminopropyl)carbodiimide)
Et$_2$O diethyl ether
EtOAc ethyl acetate
EtOH ethanol
FMOC 9-fluorenylmethyloxycarbonyl
h hour(s)
HATU 2-(7-aza-1H-benzotriazole-1-yl)-1,1,3,3-tetramethyluronium hexafluorophosphate
HPLC high pressure liquid chromatography
i-PrOH iso-propanol
LAH lithium aluminum hydride
LDA lithium diisopropylamide
mCPBA meta-chloroperoxybenzoic acid
MEM β-methoxyethoxymethyl
MeOH methanol
min minute(s)
MOM methoxymethyl
MPLC medium pressure liquid chromatography
Ms methanesulfonyl
MsCl methanesulfonyl chloride
NaHMDS sodium hexamethyldisilazide
NBS N-bromosuccinimide
NMO N-methylmorpholine N-oxide
NMP N-methyl-2-pyrrolidone
PCC pyridinium chlorochromate
Pd/C palladium on carbon
Pd(dppf)Cl$_2$ [1,1'-bis(diphenylphosphino)ferrocene]dichloropalladium(II)
Pd(Ph$_3$P)$_2$Cl$_2$ bis(triphenylphosphine)palladium(II) dichloride
(Ph)$_3$P triphenylphosphine
Piv pivaloyl
PMB p-methoxybenzyl
PTSA p-toluenesulfonic acid
PyB OP benzotriazol-1-yl-oxytripyrrolidinophosphonium hexafluorophosphate
RT room temperature
TBAF tetrabutylammonium fluoride
TBDMS tert-butyldimethylsilyl
t-BuOH tert-butyl alcohol
TEA triethylamine
Tf trifluoromethanesulfonyl
TFA trifluoroacetic acid
TFAA trifluoroacetic anhydride
THF tetrahydrofuran
THP 2-tetrahydropyranyl
TMS trimethylsilyl
TMEDA N,N,N',N'-tetramethylethylenediamine Synthesis of Compounds Compounds of the Invention can be made using conventional organic synthesis in view of this disclosure, or by the illustrative methods shown in the schemes below.

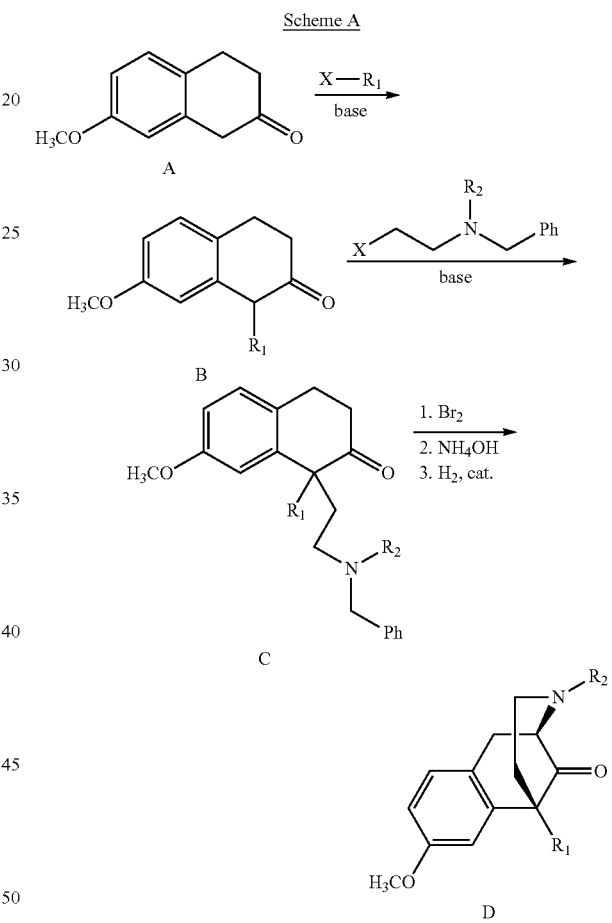

Scheme A

Compound D is prepared as generally described in U.S. Pat. No. 3,956,336A. Compound A [*J. Amer. Chem. Soc.*, 1961, 83, 1492] was alkylated with a alkyl halide, in the presence of a base (such as, pyrrolidine), in a suitable solvent (such as, toluene) to give Compound B. Compound B was treated with a haloethyl amine in the presence of a base (such as, sodium hydride), in a solvent (such as, benzene) to give Compound C. Compound C was treated with bromine in a suitable solvent (such as, acetic acid) to give the alpha-bromo ketone, which was cyclized to give the quaternary salt by treatment with a suitable base (such as, ammonium hydroxide). Hydrogenolysis of the quaternary salt in the presence of hydrogen and a suitable catalyst (such as, palladium on carbon), in a suitable solvent (such as, acetic acid), gives Compound D.

Scheme B

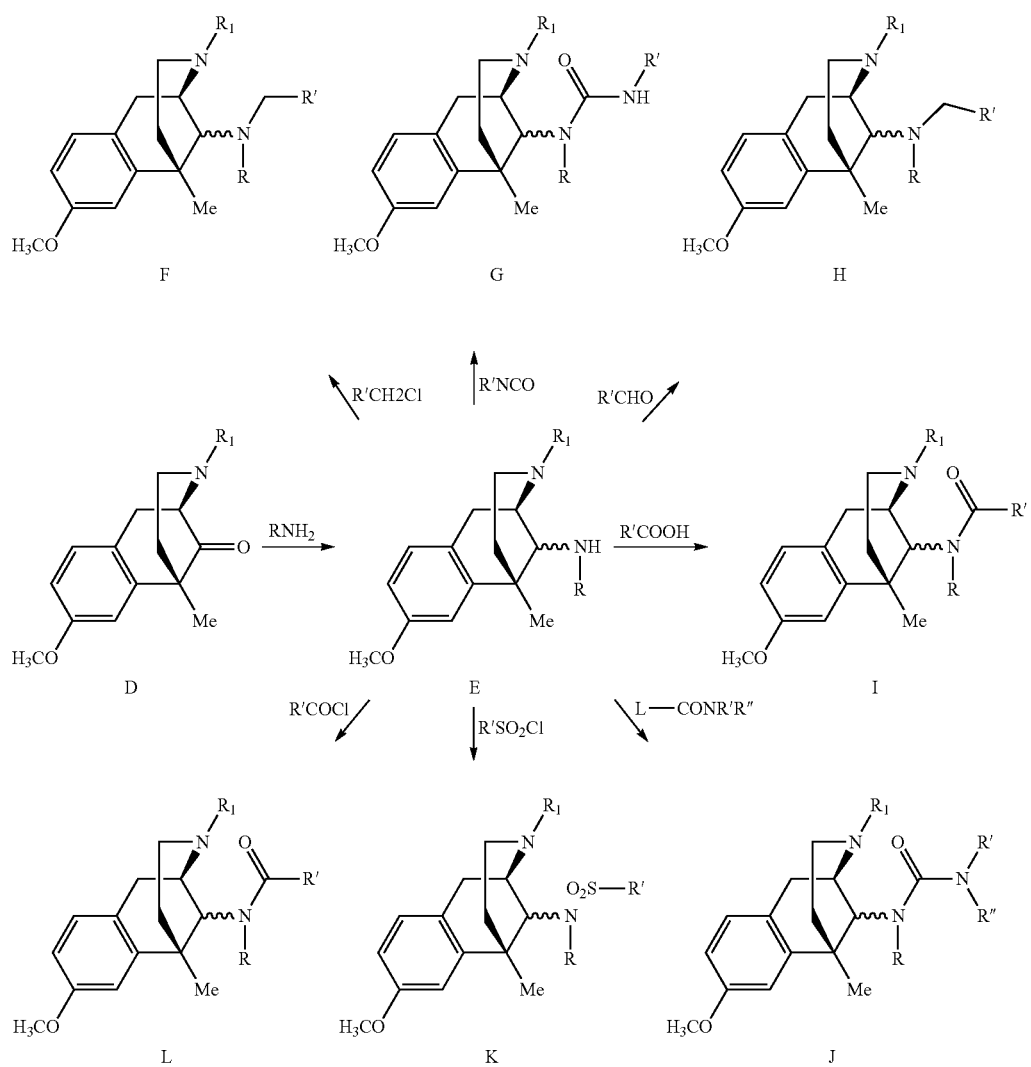

Compound D is reacted with an amine under reductive amination conditions, with a suitable reducing agent (such as, sodium triacetoxyborohydride) in a suitable solvent (such as, acetonitrile (ACN)) to give Compound E. In the alternative, Compound D is reacted with an amine, using a suitable base (such as, sodium acetate) in a suitable solvent (such as, ethanol (EtOH)). Subsequent treatment with a suitable catalyst (such as, Raney nickel) under hydrogenation conditions at elevated pressure also gives Compound E.

Compound E can be functionalized with suitable reagents (such as, acid chlorides, sulfonyl chlorides, and alkyl halides) in a suitable solvent (such as, dichloromethane (DCM)) in the presence of a suitable base (such as, triethyl amine (TEA)) to obtain Compound F, L, or K. Compound E can be functionalized with suitable reagents (such as, aldehydes) under reductive amination conditions, with a suitable reducing agent (such as, sodium triacetoxyborohydride) in a suitable solvent (such as, DCM) to obtain Compound G or H. Compound E can be functionalized with suitable reagents (such as, carboxamides) in a suitable solvent (such as, tetrahydrofuran (THF)) to obtain Compound J. Compound E can be functionalized with suitable reagents (such as, car-boxylic acids) under peptide coupling conditions, with a suitable peptide coupling agent (such as, 2-(7-aza-1H-benzotriazole-1-yl)-1,1,3,3-tetramethyluronium hexafluorophosphate (HATU)) in a suitable solvent (such as, dimethylformamide (DMF)) to obtain Compound I.

Further functionalization of Compound F, G, H, I, J, K, or L can be done by one with ordinary skill in the art using conventional organic synthesis.

Scheme C

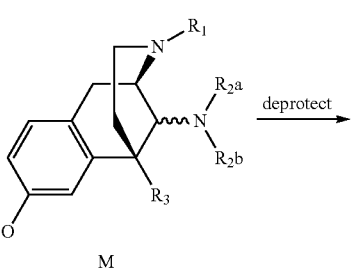

-continued

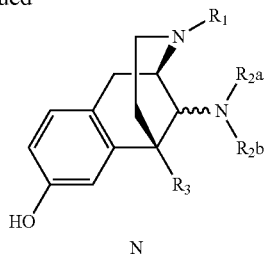

N

Compound M is cleaved to Compound N by treatment with a suitable reagent (such as, boron tribromide ($BBr_3$)) in a suitable solvent (such as, DCM) (e.g. Greene, T. W. "Protective Groups in Organic Synthesis", J. Wiley & Sons, N Y, 1981).

Scheme D

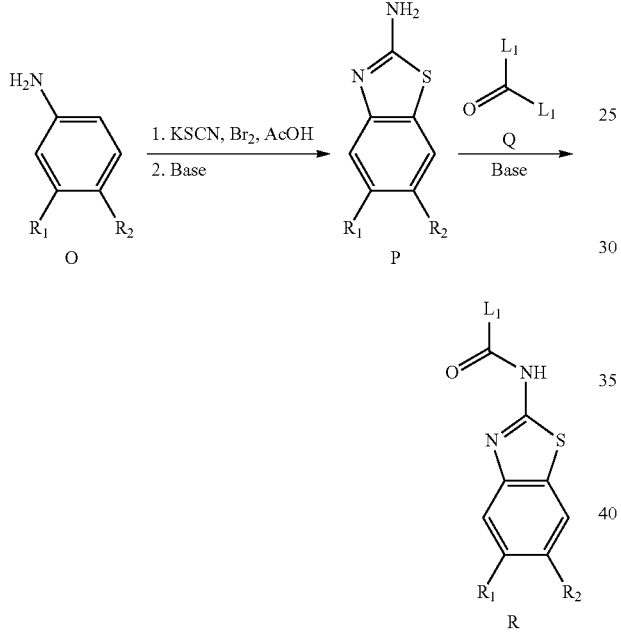

Compound O is reacted with potassium thiocyanate, in the presence of bromine, in a suitable acid (such as, acetic acid) to give Compound P. Compound P can be precipitated from solution following the addition of a suitable base (such as, ammonium hydroxide). Compounds of formula O are commercially available or can be prepared by procedures known in the art. Compound P can be functionalized with suitable reagents Q where each L1 is a suitable leaving group (such as, imidazol-1-yl) in the presence of a suitable base (such as, DIEPA). The compounds of formula Q are commercially available or can be prepared by procedures known in the art.

Scheme E

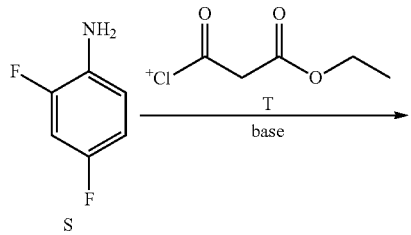

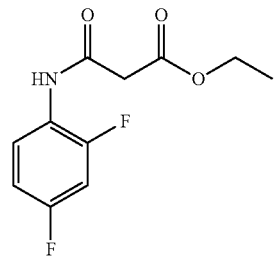

U

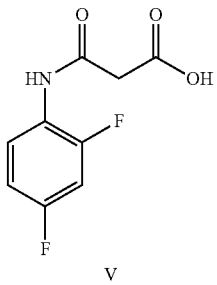

V

Compound S is converted to Compound U according to literature procedure (WO2008124118 A1) by reaction with a suitable acylating reagent (such as, Compound T) in the presence of a suitable base (such as, TEA) in a suitable solvent (such as, DCM). Compound U is converted to Compound V using standard hydrolysis conditions known by one skilled in the art, such as, according to literature procedure (e.g., those delineated in WO2008124118 A1).

Scheme F

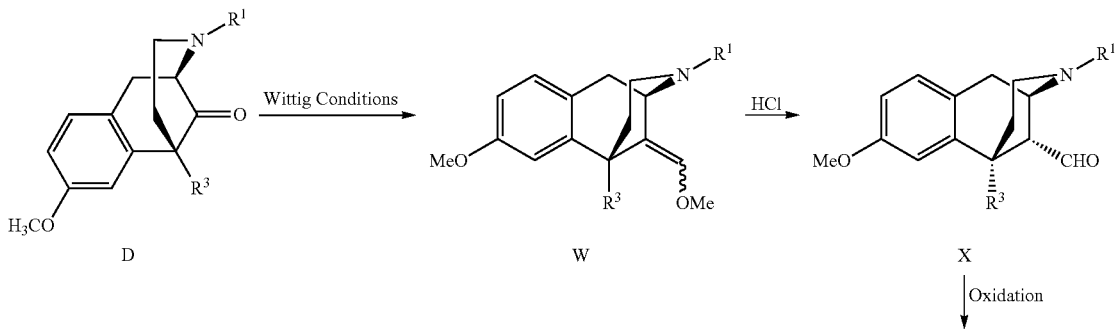

| Oxidation

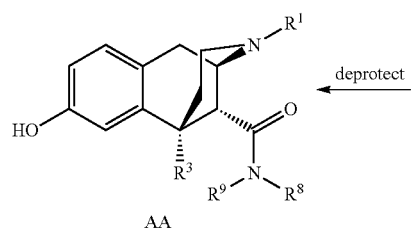
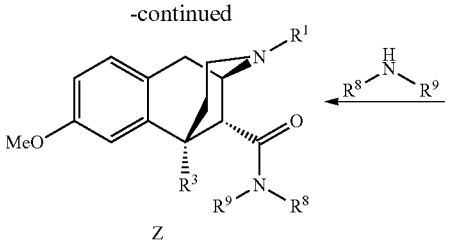
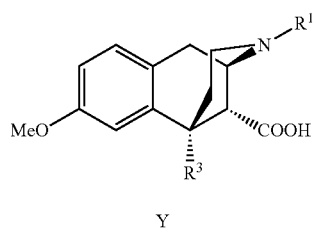

AA    Z    Y

Compound D is converted to Compound W using standard Wittig reaction conditions known by one skilled in the art, such as, by reaction with a suitable triphenyl phosphonium ylide (such as, (methoxymethyl)triphenylphosphonium chloride) in the presence of a suitable base (such as, potassium tert-butoxide (t-BuOk)) in a suitable solvent (such as, THF). Compound W is converted to Compound X by treatment with aqueous HCl in a suitable solvent (such as, THF).

Compound X is converted to Compound Y using standard oxidation conditions known by one skilled in the art, for example, according to literature procedure (*Tetrahedron*, 1981, 37, 2091-2096). Compound Y is reacted with a suitable amine (such as, piperidine) using a suitable coupling agent (such as, HATU) in a suitable solvent (such as, dimethylformamide (DMF)) to obtain Compound Z. Compound Z is converted to Compound AA by treatment with a suitable reagent (such as, boron tribromide ($BBr_3$)) in a suitable solvent (such as, DCM) (e.g. Greene, T. W. "Protective Groups in Organic Synthesis", J. Wiley & Sons, N Y, 1981).

Scheme G

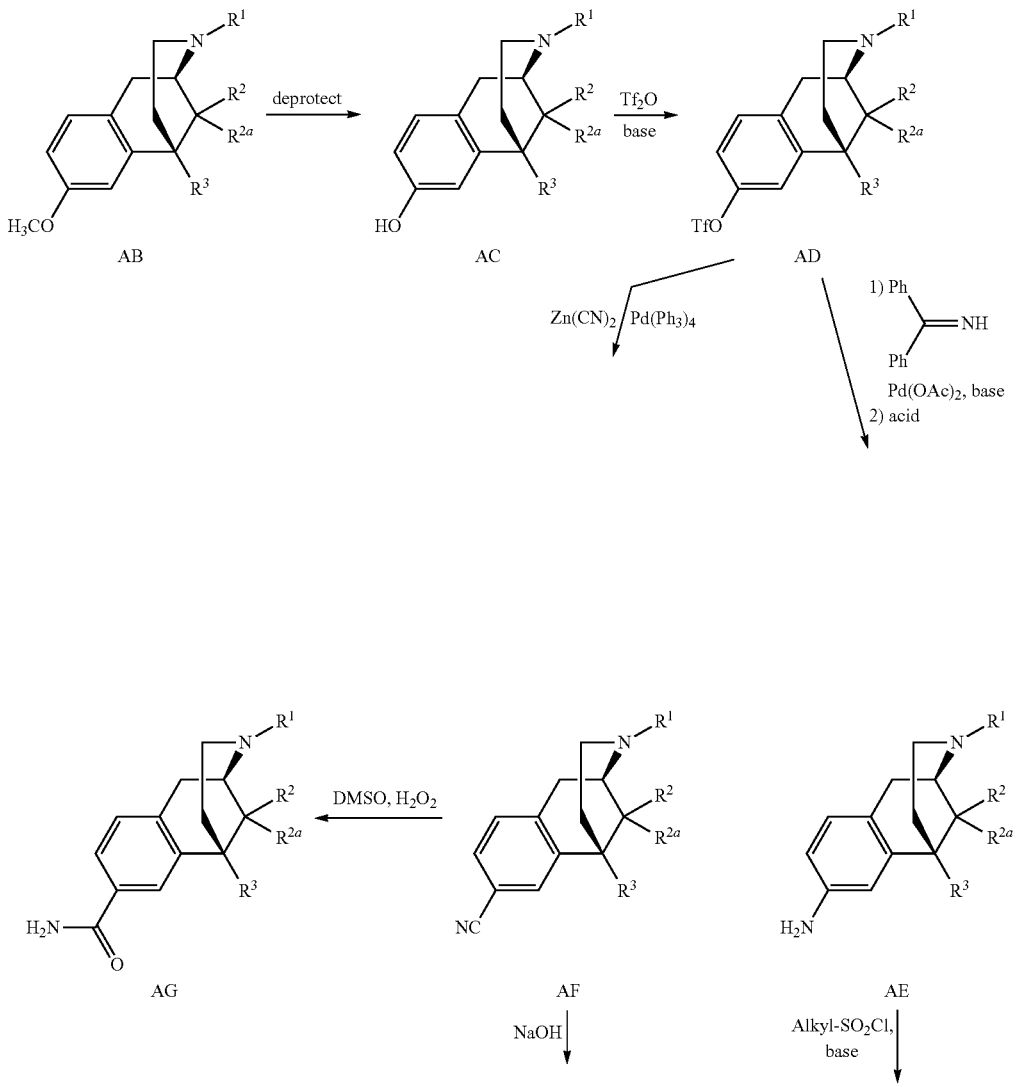

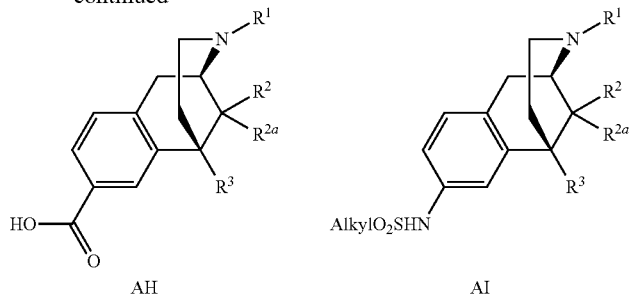

AH            AI

Compound AB is prepared in accordance with the synthetic methods delineated in WO 2014072809 (PCT application NO. PCT/IB2013/002511). Compound AB is deprotected to afford Compound AC by treatment with a suitable reagent (such as, boron tribromide ($BBr_3$)) in a suitable solvent (such as, DCM) (e.g. Greene, T. W. "Protective Groups in Organic Synthesis", J. Wiley & Sons, N Y, 1981).

Compound AC is then converted to Compound AD by reaction with triflic anhydride in the presence of a suitable base (such as, trimethylamine) in a suitable solvent (such as, DCM) (see WO 2012038813).

Compound AD can be further converted to nitrile AF, Compounds AE, AG, AH, and AI (and others) by using the conventional synthetic methods, such as, those delineated in WO 2012038813.

Testing of Compounds

μ-Opioid Receptor Binding Assay Procedures:

Radioligand dose-displacement binding assays for μ-opioid receptors used 0.3 nM [$^3$H]-diprenorphine (Perkin Elmer, Shelton, Conn.), with 5 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hr at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subsequently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISM™ v. 3.0 or higher (San Diego, Calif.), or an in-house function for one-site competition curve-fitting.

μ-Opioid Receptor Binding Data:

Generally, the lower the Ki value, the more effective the Compounds of the Invention will be at treating or preventing pain or another Condition. Typically, the Compounds of the Invention will have a Ki (nM) of about 1000 or less for binding to μ-opioid receptors. In one embodiment the Compounds of the Invention will have a Ki (nM) of about 300 or less for binding to μ-opioid receptors. In one embodiment, Compounds of the Invention will have a Ki (nM) of about 100 or less. In another embodiment, Compounds of the Invention will have a Ki (nM) of about 10 or less. In still another embodiment, Compounds of the Invention will have a Ki (nM) of about 1 or less. In still another embodiment, Compounds of the Invention will have a Ki (nM) of about 0.1 or less.

μ-Opioid Receptor Functional Assay Procedures:

[$^{35}$S]GTPγS functional assays were conducted using freshly thawed μ-receptor membranes prepared in-house from a cell line expressing recombinant opioid receptor in a HEK-293, CHO or U-2 OS cell background, or purchased from a commercial source (Perkin Elmer, Shelton, Conn.; or DiscovRx, Fremont, Calif.). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 min at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 μl of ice-cold wash buffer (10 mM $NaH_2PO_4$, 10 mM $Na_2HPO_4$, pH 7.4). Filter plates were subsequently dried at 50° C. for 2-3 hr. BetaScint scintillation cocktail (Perkin Elmer, Shelton, Conn.) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data:

μ GTP $EC_{50}$ is the concentration of a compound providing 50% of the maximal response for the compound at a μ-opioid receptor. Compounds of the Invention will typically have a μ GTP $EC_{50}$ (nM) of about 5000 or less. In certain embodiments, Compounds of the Invention will have a μ GTP $EC_{50}$ (nM) of about 2000 or less; or about 1000 or less; or about 100 or less; or about 10 or less; or about 1 or less; or about 0.1 or less.

μ GTP $E_{max}$ (%) is the maximal effect elicited by a compound relative to the effect elicited by DAMGO, a standard μ agonist. Generally, the μ GTP $E_{max}$ (%) value measures the efficacy of a compound to treat or prevent pain or other Conditions. Typically, Compounds of the Invention will have a μ GTP $E_{max}$ (%) of greater than about 10%; or greater than about 20%. In certain embodiments, Compounds of the Invention will have a μ GTP $E_{max}$ (%) of greater than about 50%; or greater than about 65%; or greater than about 75%; or greater than about 85%; or greater than about 100%.

κ-Opioid Receptor Binding Assay Procedures:

Membranes from recombinant HEK-293 cells, CHO or U-2 OS cells expressing the recombinant human κ opioid receptor (κ) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes from a cell line naturally expressing kappa opioid receptors can also be used. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at –80° C.

Radioligand dose displacement assays used 0.4 nM [$^3$H]-U69,593 (GE Healthcare, Piscataway, N.J.; 40 Ci/mmole) with 15 μg membrane protein (recombinant K opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

κ-Opioid Receptor Binding Data:

In certain embodiments, the Compounds of the Invention will have a Ki (nM) for κ receptors of about 10,000 or more (which, for purposes of this invention, is interpreted as having no binding to the κ receptors). Certain Compounds of the Invention will have a Ki (nM) of about 20,000 or less for κ receptors. In certain embodiments, Compounds of the Invention will have a Ki (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less.

κ-Opioid Receptor Functional Assay Procedures:

Functional [$^{35}$S]GTPγS binding assays were conducted as follows. K opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well.

κ-Opioid Receptor Functional Data:

κ GTP $EC_{50}$ is the concentration of a compound providing 50% of the maximal response for the compound at a κ receptor. Certain Compounds of the Invention will have a κ GTP $EC_{50}$ (nM) of about 20,000 or less to stimulate K opioid receptor function. In certain embodiments, Compounds of the Invention will have a κ GTP $EC_{50}$ (nM) of about 10,000 or less; or about 5000 or less; or about 2000 or less; or about 1500 or less; or about 1000 or less; or about 600 or less; or about 100 or less; or about 50 or less; or about 25 or less; or about 10 or less; or about 1 or less; or about 0.1 or less.

κ GTP $E_{max}$ (%) is the maximal effect elicited by a compound relative to the effect elicited by U69,593. Certain Compounds of the Invention will have a κ GTP $E_{max}$ (%) of greater than about 1%; or greater than about 5%; or greater than about 10%; or greater than about 20%. In certain embodiments, Compounds of the Invention will have a κ GTP $E_{max}$(%) of greater than about 50%; or greater than about 75%; or greater than about 90%; or greater than about 100%.

δ-Opioid Receptor Binding Assay Procedures:

δ-opioid Receptor Binding Assay Procedures can be conducted as follows. Radioligand dose-displacement assays use 0.3 nM [$^3$H]-Naltrindole (Perkin Elmer, Shelton, Conn.; 33.0 Ci/mmole) with 5 g membrane protein (Perkin Elmer, Shelton, Conn.) in a final volume of 500 μl binding buffer (5 mM $MgCl_2$, 5% DMSO, 50 mM Trizma base, pH 7.4). Non-specific binding is determined in the presence of 25 μM unlabeled naloxone. All reactions are performed in 96-deep well polypropylene plates for 1 hr at a temperature of about 25° C. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by five filtration washes with 500 μl ice-cold binding buffer. Filter plates are subsequently dried at 50° C. for 1-2 hours. Fifty l/well scintillation cocktail (Perkin Elmer, Shelton, Conn.) is added and plates are counted in a Packard Top-Count for 1 min/well.

δ-Opioid Receptor Binding Data:

In certain embodiments, the Compounds of the Invention will have a Ki (nM) for δ receptors of about 10,000 or more (which, for the purposes of this invention, is interpreted as having no binding to the δ receptors). Certain Compounds of the Invention will have a Ki (nM) of about 20,000 or less for δ receptors. In one embodiment, the Compounds of the Invention will have a Ki (nM) of about 10,000 or less; or of about 9000 or less. In another embodiment, the Compounds of the Invention will have a Ki (nM) of about 7500 or less; or of about 6500 or less; or of about 5000 or less; or of about 3000 or less; or of about 2500 or less. In another embodiment, the Compounds of the Invention will have a Ki (nM) of about 1000 or less; or of about 500 or less; or of about 350 or less; or of about 250 or less; or of about 100 or less; or of about 10 or less.

δ-Opioid Receptor Functional Assay Procedures:

Functional [$^{35}$S]GTPγS binding assays can be conducted as follows. δ opioid receptor membrane solution is prepared by sequentially adding final concentrations of 0.026 μg/μl δ membrane protein (Perkin Elmer, Shelton, Conn.), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) is transferred to 96-shallow well polypropylene plates containing 10 μl of 20× concentrated stock solutions of agonist prepared in DMSO. Plates are incubated for 30 min at a temperature of about 25° C. with shaking.

Reactions are terminated by rapid filtration onto 96-well Unifilter GF/B filter plates (Perkin Elmer, Shelton, Conn.) using a 96-well tissue harvester (Packard) and followed by three filtration washes with 200 µl ice-cold binding buffer (10 mM $NaH_2PO_4$, 10 mM $Na_2HPO_4$, pH 7.4). Filter plates are subsequently dried at 50° C. for 1-2 hours. Fifty µl/well scintillation cocktail (Perkin Elmer, Shelton, Conn.) is added and plates are counted in a Packard Top-count for 1 min/well.

δ-Opioid Receptor Functional Data:

δ GTP $EC_{50}$ is the concentration of a compound providing 50% of the maximal response for the compound at a δ receptor. Certain Compounds of the Invention will have a δ GTP $EC_{50}$ (nM) of about 20,000 or less; or about 10,000 or less. In certain embodiments, the Compounds of the Invention will have a δ GTP $EC_{50}$ (nM) of about 3500 or less; or of about 1000 or less; or of about 500 or less; or of about 100 or less; or of about 90 or less; or of about 50 or less; or of about 25 or less; or of about 10 or less.

δ GTP $E_{max}$ (%) is the maximal effect elicited by a compound relative to the effect elicited by met-enkephalin. Certain Compounds of the Invention of the invention will have a δ GTP $E_{max}$ (%) of greater than about 1%; or of greater than about 5%; or of greater than about 10%. In one embodiment, the Compounds of the Invention will have a δ GTP $E_{max}$ (%) of greater than about 30%. In other embodiments, the Compounds of the Invention will have a δ GTP $E_{max}$ (%) of greater than about 50%; or of greater than about 75%; or of greater than about 90%. In another embodiment, the Compounds of the Invention will have a δ GTP $E_{max}$ (%) of about 100% or greater.

ORL-1 Receptor Binding Assay Procedure:

Membranes from recombinant HEK-293 cells expressing the human opioid receptor-like receptor (ORL-1) (Perkin Elmer, Shelton, Conn.) are prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Radioligand binding assays (screening and dose-displacement) use 0.1 nM [$^3$H]-nociceptin (Perkin Elmer, Shelton, Conn.; 87.7 Ci/mmole) with 12 g membrane protein in a final volume of 500 al binding buffer (10 mM $MgCl_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at room temperature. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by three filtration washes with 500 µl ice-cold binding buffer. Filter plates are subsequently dried at 50° C. for 2-3 hours. Fifty µl/well scintillation cocktail (Perkin Elmer, Shelton, Conn.) is added and plates are counted in a Packard Top-Count for 1 min/well. The data from screening and dose-displacement experiments are analyzed using Microsoft Excel and the curve fitting functions in GraphPad PRISM™, v. 3.0 or higher, respectively, or an in-house function for one-site competition curve-fitting.

ORL-1 Receptor Binding Data:

Certain Compounds of the Invention will have a Ki (nM) of about 1000 or less. In one embodiment, the Compounds of the Invention will have a Ki (nM) of about 500 or less. In other embodiments, the Compounds of the Invention will have a Ki (nM) of about 300 or less; or of about 100 or less; or of about 50 or less; or of about 20 or less. In yet other embodiments, the Compounds of the Invention will have a Ki (nM) of about 10 or less; or of about 1 or less; or of about 0.1 or less.

ORL-1 Receptor Functional Assay Procedure:

Membranes from recombinant HEK-293 cells expressing the human opioid receptor-like (ORL-1) (Perkin Elmer, Shelton, Conn.) are prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Functional [$^{35}$S]GTPγS binding assays are conducted as follows. ORL-1 membrane solution is prepared by sequentially adding final concentrations of 0.026 µg/µl ORL-1 membrane protein, 10 µg/ml saponin, 3 µM GDP and 0.20 nM [$^{35}$S]GTPγS to binding buffer (100 mM NaCl, 10 mM $MgCl_2$, 20 mM HEPES, pH 7.4) on ice. The prepared membrane solution (190 µl/well) is transferred to 96-shallow well polypropylene plates containing 10 µl of 20× concentrated stock solutions of agonist/nociceptin prepared in DMSO. Plates are incubated for 30 min at room temperature with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 µl ice-cold binding buffer (10 mM $NaH_2PO_4$, 10 mM $Na_2HPO_4$, pH 7.4). Filter plates are subsequently dried at 50° C. for 2-3 hours. Fifty µl/well scintillation cocktail (Perkin Elmer, Shelton, Conn.) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data:

ORL-1 GTP $EC_{50}$ is the concentration of a compound providing 50% of the maximal response for the compound at an ORL-1 receptor. In certain embodiments, the Compounds of the Invention that have a high binding affinity (i.e. low $K_i$ value) will have an ORL-1 GTP $EC_{50}$ (nM) of greater than about 10,000 (i.e. will not stimulate at therapeutic concentrations) In certain embodiments Compounds of the Invention will have an ORL-1 GTP $EC_{50}$ (nM) of about 20,000 or less. In one embodiment, the Compounds of the Invention will have an ORL-1 GTP $EC_{50}$ (nM) of about 10,000 or less; or of about 5000 or less; or of about 1000 or less. In still other embodiments, the Compounds of the Invention will have an ORL-1 GTP $EC_{50}$ (nM) of about 100 or less; or of about 10 or less; or of about 1 or less; or of about 0.1 or less.

ORL-1 GTP $E_{max}$ % is the maximal effect elicited by a compound relative to the effect elicited by nociceptin, a standard ORL-1 agonist. In certain embodiments, Compounds of the Invention will have an ORL-1 GTP $E_{max}$ of less than 10% (which, for the purposes of this invention, is interpreted as having antagonist activity at ORL-1 receptors). Certain Compounds of the Invention will have an ORL-1 GTP $E_{max}$ (%) of greater than 1%; or of greater than 5%; or of greater than 10%. In other embodiments the Compounds of the Invention will have an ORL-1 GTP $E_{max}$ of greater than 20%; or of greater than 50%; or of greater than 75%; or of greater than 88%; or of greater than 100%.

In Vivo Assays for Prevention or Treatment of Pain

Test Animals:

Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain:

To assess the actions of a Compound of the Invention for the treatment or prevention of acute pain, the rat tail flick can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Invention. Data are expressed as tail flick latency(s) and the percentage of the maximal possible effect (% MPE), i.e., 20 seconds, is calculated as follows:

$$\% MPE = \frac{[(\text{post administration latency}) - (\text{pre-administration latency})]}{(20 \text{ s} - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

To assess the actions of a Compound of the Invention for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). Rats are placed into the cylinder on the hot plate apparatus for a maximum duration of 30 s, or until it exhibits a nocifensive behavior (behavioral endpoint), at which time it is removed from the hot plate, and the response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) escape or attempted escape from the testing device; or 4) vocalization. Data are expressed as response latency(s) and the percentage of the maximal possible effect is calculated as described above for the tail flick test. The hot plate test is described in G. Woolfe and A. D. Macdonald, *J. Pharmacol. Exp. Ther.* 80:300-307 (1944).

Inflammatory Pain:

To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \text{Reversal} = \frac{[(\text{post administration } PWT) - (\text{pre-administration } PWT)]}{[(\text{baseline } PWT) - (\text{pre-administration } PWT)]} \times 100$$

Neuropathic Pain:

To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia:

The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression:

To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., 2000 *Intensive Care Med.* (26) 585-591).

Assessment of Gastric Motility:

Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

In certain embodiments, the Compounds of the Invention are believed to be advantageously useful in human and veterinary medicine. As above described, the Compounds of the Invention are useful for treating or preventing a Condition in a subject in need thereof. The Compounds of the Invention can be administered to any animal requiring modulation of the opioid and/or ORL-1 receptors.

When administered to a subject, a Compound of the Invention can be administered as a component of a composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, thin films, suppositories, aerosols, sprays, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the invention preferably comprise a suitable amount of a pharmaceutically acceptable excipient so as to provide the form for proper administration to the subject. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release, Vol. 2, Applications and Evaluation*, R. S. Langer and D. L. Wise eds., CRC Press (1984). Other controlled- or sustained-release systems that are discussed in the review by Langer, *Science* 249:1527-1533 (1990) can be selected for use according to the present invention. In one embodiment, a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each animal's circumstances. Variations in dosing may occur depending upon typical factors such as the weight, age, gender and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Compound of the Invention, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Compound of the Invention is administered, the effective dosage amounts correspond to the total amount administered.

Where a cell capable of expressing the ORL-1 receptor is contacted with a Compound of the Invention in vitro, the amount effective for inhibiting or activating the ORL-1 receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the µ-opioid receptors is contacted with a Compound of the Invention in vitro, the amount effective for inhibiting or activating the µ-opioid receptors function in a cell will typically range from about $10^{-2}$ mol/L to about $10^{-4}$ mol/L, or from about $10^{-2}$ mol/L to about $10^{-5}$ mol/L, or from about $10^{-2}$ mol/L to about $10^{-6}$ mol/L, or from about $10^{-2}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the δ-opioid receptors is contacted with a Compound of the Invention in vitro, the amount effective for inhibiting or activating the δ-opioid receptors function in a cell will typically range from about $10^{-2}$ mol/L to about $10^{-4}$ mol/L, or from about $10^{-2}$ mol/L to about $10^{-5}$ mol/L, or from about $10^{-2}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the κ-opioid receptors is contacted with a Compound of the Invention in vitro, the amount effective for inhibiting or activating the κ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

The Compounds of the Invention can be assayed in vitro or in vivo for the desired therapeutic or prophylactic activity prior to use in humans. Animal model systems can be used to demonstrate safety and efficacy. Certain Compounds of the Invention will have an $ED_{50}$ for treating pain ranging from about 0.5 mg/kg to about 20 mg/kg. Certain Compounds of the Invention will produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the invention, methods for treating or preventing a Condition in an animal in need thereof can further comprise co-administering to the animal an effective amount of a second therapeutic agent in addition to a Compound of the Invention (i.e., a first therapeutic agent). An effective amount of the second therapeutic agent will be known or determinable by a medical practitioner in view of this disclosure and published clinical studies. In one embodiment of the invention, where a second therapeutic agent is administered to an animal for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Insel, *Analgesic-Antipyretic and Anti-inflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9$^{th}$ ed 1996); and Glen R. Hanson, *Analgesic, Antipyretic and Anti-Inflammatory Drugs* in Remington: *The Science and Practice of Pharmacy Vol IA* 1196-1221 (A. R. Gennaro ed. 19$^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the invention is prepared by a method comprising admixing a Compound of the Invention (or a pharmaceutically acceptable salt, prodrug or solvate thereof) with a pharmaceutically acceptable carrier or excipient. Admixing can be accomplished using methods known for admixing a compound (or derivative) and a pharmaceutically acceptable carrier or excipient. In one embodiment, the Compound of the Invention (or pharmaceutically acceptable salt, prodrug or solvate thereof) is present in the composition in an effective amount.

EXAMPLES

Example 1

Synthesis of (2S,6R)-8-methoxy-3,6-dimethyl-1,2,3,4,5,6-hexahydro-2,6-methano-benzo[d]azocin-11-one (Compound 6)

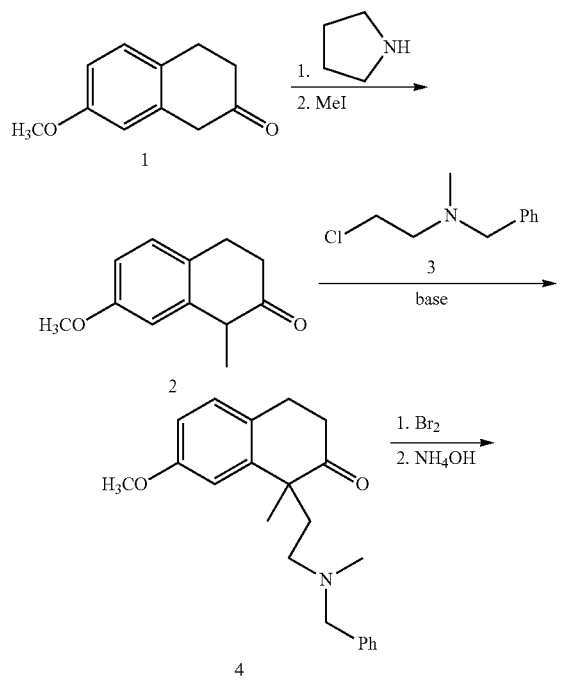

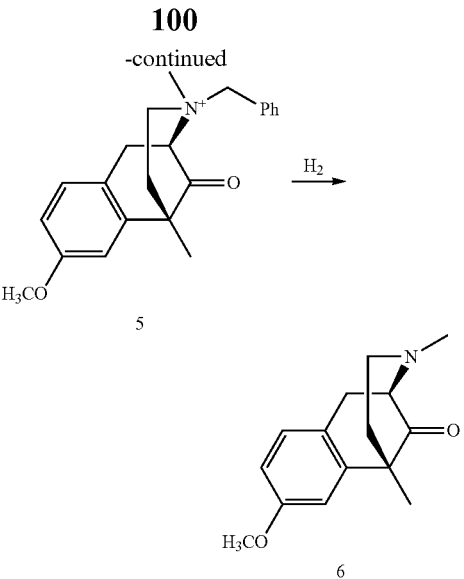

Pyrrolidine (190 mL, 2.3 mol) was added to a solution of Compound 1 (200 g, 1.1 mol) (Accela ChemBio) in 600 mL of toluene over 30 min. The azeotropic removal of water was then performed by heating the reaction mixture to 115° C. and collecting about 20 mL of water using a Dean-Stark trap. After cooling to RT, the reaction mixture was concentrated under reduced pressure to 25% of the original volume. To the remaining residue was added 1,4-dioxane (500 mL) followed by the drop-wise addition of MeI (400 g; 2.82 mol) over 30 min at RT. The reaction mixture was stirred at 40° C. for 2 h and 60° C. for 16 h. The reaction was cooled to 0° C., the solvent decanted, and the remaining residue washed with 200 mL of hexanes. Toluene (600 mL), water (600 mL), and AcOH (70 mL) was added and the resulting mixture heated at 70° C. for 16 h. The mixture was then cooled to RT, the organic layer cut away, and the remaining aqueous layer extracted with toluene (2×250 mL). The combined organics were washed with brine and evaporated in vacuo. The residue was purified by flash chromatography (SiO2, 10% EtOAc/hexanes) to give Compound 2 as colorless oil (190 g, yield 91%): $^1$H NMR (CHLOROFORM-d) δ: 7.13 (d, J=9.0 Hz, 1H), 6.65-6.84 (m, 2H), 3.81 (s, 3H), 3.49 (q, J=7.2 Hz, 1H), 2.91-3.12 (m, 2H), 2.55-2.67 (m, 1H), 2.39-2.54 (m, 1H), 1.46 (d, J=7.0 Hz, 3H).

To a mixture of NaH (55% in mineral oil, 11 g, 0.25 mol) in 200 mL toluene at 75° C. was added over 1 h Compound 2 (36 g, 0.189 mol) dissolved in 100 mL toluene. After stirring for 1 h, a solution of N-benzyl-2-chloro-N-methyl-ethanamine (Compound 3, 35 g in 150 mL toluene) was added drop-wise over 1 h. After stirring for 1 h at 75° C., the reaction was cooled to RT and poured over ice-water (200 g). The toluene layer was cut away. The aqueous layer was further extracted with 100 mL toluene. The combined toluene layers were treated with HCl (5N 150 mL) at 0° C. and stirred at RT for 1 h. The aqueous layer was cut away, cooled with ice water, neutralized with NH4OH (100 mL) to pH~9, and further extracted with toluene (2×200 mL). The new combined toluene layers were washed with brine and evaporated in vacuo. The residue was purified by flash chromatography (SiO2, 66% EtOAc/hexanes) to give Compound 4 as colorless oil (37 g, yield 56%): $^1$H NMR (CHLOROFORM-d) δ: 7.23-7.27 (m, 2H), 7.15-7.22 (m, 3H), 7.07 (d, J=8.3 Hz, 1H), 6.81 (d, J=2.6 Hz, 1H), 6.74 (dd, J=8.3, 2.6 Hz, 1H), 3.79 (s, 3H), 3.23-3.46 (m, 2H), 2.88-3.09 (m, 2H), 2.61-2.69 (m, 2H), 2.53 (d, J=13.6 Hz, 1H), 2.02-2.11 (m, 2H), 1.99 (s, 3H), 1.79-1.91 (m, 1H), 1.41 (s, 3H).

AcOH (6 g, 100 mmol) was added to a solution of Compound 4 (17 g, 50.4 mmol) in 150 mL DCM at 10-15° C. A solution of $Br_2$ (8.7 g, 0.11 mol) in 20 mL DCM was then added over 45 min, and the reaction mixture was stirred at RT for 24 h. The reaction mixture was then cooled to 0° C. and neutralized with $NH_4OH$ to pH~9. The organic layer was cut away and concentrated under reduced pressure. The residue was treated acetone (50 mL) and stirred at RT for 16 h. The resulting solids were collected via vacuum filtration under nitrogen back flow, and washed with $Et_2O$ to give Compound 5 as white solid (11 g, yield 52%): $^1$H NMR (METHANOL-d) δ: 7.48-7.72 (m, 5H), 7.13-7.37 (m, 1H), 6.85-7.06 (m, 2H), 4.91-5.03 (m, 1H), 4.72-4.87 (m, 1H), 4.31-4.67 (m, 1H), 4.08-4.29 (m, 1H), 3.84 (d, J=3.7 Hz, 3H), 3.45-3.77 (m, 3H), 2.95-3.25 (m, 3H), 2.37-2.91 (m, 1H), 2.04-2.26 (m, 1H), 1.54-1.77 (m, 3H).

To a suspension of Compound 5 (44 g, 131 mmol) in 200 mL AcOH was added Pd/C (wet, 10% on carbon, 8 g). The mixture was shaken at 30 psi under an atmosphere of hydrogen for 5 h using a Parr hydrogenator. The reaction was then quenched with water, filtered through a bed of Celite, and concentrated under reduced pressure. The residue was dissolved in 200 mL of EtOAc, cooled in an ice-water bath, and neutralized with $NH_4OH$ to pH~9. The organic layer was evaporated in vacuo. The residue was purified by flash chromatography (SiO2, 5% MeOH/DCM) to give Compound 6 as white solid (22 g, yield 69%): $^1$H NMR (CHLOROFORM-d) δ: 7.06 (d, J=8.3 Hz, 1H), 6.67-6.84 (m, 2H), 3.80 (s, 3H), 3.50 (d, J=17.8 Hz, 1H), 3.36 (d, J=6.1 Hz, 1H), 3.09 (dd, J=17.9, 6.2 Hz, 1H), 2.74 (td, J=12.7, 3.2 Hz, 1H), 2.48-2.58 (m, 1H), 2.46 (s, 3H), 2.21 (td, J=12.8, 4.8 Hz, 1H), 1.68-1.76 (m, 1H), 1.47 (s, 3H).

Example 2

Resolution of Racemic Intermediates by Chiral Column Chromatography

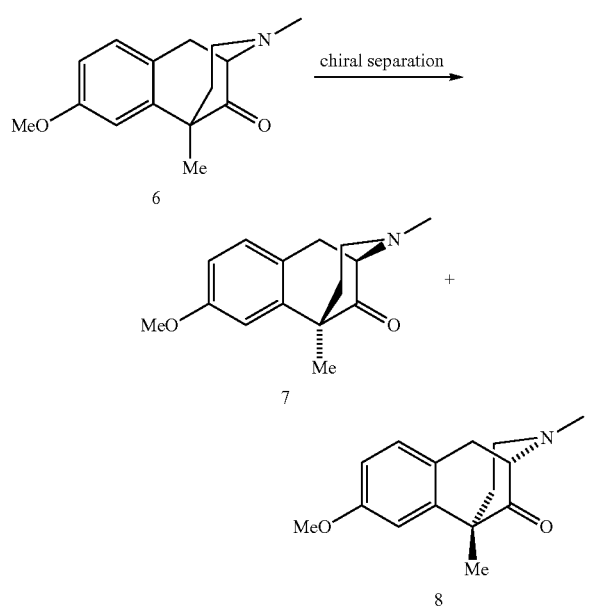

Chiral chromatography was performed on racemic Compound 6 using a RegisPack 5 column (250 mm×50 mm×5 m) eluting with 20:80 EtOH/$CO_2$ to afford optically pure Compound 7 and Compound 8.

Example 3

Synthesis of (2R,6S,11R)-3,6-dimethyl-11-((4-(methylsulfonyl)phenethyl)amino)-1,2,3,4,5,6-hexahydro-2,6-methanobenzo[d]azocin-8-ol (Compound 10) and (2R,6S,11S)-3,6-dimethyl-11-((4-(methylsulfonyl)phenethyl)amino)-1,2,3,4,5,6-hexahydro-2,6-methanobenzo[d]azocin-8-ol (Compound 11)

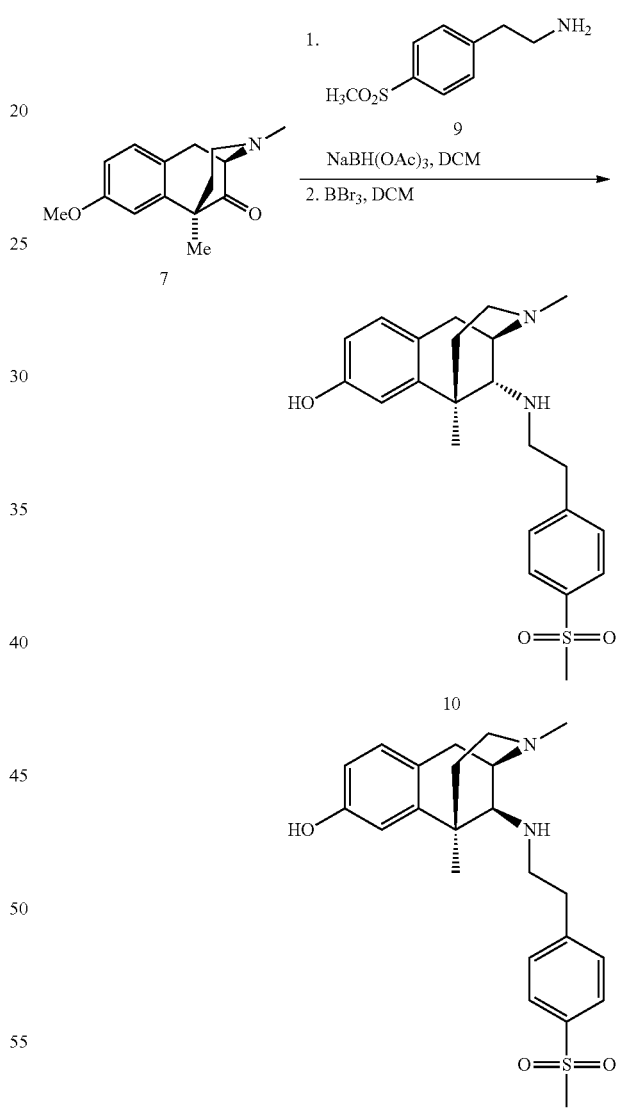

A mixture of Compound 7 (0.50 g, 1.65 mmol), 2-(4-(methylsulfonyl)phenyl)ethan-1-amine (Compound 9, 0.492 g, 2.47 mmol) (Aldrich) and pTSA (0.03 g) in toluene (40 mL) was heated to reflux for 4 h and concentrated to give a brown oil. To this oil was added ACN (20 mL) followed by NaBH(OAc)$_3$ (1.05 g, 4.94 mmol). The reaction mixture was stirred at RT for 24 h, MeOH (1 mL) was added and the mixture concentrated. Water (10 mL) and EtOAc (100 mL) were added and the pH adjusted to ~9 with conc. NH₄OH. The layers were separated and the organic layer was concentrated and purified by flash chromatography (SiO2, DCM/MeOH/NH₄OH 10/1/0.05) to give the product as a mixture of isomers.

This material was dissolved in DCM (4 mL), cooled to −78° C. and 1 M BBr₃ in DCM (2.0 mL, 2.0 mmol) was added. The mixture was stirred at −78° C. for 1 h allowed to warm to 0° C. and stirred an additional 30 min. The reaction was quenched by the addition of water (2 mL) and the pH adjusted to ~8 with conc. NH₄OH. The organic layer was cut away, dried over Na₂SO₄, and evaporated in vacuo. The residue was purified by flash chromatography (SiO2, DCM/MeOH/NH₄OH 10/1/0.05) to give Compound 10 as a white solid (0.020 g, 3%) and Compound 11 as a white solid (0.050 g, 7%).

(2R,6S,11R)-3,6-dimethyl-11-((4-(methylsulfonyl)phenethyl)amino)-1,2,3,4,5,6-hexahydro-2,6-methanobenzo[d]azocin-8-ol (Compound 10): $^1$H NMR (400 MHz, METHANOL-d4) δ: 7.84 (d, J=8.3 Hz, 2H), 7.47 (d, J=8.3 Hz, 2H), 6.88 (d, J=8.3 Hz, 1H), 6.67 (d, J=2.5 Hz, 1H), 6.57 (dd, J=8.3, 2.5 Hz, 1H), 3.21 (dd, J=5.4, 3.7 Hz, 1H), 3.10 (s, 3H), 2.97-3.06 (m, 1H), 2.81-2.96 (m, 4H), 2.75 (d, J=3.5 Hz, 1H), 2.61 (dd, J=18.3, 6.0 Hz, 1H), 2.42 (s, 3H), 2.39 (d, J=3.4 Hz, 1H), 2.10 (td, J=12.4, 3.2 Hz, 1H), 1.84 (td, J=12.9, 4.8 Hz, 1H), 1.24-1.42 (m, 4H). LC/MS, m/z=415.2, [M+H]⁺ (Calc: 414.6).

(2R,6S,11S)-3,6-dimethyl-11-((4-(methylsulfonyl)phenethyl)amino)-1,2,3,4,5,6-hexahydro-2,6-methanobenzo[d]azocin-8-ol (Compound 11): $^1$H NMR (400 MHz, METHANOL-d4) δ: 7.81 (d, J=8.3 Hz, 2H), 7.47 (d, J=8.3 Hz, 2H), 6.95 (d, J=8.4 Hz, 1H), 6.74 (d, J=2.4 Hz, 1H), 6.60 (dd, J=8.3, 2.5 Hz, 1H), 3.71 (d, J=4.5 Hz, 1H), 3.22-3.29 (m, 2H), 3.04-3.18 (m, 2H), 3.00 (s, 3H), 2.85-3.00 (m, 5H), 2.72 (s, 3H), 2.54 (td, J=12.9, 3.7 Hz, 1H), 2.14 (td, J=13.8, 4.9 Hz, 1H), 1.34 (s, 3H), 1.31 (d, J=15.2 Hz, 1H). LC/MS, m/z=415.2, [M+H]⁺ (Calc: 414.6).

In a similar manner, the following compounds were prepared from chiral amine Compound 7:

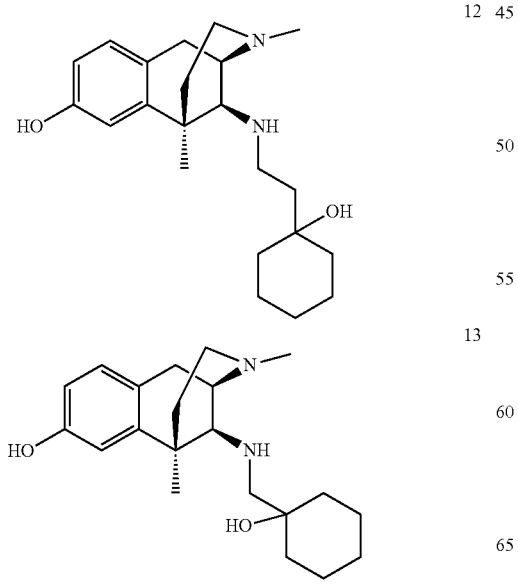

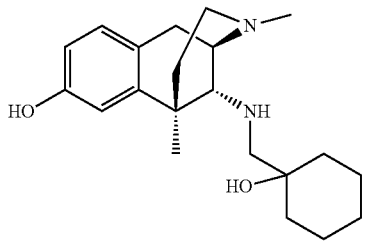

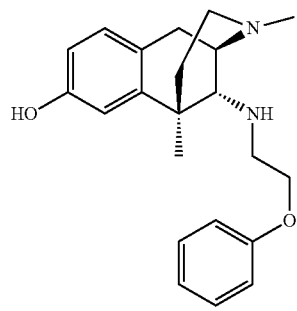

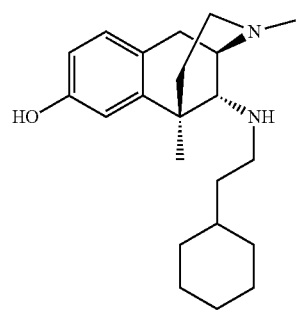

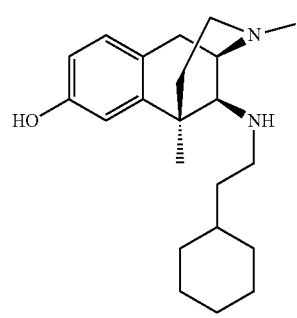

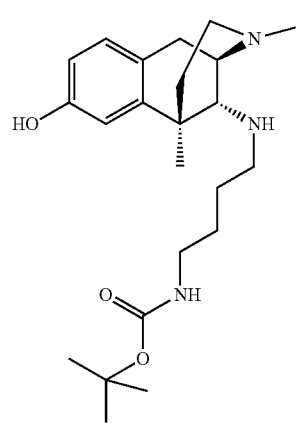

-continued

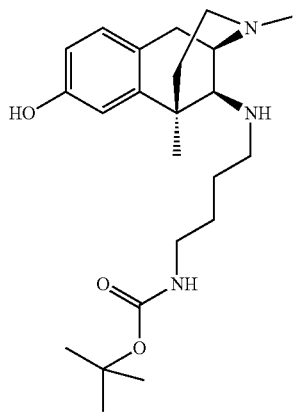

(2R,6S,11S)-11-((2-(1-hydroxycyclohexyl)ethyl)amino)-3,6-dimethyl-1,2,3,4,5,6-hexahydro-2,6-methano-benzo[d]azocin-8-ol (Compound 12)

$^1$H NMR (400 MHz, METHANOL-d4) δ: 6.95 (d, J=8.4 Hz, 1H), 6.74 (d, J=2.4 Hz, 1H), 6.61 (dd, J=8.4, 2.4 Hz, 1H), 3.75 (br. s., 1H), 3.45 (br. s., 1H), 3.24-3.39 (m, 2H), 3.08-3.19 (m, 1H), 3.03 (dd, J=18.7, 5.9 Hz, 1H), 2.78 (d, J=9.9 Hz, 1H), 2.62 (s, 3H), 2.39 (td, J=12.6, 3.0 Hz, 1H), 2.03 (td, J=13.6, 4.6 Hz, 1H), 1.76-1.89 (m, 2H), 1.46-1.63 (m, 6H), 1.30-1.46 (m, 8H). LC/MS, m/z=359.2, [M+H]$^+$ (Calc: 358.5).

(2R,6S,11S)-11-(((1-hydroxycyclohexyl)methyl)amino)-3,6-dimethyl-1,2,3,4,5,6-hexahydro-2,6-methano-benzo[d]azocin-8-ol (Compound 13)

$^1$H NMR (400 MHz, METHANOL-d4) δ: 6.95 (d, J=8.4 Hz, 1H), 6.75 (d, J=2.4 Hz, 1H), 6.60 (dd, J=8.4, 2.4 Hz, 1H), 3.72 (d, J=4.6 Hz, 1H), 3.27 (s, 1H), 3.06-3.18 (m, 1H), 2.99 (dd, J=12.7, 4.5 Hz, 1H), 2.88 (d, J=1.5 Hz, 1H), 2.76 (s, 3H), 2.71 (d, J=12.5 Hz, 1H), 2.47-2.64 (m, 2H), 2.22 (td, J=13.8, 5.0 Hz, 1H), 1.25-1.65 (m, 14H). LC/MS, m/z=359.2, [M+H]$^+$ (Calc: 358.5).

(2R,6S,11R)-11-(((1-hydroxycyclohexyl)methyl)amino)-3,6-dimethyl-1,2,3,4,5,6-hexahydro-2,6-methanobenzo[d]azocin-8-ol (Compound 14)

$^1$H NMR (400 MHz, METHANOL-d4) δ: 7.12 (d, J=8.4 Hz, 1H), 6.84 (d, J=2.4 Hz, 1H), 6.78 (dd, J=8.4, 2.4 Hz, 1H), 4.27 (d, J=2.9 Hz, 1H), 3.72 (br. s., 1H), 3.34-3.47 (m, 2H), 3.23 (dd, J=13.0, 2.9 Hz, 1H), 2.99-3.15 (m, 5H), 2.80 (t, J=12.0 Hz, 1H), 2.08-2.26 (m, 1H), 1.71-1.79 (m, 1H), 1.70 (s, 3H), 1.56-1.67 (m, 4H), 1.50 (br. s., 5H), 1.29-1.40 (m, 1H). LC/MS, m/z=359.2, [M+H]$^+$ (Calc: 358.5).

(2R,6S,11R)-3,6-dimethyl-11-((2-phenoxyethyl)amino)-1,2,3,4,5,6-hexahydro-2,6-methanobenzo[d]azocin-8-ol (Compound 15)

$^1$H NMR (400 MHz, METHANOL-d4) δ: 7.25 (dd, J=8.6, 7.5 Hz, 2H), 6.81-6.99 (m, 4H), 6.72 (d, J=2.4 Hz, 1H), 6.60 (dd, J=8.3, 2.5 Hz, 1H), 3.96-4.15 (m, 2H), 3.27 (dd, J=5.3, 3.7 Hz, 1H), 3.06-3.16 (m, 1H), 2.93-3.03 (m, 2H), 2.73-2.88 (m, 2H), 2.43 (s, 3H), 2.40 (d, J=3.3 Hz, 1H), 2.13 (td, J=12.4, 3.3 Hz, 1H), 1.87 (td, J=12.9, 4.8 Hz, 1H), 1.47 (s, 3H), 1.32-1.40 (m, 1H). LC/MS, m/z=353.0, [M+H]$^+$ (Calc: 352.3).

(2R,6S,11R)-11-((2-cyclohexylethyl)amino)-3,6-dimethyl-1,2,3,4,5,6-hexahydro-2,6-methanobenzo[d]azocin-8-ol (Compound 16)

$^1$H NMR (400 MHz, METHANOL-d4) δ: 7.16 (d, J=8.4 Hz, 1H), 6.76-6.94 (m, 2H), 4.30 (dd, J=6.0, 3.1 Hz, 1H), 3.86 (d, J=2.8 Hz, 1H), 3.38-3.53 (m, 1H), 3.12-3.31 (m, 4H), 3.06 (s, 3H), 2.78 (t, J=11.9 Hz, 1H), 2.22 (td, J=14.1, 4.5 Hz, 1H), 1.64-1.88 (m, 10H), 1.48-1.64 (m, 1H), 1.12-1.44 (m, 4H), 0.93-1.11 (m, 2H). LC/MS, m/z=343.2 [M+H]$^+$ (Calc: 342.5).

(2R,6S,11 S)-11-((2-cyclohexylethyl)amino)-3,6-dimethyl-1,2,3,4,5,6-hexahydro-2,6-methanobenzo[d]azocin-8-ol (Compound 17)

$^1$H NMR (400 MHz, METHANOL-d4) δ: 6.96 (d, J=8.3 Hz, 1H), 6.74 (d, J=2.4 Hz, 1H), 6.61 (dd, J=8.3, 2.4 Hz, 1H), 3.84 (br. s., 1H), 3.43 (br. s., 1H), 3.24-3.35 (m, 1H), 3.03-3.18 (m, 2H), 2.81-2.99 (m, 2H), 2.69 (s, 3H), 2.46 (td, J=12.7, 3.3 Hz, 1H), 2.14 (td, J=13.8, 4.7 Hz, 1H), 1.49-1.75 (m, 7H), 1.45 (s, 3H), 1.41 (d, J=14.6 Hz, 1H), 1.04-1.34 (m, 4H), 0.82-1.01 (m, 2H). LC/MS, m/z=343.2 [M+H]$^+$ (Calc: 342.5).

Tert-butyl (4-(((2R,6S,11R)-8-hydroxy-3,6-dimethyl-1,2,3,4,5,6-hexahydro-2,6-methanobenzo[d]azocin-11-yl)amino)butyl)carbamate (Compound 18)

$^1$H NMR (400 MHz, METHANOL-d4) δ: 6.83 (d, J=8.3 Hz, 1H), 6.60 (d, J=2.5 Hz, 1H), 6.48 (dd, J=8.3, 2.5 Hz, 1H), 3.09-3.17 (m, 1H), 2.81-2.99 (m, 3H), 2.57-2.76 (m, 3H), 2.45-2.56 (m, 1H), 2.32 (s, 3H), 2.29 (d, J=3.4 Hz, 1H), 2.01 (td, J=12.4, 3.2 Hz, 1H), 1.75 (td, J=13.0, 4.8 Hz, 1H), 1.30-1.43 (m, 16H), 1.25 (d, J=12.2 Hz, 1H). LC/MS, m/z=404.2 [M+H]$^+$ (Calc: 403.6).

Tert-butyl (4-(((2R,6S,11S)-8-hydroxy-3,6-dimethyl-1,2,3,4,5,6-hexahydro-2,6-methanobenzo[d]azocin-11-yl)amino)butyl)carbamate (Compound 19)

$^1$H NMR (400 MHz, METHANOL-d4) δ: 6.81 (d, J=8.3 Hz, 1H), 6.65 (d, J=2.5 Hz, 1H), 6.46 (dd, J=8.2, 2.5 Hz, 1H), 3.12 (d, J=17.6 Hz, 2H), 2.87-3.01 (m, 2H), 2.66-2.77 (m, 1H), 2.60 (dd, J=18.0, 5.7 Hz, 1H), 2.37-2.53 (m, 2H), 2.21-2.35 (m, 4H), 1.92-2.04 (m, 1H), 1.85 (td, J=12.8, 4.7 Hz, 1H), 1.44 (d, J=2.8 Hz, 4H), 1.24-1.36 (m, 12H), 1.00 (d, J=12.8 Hz, 1H). LC/MS, m/z=404.2 [M+H]$^+$ (Calc: 403.6).

Example 4

Synthesis of (2R,6S,11R)-8-methoxy-N,3,6-trimethyl-1,2,3,4,5,6-hexahydro-2,6-methanobenzo[d]azocin-11-amine (Compound 21) and (2R,6S,11S)-8-methoxy-N,3,6-trimethyl-1,2,3,4,5,6-hexahydro-2,6-methanobenzo[d]azocin-11-amine (Compound 22)

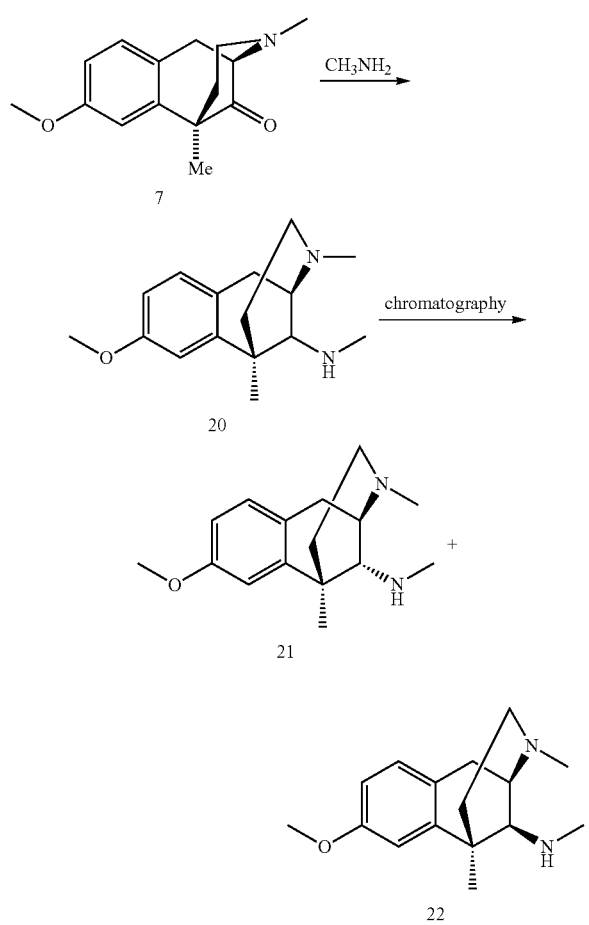

A mixture of methylamine (33% in EtOH, 10 mL), Compound 7 (1.0 g, 4 mmol), AcOH (0.25 g, 4 mmol) and 4A molecular sieves (1 g) was shaken at RT for 24 h. The reaction mixture was concentrated under reduced pressure, and both NaBH(OAc)$_3$ (1.5 g) and DCM (5 mL) were added. The mixture was shaken at RT for 5 h. The reaction was quenched with water (4 mL) and NaOH (2N, 4 mL), and extracted with EtOAc (4×30 mL). The layers were separated and the organic layer was concentrated to give crude Compound 21, which was purified by flash chromatography (DCM/MeOH/NH$_4$OH 10/0.4/0.04) to give Compound 21 (0.6 g) and Compound 22 (0.15 g) as colorless oils.

Compound 21: LC/MS, m/z=261.4 [M+H]$^+$ (Calc: 260.4); retention time (0.294 min).

Compound 22: LC/MS, m/z=261.2 [M+H]$^+$ (Calc: 260.4); retention time (0.598 min).

Example 5

Synthesis of (2R,6S,11S)-8-methoxy-3,6-dimethyl-1,2,3,4,5,6-hexahydro-2,6-methanobenzo[d]azocin-11-amine (Compound 23) and (2R,6S,11S)-8-methoxy-3,6-dimethyl-1,2,3,4,5,6-hexahydro-2,6-methanobenzo[d]azocin-11-amine (Compound 24)

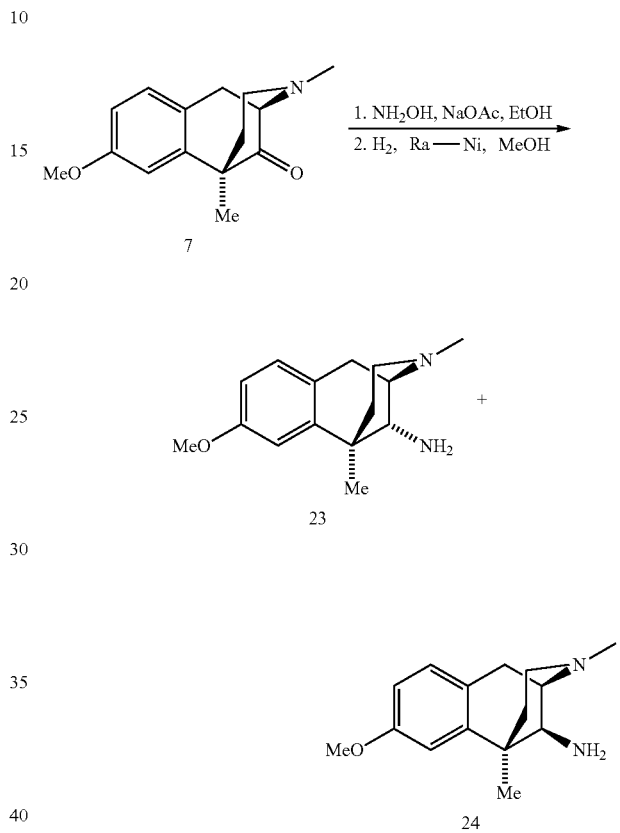

A mixture of Compound 7 (5 g, 20 mmol), hydroxylamine hydrochloride (30 mmol) and NaOAc (50 mmol) in 100 mL of EtOH was stirred at 60° C. for 24 h. The solvent was removed under reduced pressure followed by the addition of NaOH (3N, 20 mL) and EtOAc (20 mL). The reaction mixture was filtered to give a white solid, which was dissolved in MeOH (400 mL) and AcOH (1.5 mL). The resulting solution was subjected to hydrogenation using an H-cube-Midi (Raney Nickel; 60 psi; 40° C.; rate=7 mL/min). The mixture was concentrated under reduced pressure, the residue dissolved in 100 mL CHCl$_3$, and the resulting solution neutralized with 3 N NaOH to pH~10. The layers were separated and the organic layer was concentrated and purified by flash chromatography (SiO2, 10% (10% NH4OH in MeOH) in DCM) to give Compound 23 (3.0 g) and Compound 24 (0.5 g) as colorless oils.

Compound 23: LC/MS, m/z=247.2, [M+H]+(Calc: 246.3), retention time (0.298 min).

Compound 24: LC/MS, m/z=247.4, [M+H]+(Calc: 246.3), retention time (0.539 min).

Example 6

Synthesis of N-(1H-benzo[d]imidazol-2-yl)-1H-imidazole-1-carboxamide (Compound A-4) and N-(1-ethyl-1H-benzo[d]imidazol-2-yl)-1H-imidazole-1-carboxamide (Compound A-5)

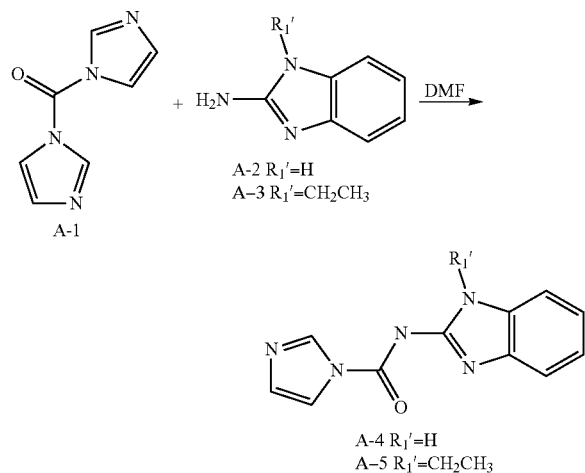

CDI (Compound A-1, 1.34 g, 8.2 mmol) was added to a solution of Compound A-2 (1.0 g, 7.5 mmol) in 6 mL DMF (and 4 mL CHCl$_3$) at 0° C. The reaction mixture was warmed to rt for 72 h. The solid was collected, and dried to give Compound A-4 as white solid (1.2 g, 70%): $^1$H NMR (DMSO-d$_6$) δ: 12.57 (br. s., 2H), 8.27 (s, 1H), 7.64 (t, J=1.3 Hz, 1H), 7.42 (dd, J=5.9, 3.2 Hz, 2H), 7.23 (dd, J=5.9, 3.2 Hz, 2H), 7.00 (t, J=1.1 Hz, 1H).

In a similar manner, Compound A-5 was prepared (white solid, 1 g, 65%): $^1$H NMR (DMSO-d$_6$) δ: 12.61 (br. s., 1H), 8.39 (s, 1H), 7.71 (t, J=1.3 Hz, 1H), 7.50-7.60 (m, 2H), 7.28 (td, J=7.4, 1.5 Hz, 2H), 6.94-7.05 (m, 1H), 4.30 (q, J=7.1 Hz, 2H), 1.33 (t, J=7.2 Hz, 3H).

Example 7

Synthesis of N$^1$-(2,4-difluorophenyl)-N$^3$—((2R,6S,11R)-8-hydroxy-3,6-dimethyl-1,2,3,4,5,6-hexahydro-2,6-methanobenzo[d]azocin-11-yl)-N$^3$-methylmalonamide (Compound 26)

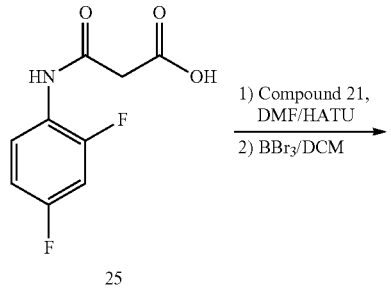

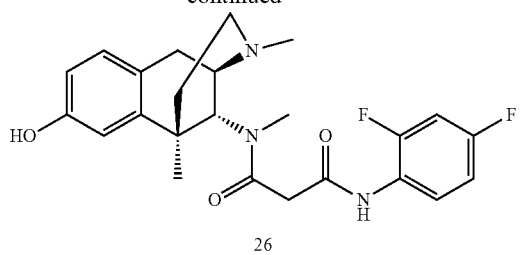

Carboxylic acid Compound 25 was prepared according to literature procedure as described in WO2008124118 A1. To a mixture of Compound 21 (0.10 g, 0.35 mmol), Compound 25 (0.054 g, 0.42 mmol) and DIPEA (0.045 g, 0.35 mmol) in DMF (1 mL) was added HATU (0.16 g, 0.42 mmol) at RT. The reaction mixture was stirred at RT for 16 h, quenched by the addition of water and the mixture extracted with EtOAc. The organic layer was concentrated and purified by flash chromatography (SiO2, 10% (10% NH4OH in MeOH) in DCM) to give the desired product. This material was dissolved in DCM (8 mL), cooled to −78° C. and 1 M BBr3 in DCM (2.0 mL, 2.0 mmol) was added. The mixture was stirred at −78° C. for 2 h allowed to warm to 0° C. and stirred an additional 30 min. The reaction was quenched by the addition of water (2 mL) and the pH adjusted to ~8 with NH$_4$OH. The organic layer was cut away and evaporated in vacuo.

The residue was purified by reverse-phase prep HPLC (C18, 0-100% 0.1% TFA in water/0.1% TFA in ACN) to give Compound 26 as a white solid: $^1$H NMR (400 MHz, METHANOL-d4) δ: 7.81 (td, J=8.9, 6.1 Hz, 1H), 6.90-7.06 (m, 2H), 6.81-6.89 (m, 1H), 6.74 (d, J=2.4 Hz, 1H), 6.64 (dd, J=8.4, 2.4 Hz, 1H), 4.68 (br. s., 1H), 3.69 (br. s., 1H), 3.50-3.65 (m, 2H), 3.2-3.3 (m, 1H), 2.92-3.14 (m, 2H), 2.85 (s, 3H), 2.51-2.74 (m, 4H), 1.99 (td, J=13.8, 4.5 Hz, 1H), 1.62 (d, J=12.3 Hz, 1H), 1.38-1.48 (m, 3H). LC/MS, m/z=444.0, [M+H]$^+$ (Calc: 443.5).

In a similar manner, the following compounds were prepared from the appropriate carboxylic acid and chiral amine Compound 20, Compound 21, Compound 23, or Compound 24:

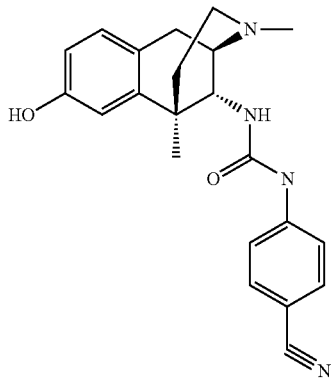

28
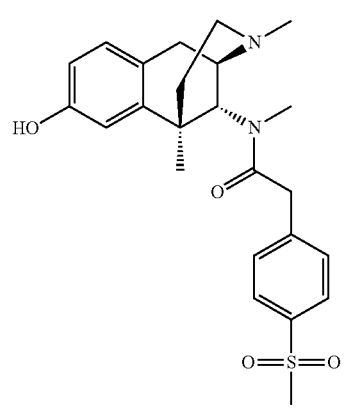
29
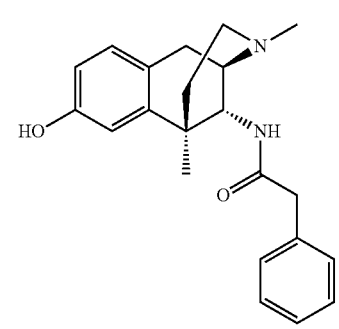
30
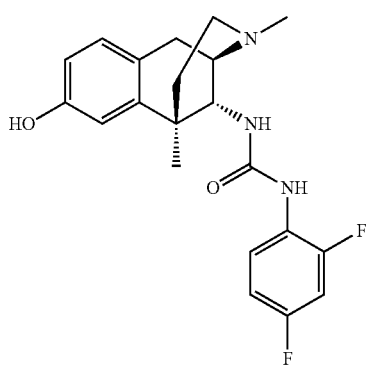
31
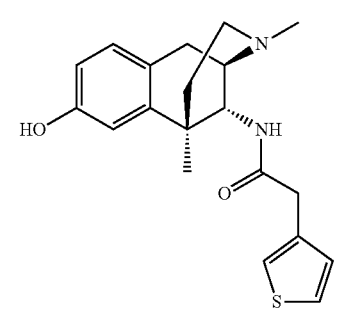
32
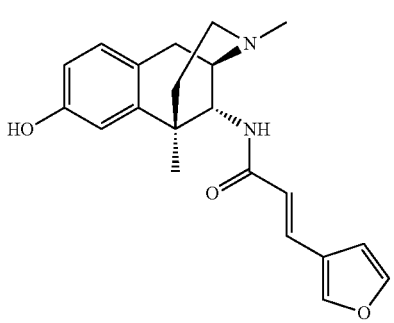
33
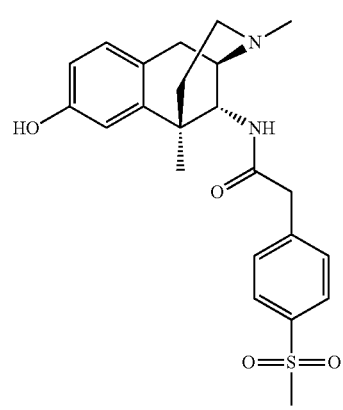
34
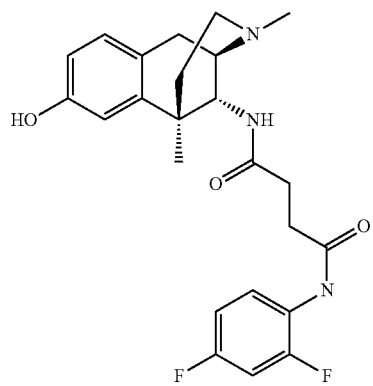
35
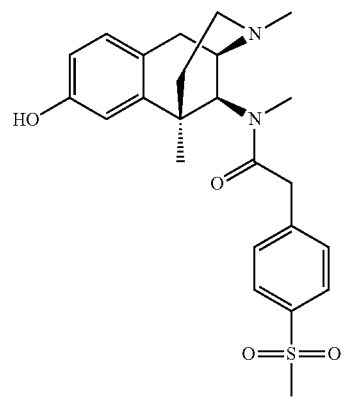
1-(4-Cyanophenyl)-3-((2R,6S,11R)-8-hydroxy-3,6-dimethyl-1,2,3,4,5,6-hexahydro-2,6-methanobenzo[d]azocin-11-yl)urea (Compound 27): 1H NMR (400 MHz, METHANOL-d4) δ: 7.54-7.62 (m, 2H), 7.46-7.53 (m, 2H), 7.03 (d, J=8.4 Hz, 1H), 6.78 (d, J=2.5 Hz, 1H), 6.67 (dd, J=8.3, 2.5 Hz, 1H), 4.06 (d, J=3.6 Hz, 1H), 3.21-3.29 (m, 1H), 3.09 (d, J=18.6 Hz, 1H), 2.80 (dd, J=18.6, 6.1 Hz, 1H), 2.36-2.50 (m, 4H), 2.16 (td, J=12.4, 3.1 Hz, 1H), 1.96 (td, J=12.9, 4.7 Hz, 1H), 1.40-1.56 (m, 4H). LC/MS, m/z=377.0, [M+H]+(Calc: 376.4).

N-((2R,6S,11R)-8-hydroxy-3,6-dimethyl-1,2,3,4,5,6-hexahydro-2,6-methanobenzo[d]azocin-11-yl)-N-methyl-2-(4-(methylsulfonyl)phenyl)acetamide (Compound 28): $^1$H NMR (400 MHz, METHANOL-d4) δ: 7.82 (d, J=8.4 Hz, 2H), 7.41 (d, J=8.3 Hz, 2H), 6.97 (d, J=8.3 Hz, 1H), 6.71 (d, J=2.5 Hz, 1H), 6.62 (dd, J=8.3, 2.5 Hz, 1H), 4.71 (br. s., 1H), 3.75-3.96 (m, 2H), 3.60 (br. s., 1H), 3.15 (s, 1H), 2.91-3.06 (m, 5H), 2.84 (s, 3H), 2.69 (s, 3H), 2.54-2.65 (m, 1H), 1.95-2.13 (m, 1H), 1.56 (dd, J=14.2, 2.0 Hz, 1H), 1.39 (s, 3H). LC/MS, m/z=443.2, [M+H]+ (Calc: 442.6).

N-((2R,6S,11R)-8-hydroxy-3,6-dimethyl-1,2,3,4,5,6-hexahydro-2,6-methanobenzo[d]azocin-11-yl)-2-phenylacetamide (Compound 29): $^1$H NMR (400 MHz, METHANOL-d4) δ: 7.11-7.18 (m, 2H), 7.04-7.11 (m, 3H), 6.84 (d, J=8.3 Hz, 1H), 6.59 (d, J=2.5 Hz, 1H), 6.52 (dd, J=8.3, 2.5 Hz, 1H), 4.01 (d, J=3.6 Hz, 1H), 3.38 (s, 2H), 2.99-3.08 (m, 1H), 2.88 (d, J=18.5 Hz, 1H), 2.52 (dd, J=18.5, 6.0 Hz, 1H), 2.30 (d, J=3.1 Hz, 1H), 2.27 (s, 3H), 1.90-2.06 (m, 1H), 1.69-1.84 (m, 1H), 1.26-1.32 (m, 1H), 1.23 (s, 3H). LC/MS, m/z=351.0, [M+H]+(Calc: 350.4).

$N^1$-(2,4-difluorophenyl)-$N^3$—((2R,6S,11R)-8-hydroxy-3,6-dimethyl-1,2,3,4,5,6-hexahydro-2,6-methanobenzo[d]azocin-11-yl)malonamide (Compound 30)

$^1$H NMR (DMSO-d6) δ: 9.87 (s, 1H), 8.97 (s, 1H), 7.77 (td, J=9.0, 6.2 Hz, 1H), 7.49 (d, J=8.5 Hz, 1H), 7.25 (ddd, J=11.3, 8.9, 2.9 Hz, 1H), 6.93-7.04 (m, 1H), 6.85 (d, J=8.3 Hz, 1H), 6.57 (d, J=2.4 Hz, 1H), 6.49 (dd, J=8.2, 2.5 Hz, 1H), 3.85 (dd, J=8.5, 3.5 Hz, 1H), 3.28 (s, 2H), 2.88 (t, J=4.3 Hz, 1H), 2.79 (d, J=18.0 Hz, 1H), 2.51-2.61 (m, 1H), 2.12-2.30 (m, 4H), 1.83 (td, J=12.0, 2.6 Hz, 1H), 1.68 (td, J=12.4, 4.6 Hz, 1H), 1.11-1.31 (m, 4H). LC/MS, m/z=430.0, [M+H]+(Calc: 429.5).

N-((2R,6S,11R)-8-hydroxy-3,6-dimethyl-1,2,3,4,5,6-hexahydro-2,6-methanobenzo[d]azocin-11-yl)-2-(thiophen-3-yl)acetamide (Compound 31)

1H NMR (METHANOL-d4) δ: 7.20 (dd, J=5.0, 3.0 Hz, 1H), 6.97-7.01 (m, 1H), 6.85 (d, J=8.3 Hz, 1H), 6.82 (dd, J=5.0, 1.2 Hz, 1H), 6.60 (d, J=2.5 Hz, 1H), 6.53 (dd, J=8.3, 2.5 Hz, 1H), 4.01 (d, J=3.6 Hz, 1H), 3.41 (d, J=2.3 Hz, 2H), 3.01-3.08 (m, 1H), 2.89 (d, J=18.5 Hz, 1H), 2.52 (dd, J=18.5, 6.0 Hz, 1H), 2.25-2.34 (m, 4H), 1.99 (td, J=12.4, 3.1 Hz, 1H), 1.79 (td, J=12.9, 4.7 Hz, 1H), 1.26-1.34 (m, 1H), 1.24 (s, 3H). LC/MS, m/z=357.0, [M+H]+(Calc: 356.5).

(E)-3-(furan-3-yl)-N-((2R,6S,11R)-8-hydroxy-3,6-dimethyl-1,2,3,4,5,6-hexahydro-2,6-methanobenzo[d]azocin-11-yl)acrylamide (Compound 32)

1H NMR (METHANOL-d4) δ: 7.65 (s, 1H), 7.39 (s, 1H), 7.31 (d, J=15.6 Hz, 1H), 6.91 (d, J=8.3 Hz, 1H), 6.66 (d, J=2.5 Hz, 1H), 6.55 (dd, J=8.3, 2.5 Hz, 1H), 6.49 (d, J=1.8 Hz, 1H), 6.35 (d, J=15.6 Hz, 1H), 4.19 (d, J=3.6 Hz, 1H), 3.09-3.17 (m, 1H), 2.96 (d, J=18.5 Hz, 1H), 2.69 (dd, J=18.5, 5.9 Hz, 1H), 2.20-2.41 (m, 4H), 2.04 (td, J=12.4, 3.1 Hz, 1H), 1.69-1.93 (m, 1H), 1.20-1.40 (m, 4H). LC/MS, m/z=353.0, [M+H]+(Calc: 352.4).

N-((2R,6S,11R)-8-hydroxy-3,6-dimethyl-1,2,3,4,5,6-hexahydro-2,6-methanobenzo[d]azocin-11-yl)-2-(4-(methylsulfonyl)phenyl)acetamide (Compound 33)

1H NMR (METHANOL-d4) δ: 7.76 (d, J=8.4 Hz, 2H), 7.38 (d, J=8.4 Hz, 2H), 6.89 (d, J=8.3 Hz, 1H), 6.63 (d, J=2.5 Hz, 1H), 6.55 (dd, J=8.3, 2.5 Hz, 1H), 4.04 (d, J=3.5 Hz, 1H), 3.53 (s, 2H), 3.02-3.11 (m, 1H), 3.00 (s, 3H), 2.93 (d, J=18.4 Hz, 1H), 2.59 (dd, J=18.5, 5.9 Hz, 1H), 2.24-2.35 (m, 4H), 2.00 (td, J=12.4, 3.1 Hz, 1H), 1.79 (td, J=12.9, 4.7 Hz, 1H), 1.20-1.37 (m, 4H). LC/MS, m/z=429.0, [M+H]+(Calc: 428.5).

$N^1$-(2,4-difluorophenyl)-N4-((2R,6S,11R)-8-hydroxy-3,6-dimethyl-1,2,3,4,5,6-hexahydro-2,6-methanobenzo[d]azocin-11-yl)succinamide (Compound 34)

1H NMR (METHANOL-d4) δ: 7.52-7.78 (m, 1H), 6.73-6.99 (m, 3H), 6.64 (d, J=2.5 Hz, 1H), 6.53 (dd, J=8.3, 2.5 Hz, 1H), 4.07 (d, J=3.5 Hz, 1H), 3.01-3.14 (m, 1H), 2.83-2.97 (m, 1H), 2.64-2.77 (m, 1H), 2.49-2.64 (m, 2H), 2.37-2.47 (m, 2H), 2.24-2.36 (m, 4H), 2.02 (td, J=12.4, 3.1 Hz, 1H), 1.80 (td, J=12.9, 4.6 Hz, 1H), 1.22-1.39 (m, 4H). LC/MS, m/z=444.0, [M+H]+(Calc: 443.5).

N-((2R,6S,11S)-8-hydroxy-3,6-dimethyl-1,2,3,4,5,6-hexahydro-2,6-methanobenzo[d]azocin-11-yl)-N-methyl-2-(4-(methylsulfonyl)phenyl)acetamide (Compound 35): $^1$H NMR (400 MHz, METHANOL-d4) δ: 7.85 (d, J=8.4 Hz, 2H), 7.50 (d, J=8.4 Hz, 2H), 6.97 (d, J=8.4 Hz, 1H), 6.69 (d, J=2.4 Hz, 1H), 6.61 (dd, J=8.3, 2.4 Hz, 1H), 4.01-4.15 (m, 1H), 3.91-3.99 (m, 2H), 3.85 (s, 1H), 3.32 (d, J=3.5 Hz, 2H), 3.22 (br. s., 2H), 3.10 (dd, J=12.7, 3.9 Hz, 1H), 3.03 (s, 3H), 2.79 (s, 3H), 2.65 (td, J=13.0, 3.5 Hz, 1H), 2.21 (td, J=13.9, 4.6 Hz, 1H), 1.41-1.45 (m, 4H). LC/MS, m/z=443.0, [M+H]+(Calc: 442.6).

Further, by using a starting material with —CONH$_2$ as the R$^4$ group (which can be prepared in accordance with Scheme G provided above), the following compounds was prepared in a similar manner:

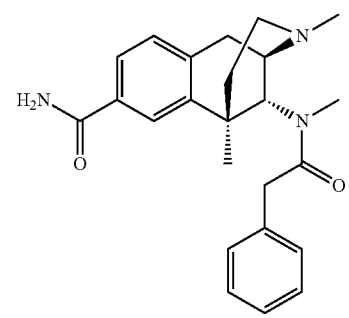

(2R,6S,11R)-3,6-dimethyl-11-(N-methyl-2-phenylacetamido)-1,2,3,4,5,6-hexahydro-2,6-methanobenzo[d]azocine-8-carboxamide (Compound 124): LC/MS, m/z=392.1, [M+H]+ (Calc: 391.2).

Example 8

Synthesis of N-(6-fluorobenzo[d]thiazol-2-yl)-2-(((2R,6S,11R)-8-hydroxy-3,6-dimethyl-1,2,3,4,5,6-hexahydro-2,6-methanobenzo[d]azocin-11-yl)(methyl)amino)acetamide (Compound 40)

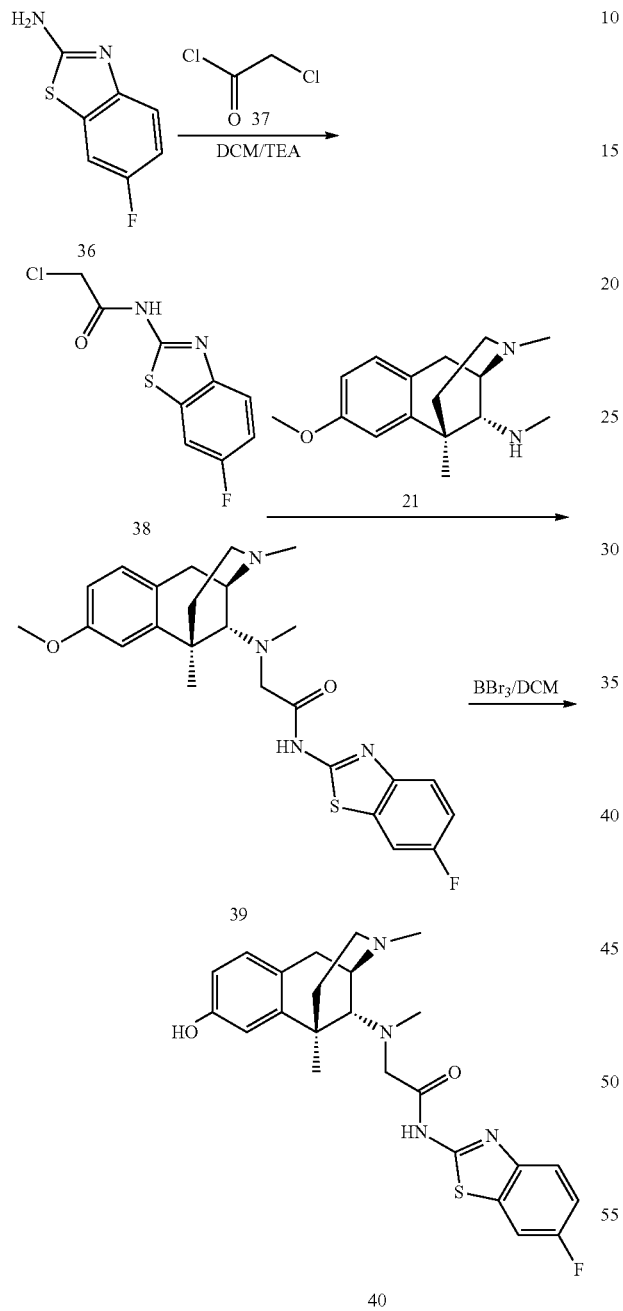

Compound 38 was prepared from Compound 36 and Compound 37 as described in PCT Publication No. WO2007118853. A mixture of Compound 38 (113 mg, 0.46 mmol), Compound 21 (100 mg, 0.38 mmol), KI (50 mg) and $K_2CO_3$ (0.1 g, 0.76 mmol) in 4 mL $CH_3CN$/0.1 mL water was stirred at 40° C. for 24 h. After cooling to RT, the reaction was quenched with water (6 mL), extracted with EtOAc (2×15 mL), and evaporated in vacuo. The residue was purified by flash chromatography (SiO2, 10/1/0.1 DCM/MeOH/NH4OH) to give Compound 39 as white solid: LC/MS, m/z=469.0, [M+H]+ (Calc: 468.6).

Compound 39 was dissolved in DCM (6 mL), and cooled to –78° C. A solution of $BBr_3$ (1N in DCM, 2 mL) was added. After stirring for 2 h at –78° C., the reaction mixture was warmed to 0° C. and allowed to stir at that temperature for 1 h. The reaction was quenched with water (2 mL) and neutralized with NH4OH. The organic layer was separated and concentrated to dryness. The residue was purified by reverse-phase prep HPLC (C18, 0-100% 0.1% TFA in water/0.1% TFA in ACN) to give Compound 40 as a white solid (TFA-salt, 55 mg): $^1$H NMR (400 MHz, METHANOL-d4) δ: 7.66 (dd, J=8.9, 4.5 Hz, 1H), 7.59 (dd, J=8.3, 2.5 Hz, 1H), 7.13-7.25 (m, 1H), 7.07 (d, J=8.4 Hz, 1H), 6.67-6.83 (m, 2H), 5.10 (br. s., 1H), 5.04 (d, J=15.6 Hz, 1H), 4.33 (d, J=15.6 Hz, 1H), 4.11 (br. s., 0.7H), 4.03 (br. s., 0.3H), 3.43-3.66 (m, 5H), 3.26 (d, J=6.4 Hz, 1H), 3.00-3.18 (m, 1H), 2.68-2.82 (m, 3H), 2.25-2.45 (m, 1H), 1.71 (d, J=15.6 Hz, 1H), 1.63 (s, 3H). LC/MS, m/z=455.2, [M+H]+ (Calc: 454.6).

In a similar manner, the following compound was prepared:

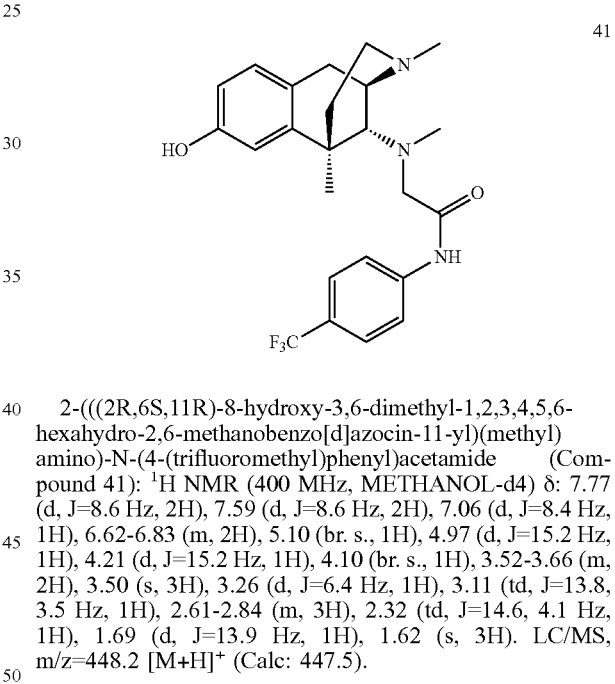

2-(((2R,6S,11R)-8-hydroxy-3,6-dimethyl-1,2,3,4,5,6-hexahydro-2,6-methanobenzo[d]azocin-11-yl)(methyl)amino)-N-(4-(trifluoromethyl)phenyl)acetamide (Compound 41): $^1$H NMR (400 MHz, METHANOL-d4) δ: 7.77 (d, J=8.6 Hz, 2H), 7.59 (d, J=8.6 Hz, 2H), 7.06 (d, J=8.4 Hz, 1H), 6.62-6.83 (m, 2H), 5.10 (br. s., 1H), 4.97 (d, J=15.2 Hz, 1H), 4.21 (d, J=15.2 Hz, 1H), 4.10 (br. s., 1H), 3.52-3.66 (m, 2H), 3.50 (s, 3H), 3.26 (d, J=6.4 Hz, 1H), 3.11 (td, J=13.8, 3.5 Hz, 1H), 2.61-2.84 (m, 3H), 2.32 (td, J=14.6, 4.1 Hz, 1H), 1.69 (d, J=13.9 Hz, 1H), 1.62 (s, 3H). LC/MS, m/z=448.2 [M+H]+ (Calc: 447.5).

Example 9

Synthesis of N-((2R,6S,11R)-8-methoxy-3,6-dimethyl-1,2,3,4,5,6-hexahydro-2,6-methanobenzo[d]azocin-11-yl)-N-methyl-2-(3-oxopiperazin-1-yl)acetamide (Compound 44)

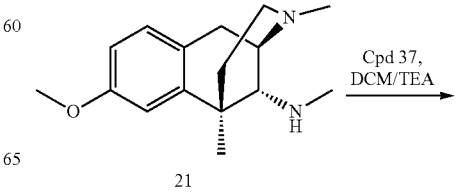

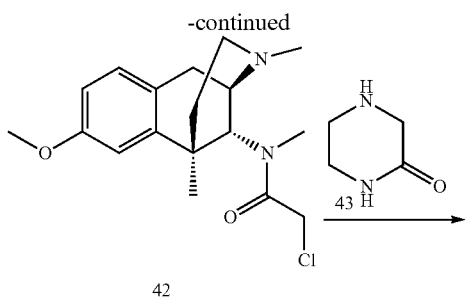

Compound 37 (45 mg, 0.38 mmol) was added to a solution of Compound 21 (0.1 g, 0.38 mmol) and TEA (80 mg) in 10 mL of DCM at −10° C. The reaction was warmed to RT, stirred for 14 h, and then quenched with water. The organic layer was cut away, and concentrated under reduced pressure to give crude Compound 42: LC/MS, m/z=337.2 [M+H]$^+$ (Calc: 336.9).

To a mixture of Compound 43 (154 mg, 1.54 mmol), $K_2CO_3$ (213 mg, 1.54 mmol) and the crude Compound 42 was added $CH_3CN$ (10 mL). The reaction mixture was concentrated under reduced pressure to about 10 mL and stirred at 65° C. for two days. After cooling to RT, the mixture was quenched with water and extracted with EtOAc (3×20 mL). The organic layer were combined and evaporated in vacuo.

The residue was purified by flash chromatography (SiO2, 10/1.5/0.1 DCM/MeOH/NH$_4$OH) to give still impure Compound 44. The compound was re-purified by reverse-phase prep HPLC (C18, 0-100% 0.1% TFA in water/0.1% TFA in ACN) to give pure Compound 44 as a white solid (TFA-salt, 50 mg): $^1$H NMR (400 MHz, METHANOL-d4) δ: 7.11 (d, J=8.4 Hz, 1H), 6.85 (d, J=2.4 Hz, 1H), 6.81 (dd, J=8.5, 2.5 Hz, 1H), 4.71 (br. s., 1H), 3.89-4.10 (m, 2H), 3.62-3.75 (m, 6H), 3.45 (t, J=5.6 Hz, 2H), 3.24-3.35 (m, 3H), 3.01-3.16 (m, 2H), 2.87 (s, 3H), 2.50-2.67 (m, 4H), 1.95-2.07 (m, 1H), 1.66 (d, J=13.4 Hz, 1H), 1.39-1.50 (m, 3H). LC/MS, m/z=401.2 [M+H]$^+$ (Calc: 400.5).

Example 10

Synthesis of (2R,6S,11R)-8-methoxy-N,3,6-trimethyl-N-(piperidin-4-ylmethyl)-1,2,3,4,5,6-hexahydro-2,6-methanobenzo[d]azocin-11-amine (Compound 48)

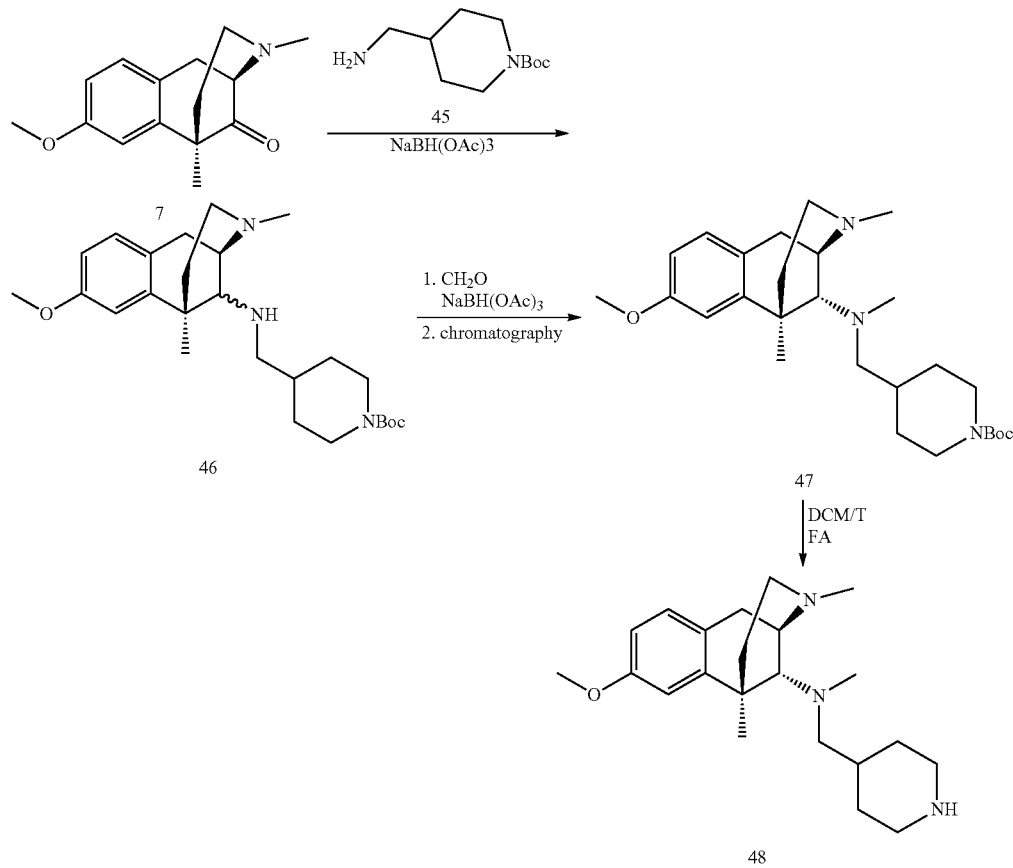

A mixture of Compound 7 (1.0 g, 4 mmol), tert-butyl 4-(aminomethyl)piperidine-1-carboxylate (Compound 45) (1 g, 4.8 mmol) (Aldrich) and 4A molecular sieves (2 g) in 20 mL CHCl$_3$ was shaken at 60° C. for 14 h. The reaction mixture was cooled to RT and NaBH(OAc)$_3$ (1.8 g, 8.2 mmol) was added. The reaction mixture was shaken at RT for 24 h, and quenched with NaOH (1 N, 10 mL). An additional amount of CHCl$_3$ (20 mL) was added. The organic layer was cut away, dried over Na$_2$SO$_4$ and evaporated in vacuo to give crude Compound 46.

To crude Compound 46 was added in order 20 mL of CHCl$_3$, formaldehyde (37% aqu., 0.6 mL), 4A molecular seives and NaBH(OAc)$_3$ (1.8 g). The mixture was shaken at RT for 16 h. The reaction was then quenched with water/NH$_4$OH (10/5 mL) at RT. The mixture was allowed to stir for 30 min. The organic layer was cut away and evaporated in vacuo. The residue was purified by flash chromatography (SiO2, 10/0.2/0.02 DCM/MeOH/NH$_4$OH) to give Compound 47 as a colorless oil (0.9 g, yield 48%): $^1$H NMR (400 MHz, CHLOROFORM-d) δ: 6.89 (d, J=8.4 Hz, 1H), 6.72 (d, J=2.6 Hz, 1H), 6.59 (dd, J=8.3, 2.5 Hz, 1H), 3.72 (s, 3H), 2.95-3.12 (m, 2H), 2.72 (d, J=2.0 Hz, 1H), 2.46-2.68 (m, 4H), 2.26-2.38 (m, 7H), 2.13 (s, 3H), 2.03 (d, J=7.3 Hz, 2H), 1.79 (d, J=4.8 Hz, 1H), 1.44-1.59 (m, 2H), 1.32-1.4 (m, 18H), 1.23 (dd, J=11.0, 1.5 Hz, 1H), 0.76-1.08 (m, 3H). LC/MS, m/z=458.2, [M+H]$^+$ (Calc: 457.6).

TFA (1.5 mL, 19 mmol) was added to a solution of Compound 47 (0.8 g, 1.8 mmol) in 50 mL of DCM at 0° C. The reaction mixture was stirred at 0° C. for 4 h and then allowed to warm to RT. After stirring at RT for 16 h, the mixture was concentrated under reduced pressure and CHCl$_3$ (100 mL) was added. The mixture was cooled in an ice-water bath and neutralized to pH~9 with NH$_4$OH. The organic layer was cut away, dried over Na$_2$SO$_4$, and evaporated in vacuo to give Compound 48 as an orange oil (0.5 g): $^1$H NMR (400 MHz, METHANOL-d4) δ: 6.90 (d, J=8.4 Hz, 1H), 6.70 (d, J=2.6 Hz, 1H), 6.61 (dd, J=8.4, 2.6 Hz, 1H), 3.66 (s, 3H), 3.11 (dd, J=5.7, 2.4 Hz, 1H), 3.05 (d, J=18.7 Hz, 1H), 2.88-3.00 (m, 3H), 2.72 (d, J=1.8 Hz, 1H), 2.42-2.62 (m, 4H), 2.29-2.39 (m, 3H), 2.28 (s, 3H), 2.07 (d, J=7.0 Hz, 1H), 2.01 (s, 3H), 1.99 (d, J=3.5 Hz, 1H), 1.71-1.82 (m, 1H), 1.65-1.69 (m, 2H), 1.52-1.63 (m, 1H), 1.39 (s, 3H), 1.21 (dd, J=12.9, 1.4 Hz, 1H), 0.86-1.07 (m, 3H). LC/MS, m/z=358.2, [M+H]$^+$ (Calc: 357.5).

In a similar manner, the following compound was prepared from Compound 46:

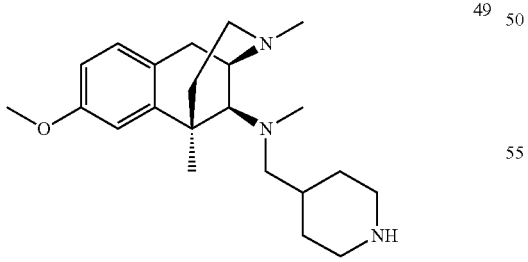

(2R,6S,11S)-8-methoxy-N,3,6-trimethyl-N-(piperidin-4-ylmethyl)-1,2,3,4,5,6-hexahydro-2,6-methanobenzo[d]azocin-11-amine (Compound 49)

$^1$H NMR (400 MHz, METHANOL-d4) δ: 6.98 (d, J=8.4 Hz, 1H), 6.81 (d, J=2.6 Hz, 1H), 6.68 (dd, J=8.4, 2.6 Hz, 1H), 3.76 (s, 3H), 3.21-3.29 (m, 2H), 3.03-3.15 (m, 3H), 2.57-2.70 (m, 3H), 2.56 (s, 3H), 2.52 (s, 1H), 2.33-2.47 (m, 3H), 2.31 (s, 3H), 2.16-2.25 (m, 1H), 2.01-2.11 (m, 1H), 1.92 (d, J=13.9 Hz, 1H), 1.81 (d, J=13.4 Hz, 1H), 1.72 (dt, J=7.2, 3.7 Hz, 1H), 1.44 (s, 3H), 1.05-1.25 (m, 3H). LC/MS, m/z=358.2, [M+H]$^+$ (Calc: 357.5).

Example 11

Synthesis of 1-(4-((((2R,6S,11R)-8-hydroxy-3,6-dimethyl-1,2,3,4,5,6-hexahydro-2,6-methanobenzo[d]azocin-11-yl)(methyl)amino)methyl)piperidin-1-yl)-2,2-dimethylpropan-1-one (Compound 52)

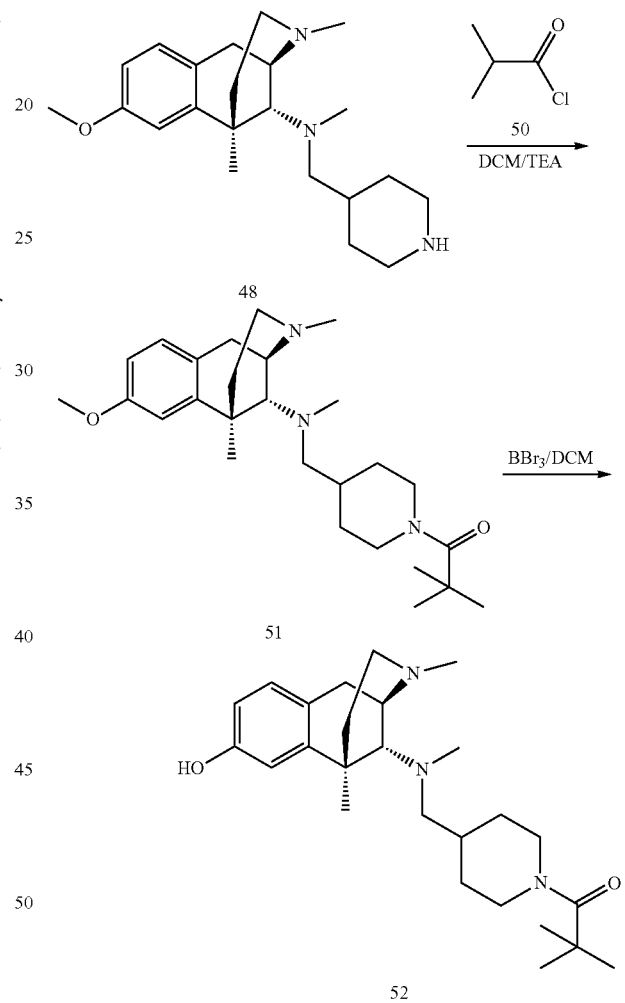

Compound 50 (80 mg, 0.67 mmol) was added to a solution of Compound 48 (0.12 g, 0.34 mmol) and TEA (0.1 g, 1.0 mmol) in 5 mL of DCM at 0° C. The mixture was warmed to RT for 16 h. After subsequent quenching with water (1 mL), the organic layer was cut away and concentrated to give crude Compound 51 as brown oil: LC/MS, m/z=442.4, [M+H]$^+$ (Calc: 441.6).

Crude Compound 51 was dissolved in 8 mL of DCM and cooled to −78° C. A solution of BBr$_3$ (1N in DCM, 2 mL) was added under an atmosphere of argon. The mixture was stirred at −78° C. for 1 h, warmed to 0° C., and allowed to stir at 0° C. for 1 h. The reaction was quenched with water and neutralized with NH₄OH to pH~9. The organic layer was cut away, dried over Na₂SO₄, and evaporated in vacuo.

The residue was purified by flash chromatography (SiO2, DCM/MeOH/NH₄OH 10/1/0.05) to give Compound 52 as white solid (70 mg, yield 48%): ¹H NMR (400 MHz, METHANOL-d4) δ: 6.90 (d, J=8.3 Hz, 1H), 6.72 (d, J=2.5 Hz, 1H), 6.58 (dd, J=8.2, 2.5 Hz, 1H), 4.35 (t, J=10.4 Hz, 2H), 3.23 (d, J=3.5 Hz, 1H), 3.13 (d, J=18.8 Hz, 1H), 2.75-2.94 (m, 3H), 2.66 (dd, J=18.6, 6.0 Hz, 1H), 2.32-2.49 (m, 6H), 2.08-2.21 (m, 4H), 1.73-1.92 (m, 4H), 1.47 (s, 3H), 1.19-1.36 (m, 10H), 0.87-1.08 (m, 2H). LC/MS, m/z=428.2, [M+H]⁺ (Calc: 427.6).

Example 12

Synthesis of (2R,6S,11R)-3,6-dimethyl-11-(methyl ((1-(methylsulfonyl)piperidin-4-yl)methyl)amino)-1,2,3,4,5,6-hexahydro-2,6-methanobenzo[d]azocin-8-ol (Compound 54)

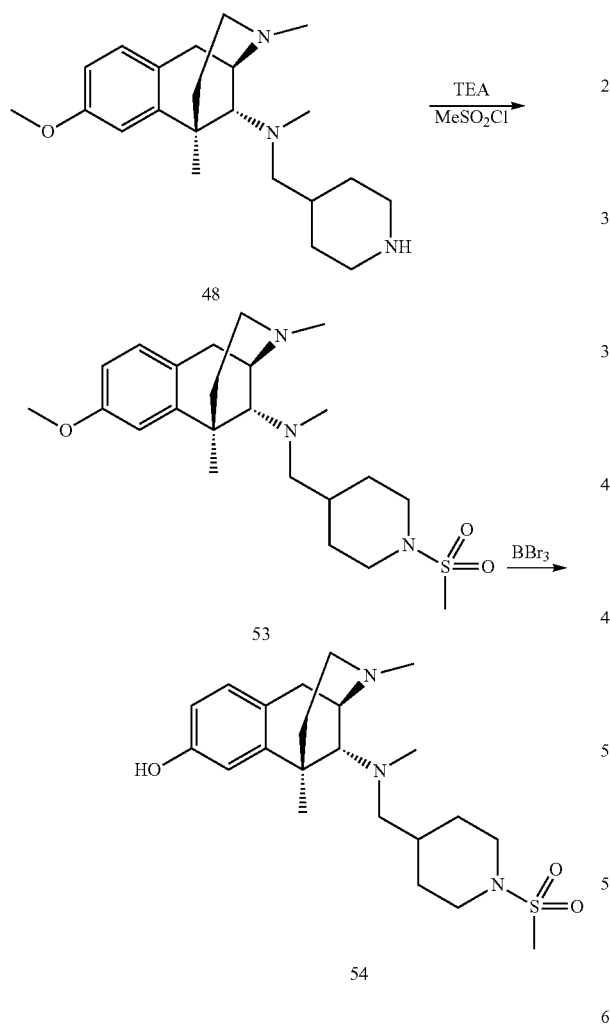

Methane sulfonylchloride (80 mg, 0.67 mmol) was added to a solution of Compound 48 (0.12 g, 0.34 mmol) and TEA (0.1 g, 1.0 mmol) in 5 mL of DCM at 0° C. The mixture was warmed to RT for 16 h. After subsequent quenching with water (1 mL), the organic layer was cut away and concentrated to give crude Compound 53 as yellow oil: LC/MS, m/z=436.2, [M+H]⁺ (Calc: 435.6).

Crude Compound 53 was dissolved in 8 mL of DCM and cooled to −78° C. A solution of BBr₃ (1N in DCM, 2 mL) was added under an atmosphere of argon. The mixture was stirred at −78° C. for 1 h, warmed to 0° C., and allowed to stir at 0° C. for 1 h. The reaction was quenched with water and neutralized with NH₄OH to pH~9. The organic layer was cut away, dried over Na₂SO₄, and evaporated in vacuo.

The residue was purified by flash chromatography (SiO2, DCM/MeOH/NH₄OH 10/1/0.05) to give Compound 54 as white solid (60 mg, yield 42%): ¹H NMR (400 MHz, METHANOL-d4) δ: 6.91 (d, J=8.3 Hz, 1H), 6.73 (d, J=2.5 Hz, 1H), 6.58 (dd, J=8.2, 2.5 Hz, 1H), 3.55-3.69 (m, 2H), 3.23 (d, J=3.3 Hz, 1H), 3.13 (d, J=18.5 Hz, 1H), 2.78-2.86 (m, 4H), 2.61-2.78 (m, 3H), 2.47 (d, J=7.3 Hz, 2H), 2.41 (s, 4H), 2.07-2.21 (m, 4H), 1.75-1.95 (m, 3H), 1.66 (ddd, J=10.9, 7.3, 3.7 Hz, 1H), 1.47 (s, 3H), 1.32 (d, J=11.5 Hz, 1H), 1.03-1.24 (m, 2H). LC/MS, m/z=422.2, [M+H]⁺ (Calc: 421.6).

In a similar manner, the following compounds were prepared from the appropriate sulfonyl chloride and Compound 48:

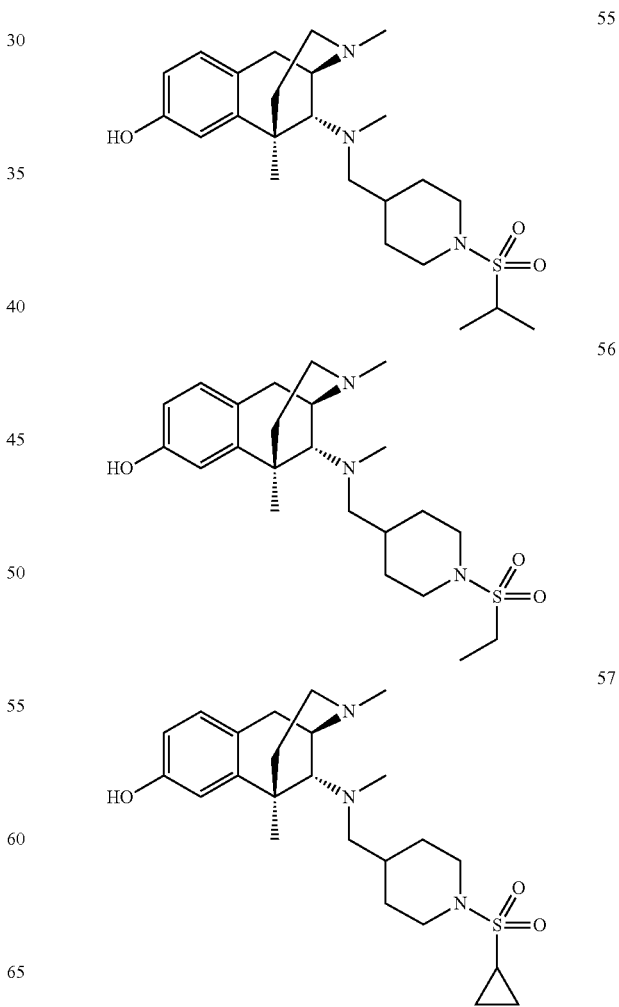

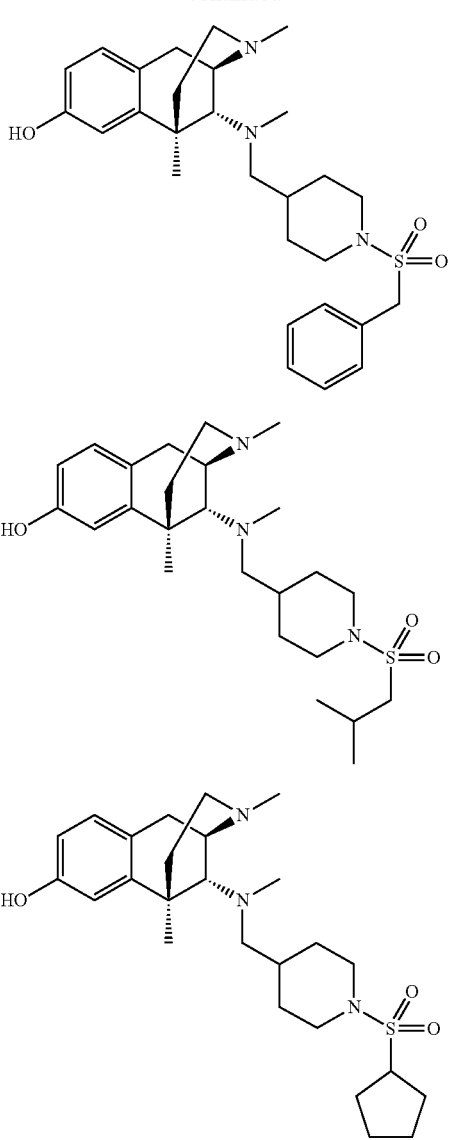

(2R,6S,11R)-11-(((1-(isopropylsulfonyl)piperidin-4-yl)methyl)(methyl)amino)-3,6-dimethyl-1,2,3,4,5,6-hexahydro-2,6-methanobenzo[d]azocin-8-ol (Compound 55)

$^1$H NMR (400 MHz, METHANOL-d4) δ: 6.79 (d, J=8.3 Hz, 1H), 6.61 (d, J=2.5 Hz, 1H), 6.46 (dd, J=8.2, 2.5 Hz, 1H), 3.60 (td, J=8.0, 4.0 Hz, 2H), 3.12-3.20 (m, 1H), 3.11 (dt, J=5.5, 2.6 Hz, 1H), 3.01 (d, J=18.7 Hz, 1H), 2.78 (tdd, J=12.2, 6.6, 2.4 Hz, 1H), 2.69 (d, J=1.9 Hz, 2H), 2.54 (dd, J=18.6, 6.1 Hz, 1H), 2.20-2.40 (m, 6H), 1.97-2.10 (m, 4H), 1.63-1.83 (m, 3H), 1.57 (ddd, J=11.0, 7.3, 3.6 Hz, 1H), 1.35 (s, 3H), 1.12-1.26 (m, 7H), 0.84-1.07 (m, 2H). LC/MS, m/z=450.2, [M+H]+(Calc: 449.6).

(2R,6S,11R)-11-(((1-(ethylsulfonyl)piperidin-4-yl)methyl)(methyl)amino)-3,6-dimethyl-1,2,3,4,5,6-hexahydro-2,6-methanobenzo[d]azocin-8-ol (Compound 56)

$^1$H NMR (400 MHz, METHANOL-d4) δ: 7.05 (d, J=8.4 Hz, 1H), 6.81 (d, J=2.5 Hz, 1H), 6.71 (dd, J=8.3, 2.5 Hz, 1H), 3.99 (br. s., 1H), 3.62-3.80 (m, 2H), 3.29 (br. s., 1H), 3.06-3.23 (m, 3H), 2.93-3.05 (m, 5H), 2.68-2.89 (m, 3H), 2.58 (d, J=6.7 Hz, 2H), 2.24 (s, 3H), 1.97-2.13 (m, 1H), 1.68-1.90 (m, 3H), 1.52-1.67 (m, 4H), 1.32 (t, J=7.4 Hz, 3H), 1.01-1.24 (m, 2H). LC/MS, m/z=436.2, [M+H]+ (Calc: 435.6).

(2R,6S,11R)-11-(((1-(cyclopropylsulfonyl)piperidin-4-yl)methyl)(methyl)amino)-3,6-dimethyl-1,2,3,4,5,6-hexahydro-2,6-methanobenzo[d]azocin-8-ol (Compound 57)

$^1$H NMR (METHANOL-d4) δ: 7.06 (d, J=8.4 Hz, 1H), 6.82 (d, J=2.4 Hz, 1H), 6.71 (dd, J=8.3, 2.5 Hz, 1H), 4.00 (br. s., 1H), 3.69 (t, J=10.8 Hz, 2H), 3.27-3.32 (m, 1H), 3.07-3.25 (m, 3H), 2.98 (s, 3H), 2.82-2.93 (m, 2H), 2.75 (br. s., 1H), 2.59 (d, J=6.9 Hz, 2H), 2.43 (tt, J=7.7, 5.1 Hz, 1H), 2.26 (s, 3H), 1.98-2.15 (m, 1H), 1.85 (d, J=13.2 Hz, 2H), 1.68-1.79 (m, 1H), 1.50-1.66 (m, 4H), 1.09-1.27 (m, 2H), 0.94-1.08 (m, 4H). LC/MS, m/z=448.2, [M+H]+ (Calc: 447.6).

(2R,6S,11R)-11-(((1-(benzylsulfonyl)piperidin-4-yl)methyl)(methyl)amino)-3,6-dimethyl-1,2,3,4,5,6-hexahydro-2,6-methanobenzo[d]azocin-8-ol (Compound 58)

$^1$H NMR (400 MHz, METHANOL-d4) δ: 7.17-7.36 (m, 5H), 6.92 (d, J=8.4 Hz, 1H), 6.69 (d, J=2.4 Hz, 1H), 6.59 (dd, J=8.3, 2.5 Hz, 1H), 4.19 (s, 2H), 3.81 (br. s., 1H), 3.50 (td, J=6.2, 2.2 Hz, 2H), 3.16 (br. s., 1H), 2.94-3.09 (m, 2H), 2.76-2.92 (m, 4H), 2.55 (tdd, J=12.2, 6.8, 2.4 Hz, 3H), 2.28-2.44 (m, 2H), 2.06 (s, 3H), 1.80-1.97 (m, 1H), 1.61 (t, J=12.0 Hz, 2H), 1.36-1.55 (m, 5H), 0.77-1.01 (m, 2H). LC/MS, m/z=498.3, [M+H]+(Calc: 497.7).

(2R,6S,11R)-11-(((1-(isobutylsulfonyl)piperidin-4-yl)methyl)(methyl)amino)-3,6-dimethyl-1,2,3,4,5,6-hexahydro-2,6-methanobenzo[d]azocin-8-ol (Compound 59)

$^1$H NMR (400 MJz, TFA-salt; METHANOL-d4) δ: 7.04 (d, J=8.3 Hz, 1H), 6.81 (d, J=2.4 Hz, 1H), 6.70 (dd, J=8.3, 2.5 Hz, 1H), 3.94 (br. s., 1H), 3.69 (dd, J=7.0, 3.2 Hz, 2H), 3.28 (br. s., 1H), 3.16 (d, J=7.0 Hz, 2H), 2.97 (br. s., 4H), 2.83 (d, J=6.5 Hz, 2H), 2.76 (tdd, J=12.0, 6.6, 2.4 Hz, 3H), 2.42-2.62 (m, 2H), 2.11-2.29 (m, 4H), 2.01 (br. s., 1H), 1.84 (dd, J=18.7, 15.7 Hz, 2H), 1.58-1.75 (m, 2H), 1.56 (s, 3H), 1.01-1.23 (m, 8H). LC/MS, m/z=464.2, [M+H]+ (Calc: 463.7).

(2R,6S,11R)-11-(((1-(cyclopentylsulfonyl)piperidin-4-yl)methyl)(methyl)amino)-3,6-dimethyl-1,2,3,4,5,6-hexahydro-2,6-methanobenzo[d]azocin-8-ol (Compound 60)

$^1$H NMR (400 MHz, METHANOL-d4) δ: 6.92 (d, J=8.3 Hz, 1H), 6.69 (d, J=2.4 Hz, 1H), 6.59 (dd, J=8.3, 2.5 Hz, 1H), 3.81 (br. s., 1H), 3.62 (dd, J=7.3, 3.3 Hz, 2H), 3.46 (quin, J=8.0 Hz, 1H), 3.16 (br. s., 1H), 2.95-3.11 (m, 2H), 2.78-2.92 (m, 4H), 2.73 (tdd, J=12.1, 6.8, 2.3 Hz, 2H), 2.52-2.65 (m, 1H), 2.31-2.48 (m, 2H), 2.06 (s, 3H), 1.77-1.95 (m, 5H), 1.47-1.76 (m, 8H), 1.44 (s, 3H), 0.86-1.10 (m, 2H). LC/MS, m/z=476.2, [M+H]+ (Calc: 475.7).

Example 13

Synthesis of (2R,6S,11R)-11-(((1-(isopropylsulfonyl)piperidin-4-yl)methyl)amino)-3,6-dimethyl-1,2,3,4,5,6-hexahydro-2,6-methanobenzo[d]azocin-8-ol (Compound 65)

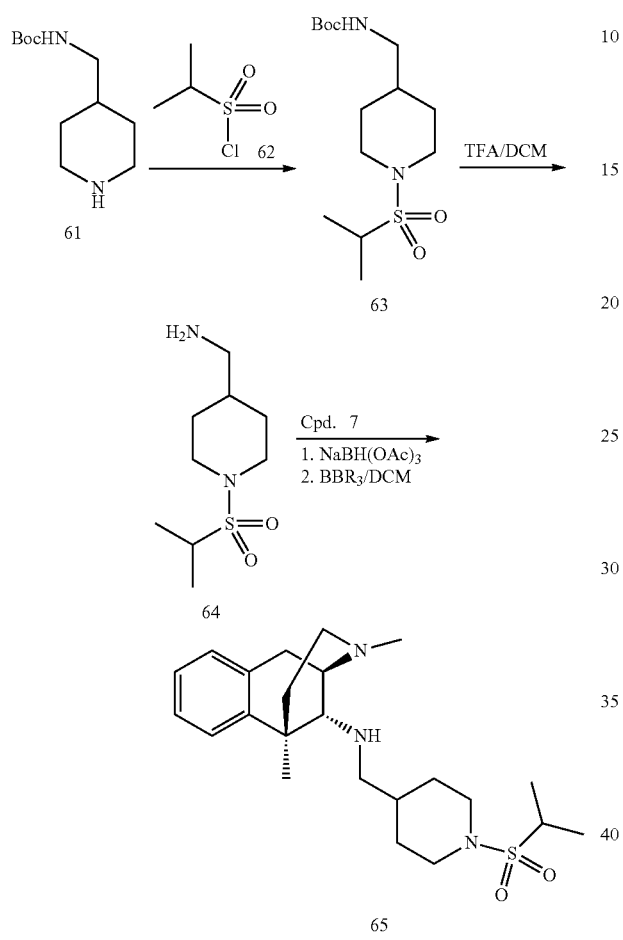

Propane-2-sulfonyl chloride (Compound 62) (2.4 g, 16.8 mmol) (Aldrich) was added to a solution of Compound 61 (3 g, 14 mmol) and TEA (3 mL, 21 mmol) in 50 mL of CHCl₃ at 0° C. over 15 min. The reaction mixture was warmed to RT overnight. The reaction was quenched with water (5 mL), and washed with saturated NaHCO₃. The organic layer was concentrated to give crude Compound 63 as yellow oil: LC/MS, m/z=343.2, [M+Na]+ (Calc: 320.4).

Compound 63 was dissolved in DCM (50 mL) and cooled with ice-water. TFA (6 mL) was added, and the mixture was warmed to RT for 72 h. The solvent was removed under reduced pressure, the residue dissolved in 100 mL of EtOAc, and the resulting solution neutralized with NaOH (1N) to pH~7. The organic layer was cut away, dried over Na₂SO₄, and evaporated in vacuo.

The residue was purified by flash chromatography (SiO2, DCM/MeOH/NH₄OH 10/1/0.05) to give Compound 64 as brown oil (2 g): ¹H NMR (400 MHz, CHLOROFORM-d) δ: 4.32 (q, J=7.1 Hz, 2H), 3.83 (br. s., 1H), 3.23-3.38 (m, 1H), 3.15 (d, J=7.3 Hz, 1H), 2.77-2.97 (m, 1H), 1.69-1.92 (m, 1H), 1.38-1.47 (m, 10H), 1.30-1.37 (m, 3H), 1.19-1.28 (m, 1H). LC/MS, m/z=221.4, [M+H]+(Calc: 220.3).

A mixture of Compound 7 (0.50 g, 1.65 mmol), Compound 64 (0.554 g, 2.47 mmol) and pTSA (0.03 g) in toluene (40 mL) was heated to reflux for 4 h and concentrated to give a brown oil. To this oil was added ACN (20 mL) followed by NaBH(OAc)₃ (1.05 g, 4.94 mmol). The reaction mixture was stirred at RT for 24 h, MeOH (1 mL) was added and the mixture concentrated. Water (10 mL) and EtOAc (100 mL) were added and the pH adjusted to ~9 with NH₄OH. The layers were separated and the organic layer was concentrated and purified by flash chromatography (SiO₂, 10% (10% NH₄OH in MeOH) in DCM) to give the product as a mixture of isomers. This material was dissolved in DCM (4 mL), cooled to −78° C. and 1 M BBr₃ in DCM (2.0 mL, 2.0 mmol) was added. The mixture was stirred at −78° C. for 1 h allowed to warm to 0° C. and stirred an additional 30 min. The reaction was quenched by the addition of water (2 mL) and the pH adjusted to ~8 with NH₄OH. The organic layer was cut away, dried over Na₂SO₄, and evaporated in vacuo.

The residue was purified by flash chromatography (SiO2, DCM/MeOH/NH₄OH 10/1/0.05) to give Compound 65 as a white solid: ¹H NMR (400 MHz, METHANOL-d4) δ: 7.04 (d, J=8.4 Hz, 1H), 6.74 (d, J=2.4 Hz, 1H), 6.70 (dd, J=8.4, 2.5 Hz, 1H), 4.19 (dd, J=5.6, 2.9 Hz, 1H), 3.78 (d, J=3.0 Hz, 1H), 3.71 (dd, J=12.8, 1.5 Hz, 2H), 3.26-3.37 (m, 1H), 3.10-3.21 (m, 3H), 3.03 (dd, J=13.1, 5.3 Hz, 1H), 2.94 (s, 3H), 2.77-2.91 (m, 3H), 2.59-2.72 (m, 1H), 2.14 (td, J=14.1, 4.5 Hz, 1H), 1.85-1.98 (m, 1H), 1.69-1.80 (m, 2H), 1.65 (dd, J=14.6, 1.8 Hz, 1H), 1.58 (s, 3H), 1.12-1.28 (m, 8H). LC/MS, m/z=436.2, [M+Na]+(Calc: 435.6).

Example 14

Synthesis of (2R,6S,11R)—N-(4-fluorophenethyl)-8-methoxy-3,6-dimethyl-1,2,3,4,5,6-hexahydro-2,6-methanobenzo[d]azocin-11-amine (Compound 68)

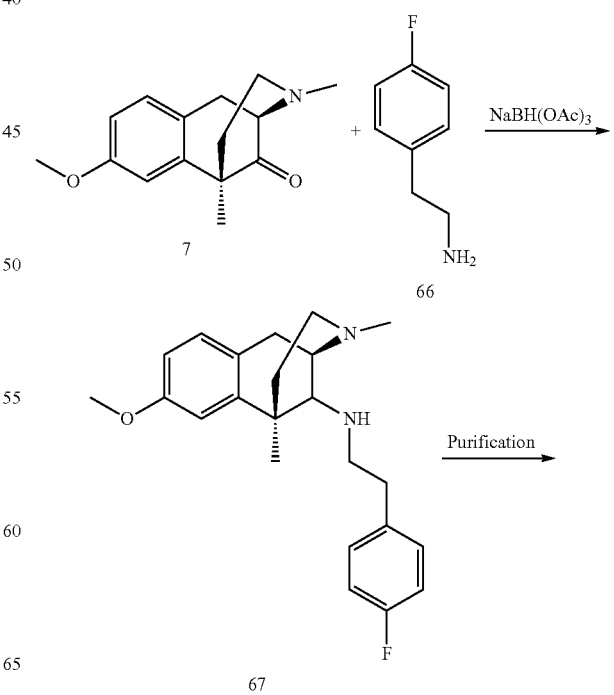

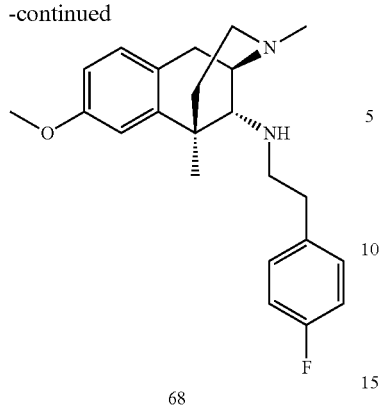
68

A mixture of Compound 7 (1.0 g, 4 mmol), 2-(4-fluorophenyl)ethan-1-amine (Compound 66) (1 g, 4.8 mmol) (Aldrich) and 4A molecular sieves (2 g) in 20 mL CHCl₃ was shaken at 60° C. for 14 h. The reaction mixture was cooled to RT and NaBH(OAc)₃ (1.8 g, 8.2 mmol) was added. The reaction mixture was shaken at RT for 24 h and quenched with NaOH (1 N, 10 mL). An additional amount of CHCl₃ (20 mL) was added. The organic layer was cut away, dried over Na₂SO₄ and evaporated in vacuo to give Compound 67, which was purified by flash chromatography (SiO2, DCM/MeOH/NH₄OH 10/1/0.05) to give Compound 68 as a yellow oil with the yield of 50%. LC/MS, m/z=369.2, [M+H]⁺ (Calc: 368.5); retention time (0.945 min)

In a similar manner, the following compounds were prepared:

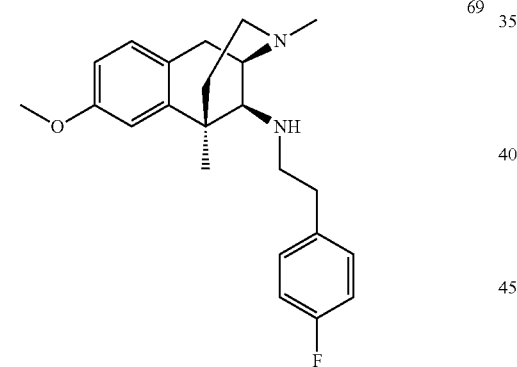
69

(2R,6S,11S)—N-(4-fluorophenethyl)-8-methoxy-3,6-dimethyl-1,2,3,4,5,6-hexahydro-2,6-methanobenzo[d]azocin-11-amine (Compound 69): LC/MS, m/z=369.2, [M+H]⁺ (Calc: 368.5); retention time (1.489 min);

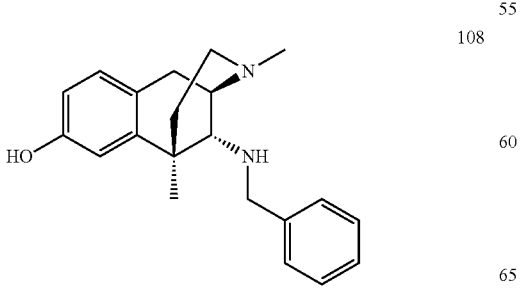
108

(2R,6S,11R)-11-(benzylamino)-3,6-dimethyl-1,2,3,4,5,6-hexahydro-2,6-methanobenzo[d]azocin-8-ol (Compound 108): LC/MS, m/z=323.3 [M+H]⁺ (Calc: 322.2); and

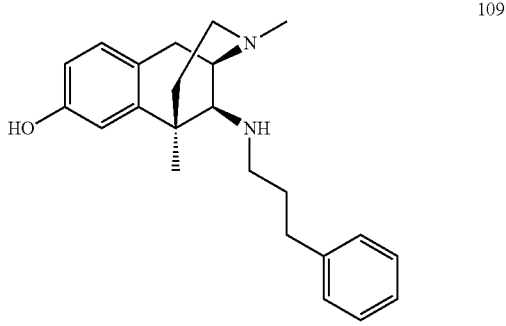
109

(2R,6S,11S)-3,6-dimethyl-11-((3-phenylpropyl)amino)-1,2,3,4,5,6-hexahydro-2,6-methanobenzo-[d]azocin-8-ol (Compound 109): LC/MS, m/z=351.1 [M+H]⁺ (Calc: 350.2).

Further, by using starting materials with various R⁴ groups (which can be prepared in accordance with Scheme G provided above), the following compounds were prepared in a similar manner:

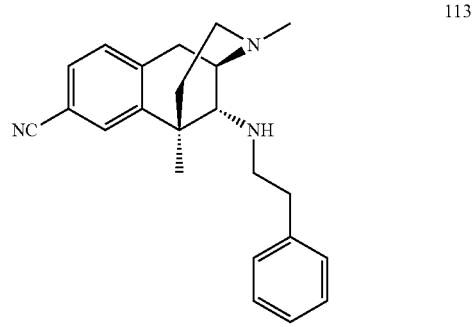
113

(2R,6S,11R)-3,6-dimethyl-11-(phenethylamino)-1,2,3,4,5,6-hexahydro-2,6-methanobenzo[d]azocine-8-carbonitrile (Compound 113): LC/MS, m/z=346.2 [M+H]⁺ (Calc: 345.2);

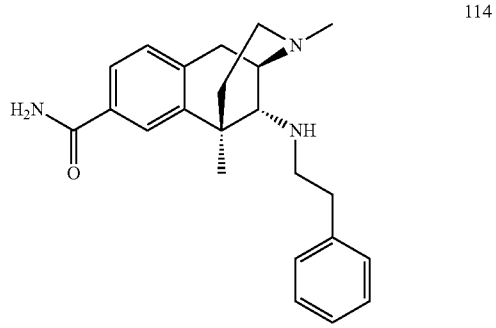
114

(2R,6S,11R)-3,6-dimethyl-11-(phenethylamino)-1,2,3,4,5,6-hexahydro-2,6-methanobenzo[d]azocine-8-carboxamide (Compound 114): LC/MS, m/z=364.2 [M+H]⁺ (Calc: 363.2);

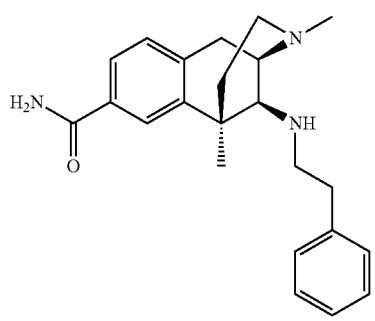

(2R,6S,11S)-3,6-dimethyl-11-(phenethylamino)-1,2,3,4,5,6-hexahydro-2,6-methanobenzo[d]azocine-8-carboxamide (Compound 115): LC/MS, m/z=364.2 [M+H]+ (Calc: 363.2);

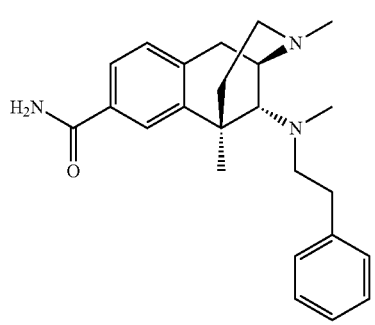

(2R,6S,11R)-3,6-dimethyl-11-(methyl(phenethyl)amino)-1,2,3,4,5,6-hexahydro-2,6-methanobenzo[d]azocine-8-carboxamide (Compound 123): LC/MS, m/z=378.1 [M+H]+ (Calc: 377.3);

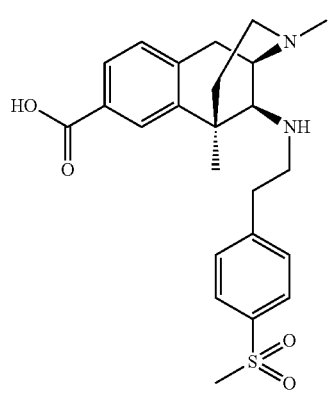

(2R,6S,11S)-3,6-dimethyl-11-((4-(methylsulfonyl)phenethyl)amino)-1,2,3,4,5,6-hexahydro-2,6-methanobenzo[d]azocine-8-carboxylic acid (Compound 125): LC/MS, m/z=443.1 [M+H]+ (Calc: 442.2); and

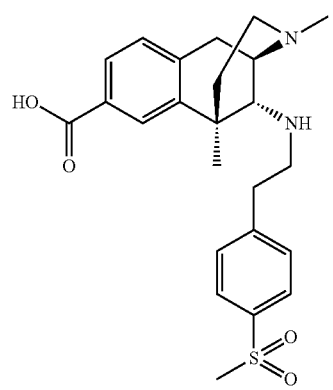

(2R,6S,11S)-3,6-dimethyl-11-((4-(methylsulfonyl)phenethyl)amino)-1,2,3,4,5,6-hexahydro-2,6-methanobenzo[d]azocine-8-carboxylic acid (Compound 126): LC/MS, m/z=443.1 [M+H]+ (Calc: 442.2).

Example 15

Synthesis of N-(4-fluorophenethyl)-N-((2R,6S,11S)-8-hydroxy-3,6-dimethyl-1,2,3,4,5,6-hexahydro-2,6-methanobenzo[d]azocin-11-yl)glycine (Compound 72)

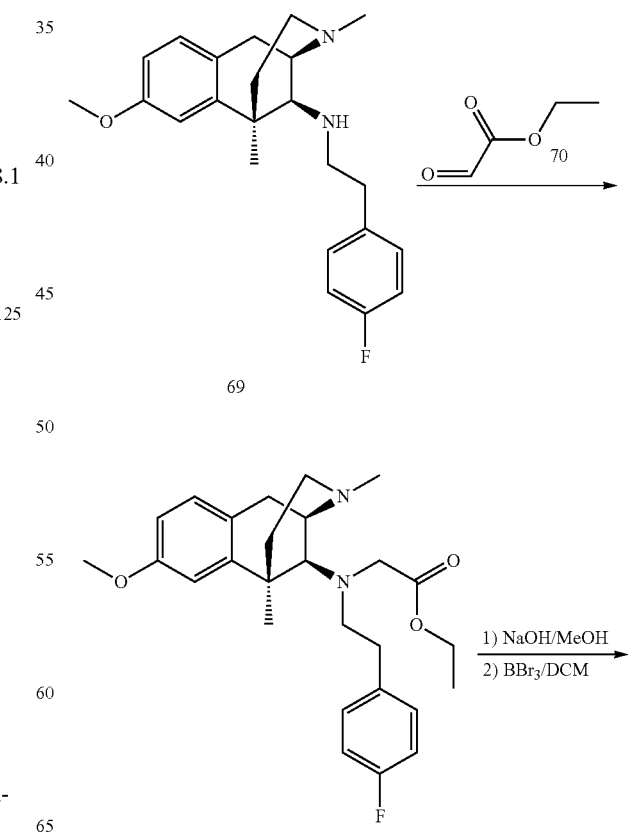

-continued

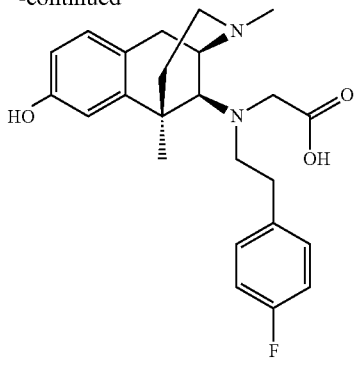

72

To a solution of Compound 69 (0.15 g, 0.4 mmol) and Compound 70 (~50% in toluene, 125 mg) in 2 mL CHCl$_3$ at RT was added NaBH(OAc)$_3$ (0.17 g, 0.8 mmol). The mixture was shaken at RT for 24 h. The reaction was quenched with 1 mL water, 2 mL NH$_4$OH, and extracted with CHCl$_3$ (3×15 mL). The combined organic layers were concentrated under reduced pressure to give crude Compound 71 as brown oil: LC/MS, m/z=455.2 [M+H]$^+$ (Calc: 454.6), The crude Compound 71 was dissolved in 4 mL of MeOH and 0.5 mL 2N NaOH at RT. The mixture was shaken at 40° C. for 2 h. After cooling to RT the mixture was concentrated under reduced pressure. The residue was dissolved in 6 mL of DCM at −78° C., and was added BBr$_3$ (1.0N in DCM, 3 mL). After 1 h, the reaction mixture was warmed to 0° C. and allowed to stir at 0° C. for 1 h. After quenching with water (2 mL) and stirring at RT for 2 h, the mixture was neutralized with NH$_4$OH to pH~9. The organic layer was cut away, washed with brine, and evaporated in vacuo.

The residue was purified by reverse-phase prep HPLC (C18, 0-100% 0.1% TFA in water/0.1% TFA in ACN) to give Compound 72 as a white solid (TFA-salt, 50 mg):

1H NMR (400 MHz, METHANOL-d4) δ: 7.14 (dd, J=8.6, 5.5 Hz, 2H), 6.82-6.96 (m, 3H), 6.68 (d, J=2.4 Hz, 1H), 6.58 (dd, J=8.3, 2.5 Hz, 1H), 3.98 (d, J=18.3 Hz, 1H), 3.87 (d, J=5.5 Hz, 1H), 3.68 (d, J=18.3 Hz, 1H), 3.22-3.31 (m, 2H), 3.18 (d, J=5.9 Hz, 1H), 3.03-3.14 (m, 2H), 2.93 (dt, J=13.8, 7.1 Hz, 1H), 2.83 (s, 3H), 2.55-2.75 (m, 3H), 2.20 (td, J=14.1, 5.1 Hz, 1H), 1.40 (dd, J=15.2, 3.5 Hz, 1H), 1.31 (s, 3H). LC/MS, m/z=413.0 [M+H]+(Calc: 412.5).

In a similar manner, the following compounds were prepared:

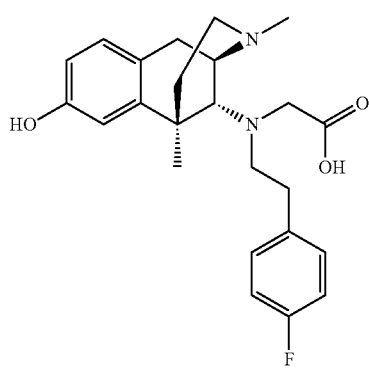

73

2-((4-fluorophenethyl)((2R,6S,11R)-8-hydroxy-3,6-dimethyl-1,2,3,4,5,6-hexahydro-2,6-methanobenzo[d]azocin-11-yl)amino)acetamide (Compound 73): $^1$H NMR (DMSO-d$_6$) δ: 6.83-7.04 (m, 5H), 6.61 (d, J=2.4 Hz, 1H), 6.56 (dd, J=8.2, 2.4 Hz, 1H), 3.35 (br. s., 1H), 3.12-3.22 (m, 3H), 3.02 (br. s., 1H), 2.92 (d, J=18.7 Hz, 1H), 2.63-2.78 (m, 3H), 2.53 (br. s., 2H), 2.43 (s, 3H), 1.99-2.14 (m, 1H), 1.77-1.91 (m, 1H), 1.35 (s, 3H), 1.23 (d, J=12.5 Hz, 1H).
LC/MS, m/z=413.2 [M+H]$^+$ (Calc: 412.5).

Example 16

Synthesis of N-(4-fluorophenethyl)-N-((2R,6S,11R)-8-hydroxy-3,6-dimethyl-1,2,3,4,5,6-hexahydro-2,6-methanobenzo[d]azocin-11-yl)glycine (Compound 74)

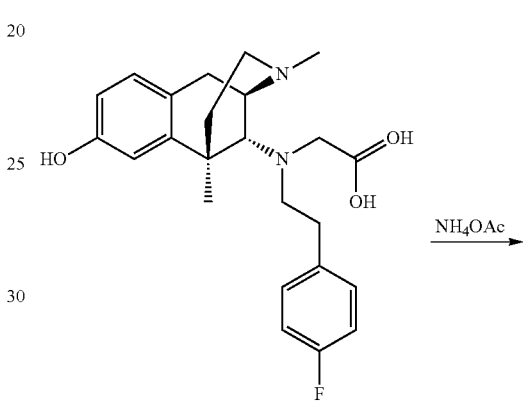

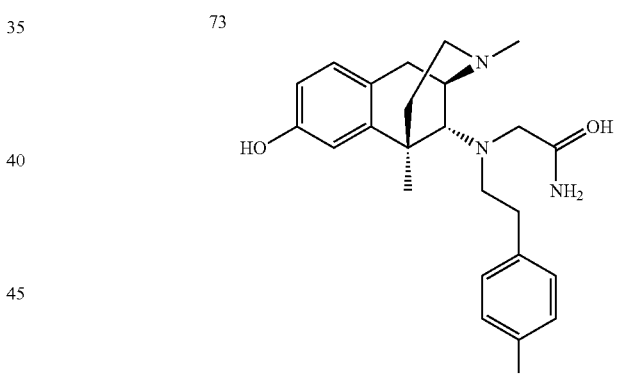

74

A mixture of HATU (50 mg, 0.4 mmol), Compound 73 (20 mg, 0.05 mmol), NH$_4$OAc (30 mg, 0.4 mmol) and DIPEA (0.1 mL) in 2 mL of DMF was shaken at RT for 48 h. The reaction mixture was quenched with water (1 mL) and extracted with EtOAc (2×4 mL). The organic layers were combined, washed with brine, and evaporated in vacuo.

The residue was purified by reverse-phase prep HPLC (C18, 0-100% 0.1% TFA in water/0.1% TFA in ACN) to give Compound 74 as a white solid (TFA-salt, 15 mg).

$^1$H NMR (METHANOL-d4) δ: 6.91-6.99 (m, 3H), 6.80-6.89 (m, 2H), 6.67 (d, J=2.4 Hz, 1H), 6.60 (dd, J=8.3, 2.5 Hz, 1H), 3.92 (d, J=3.9 Hz, 1H), 3.22-3.30 (m, 1H), 3.16 (s, 2H), 2.95-3.06 (m, 3H), 2.87 (s, 3H), 2.53-2.82 (m, 5H), 1.90 (td, J=13.9, 4.6 Hz, 1H), 1.52 (dd, J=14.3, 2.1 Hz, 1H), 1.37 (s, 3H). LC/MS, m/z=412.2 [M+H]$^+$ (Calc: 411.5).

Example 17

Synthesis of (2R,6S,11S)-11-((4-fluorophenethyl)(2-hydroxyethyl)amino)-3,6-dimethyl-1,2,3,4,5,6-hexahydro-2,6-methanobenzo[d]azocin-8-ol (Compound 77)

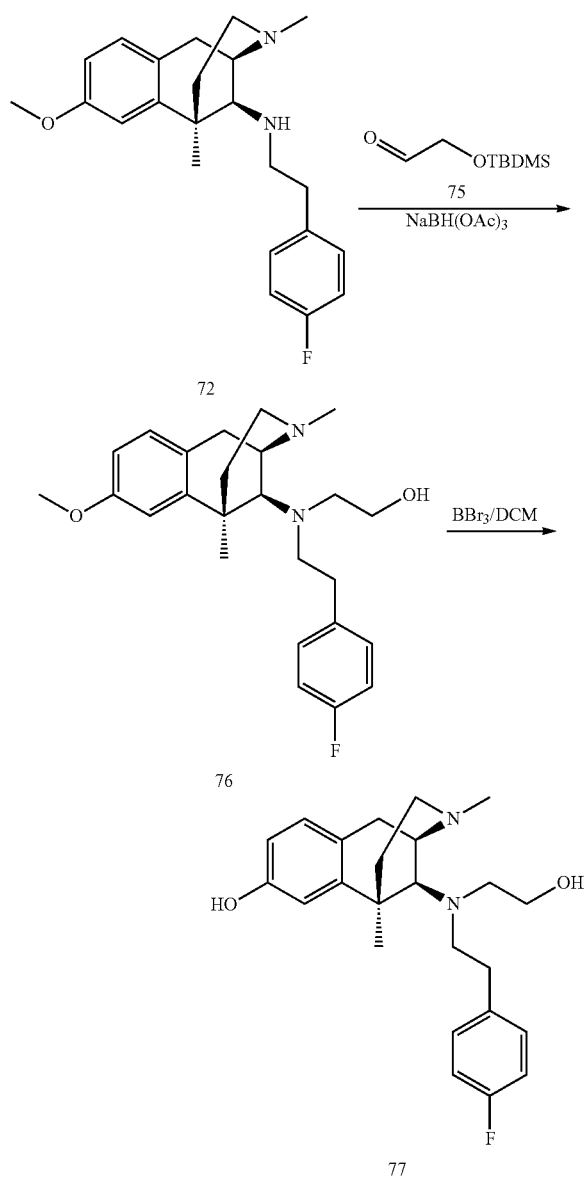

A mixture of Compound 72 (0.1 g, 0.27 mmol) and 2-((tert-butyldimethylsilyl)oxy)-acetaldehyde (Compound 75) (0.1 g, 0.58 mmol) (Aldrich) in 3 mL CHCl$_3$ was shaken at 60° C. for 1 h. After cooling to RT NaBH(OAc)$_3$ (0.2 g, 0.9 mmol) was added. The reaction mixture was shaken at RT for 24 h, quenched with water (1 mL), and the organic layer cut away. The organic layer was concentrated under reduced pressure to give a yellow oil, which was dissolved in 8 mL of MeOH and 1 mL of HCl (5N aqueous). The acidic mixture was shaken at RT for 4 h, then cooled in an ice-water bath, and finally neutralized with NH$_4$OH to pH~9. The mixture was extracted with CHCl$_3$ (3×5 mL). The combined organic layers were dried over Na$_2$SO$_4$ and concentrated under reduced pressure to give Compound 76. LC/MS, m/z=413.2, [M+H]$^+$ (Calc: 412.5).

To a solution of the crude Compound 76 in 8 mL of DCM at −78° C. was added BBr$_3$ (1.0N in DCM, 3 mL). After 1 h the reaction mixture was warmed to 0° C. After stirring at 0° C. for 1 h, the reaction was quenched with water and neutralized with NH$_4$OH to pH~9. The organic layer was cut away, washed with brine, and evaporated in vacuo.

The residue was purified by reverse-phase prep HPLC (C18, 0-100% 0.1% TFA in water/0.1% TFA in ACN) to yield Compound 77 as a white solid (TFA-salt, 30 mg): $^1$H NMR (METHANOL-d4) δ: 7.12 (dd, J=8.6, 5.5 Hz, 2H), 6.89 (q, J=8.6 Hz, 3H), 6.69 (d, J=2.5 Hz, 1H), 6.57 (dd, J=8.3, 2.4 Hz, 1H), 3.68-3.82 (m, 2H), 3.56 (dt, J=10.5, 3.0 Hz, 1H), 3.37-3.46 (m, 1H), 3.25 (s, 2H), 3.00-3.18 (m, 4H), 2.89-2.98 (m, 1H), 2.60-2.80 (m, 6H), 2.47 (td, J=14.1, 5.2 Hz, 1H), 1.31-1.42 (m, 4H). LC/MS, m/z=399.2, [M+H]$^+$ (Calc: 398.5).

Example 18

The following compounds were prepared according to literature procedures.

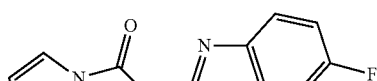

78

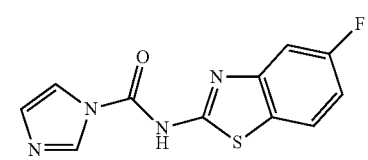

79

N-(6-fluorobenzo[d]thiazol-2-yl)-1H-imidazole-1-carboxamide (Compound 78) and N-(5-fluorobenzo[d]thiazol-2-yl)-1H-imidazole-1-carboxamide (Compound 79) were prepared in the same/similar manners as those described in PCT patent publication No. WO2013021276.

Example 19

Synthesis of 3-(6-fluorobenzo[d]thiazol-2-yl)-1-((2R,6S,11R)-8-hydroxy-3,6-dimethyl-1,2,3,4,5,6-hexahydro-2,6-methanobenzo[d]azocin-11-yl)-1-methylurea (Compound 81)

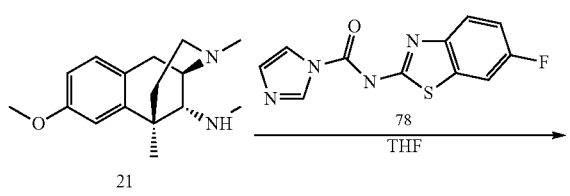

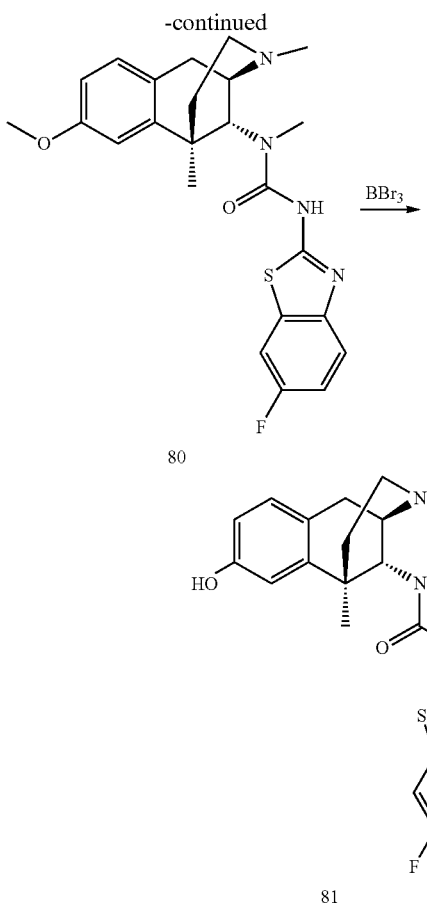

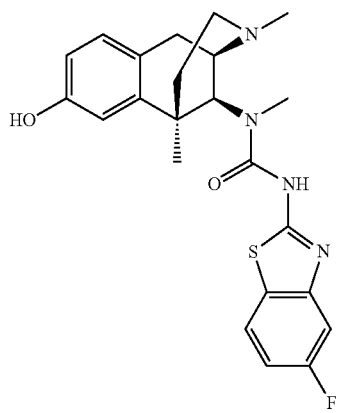

A mixture of Compound 21 (0.1 g, 0.38 mmol) and Compound 78 (0.1 g, 0.38 mmol) in 10 mL of THF was shaken at 65° C. for 4 h. After cooling to RT, the mixture was concentrated under reduced pressure. The residue was dissolved in 15 mL of EtOAc and washed with 10% NH₄Cl (4 mL). The organic layer was cut away, and concentrated under reduced pressure to give crude Compound 80 as a brown oil: LC/MS, m/z=455.0, [M+H]⁺ (Calc: 454.6).

To a mixture of crude Compound 80 in 6 mL of DCM at −78° C. was added BBr₃ (1.0N in DCM, 3 mL). After stirring for 1 h, the reaction mixture was warmed to 0° C. and allowed to stir at 0° C. for 1 h. The reaction was quenched with water (2 mL) and further stirred at RT for 2 h, and then neutralized with NH₄OH to pH~9. The organic layer was cut away, dried over Na₂SO₄ and evaporated in vacuo.

The residue was purified by flash chromatography (SiO2, DCM/MeOH/NH4OH 10/1/0.1) to give Compound 81 as a white solid (50 mg, yield 29%): ¹H NMR (400 MHz, METHANOL-d4) δ: 7.29-7.49 (m, 2H), 6.90-7.14 (m, 2H), 6.73-6.80 (m, 1H), 6.60-6.70 (m, 1H), 4.63 (br. s., 1H), 3.65-3.85 (m, 1H), 3.34-3.58 (m, 1H), 3.26 (s, 1H), 2.98-3.19 (m, 3H), 2.88 (s, 2H), 2.72-2.80 (m, 1H), 2.71 (s, 1H), 2.58-2.69 (m, 1H), 1.94-2.44 (m, 1H), 1.53-1.72 (m, 1H), 1.34-1.52 (m, 3H). LC/MS, m/z=441.2, [M+H]⁺ (Calc: 440.2).

In a similar manner, the following compounds were prepared:

1-(5-fluorobenzo[d]thiazol-2-yl)-3-((2R,6S,11S)-8-hydroxy-3,6-dimethyl-1,2,3,4,5,6-hexahydro-2,6-methanobenzo[d]azocin-11-yl)-1,3-dimethylurea (Compound 82):

¹H NMR (400 MHz, METHANOL-d4) δ: 7.74 (dd, J=8.7, 5.4 Hz, 1H), 7.31 (dd, J=10.1, 2.4 Hz, 1H), 6.90-7.11 (m, 2H), 6.78 (d, J=2.4 Hz, 1H), 6.67 (dd, J=8.3, 2.4 Hz, 1H), 3.81 (s, 1H), 3.61 (d, J=5.4 Hz, 1H), 3.35-3.45 (m, 1H), 3.19 (s, 3H), 3.11 (dd, J=17.9, 5.7 Hz, 1H), 3.00 (dd, J=12.0, 3.7 Hz, 1H), 2.65 (s, 3H), 2.47 (td, J=12.4, 3.4 Hz, 1H), 2.30 (td, J=13.3, 4.7 Hz, 1H), 1.48 (s, 3H), 1.36 (d, J=14.0 Hz, 1H); LC/MS, m/z=441.0 [M+H]⁺ (Calc: 440.5); and

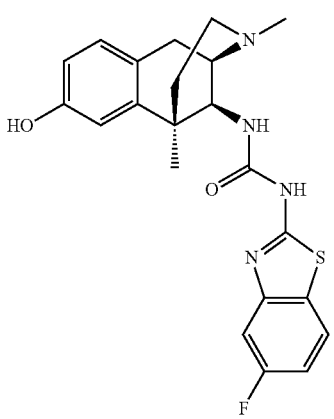

1-(5-Fluorobenzo[d]thiazol-2-yl)-3-((2R,6S,11S)-8-hydroxy-3,6-dimethyl-1,2,3,4,5,6-hexahydro-2,6-methanobenzo[d]azocin-11-yl)urea (Compound 122): LC/MS, m/z=427.0 [M+H]⁺ (Calc: 426.2).

Further, by using suitable benzo[d]imidazole building blocks such as, Compounds A-4 and A-5, the following compounds were also prepared:

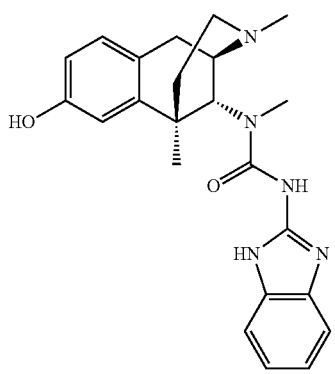

107

3-(1H-benzo[d]imidazol-2-yl)-1-((2R,6S,11R)-8-hydroxy-3,6-dimethyl-1,2,3,4,5,6-hexahydro-2,6-methanobenzo[d]azocin-11-yl)-1-methylurea (Compound 107): LC/MS, m/z=406.2 [M+H]+ (Calc: 405.5);

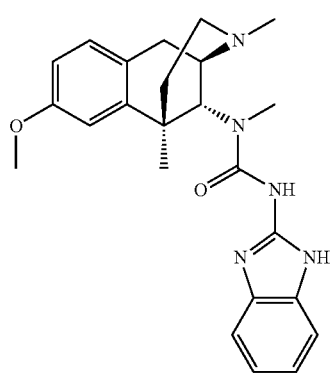

110

3-(1-Ethyl-1H-benzo[d]imidazol-2-yl)-1-((2R,6S,11R)-8-methoxy-3,6-dimethyl-1,2,3,4,5,6-hexahydro-2,6-methanobenzo[d]azocin-11-yl)-1-methylurea (Compound 110): LC/MS, m/z=448.4 [M+H]+ (Calc: 447.3);

111

3-(1H-benzo[d]imidazol-2-yl)-1-((2R,6S,11R)-8-methoxy-3,6-dimethyl-1,2,3,4,5,6-hexahydro-2,6-methanobenzo[d]azocin-11-yl)-1-methylurea (Compound 111): LC/MS, m/z=420.3 [M+H]+ (Calc: 419.2); and

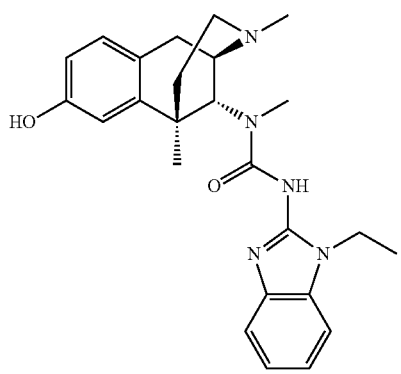

112

3-(1-ethyl-1H-benzo[d]imidazol-2-yl)-1-((2R,6S,11R)-8-hydroxy-3,6-dimethyl-1,2,3,4,5,6-hexahydro-2,6-methanobenzo[d]azocin-11-yl)-1-methylurea (Compound 112): LC/MS, m/z=434.2 [M+H]+ (Calc: 433.3).

The following compound was also prepared using a similar process by using a suitable benzo[d]oxazole building block:

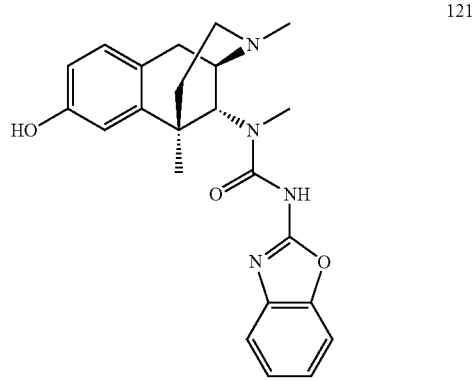

121

3-(Benzo[d]oxazol-2-yl)-1-((2R,6S,11R)-8-hydroxy-3,6-dimethyl-1,2,3,4,5,6-hexahydro-2,6-methanobenzo[d]azocin-11-yl)-1-methylurea (Compound 121): LC/MS, m/z=407.1 [M+H]+ (Calc: 406.2).

Example 20

The following compounds were prepared in a similar manner as described in Example 4 from the appropriate primary amine:

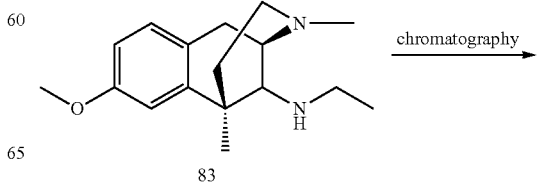

83

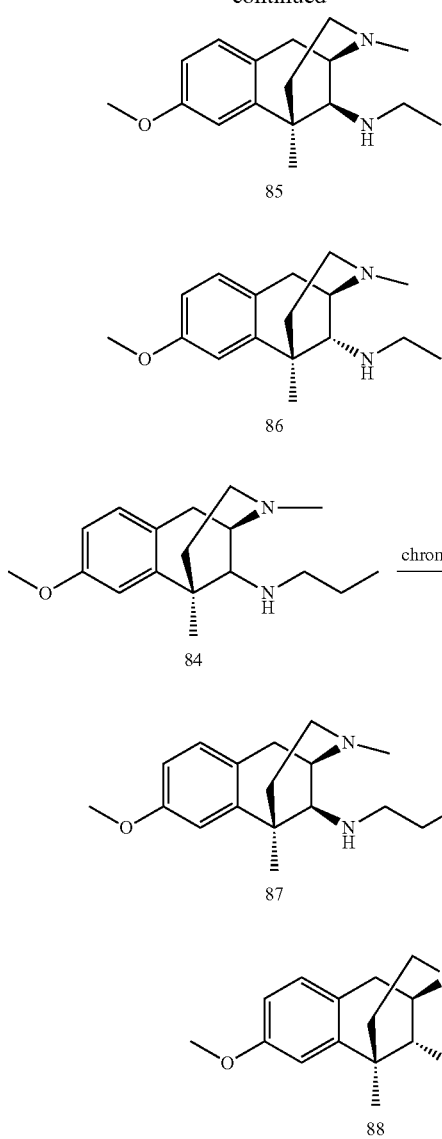

(2R,6S,11S)—N-ethyl-8-methoxy-3,6-dimethyl-1,2,3,4,5,6-hexahydro-2,6-methanobenzo[d]azocin-11-amine (Compound 85): LC/MS, m/z=275.4, [M+H]$^+$ (Calc: 274.4); retention time (0.678 min).

(2R,6S,11R)—N-ethyl-8-methoxy-3,6-dimethyl-1,2,3,4,5,6-hexahydro-2,6-methanobenzo[d]azocin-11-amine (Compound 86): LC/MS, m/z=275.2, [M+H]$^+$ (Calc: 274.4); retention time (0.289 min).

(2R,6S,11S)-8-methoxy-3,6-dimethyl-N-propyl-1,2,3,4,5,6-hexahydro-2,6-methanobenzo[d]azocin-11-amine (Compound 87): LC/MS, m/z=289.2, [M+H]$^+$ (Calc: 288.4); retention time (0.826 min).

(2R,6S,11R)-8-methoxy-3,6-dimethyl-N-propyl-1,2,3,4,5,6-hexahydro-2,6-methanobenzo[d]azocin-11-amine (Compound 88): LC/MS, m/z=289.2, [M+H]$^+$ (Calc: 288.4); retention time (0.401 min).

Example 21

Synthesis of 3-(4-cyanophenyl)-1-ethyl-1-((2R,6S,11R)-8-hydroxy-3,6-dimethyl-1,2,3,4,5,6-hexahydro-2,6-methanobenzo[d]azocin-11-yl)urea (Compound 91)

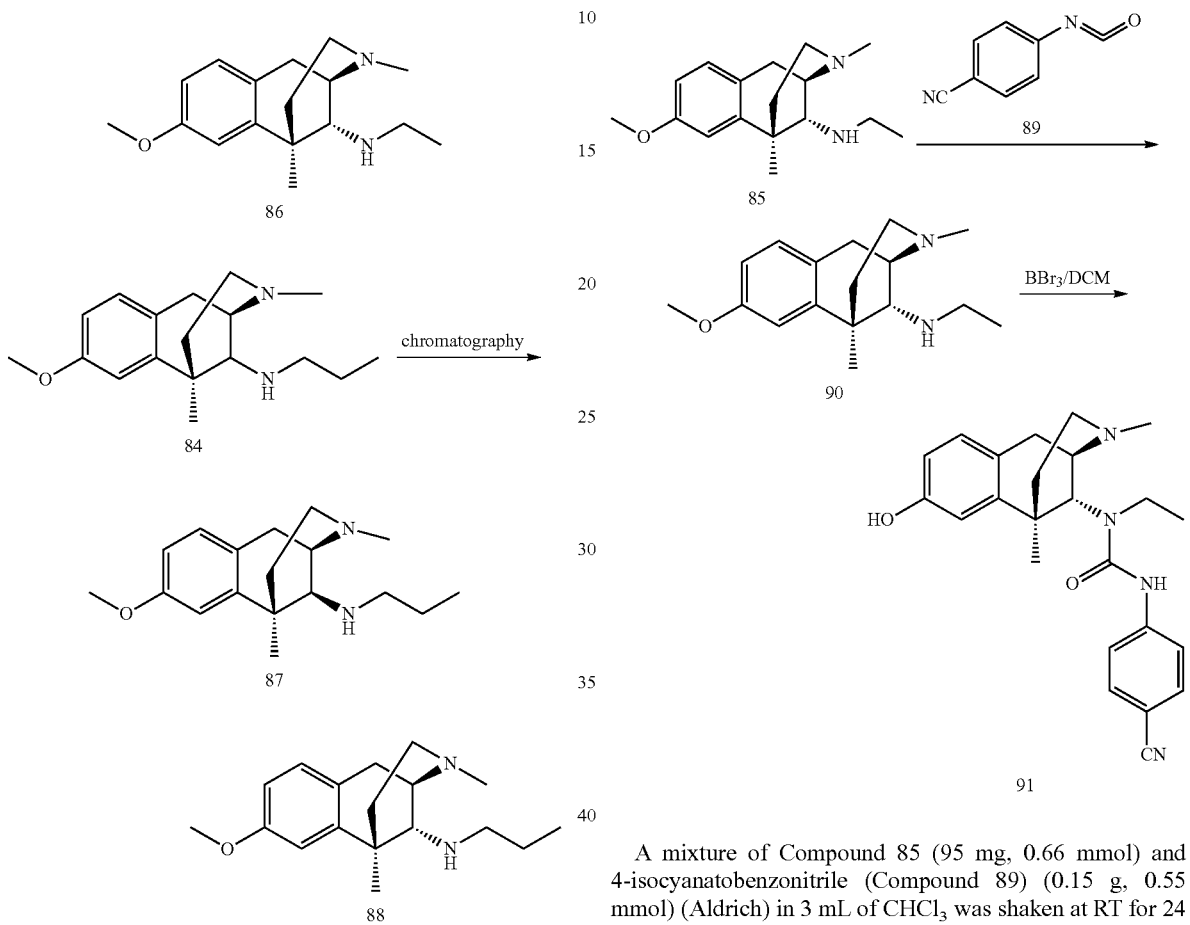

A mixture of Compound 85 (95 mg, 0.66 mmol) and 4-isocyanatobenzonitrile (Compound 89) (0.15 g, 0.55 mmol) (Aldrich) in 3 mL of CHCl$_3$ was shaken at RT for 24 h. The mixture was then warmed to 50° C. and shaken at 50° C. for 2 h. After cooling to RT, the reaction mixture was concentrated under reduced pressure to give crude Compound 90: LC/MS, m/z=275.2, [M+H]$^+$ (Calc: 274.4).

Crude Compound 90 was dissolved in DCM (8 mL), cooled to −78° C., and BBr$_3$ (1N in DCM, 2 mL) was added. After 1 h the reaction mixture was warmed to 0° C. and stirred for 2 h. The reaction was then quenched with water and neutralized with NH$_4$OH to pH~9. The organic layer was cut away, dried over Na$_2$SO$_4$, and evaporated in vacuo.

The residue was purified by flash chromatography (SiO2, DCM/MeOH/NH$_4$OH 10/1/0.1) to give Compound 91 as white solid (60 mg, yield 27%): $^1$H NMR (400 MHz, METHANOL-d4) δ: 6.90 (d, J=8.3 Hz, 1H), 6.65 (d, J=2.5 Hz, 1H), 6.54 (dd, J=8.3, 2.5 Hz, 1H), 4.20 (br. s., 1H), 3.01-3.20 (m, 3H), 2.85-3.00 (m, 1H), 2.73 (dd, J=18.8, 5.8 Hz, 1H), 2.41 (dd, J=12.3, 3.4 Hz, 1H), 2.36 (s, 3H), 2.08 (td, J=12.4, 3.3 Hz, 1H), 1.88 (td, J=12.9, 4.7 Hz, 1H), 1.35 (s, 3H), 1.27-1.34 (m, 1H), 0.91 (t, J=6.9 Hz, 3H). LC/MS, m/z=405.2, [M+H]$^+$ (Calc: 404.5).

In a similar manner, the following compounds were prepared using the appropriate chiral amine from Example 20:

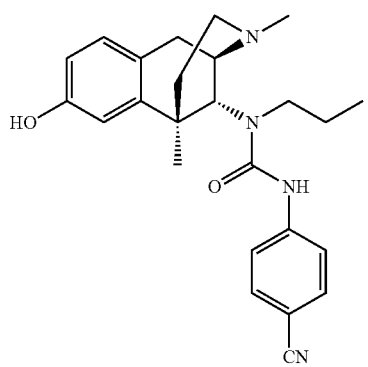

92

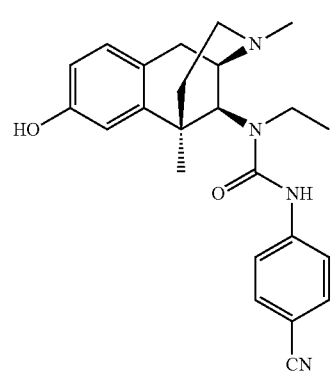

93

3-(4-cyanophenyl)-1-((2R,6S,11R)-8-hydroxy-3,6-dimethyl-1,2,3,4,5,6-hexahydro-2,6-methanobenzo[d]azocin-11-yl)-1-propylurea (Compound 92)

$^1$H NMR (400 MHz, METHANOL-d4) δ: 7.52 (s, 4H), 6.90 (d, J=8.3 Hz, 1H), 6.65 (d, J=2.5 Hz, 1H), 6.55 (dd, J=8.3, 2.5 Hz, 1H), 4.16 (br. s., 1H), 2.95-3.12 (m, 3H), 2.59-2.81 (m, 2H), 2.39 (dd, J=12.2, 3.5 Hz, 1H), 2.34 (s, 3H), 2.08 (td, J=12.4, 3.3 Hz, 1H), 1.87 (td, J=12.8, 4.7 Hz, 1H), 1.47-1.68 (m, 1H), 1.29-1.41 (m, 4H), 1.23 (tdd, J=12.0, 7.5, 4.6 Hz, 1H), 0.42 (t, J=7.4 Hz, 3H). LC/MS, m/z=419.2, [M+H]$^+$ (Calc: 418.5).

3-(4-cyanophenyl)-1-ethyl-1-((2R,6S,11 S)-8-hydroxy-3,6-dimethyl-1,2,3,4,5,6-hexahydro-2,6-methanobenzo[d]azocin-11-yl)urea (Compound 93)

$^1$H NMR (400 MHz, METHANOL-d4) δ: 7.44-7.80 (m, 4H), 6.99 (d, J=8.4 Hz, 1H), 6.71 (d, J=2.5 Hz, 1H), 6.62 (dd, J=8.3, 2.4 Hz, 1H), 4.01 (d, J=4.6 Hz, 1H), 3.75-3.94 (m, 2H), 3.28-3.51 (m, 2H), 3.07-3.19 (m, 2H), 2.85 (s, 3H), 2.69 (td, J=13.0, 3.6 Hz, 1H), 2.37 (td, J=13.8, 4.7 Hz, 1H), 1.45 (s, 3H), 1.39 (d, J=14.4 Hz, 1H), 1.17 (t, J=7.0 Hz, 3H); LC/MS, m/z=405.2, [M+H]$^+$ (Calc: 404.5).

Further, by using starting materials with various R$^4$ groups (which can be prepared in accordance with Scheme G provided above), the following compounds were prepared in a similar manner:

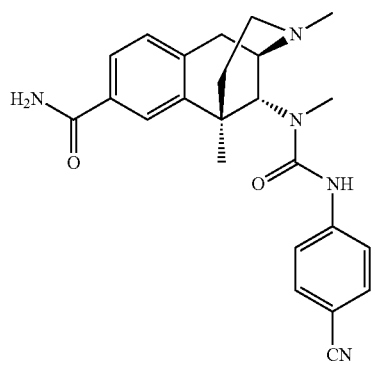

119

(2R,6S,11R)-11-(3-(4-cyanophenyl)-1-methylureido)-3,6-dimethyl-1,2,3,4,5,6-hexahydro-2,6-methanobenzo[d]azocine-8-carboxamide (Compound 119): LC/MS, m/z=418.2, [M+H]$^+$ (Calc: 417.2); and

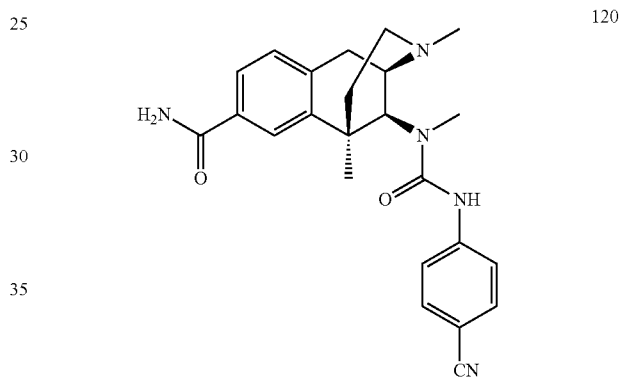

120

(2R,6S,11S)-11-(3-(4-cyanophenyl)-1-methylureido)-3,6-dimethyl-1,2,3,4,5,6-hexahydro-2,6-methanobenzo[d]azocine-8-carboxamide (Compound 120): LC/MS, m/z=418.2, [M+H]$^+$ (Calc: 417.2).

Example 22

Synthesis of N-(tert-butyl)-4-(((((2R,6S,11R)-8-hydroxy-3,6-dimethyl-1,2,3,4,5,6-hexahydro-2,6-methanobenzo[d]azocin-11-yl)(methyl)amino)methyl)piperidine-1-carboxamide (Compound 95)

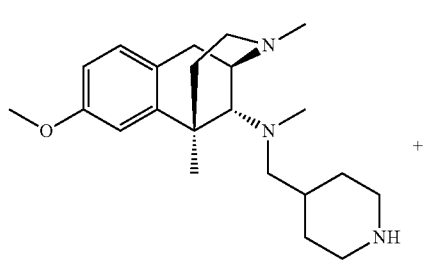

48

-continued

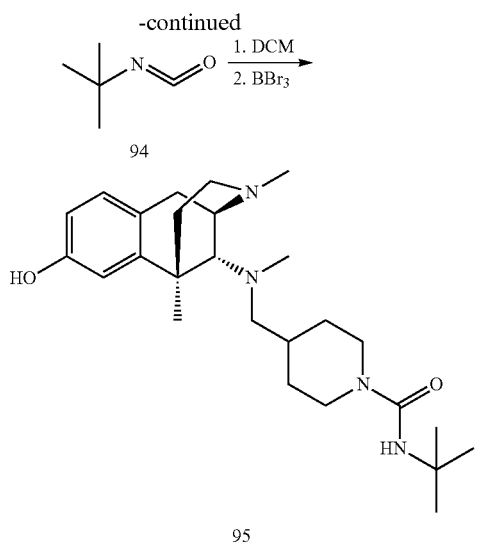

Compound 94 (33 mg, 0.34 mmol) was added to a solution of Compound 48 (0.1 g, 0.28 mmol) in 2 mL CHCl₃ at 0° C. The reaction mixture was shaken first at RT for 2 h and then at 50° C. for 14 h. The reaction mixture was cooled to RT and quenched with 0.5 mL of NH₄OH. The organic layer was cut away and concentrated under reduced pressure. The residue was dissolved in 6 mL of DCM and cooled to −78° C. under argon. A solution of BBr₃ (2 mL, 1 N in DCM) was added, and the mixture was stirred at −78° C. for 1 h. The mixture was then warmed to RT and further stirred for 1 h. The reaction was quenched with water (1 mL) and neutralized with NH₄OH. The aqueous layer was extracted with CHCl₃ (2×4 mL). The combined organic layers were dried over Na₂SO₄ and evaporated in vacuo.

The residue was purified by flash chromatography (SiO2, DCM/MeOH/NH₄OH 10/1/0.1) to give Compound 95 as white solid (20 mg, yield 16%): $^1$H NMR (400 MHz, METHANOL-d4) δ: 6.87 (d, J=8.3 Hz, 1H), 6.66 (d, J=2.4 Hz, 1H), 6.54 (dd, J=8.3, 2.4 Hz, 1H), 3.75-3.91 (m, 2H), 3.57 (br. s., 1H), 3.11 (d, J=19.5 Hz, 1H), 2.74-2.97 (m, 3H), 2.51-2.71 (m, 5H), 2.28-2.49 (m, 3H), 2.03 (s, 3H), 1.85 (td, J=13.5, 4.6 Hz, 1H), 1.51-1.69 (m, 3H), 1.33-1.45 (m, 4H), 1.22 (s, 9H), 0.73-0.99 (m, 2H). LC/MS, m/z=443.4, [M+H]⁺ (Calc: 442.6).

Example 23

Synthesis of (2R,6S,11R)-11-(((1-(2-hydroxy-2-methylpropyl)piperidin-4-yl)methyl)(methyl)amino)-3,6-dimethyl-1,2,3,4,5,6-hexahydro-2,6-methanobenzo[d]azocin-8-ol (Compound 97)

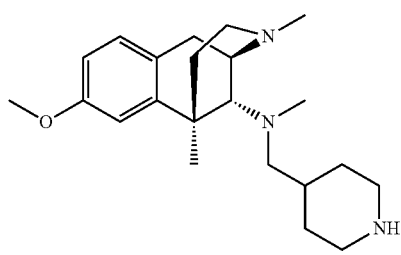

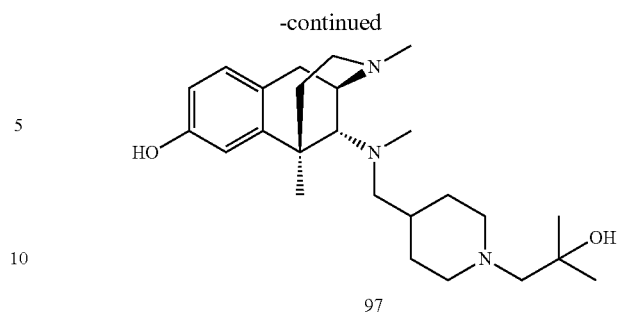

A mixture of Compound 48 (0.1 g, 0.28 mmol), water (10 µL) and Compound 96 (0.5 g, 6.9 mmol) was shaken at 50° C. for 14 h. After cooling to RT, the mixture was diluted with CHCl₃ (10 mL), washed with 0.5 mL of water, and concentrated under reduced pressure. The residue was dissolved in 6 mL of DCM and cooled to −78° C. A solution of BBr₃ (3 mL, 1 N in DCM) was added, and the reaction was stirred at −78° C. for 1 h. The reaction was then warmed to 0° C., stirred for 1 h, quenched with water (1 mL), and neutralized with NH₄OH. The aqueous layer was extracted with CHCl₃ (2×4 mL). The combined organic layers were dried over Na₂SO₄ and evaporated in vacuo.

The residue was purified by flash chromatography (SiO2, DCM/MeOH/NH₄OH 10/1/0.1) to give Compound 97 as white solid (25 mg, yield 20%): $^1$H NMR (400 MHz, METHANOL-d4) δ: 6.79 (d, J=8.3 Hz, 1H), 6.61 (d, J=2.5 Hz, 1H), 6.46 (dd, J=8.3, 2.5 Hz, 1H), 3.11 (dd, J=5.6, 2.3 Hz, 1H), 3.00 (d, J=18.7 Hz, 1H), 2.84 (br. s., 2H), 2.70 (d, J=1.9 Hz, 1H), 2.54 (dd, J=18.6, 6.0 Hz, 1H), 2.25-2.36 (m, 6H), 2.22 (s, 2H), 2.07-2.16 (m, 2H), 1.97-2.06 (m, 4H), 1.74 (td, J=12.8, 4.8 Hz, 1H), 1.57 (d, J=12.9 Hz, 2H), 1.29-1.45 (m, 4H), 1.15-1.25 (m, 1H), 0.98-1.14 (m, 8H). LC/MS, m/z=430.3 [M+H]⁺ (Calc: 429.6).

Example 24

Synthesis of (2R,6S,11R)-11-(ethyl(4-(methylsulfonyl)phenethyl)amino)-3,6-dimethyl-1,2,3,4,5,6-hexahydro-2,6-methanobenzo[d]azocin-8-ol (Compound 98)

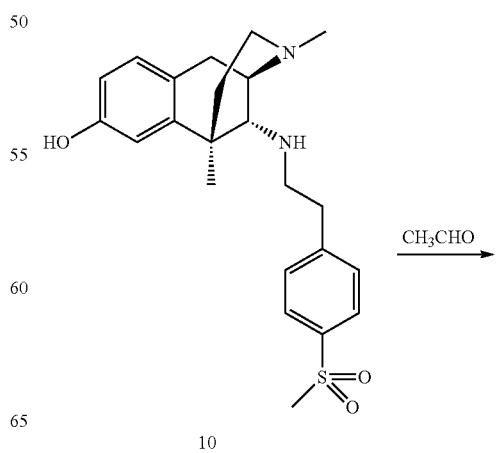

-continued

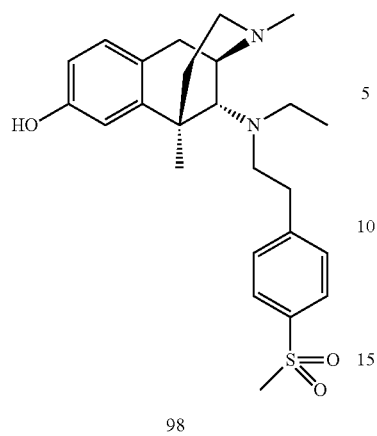

98

To a mixture of Compound 10 (50 mg, 0.12 mmol) in 2 mL CHCl$_3$ was added acetaldehyde (53 mg, 1.2 mmol). The mixture was shaken at RT for 20 min, and NaBH(OAc)$_3$ was then added. The reaction mixture was shaken at RT for 16 h, quenched with water, and purified by reverse-phase prep HPLC (C18, 0-100% 0.1% TFA in water/0.1% TFA in ACN) to give Compound 98 as a white solid (TFA-salt, 65 mg, yield 80%): $^1$H NMR (400 MHz, METHANOL-d4) δ: 7.68 (d, J=8.3 Hz, 2H), 7.07 (d, J=8.3 Hz, 2H), 6.89 (d, J=8.1 Hz, 1H), 6.57-6.68 (m, 2H), 3.68 (br. s., 1H), 2.92-3.14 (m, 6H), 2.79-2.92 (m, 4H), 2.50-2.78 (m, 7H), 1.89 (br. s., 1H), 1.47 (d, J=13.7 Hz, 1H), 1.28 (s, 3H), 0.96 (t, J=7.0 Hz, 3H). LC/MS, m/z=443.2 [M+H]$^+$ (Calc: 442.6).

Example 25

Synthesis of N-((2R,6S,11R)-8-hydroxy-3,6-dimethyl-1,2,3,4,5,6-hexahydro-2,6-methanobenzo[d]azocin-11-yl)-N-methyl-1-phenylmethane-sulfonamide (Compound 100)

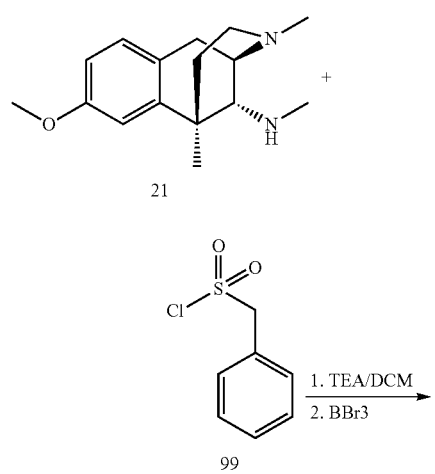

-continued

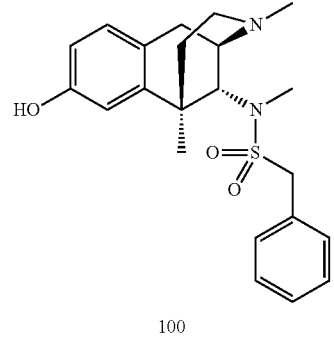

100

To a solution of Compound 21 (0.1 g, 0.38 mmol) in 4 mL DCM at −30° C. was added Compound 99 (110 mg, 0.58 mmol) and TEA (80 mg, 0.78 mmol). The mixture was warmed to RT and shaken at RT for 24 h. The reaction was quenched with water, extracted with CHCl$_3$, and concentrated under reduced pressure. The residue was dissolved in 6 mL of DCM and cooled to −78° C. under an atmosphere of argon. A solution of BBr$_3$ (1N in DCM, 2 mL) was added and the mixture was stirred at −78° C. for 1 h. The mixture was then warmed 0° C. and further stirred for 1 h. The reaction was quenched with water and neutralized to pH~9 with NH$_4$OH. The organic layer was cut away, dried over Na$_2$SO$_4$ and evaporated in vacuo.

The residue was purified by flash chromatography (SiO2, DCM/MeOH/NH$_4$OH 10/1/0.1) to give Compound 100 as white solid: $^1$H NMR (400 MHz, METHANOL-d4) δ: 7.22-7.61 (m, 5H), 6.93 (d, J=8.3 Hz, 1H), 6.71 (d, J=2.5 Hz, 1H), 6.61 (dd, J=8.3, 2.5 Hz, 1H), 4.30-4.54 (m, 2H), 4.00 (d, J=2.6 Hz, 1H), 2.99 (d, J=18.8 Hz, 1H), 2.59 (dd, J=18.8, 5.9 Hz, 1H), 2.54 (s, 3H), 2.27-2.36 (m, 2H), 2.23 (s, 3H), 2.04 (td, J=12.4, 3.3 Hz, 1H), 1.85 (td, J=12.8, 4.8 Hz, 1H), 1.40 (s, 3H), 1.33 (dd, J=13.0, 1.3 Hz, 1H). LC/MS, m/z=401.2, [M+H]$^+$ (Calc: 400.5).

In a similar manner, the following compounds were prepared using the appropriate chiral amine Compound 23:

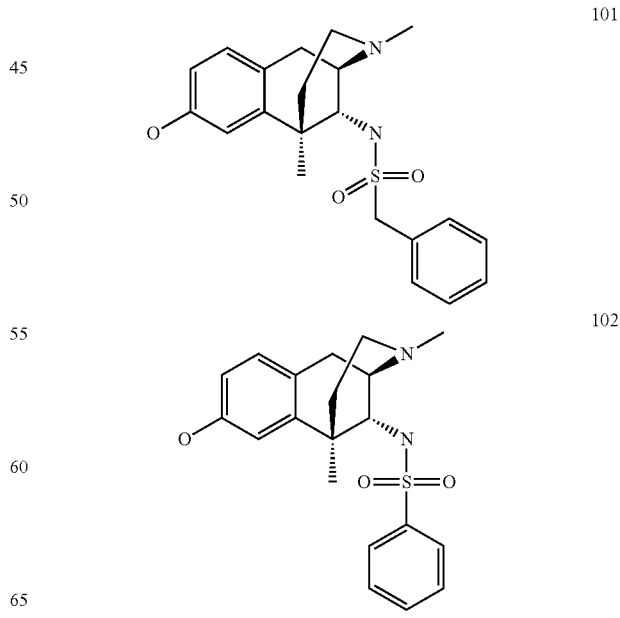

N-((2R,6S,11R)-8-hydroxy-3,6-dimethyl-1,2,3,4,5,6-hexahydro-2,6-methanobenzo[d]azocin-11-yl)benzenesulfonamide (Compound 102)

1H NMR (METHANOL-d4) δ: 7.74-7.89 (m, 2H), 7.34-7.63 (m, 3H), 6.85 (d, J=8.1 Hz, 1H), 6.43-6.59 (m, 2H), 3.28 (d, J=3.6 Hz, 1H), 2.91 (t, J=4.5 Hz, 1H), 2.80-2.87 (m, 1H), 2.63-2.77 (m, 1H), 2.15-2.29 (m, 4H), 1.84-2.00 (m, 1H), 1.61 (td, J=12.9, 4.7 Hz, 1H), 1.17-1.29 (m, 1H), 0.95 (s, 3H). LC/MS, m/z=373.0, [M+H]+(Calc: 372.5).

Example 26

Synthesis of ((2R,6S,11S)-8-hydroxy-3,6-dimethyl-1,2,3,4,5,6-hexahydro-2,6-methanobenzo[d]azocin-11-yl)(piperidin-1-yl)methanone (Compound 106)

flash chromatography (DCM to DCM/MeOH/NH$_4$OH 10/0.1/0.01 1/1) to give Compound 105 as white solid (0.35 g, Yield 31%): $^1$H NMR (400 MHz, METHANOL-d$_4$) δ: 7.03 (d, J=8.4 Hz, 1H), 6.86 (d, J=2.4 Hz, 1H), 6.74 (dd, J=8.4, 2.6 Hz, 1H), 3.92 (dd, J=5.2, 3.2 Hz, 1H), 3.77 (s, 3H), 3.24-3.32 (m, 1H), 3.08 (d, J=18.9 Hz, 1H), 2.97 (dd, J=12.9, 3.9 Hz, 1H), 2.85 (s, 3H), 2.78 (d, J=2.2 Hz, 1H), 2.62 (td, J=13.2, 3.5 Hz, 1H), 1.92 (td, J=13.8, 4.5 Hz, 1H), 1.64 (s, 3H), 1.43 (dd, J=14.2, 1.7 Hz, 1H). LC/MS, m/z=276.0, [M+H]+(Calc: 275.3).

DIEPA (0.12 mL, 0.72 mmol) was added to a solution of Compound 105 (0.1 g, 0.36 mmol), piperidine (62 mg, 0.72 mmol) and HATU (0.28 g, 0.7 mmol) in 4 mL DMF at RT. The mixture was shaken at RT for 24 h, quenched with water (2 mL), extracted with EtOAc (10 mL), and concentrated under reduced pressure to give a brown oil. This brown oil

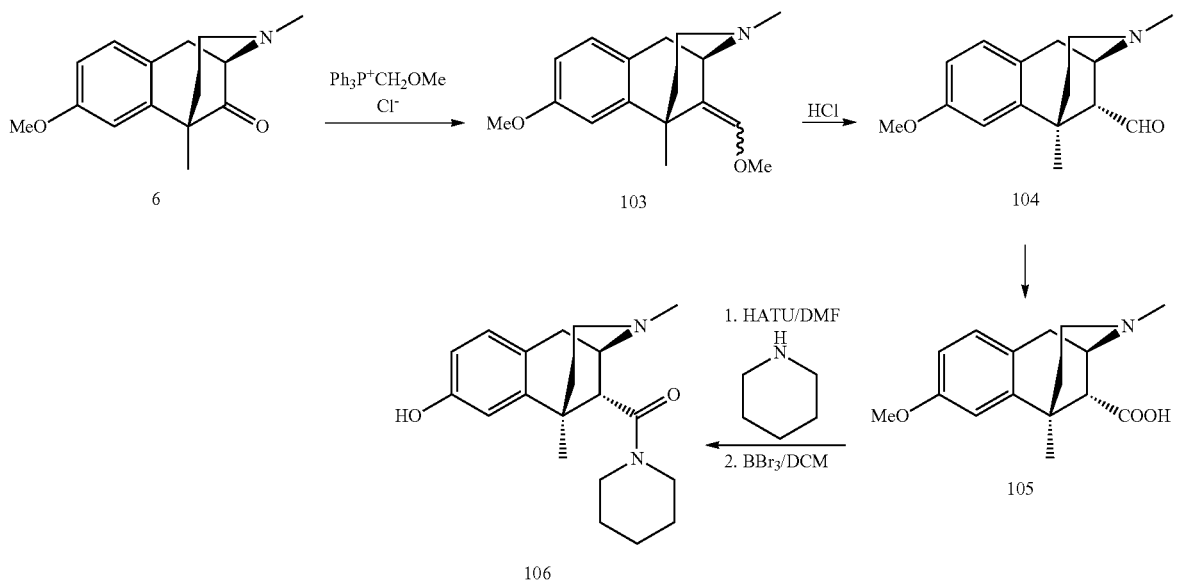

To a solution of Compound 6 (1 g, 4 mmol) and (methoxymethyl)triphenylphosphonium chloride (1.7 g, 5 mmol) (Aldrich) in 10 mL of THF at RT was added t-BuOk (1M in THF, 5 mL). The reaction mixture was stirred at RT for 16 h. After aqueous work-up, the resulting mixture was extracted with EtOAc, and purified by flash chromatography (SiO2, 3% MeOH/DCM) to give Compound 103 as a yellow oil: LC/MS, m/z=274.2 [M+H]$^+$ (Calc: 273.4).

Compound 103 was dissolved in THF (30 mL) and HCl (3N aq, 30 mL). The mixture was shaken under nitrogen at 50° C. for 24 h. After cooling to 0° C., the reaction mixture was diluted with EtOAc (15 mL) and neutralized with saturated NaOH (6N aqu) to pH ~10. The organic layer was concentrated to give crude Compound 104: LC/MS, m/z=260.4 [M+H]$^+$ (Calc: 259.3).

Crude Compound 104 was dissolved in water (12 mL), t-BuOH (50 mL), NaH$_2$PO$_4$ (1.8 g) and cyclohexene (10 mL) at RT. To this mixture was added NaClO$_2$ (0.75 g). The mixture was stirred at RT for 1 h. The mixture was then cooled with ice-water, and NH$_4$OH (1 mL), NaCl (20 g), and EtOAc (100 mL) was added. The organic layer was cut away, concentrated under reduced pressure, and purified by was dissolved in 8 mL of DCM, cooled to −78° C., and BBr$_3$ (1N in DCM, 2 mL) was added. The mixture was stirred at −78° C. for 1 h, 0° C. for 1 h, and finally RT 2 h. The reaction was quenched with water (1 mL) at 0° C. After stirring for 30 min, the mixture was neutralized with NH$_4$OH to pH~9. The organic layer was cut away, dried over Na$_2$SO$_4$, and purified by reverse-phase prep HPLC (C18, 0-100% 0.1% TFA in water/0.1% TFA in ACN) to give Compound 106 (20 mg, yield 15%): $^1$H NMR (400 MHz, TFA-SALT, METHANOL-d$_4$) δ: 6.87 (d, J=8.3 Hz, 1H), 6.66 (d, J=2.4 Hz, 1H), 6.52 (dd, J=8.3, 2.4 Hz, 1H), 3.77 (br. s., 1H), 3.43-3.67 (m, 3H), 3.11 (d, J=19.1 Hz, 3H), 2.98 (d, J=5.6 Hz, 1H), 2.89 (s, 3H), 2.66 (d, J=3.2 Hz, 1H), 1.91 (td, J=13.9, 4.5 Hz, 1H), 1.29-1.68 (m, 11H). LC/MS, m/z=329.4, [M+H]$^+$ (Calc: 328.4).

Example 27

The following compounds were prepared in similar manners as those above delineated (including such as, Scheme G) and conventional synthetic methods (such as, those described in WO2014072809)

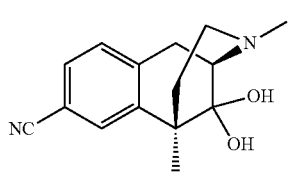

(2R,6S)-11,11-dihydroxy-3,6-dimethyl-1,2,3,4,5,6-hexahydro-2,6-methanobenzo[d]azocine-8-carbonitrile (Compound 116): LC/MS, m/z=259.2, [M+H]$^+$ (Calc: 258.1);

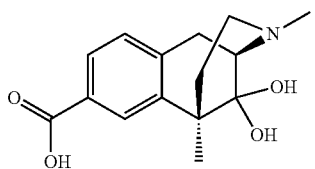

(2R,6S)-11,11-dihydroxy-3,6-dimethyl-1,2,3,4,5,6-hexahydro-2,6-methanobenzo[d]azocine-8-carboxylic acid (Compound 117): LC/MS, m/z=278.1, [M+H]$^+$ (Calc: 277.1); and

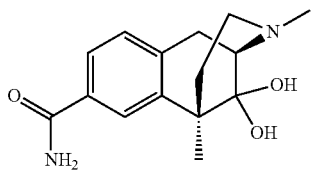

(2R,6S)-11,11-dihydroxy-3,6-dimethyl-1,2,3,4,5,6-hexahydro-2,6-methanobenzo[d]azocine-8-carboxamide (Compound 118): LC/MS, m/z=278277.2, [M+H]$^+$ (Calc: 276.2).

Example 28

The following Tables provide the results on the efficacy of binding and activity response of certain exemplified Compounds of the Invention at the ORL1, μ, and κ-opioid receptors.

In TABLE 3, binding affinity of certain Compounds of the Invention to the ORL-1, μ-, and κ-opioid receptors was determined as described above in HEK-293 or CHO cells.

In TABLE 4, activity response of certain Compounds of the Invention to the μ- and κ-opioid receptors was determined as described above for functional assays using HEK-293 or CHO cells.

In TABLE 5, activity response of certain Compounds of the Invention to the μ- and κ-opioid receptors was determined as described above for functional assays using U-2 OS cells.

TABLE 3

Binding Affinity of Exemplified Compounds of the Invention

| | Ki (nM) Opioid Receptor | |
|---|---|---|
| Cpd. No. | μ | κ |
| 10 | | 301.1 ± 9.79 |
| 55 | | >20 uM |
| 97 | | 2.12 ± 0.55 |

TABLE 4

Activity Response of Exemplified Compounds of the Invention in HEK-293 or CHO Cells

| | GTPγS (EC$_{50}$: nM, E$_{max}$: %) | | | |
|---|---|---|---|---|
| | μ | | κ | |
| Cpd No. | EC$_{50}$ | E$_{max}$ | EC$_{50}$ | E$_{max}$ |
| 10 | 224.9 ± 60.8 | 38.5 ± 2.33 | >20 uM | 1.00 |
| 11 | 35.6 ± 5.9 | 16.7 ± 0.33 | | |
| 12 | 222.8 ± 29.8 | 47.7 ± 4.84 | | |
| 13 | 1068 ± 172 | 45.7 ± 1.76 | | |
| 14 | 8694 ± 2274 | 15 ± 1.58 | | |
| 15 | 124.5 ± 20.4 | 97.7 ± 1.76 | | |
| 16 | 1269 ± 90.1 | 77.3 ± 3.84 | | |
| 17 | 92.9 ± 0.79 | 55.3 ± 4.1 | | |
| 18 | 124.3 ± 18.3 | 48.4 ± 3.28 | | |
| 19 | >20 uM | 0 | | |
| 26 | 3.97 ± 0.25 | 76.7 ± 2.73 | | |
| 27 | >20uM | 0 | | |
| 28 | 182.4 ± 12 | 84.7 ± 1.2 | | |
| 29 | >20 uM | 1 | | |
| 30 | >20 uM | 2.67 ± 3.67 | | |
| 31 | >20 uM | 1 | | |
| 32 | >20 uM | 2.33 ± 0.88 | | |
| 33 | 5281 ± 1258 | 13 ± 0 | | |
| 34 | >20 uM | 2.67 ± 0.33 | | |
| 35 | >20 uM | 2 ± 0.41 | | |
| 41 | >20 uM | 5.33 ± 1.45 | | |
| 44 | >20 uM | 43 ± 2.52 | | |
| 52 | 1.22 ± 0.2 | 31.3 ± 0.88 | | |
| 54 | 5.44 ± 2.35 | 74 ± 3.15 | | |
| 55 | 3.28 ± 0.39 | 52 ± 4.85 | | |
| 56 | 96.7 ± 9.87 | 62 ± 1.53 | | |
| 57 | 90.5 ± 18.1 | 43 ± 1.53 | | |
| 58 | 13.2 ± 0.71 | 58 ± 7.55 | | |
| 59 | 52.8 ± 5 | 27 ± 1.53 | | |
| 60 | 12 ± 1.74 | 22.3 ± 2.34 | | |
| 65 | 853.5 ± 65.3 | 34.9 ± 1.2 | | |
| 72 | 337.6 ± 60.9 | 100.8 ± 2.91 | | |
| 73 | 57.2 ± 12.7 | 68.8 ± 1.77 | | |
| 74 | 1.12 ± 0.17 | 83.2 ± 3.47 | | |
| 77 | 7.96 ± 0.69 | 87 ± 1.73 | | |
| 81 | >20 uM | −1 | | |
| 82 | >20 uM | 1 | | |
| 91 | 46.3 ± 4.1 | 75.3 ± 2.19 | | |
| 92 | 96.4 ± 3.52 | 43.8 ± 1.03 | | |
| 93 | 2286 ± 404 | 32 ± 2.48 | | |
| 95 | 8 ± 1.64 | 17.7 ± 2.6 | | |
| 97 | 22.6 ± 2.34 | 47 ± 1.53 | | |
| 98 | 0.64 ± 0.082 | 44.6 ± 0.6 | | |
| 100 | 8948 ± 2043 | 25 ± 1.53 | | |
| 101 | >20 uM | 6 ± 4.06 | | |
| 102 | >20 uM | −1 | | |
| 106 | 4094 ± 333.6 | 49 ± 1.73 | | |
| 107 | 6.81 ± 2.86 | 30.6 ± 1.51 | | |
| 108 | 11708 ± 3287 | 17.1 ± 0.67 | | |
| 109 | 649.2 ± 113.7 | 59.6 ± 2.50 | | |
| 110 | 851.5 ± 161.3 | 89.2 ± 6.05 | | |
| 111 | 790.3 ± 98.5 | 67.4 ± 3.48 | | |
| 112 | 14.1 ± 0.52 | 84.2 ± 0.94 | | |
| 113 | 11740 ± 2809 | 10.3 ± 1.10 | | |
| 114 | 8620 ± 750.9 | 71.0 ± 2.18 | | |

TABLE 4-continued

Activity Response of Exemplified Compounds of the Invention in HEK-293 or CHO Cells

| | GTPγS ($EC_{50}$: nM, $E_{max}$: %) | | | |
|---|---|---|---|---|
| | μ | | κ | |
| Cpd No. | $EC_{50}$ | $E_{max}$ | $EC_{50}$ | $E_{max}$ |
| 115 | 524.8 ± 26.3 | 83.4 ± 1.58 | | |
| 116 | >20 uM | 0.00 | | |
| 117 | >20 uM | 0.00 | | |
| 118 | 17010 ± 565.7 | 6.56 ± 0.60 | | |
| 119 | 4952 ± 508.4 | 43.9 ± 1.88 | | |
| 120 | >20 uM | −0.33 ± 0.67 | | |
| 121 | 82.4 ± 10.4 | 60.1 ± 4.74 | | |
| 122 | 374.5 ± 105.5 | 13.6 ± 1.14 | | |
| 123 | 23.3 ± 4.47 | 97.4 ± 0.20 | | |
| 124 | 3541 ± 479.8 | 81.6 ± 3.37 | | |
| 125 | >20 uM | 0.00 | | |
| 126 | >20 uM | 18.4 ± 0.30 | | |

TABLE 5

Activity Response of Exemplified Compounds of the Invention in U-2 OS Cells

| | GTPγS ($EC_{50}$: nM, $E_{max}$: %) | | | |
|---|---|---|---|---|
| Ref. | μ | | κ | |
| No. | $EC_{50}$ | $E_{max}$ | $EC_{50}$ | $E_{max}$ |
| 12 | 33.6 ± 1.43 | 100.3 ± 1.67 | 136.7 ± 20.1 | 54 ± 5.92 |
| 26 | 0.33 ± 0.025 | 107 ± 3.06 | 54.3 ± 9.45 | 81.7 ± 10.7 |
| 40 | 538.7 ± 62.8 | 18.7 ± 0.67 | 10946 ± 1408 | 45.2 ± 4.82 |

The in vitro test results of Tables 3 to 5 show that representative Compounds of the Invention generally have good binding affinity for opioid receptors, and that these compounds activate these receptors as partial to full agonists. Compounds of the Invention are therefore expected to be useful to treat Conditions, particularly pain, that are responsive to the activation of one or more opioid receptors.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed is:

1. A compound of Formula C, or a pharmaceutically acceptable salt thereof:

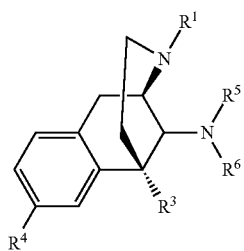

C wherein
$R^1$ is ($C_1$-$C_{10}$)alkyl;
$R^3$ is —($C_1$-$C_6$)alkyl;
$R^4$ is selected from —OH, —CN, —COOH, —CONH$_2$, and —($C_1$-$C_5$)alkoxy;
$R^5$ is selected from the group consisting of
  i) —($C_1$-$C_6$)alkyl optionally substituted by one, two, or three substituents independently selected from the group consisting of —OH; —CONR$^8$R$^9$; —NR$^8$R$^9$, —OR$^{12}$; —($C_3$-$C_{12}$)cycloalkyl; -(6- to 14-membered)aryl optionally substituted by —SO$_2$—($C_1$-$C_6$)alkyl; and hydroxy($C_3$-$C_{12}$)cycloalkyl-;
  ii) —C(=O)—($C_1$-$C_6$)alkyl or —C(=O)—($C_1$-$C_5$)alkyl-(6- to 14-membered)aryl, each optionally substituted by -(3- to 12-membered)heterocycle, —SO$_2$—($C_1$-$C_6$)alkyl, or —CONR$^8$R$^9$;
  iii) ((6- to 14-membered)aryl)-($C_1$-$C_6$)alkyl- optionally substituted with 1 or 2 substituents independently selected from the group of halo, —C(halo)$_3$, CN, and —SO$_2$—($C_1$-$C_6$)alkyl;
  iv) ((3- to 12 membered)heterocycle)-($C_1$-$C_6$)alkyl- optionally substituted with 1 or 2 substituents independently selected from the group of —C(=O)—($C_1$-$C_6$)alkyl, —SO$_2$—($C_1$-$C_6$)alkyl, —CONR$^8$R$^9$, hydroxy($C_1$-$C_6$)alkyl-, —SO$_2$—($C_1$-$C_6$)alkyl-phenyl, and —SO$_2$—(($C_3$-$C_{12}$)cycloalkyl);
  v) —CONR$^8$R$^9$;
  vi) —SO$_2$—($C_1$-$C_6$)alkyl optionally substituted by -(6- to 14-membered)aryl;
  vii) —SO$_2$-((6- to 14-membered)aryl); and
  viii) —C(=O)—($C_2$-$C_6$)alkenyl substituted by -(5- to 12-membered)heteroaryl;
$R^6$ is selected from the group consisting of H, —($C_1$-$C_6$)alkyl, —($C_1$-$C_6$)alkyl-CO—OR$^{10}$, —($C_1$-$C_6$)alkyl-OR$^{10}$, and —($C_1$-$C_6$)alkyl-CONR$^8$R$^9$;
$R^8$ and $R^9$ are each independently selected from the group consisting of hydrogen; —COOR$^{10}$; —($C_1$-$C_6$)alkyl-COOR$^{10}$; —CONH$_2$; ($C_1$-$C_6$)alkyl-CONH—; ((6- to 14-membered)aryl) optionally substituted with 1, 2, or 3 independently selected R$^b$ groups; and -((5- to 12-membered)heteroaryl) optionally substituted with 1 or 2 independently selected R$^b$ groups;
each R$^{10}$ is independently hydrogen or —($C_1$-$C_6$)alkyl
each R$^{12}$ is independently (6- to 14-membered)aryl, ((6- to 14-membered)aryl)-($C_1$-$C_6$)alkyl-, (5- to 12-membered)heteroaryl, or ((5- to 12-membered)heteroaryl)-($C_1$-$C_6$)alkyl-;
each R$^b$ is independently selected from the group consisting of —C(halo)$_3$, —CH(halo)$_2$, —CH$_2$(halo), halo, —($C_1$-$C_6$)alkyl, and CN;
Provided that
  i) when $R^1$ is methyl, and $R^5$ is ((3- to 12 membered)-heterocycle)-($C_1$-$C_6$)alkyl-, then
    the ((3- to 12 membered)heterocycle) moiety in said ((3- to 12 membered)heterocycle)-($C_1$-$C_6$)alkyl- of $R^5$ is further substituted by a substituent selected from the group consisting of —SO$_2$—($C_1$-$C_6$)alkyl, —CONR$^8$R$^9$, hydroxy($C_1$-$C_6$)alkyl-, —C(=O)—($C_1$-$C_6$)alkyl, and —SO$_2$—(($C_3$-$C_{12}$)cycloalkyl);
  ii) when both of $R^1$ and $R^3$ are methyl, and $R^4$ is methoxy, then
    $R^6$ is —($C_1$-$C_6$)alkyl, and $R^5$ is —C(=O)—($C_1$-$C_6$)alkyl substituted by -(3- to 12-membered)heterocycle; and
  iii) when $R^1$ is methyl, $R^6$ is H or —($C_1$-$C_6$)alkyl, and $R^5$ is optionally-substituted —CONR$^8$R$^9$, then
    $R^3$ is methyl, $R^4$ is —OH, and $R^5$ is selected from the group consisting of

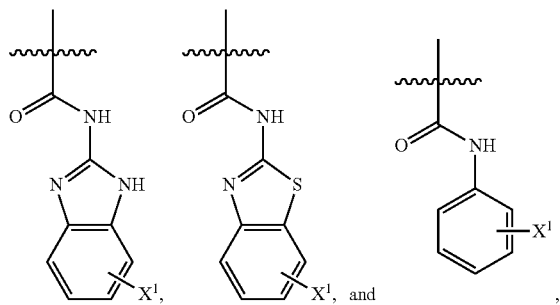

wherein $X^1$ is H, halo, or CN;

iv) when $R^1$ is methyl, and $R^5$ is selected from the group consisting of a) —($C_1$-$C_6$)alkyl substituted by -(6- to 14-membered)aryl; and b) ((6- to 14-membered)aryl)-($C_1$-$C_6$)alkyl- optionally substituted by one or two halos, then
$R^6$ is a group other than H; and v) when $R^5$ is —C(=O)—($C_2$-$C_6$)alkenyl substituted by -(5- to 12-membered)heteroaryl, then
$R^4$ is —OH; and $R^6$ is H;

and further provided that
said compound is not selected from the group consisting of N-((2R,6R,11S)-8-hydroxy-3,6-dimethyl-1,2,3,4,5,6-hexahydro-2,6-methanobenzo[d]azocin-11-yl)-N-methyl-2-(4-(methylsulfonyl)phenyl)acetamide;

(2R,6R,11S)-3,6-dimethyl-11-(methyl(phenethyl) amino)-1,2,3,4,5,6-hexahydro-2,6-methanobenzo[d]azocin-8-ol;

N-((2R,6S,11S)-8-hydroxy-3,6-dimethyl-1,2,3,4,5,6-hexahydro-2,6-methanobenzo[d]azocin-11-yl)-N-methyl-2-phenylacetamide;

N-((2R,6S,11R)-8-hydroxy-3,6-dimethyl-1,2,3,4,5,6-hexahydro-2,6-methanobenzo[d]azocin-11-yl)-N-methyl-2-phenylacetamide;

tert-butyl (3-(((2R,6S,11S)-8-hydroxy-3,6-dimethyl-1,2,3,4,5,6-hexahydro-2,6-methanobenzo[d]azocin-11-yl) amino)propyl)carbamate;

N-((2R,6S,11R)-8-hydroxy-3,6-dimethyl-1,2,3,4,5,6-hexahydro-2,6-methanobenzo[d]azocin-11-yl)-N,4-dimethylpentanamide;

tert-butyl (2-(((2R,6S,11S)-8-hydroxy-3,6-dimethyl-1,2,3,4,5,6-hexahydro-2,6-methanobenzo[d]azocin-11-yl) amino)ethyl)carbamate;

3-(5-fluorobenzo[d]thiazol-2-yl)-1-((2R,6S,11R)-8-hydroxy-3,6-dimethyl-1,2,3,4,5,6-hexahydro-2,6-methanobenzo[d]azocin-11-yl)-1-methylurea; and 1-(5-fluorobenzo[d]thiazol-2-yl)-3-((2R,6S,11R)-8-hydroxy-3,6-dimethyl-1,2,3,4,5,6-hexahydro-2,6-methanobenzo[d]azocin-11-yl)urea.

2. The compound of claim 1, wherein $R^5$ is —($C_1$-$C_6$) alkyl optionally substituted by one, two, or three substituents independently selected from the group consisting of —OH, —CONR$^8$R$^9$, —NR$^8$R$^9$, —OR$^{12}$, —($C_3$-$C_{12}$)cycloalkyl, -(6- to 14-membered)aryl, and hydroxy($C_3$-$C_{12}$)cycloalkyl-.

3. The compound of claim 1, wherein $R^5$ is —C(=O)— ($C_1$-$C_6$)alkyl optionally substituted by -(3- to 12-membered) heterocycle or —CONR$^8$R$^9$, wherein one of R$^8$ and R$^9$ is H, and the other is ((6- to 14-membered)aryl) optionally substituted with 1 or 2 independently selected R$^b$ groups, or -((5- to 12-membered)heteroaryl) optionally substituted with 1 or 2 independently selected R$^b$ groups, and wherein R$^b$ each independently is halo or —C(halo)$_3$.

4. The compound of claim 1, wherein $R^5$ is ((6- to 14-membered)aryl)-($C_1$-$C_6$)alkyl- optionally substituted with 1 or 2 substituents independently selected from the group of halo, —C(halo)$_3$, CN, and —SO$_2$—($C_1$-$C_6$)alkyl.

5. The compound of claim 1, wherein $R^5$ is ((3- to 12 membered)-heterocycle)-($C_1$-$C_6$)alkyl- optionally substituted with 1 or 2 substituents independently selected from the group of —C(=O)—($C_1$-$C_6$)alkyl, —SO$_2$—($C_1$-$C_6$) alkyl, —CONR$^8$R$^9$, hydroxy($C_1$-$C_6$)alkyl-, —SO$_2$—($C_1$-$C_6$)alkyl-phenyl, and —SO$_2$—(($C_3$-$C_{12}$)cycloalkyl), wherein one of R$^8$ and R$^9$ is H, and the other is —($C_1$-$C_6$) alkyl.

6. The compound of claim 1, wherein $R^5$ is —CONR$^8$R$^9$, wherein one of said R$^8$ and said R$^9$ is H, and the other is phenyl or benzo[d]thiazolyl, wherein each of said phenyl and said benzo[d]thiazolyl is optionally substituted with 1 or 2 R$^b$ groups independently selected from the group of CN, halo, and —C(halo)$_3$.

7. The compound of claim 1, wherein $R^5$ is —C(=O)— ($C_2$-$C_6$)alkenyl substituted by -(5- to 12-membered)heteroaryl.

8. The compound of claim 1, wherein $R^6$ is H, —($C_1$-$C_6$) alkyl, —CH$_2$—COOH, —CH$_2$CH$_2$OH, or —CH$_2$CONH$_2$.

9. The compound of claim 1, wherein $R^1$ is ($C_1$-$C_3$)alkyl.

10. The compound of claim 1, wherein $R^4$ is OH or —($C_1$-$C_3$)alkoxy.

11. A compound of Formula H, or a pharmaceutically acceptable salt thereof:

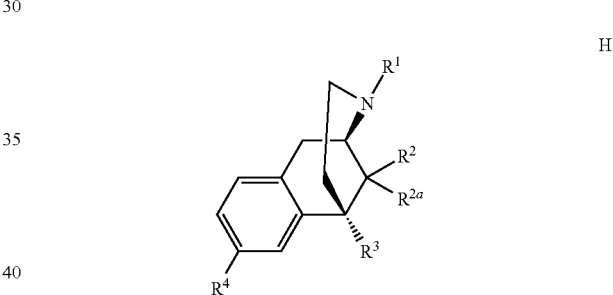

wherein
$R^1$ is ($C_1$-$C_6$)alkyl;
$R^2$ is —OH or ($C_1$-$C_6$)alkoxy;
$R^{2a}$ is —OH or ($C_1$-$C_6$)alkoxy;
$R^3$ is —($C_1$-$C_6$)alkyl; and
$R^4$ is —CN, —COOH, or —CONH$_2$.

12. A compound selected from the group consisting of:
(2R,6S,11R)-3,6-dimethyl-11-((4-(methylsulfonyl)-phenethyl)amino)-1,2,3,4,5,6-hexahydro-2,6-methanobenzo[d]azocin-8-ol (Compound 10);
(2R,6S,11S)-3,6-dimethyl-11-((4-(methylsulfonyl)phenethyl)-amino)-1,2,3,4,5,6-hexahydro-2,6-methanobenzo[d]azocin-8-ol (Compound 11);
(2R,6S,11S)-11-((2-(1-hydroxycyclohexyl)ethyl)amino)-3,6-dimethyl-1,2,3,4,5,6-hexahydro-2,6-methanobenzo[d]azocin-8-ol (Compound 12);
(2R,6S,11S)-11-(((1-hydroxycyclohexyl)methyl)amino)-3,6-dimethyl-1,2,3,4,5,6-hexahydro-2,6-methanobenzo[d]azocin-8-ol (Compound 13);
(2R,6S,11R)-11-(((1-hydroxycyclohexyl)methyl)amino)-3,6-dimethyl-1,2,3,4,5,6-hexahydro-2,6-methanobenzo[d]azocin-8-ol (Compound 14);
(2R,6S,11R)-3,6-dimethyl-11-((2-phenoxyethyl)amino)-1,2,3,4,5,6-hexahydro-2,6-methanobenzo[d]azocin-8-ol (Compound 15);

(2R,6S,11R)-11-((2-cyclohexylethyl)amino)-3,6-dimethyl-1,2,3,4,5,6-hexahydro-2,6-methanobenzo[d]azocin-8-ol (Compound 16);

(2R,6S,11S)-11-((2-cyclohexylethyl)amino)-3,6-dimethyl-1,2,3,4,5,6-hexahydro-2,6-methanobenzo[d]azocin-8-ol (Compound 17);

tert-Butyl (4-(((2R,6S,11R)-8-hydroxy-3,6-dimethyl-1,2,3,4,5,6-hexahydro-2,6-methanobenzo[d]azocin-11-yl)amino)butyl)carbamate (Compound 18);

tert-Butyl (4-(((2R,6S,11S)-8-hydroxy-3,6-dimethyl-1,2,3,4,5,6-hexahydro-2,6-methanobenzo[d]azocin-11-yl)amino)butyl)carbamate (Compound 19);

$N^1$-(2,4-difluorophenyl)-$N^3$-((2R,6S,11R)-8-hydroxy-3,6-dimethyl-1,2,3,4,5,6-hexahydro-2,6-methanobenzo[d]azocin-11-yl)-$N^3$-methylmalonamide (Compound 26);

1-(4-cyanophenyl)-3-((2R,6S,11R)-8-hydroxy-3,6-dimethyl-1,2,3,4,5,6-hexahydro-2,6-methanobenzo[d]azocin-11-yl)urea (Compound 27);

N-((2R,6S,11R)-8-hydroxy-3,6-dimethyl-1,2,3,4,5,6-hexahydro-2,6-methanobenzo[d]azocin-11-yl)-N-methyl-2-(4-(methyl-sulfonyl)phenyl)acetamide (Compound 28);

N-((2R,6S,11S)-8-hydroxy-3,6-dimethyl-1,2,3,4,5,6-hexahydro-2,6-methanobenzo[d]azocin-11-yl)-2-phenylacetamide (Compound 29);

$N^1$-(2,4-difluorophenyl)-$N^3$-((2R,6S,11R)-8-hydroxy-3,6-dimethyl-1,2,3,4,5,6-hexahydro-2,6-methanobenzo[d]azocin-11-yl)malonamide (Compound 30);

N-((2R,6S,11S)-8-hydroxy-3,6-dimethyl-1,2,3,4,5,6-hexahydro-2,6-methanobenzo-[d]azocin-11-yl)-2-(thiophen-3-yl)acetamide (Compound 31);

(E)-3-(furan-3-yl)-N-((2R,6S,11S)-8-hydroxy-3,6-dimethyl-1,2,3,4,5,6-hexahydro-2,6-methanobenzo[d]azocin-11-yl)acrylamide (Compound 32);

N-((2R,6S,11R)-8-hydroxy-3,6-dimethyl-1,2,3,4,5,6-hexahydro-2,6-methanobenzo[d]azocin-11-yl)-2-(4-(methylsulfonyl)-phenyl)acetamide (Compound 33);

$N^1$-(2,4-difluorophenyl)-$N^4$-((2R,6S,11S)-8-hydroxy-3,6-dimethyl-1,2,3,4,5,6-hexahydro-2,6-methanobenzo[d]azocin-11-yl)succinamide (Compound 34);

N-((2R,6S,11S)-8-hydroxy-3,6-dimethyl-1,2,3,4,5,6-hexahydro-2,6-methanobenzo[d]azocin-11-yl)-N-methyl-2-(4-(methyl-sulfonyl)-phenyl)acetamide (Compound 35);

N-(6-fluorobenzo[d]thiazol-2-yl)-2-(((2R,6S,11R)-8-hydroxy-3,6-dimethyl-1,2,3,4,5,6-hexahydro-2,6-methano-benzo[d]azocin-11-yl)-(methyl)amino)acetamide (Compound 40);

2-(((2R,6S,11R)-8-hydroxy-3,6-dimethyl-1,2,3,4,5,6-hexahydro-2,6-methanobenzo[d]azocin-11-yl)(methyl)amino)-N-(4-(tri-fluoromethyl)phenyl)acetamide (Compound 41);

N-((2R,6S,11R)-8-methoxy-3,6-dimethyl-1,2,3,4,5,6-hexahydro-2,6-methanobenzo[d]azocin-11-yl)-N-methyl-2-(3-oxopiperazin-1-yl)acetamide (Compound 44);

(2R,6S,11S)-8-methoxy-N,3,6-trimethyl-N-(piperidin-4-ylmethyl)-1,2,3,4,5,6-hexahydro-2,6-methanobenzo[d]azocin-11-amine (Compound 49);

1-(4-((((2R,6S,11R)-8-hydroxy-3,6-dimethyl-1,2,3,4,5,6-hexahydro-2,6-methano-benzo[d]azocin-11-yl)-(methyl)amino)methyl)piperidin-1-yl)-2,2-dimethylpropan-1-one (Compound 52);

(2R,6S,11R)-3,6-dimethyl-11-(methyl((1-(methylsulfonyl)-piperidin-4-yl)methyl)amino)-1,2,3,4,5,6-hexahydro-2,6-methanobenzo[d]azocin-8-ol (Compound 54);

(2R,6S,11R)-11-(((1-(isopropylsulfonyl)piperidin-4-yl)methyl)(methyl)amino)-3,6-dimethyl-1,2,3,4,5,6-hexahydro-2,6-methanobenzo[d]azocin-8-ol (Compound 55);

(2R,6S,11R)-11-(((1-(ethylsulfonyl)piperidin-4-yl)methyl)(methyl)amino)-3,6-dimethyl-1,2,3,4,5,6-hexahydro-2,6-methanobenzo[d]azocin-8-ol (Compound 56);

(2R,6S,11R)-11-(((1-(cyclopropylsulfonyl)piperidin-4-yl)methyl)(methyl)amino)-3,6-dimethyl-1,2,3,4,5,6-hexahydro-2,6-methanobenzo[d]azocin-8-ol (Compound 57);

(2R,6S,11S)-11-(((1-(benzylsulfonyl)piperidin-4-yl)methyl)(methyl)amino)-3,6-dimethyl-1,2,3,4,5,6-hexahydro-2,6-methanobenzo[d]azocin-8-ol (Compound 58);

(2R,6S,11S)-11-(((1-(isobutylsulfonyl)piperidin-4-yl)methyl)(methyl)amino)-3,6-dimethyl-1,2,3,4,5,6-hexahydro-2,6-methanobenzo[d]azocin-8-ol (Compound 59);

(2R,6S,11S)-11-(((1-(cyclopentylsulfonyl)piperidin-4-yl)methyl)(methyl)amino)-3,6-dimethyl-1,2,3,4,5,6-hexahydro-2,6-methanobenzo[d]azocin-8-ol (Compound 60);

(2R,6S,11S)-11-(((1-(isopropylsulfonyl)piperidin-4-yl)methyl)amino)-3,6-dimethyl-1,2,3,4,5,6-hexahydro-2,6-methanobenzo[d]azocin-8-ol (Compound 65);

N-(4-fluorophenethyl)-N-((2R,6S,11S)-8-hydroxy-3,6-dimethyl-1,2,3,4,5,6-hexahydro-2,6-methanobenzo[d]azocin-11-yl)glycine (Compound 72);

N-(4-fluorophenethyl)-N-((2R,6S,11R)-8-hydroxy-3,6-dimethyl-1,2,3,4,5,6-hexahydro-2,6-methanobenzo[d]azocin-11-yl)glycine (Compound 73);

2-((4-fluorophenethyl)-((2R,6S,11R)-8-hydroxy-3,6-dimethyl-1,2,3,4,5,6-hexahydro-2,6-methanobenzo[d]azocin-11-yl)amino)acetamide (Compound 74);

(2R,6S,11S)-11-((4-fluoro-phenethyl)(2-hydroxyethyl)-amino)-3,6-dimethyl-1,2,3,4,5,6-hexahydro-2,6-methanobenzo-[d]azocin-8-ol (Compound 77);

3-(6-fluorobenzo[d]thiazol-2-yl)-1-((2R,6S,11R)-8-hydroxy-3,6-dimethyl-1,2,3,4,5,6-hexahydro-2,6-methanobenzo[d]azocin-11-yl)-1-methylurea (Compound 81);

3-(5-fluorobenzo[d]thiazol-2-yl)-1-((2R,6S,11S)-8-hydroxy-3,6-dimethyl-1,2,3,4,5,6-hexahydro-2,6-methanobenzo[d]azocin-11-yl)-1-methylurea (Compound 82);

3-(4-cyanophenyl)-1-ethyl-1-((2R,6S,11R)-8-hydroxy-3,6-dimethyl-1,2,3,4,5,6-hexahydro-2,6-methanobenzo[d]azocin-11-yl)urea (Compound 91);

3-(4-cyanophenyl)-1-((2R,6S,11R)-8-hydroxy-3,6-dimethyl-1,2,3,4,5,6-hexahydro-2,6-methanobenzo[d]azocin-11-yl)-1-propylurea (Compound 92);

3-(4-cyanophenyl)-1-ethyl-1-((2R,6S,11S)-8-hydroxy-3,6-dimethyl-1,2,3,4,5,6-hexahydro-2,6-methanobenzo[d]azocin-11-yl)urea (Compound 93);

N-(tert-butyl)-4-(((((2R,6S,11R)-8-hydroxy-3,6-dimethyl-1,2,3,4,5,6-hexahydro-2,6-methanobenzo[d]azocin-11-yl)(methyl)amino)methyl)piperidine-1-carboxamide (Compound 95);

(2R,6S,11R)-11-(((1-(2-hydroxy-2-methylpropyl)piperidin-4-yl)methyl)-(methyl)amino)-3,6-dimethyl-1,2,3,4,5,6-hexahydro-2,6-methanobenzo[d]azocin-8-ol (Compound 97);

(2R,6S,11R)-11-(ethyl(4-(methylsulfonyl)phenethyl)amino)-3,6-dimethyl-1,2,3,4,5,6-hexahydro-2,6-methano-benzo[d]azocin-8-ol (Compound 98);

N-((2R,6S,11R)-8-hydroxy-3,6-dimethyl-1,2,3,4,5,6-hexahydro-2,6-methanobenzo[d]azocin-11-yl)-N-methyl-1-phenylmethane-sulfonamide (Compound 100);

N-((2R,6S,11S)-8-hydroxy-3,6-dimethyl-1,2,3,4,5,6-hexahydro-2,6-methanobenzo[d]azocin-11-yl)-1-phenylmethanesulfonamide (Compound 101);

N-((2R,6S,11S)-8-hydroxy-3,6-dimethyl-1,2,3,4,5,6-hexahydro-2,6-methanobenzo-[d]azocin-11-yl)benzenesulfonamide (Compound 102); and 3-(1H-benzo[d]imidazol-2-yl)-1-((2R,6S,11R)-8-hydroxy-3,6-dimethyl-1,2,3,4,5,6-hexahydro-2,6-methanobenzo[d]azocin-11-yl)-1-methylurea (Compound 107), and pharmaceutically acceptable salts thereof.

13. A compound selected from the group consisting of:
(2R,6S,11R)-11-(benzylamino)-3,6-dimethyl-1,2,3,4,5,6-hexahydro-2,6-methanobenzo[d]azocin-8-ol;

(2R,6S,11S)-3,6-dimethyl-11-((3-phenylpropyl)amino)-1,2,3,4,5,6-hexahydro-2,6-methanobenzo-[d]azocin-8-ol;

3-(1-ethyl-1H-benzo[d]imidazol-2-yl)-1-((2R,6S,11R)-8-methoxy-3,6-dimethyl-1,2,3,4,5,6-hexahydro-2,6-methanobenzo[d]azocin-11-yl)-1-methylurea;

3-(1H-benzo[d]imidazol-2-yl)-1-((2R,6S,11R)-8-methoxy-3,6-dimethyl-1,2,3,4,5,6-hexahydro-2,6-methanobenzo[d]azocin-11-yl)-1-methylurea;

3-(1-ethyl-1H-benzo[d]imidazol-2-yl)-1-((2R,6S,11R)-8-hydroxy-3,6-dimethyl-1,2,3,4,5,6-hexahydro-2,6-methanobenzo[d]azocin-11-yl)-1-methylurea;

(2R,6S,11R)-3,6-dimethyl-11-(phenethylamino)-1,2,3,4,5,6-hexahydro-2,6-methanobenzo[d]azocine-8-carbonitrile;

(2R,6S,11R)-3,6-dimethyl-11-(phenethylamino)-1,2,3,4,5,6-hexahydro-2,6-methanobenzo-[d]azocine-8-carboxamide;

(2R,6S,11S)-3,6-dimethyl-11-(phenethylamino)-1,2,3,4,5,6-hexahydro-2,6-methanobenzo[d]azocine-8-carboxamide;

(2R,6S)-11,11-dihydroxy-3,6-dimethyl-1,2,3,4,5,6-hexahydro-2,6-methanobenzo[d]azocine-8-carbonitrile;

(2R,6S)-11,11-dihydroxy-3,6-dimethyl-1,2,3,4,5,6-hexahydro-2,6-methanobenzo[d]azocine-8-carboxylic acid;

(2R,6S)-11,11-dihydroxy-3,6-dimethyl-1,2,3,4,5,6-hexahydro-2,6-methanobenzo[d]azocine-8-carboxamide;

(2R,6S,11R)-11-(3-(4-cyanophenyl)-1-methylureido)-3,6-dimethyl-1,2,3,4,5,6-hexahydro-2,6-methanobenzo[d]azocine-8-carboxamide;

(2R,6S,11S)-11-(3-(4-cyanophenyl)-1-methylureido)-3,6-dimethyl-1,2,3,4,5,6-hexahydro-2,6-methanobenzo[d]azocine-8-carboxamide;

3-(benzo[d]oxazol-2-yl)-1-((2R,6S,11R)-8-hydroxy-3,6-dimethyl-1,2,3,4,5,6-hexahydro-2,6-methanobenzo[d]azocin-11-yl)-1-methylurea;

1-(5-fluorobenzo[d]thiazol-2-yl)-3-((2R,6S,11S)-8-hydroxy-3,6-dimethyl-1,2,3,4,5,6-hexahydro-2,6-methanobenzo[d]azocin-11-yl)urea;

(2R,6S,11R)-3,6-dimethyl-11-(methyl(phenethyl)amino)-1,2,3,4,5,6-hexahydro-2,6-methanobenzo[d]azocine-8-carboxamide;

(2R,6S,11R)-3,6-dimethyl-11-(N-methyl-2-phenylacetamido)-1,2,3,4,5,6-hexahydro-2,6-methanobenzo[d]azocine-8-carboxamide;

(2R,6S,11 S)-3,6-dimethyl-11-((4-(methylsulfonyl)phenethyl)amino)-1,2,3,4,5,6-hexahydro-2,6-methanobenzo[d]azocine-8-carboxylic acid; and (2R,6S,11R)-3,6-dimethyl-11-((4-(methylsulfonyl)phenethyl)amino)-1,2,3,4,5,6-hexahydro-2,6-methanobenzo[d]azocine-8-carboxylic acid;

and pharmaceutically acceptable salts thereof.

14. A pharmaceutical composition comprising an effective amount of a compound of claim 1, or a pharmaceutically acceptable salt thereof, and a pharmaceutically acceptable carrier or excipient.

15. A pharmaceutical composition comprising an effective amount of a compound of claim 12, or a pharmaceutically acceptable salt thereof, and a pharmaceutically acceptable carrier or excipient.

16. A pharmaceutical composition comprising an effective amount of a compound of claim 13, or a pharmaceutically acceptable salt thereof, and a pharmaceutically acceptable carrier or excipient.

17. A pharmaceutical composition comprising an effective amount of a compound of claim 11, or a pharmaceutically acceptable salt thereof, and a pharmaceutically acceptable carrier or excipient.

\* \* \* \* \*